(12) United States Patent
Ashraf et al.

(10) Patent No.: US 11,160,694 B2
(45) Date of Patent: Nov. 2, 2021

(54) THREE-DIMENSIONAL SUBSTRATES AND ABSORBENT ARTICLES HAVING THE SAME

(71) Applicant: The Procter & Gamble Company, Cincinnati, OH (US)

(72) Inventors: Arman Ashraf, Mason, OH (US); Kelyn Anne Arora, Cincinnati, OH (US); Matthew Steven Ritter, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/795,713

(22) Filed: Feb. 20, 2020

(65) Prior Publication Data

US 2020/0268572 A1 Aug. 27, 2020

Related U.S. Application Data

(63) Continuation of application No. 15/881,910, filed on Jan. 29, 2018, now abandoned.
(Continued)

(51) Int. Cl.
*A61F 13/511* (2006.01)
*A61F 13/512* (2006.01)
(Continued)

(52) U.S. Cl.
CPC ...... *A61F 13/51104* (2013.01); *A61F 13/511* (2013.01); *A61F 13/512* (2013.01);
(Continued)

(58) Field of Classification Search
None
See application file for complete search history.

(56) References Cited

U.S. PATENT DOCUMENTS 3,274,018 A * 9/1966 Russell .................... D04H 1/74
427/275
4,079,739 A * 3/1978 Whitehead ........ A61F 13/15674
604/365
(Continued)

FOREIGN PATENT DOCUMENTS

CN 1302194 A 7/2001
CN 1135275 C 1/2004
(Continued)

OTHER PUBLICATIONS

Machine Translation of JP 2009000512 A, Jan. 2009 (Year: 2009).*
(Continued)

*Primary Examiner* — Jeffrey A Vonch
(74) *Attorney, Agent, or Firm* — Christian M. Best

(57) ABSTRACT

A three-dimensional substrate has a central longitudinal axis extending perpendicular to a central lateral axis. A line taken in a direction parallel to or perpendicular to the central lateral axis of the three-dimensional substrate has a non-apertured, first visually discernible zone in the substrate and a second visually discernible zone in the substrate. The first visually discernable zone has a pattern of three-dimensional features on a first surface or a second surface. At least some of the three-dimensional features define a microzone having a first region and a second region. The first region and the second region have a difference in value for an intensive property. The second visually discernable zone defines apertures. The apertures have an Effective Aperture Area in a range of about 0.3 mm² to about 15 mm².

24 Claims, 59 Drawing Sheets

Related U.S. Application Data

(60) Provisional application No. 62/452,425, filed on Jan. 31, 2017.

(51) Int. Cl.

| | |
|---|---|
| *A61F 13/513* | (2006.01) |
| *A61F 13/551* | (2006.01) |
| *B32B 3/24* | (2006.01) |
| *B32B 3/26* | (2006.01) |
| *B32B 3/28* | (2006.01) |
| *B32B 3/30* | (2006.01) |
| *B32B 5/02* | (2006.01) |
| *B32B 5/14* | (2006.01) |
| *A61F 13/49* | (2006.01) |
| *D04H 3/007* | (2012.01) |
| *D04H 3/16* | (2006.01) |
| *B32B 3/02* | (2006.01) |
| *A61F 13/51* | (2006.01) |

(52) U.S. Cl.
CPC .... *A61F 13/5126* (2013.01); *A61F 13/51394* (2013.01); *B32B 3/26* (2013.01); *B32B 3/266* (2013.01); *B32B 3/28* (2013.01); *B32B 3/30* (2013.01); *B32B 5/022* (2013.01); *B32B 5/142* (2013.01); *B32B 5/147* (2013.01); *A61F 13/49011* (2013.01); *A61F 13/51305* (2013.01); *A61F 13/551* (2013.01); *A61F 2013/49093* (2013.01); *A61F 2013/5127* (2013.01); *A61F 2013/5128* (2013.01); *A61F 2013/51078* (2013.01); *A61F 2013/51178* (2013.01); *A61F 2013/51338* (2013.01); *A61F 2013/51377* (2013.01); *B32B 3/02* (2013.01); *B32B 2307/50* (2013.01); *B32B 2307/718* (2013.01); *B32B 2307/72* (2013.01); *B32B 2307/722* (2013.01); *B32B 2555/02* (2013.01); *D04H 3/007* (2013.01); *D04H 3/16* (2013.01); *Y10T 428/2495* (2015.01); *Y10T 428/24273* (2015.01); *Y10T 428/24298* (2015.01); *Y10T 428/24479* (2015.01); *Y10T 428/24603* (2015.01); *Y10T 428/24628* (2015.01); *Y10T 428/24736* (2015.01); *Y10T 428/24942* (2015.01); *Y10T 428/24992* (2015.01); *Y10T 442/601* (2015.04); *Y10T 442/659* (2015.04); *Y10T 442/681* (2015.04)

(56) References Cited

U.S. PATENT DOCUMENTS

| | | | | |
|---|---|---|---|---|
| 4,333,979 | A * | 6/1982 | Sciaraffa | D04H 3/14 |
| | | | | 428/179 |
| 4,741,941 | A * | 5/1988 | Englebert | A61F 13/51104 |
| | | | | 428/71 |
| 4,970,104 | A | 11/1990 | Radwanski | |
| 5,277,761 | A * | 1/1994 | Phan | D21F 11/00 |
| | | | | 162/109 |
| 5,334,289 | A | 8/1994 | Trokhan et al. | |
| 5,514,523 | A | 5/1996 | Trokhan et al. | |
| 5,575,874 | A * | 11/1996 | Griesbach, III | A61F 13/512 |
| | | | | 156/167 |
| 5,599,420 | A | 2/1997 | Yeo et al. | |
| 5,628,097 | A * | 5/1997 | Benson | A61F 13/15731 |
| | | | | 28/165 |
| 5,643,653 | A | 7/1997 | Griesbach, III | A61F 13/512 |
| | | | | 428/120 |
| 5,708,034 | A * | 1/1998 | Kleemann | A61P 9/12 |
| | | | | 514/618 |
| 5,714,107 | A * | 2/1998 | Levy | D04H 1/54 |
| | | | | 264/146 |
| 5,725,927 | A | 3/1998 | Zilg et al. | |
| 5,858,504 | A | 1/1999 | Steven | |
| 5,895,623 | A | 4/1999 | Trokhan et al. | |
| 5,916,661 | A | 6/1999 | Benson et al. | |
| 6,039,555 | A * | 3/2000 | Tsuji | A61F 13/51121 |
| | | | | 425/362 |
| 6,139,941 | A | 10/2000 | Jankevics et al. | |
| 6,319,239 | B1 * | 11/2001 | Daniels | A61F 13/539 |
| | | | | 604/378 |
| 6,319,455 | B1 | 11/2001 | Kauschke et al. | |
| 6,331,268 | B1 | 12/2001 | Kauschke et al. | |
| 6,331,345 | B1 | 12/2001 | Kauschke et al. | |
| 6,361,638 | B2 * | 3/2002 | Takai | A61F 13/42 |
| | | | | 156/209 |
| 6,383,431 | B1 | 5/2002 | Dobrin et al. | |
| 6,395,957 | B1 | 5/2002 | Chen et al. | |
| 6,436,512 | B1 | 8/2002 | Kauschke et al. | |
| 6,437,214 | B1 * | 8/2002 | Everett | A61F 13/15203 |
| | | | | 604/378 |
| 6,586,076 | B1 * | 7/2003 | Mizutani | A61F 13/511 |
| | | | | 428/173 |
| 6,632,504 | B1 * | 10/2003 | Gillespie | D04H 3/16 |
| | | | | 428/131 |
| D483,187 | S * | 12/2003 | Cheng | D5/53 |
| 6,673,418 | B1 | 1/2004 | DeOlivera et al. | |
| 6,818,802 | B2 | 11/2004 | Takai et al. | |
| 6,911,574 | B1 * | 6/2005 | Mizutani | A61F 13/512 |
| | | | | 604/380 |
| 7,371,919 | B1 * | 5/2008 | Busam | B29C 66/83411 |
| | | | | 604/367 |
| 7,507,463 | B2 | 3/2009 | Noda et al. | |
| 7,553,535 | B2 | 6/2009 | Noda et al. | |
| 7,662,462 | B2 | 2/2010 | Noda et al. | |
| 7,897,240 | B2 | 3/2011 | Noda et al. | |
| 7,954,213 | B2 | 6/2011 | Mizutani | |
| 7,955,549 | B2 | 6/2011 | Noda et al. | |
| 8,143,177 | B2 | 3/2012 | Noda et al. | |
| 8,183,431 | B2 | 5/2012 | Noda et al. | |
| 8,273,941 | B2 | 9/2012 | Uematsu et al. | |
| 8,304,600 | B2 | 11/2012 | Noda et al. | |
| 8,574,209 | B2 | 11/2013 | Nishitani et al. | |
| 8,585,666 | B2 | 11/2013 | Weisman et al. | |
| 8,758,569 | B2 | 6/2014 | Aberg et al. | |
| 8,853,108 | B2 | 10/2014 | Ahoniemi et al. | |
| 8,865,965 | B2 | 10/2014 | Sato et al. | |
| 8,906,275 | B2 | 12/2014 | Davis et al. | |
| 9,095,477 | B2 | 8/2015 | Yamaguchi et al. | |
| 9,156,229 | B2 | 10/2015 | Yoda et al. | |
| 9,205,005 | B2 | 12/2015 | Kikuchi et al. | |
| 9,453,303 | B2 | 9/2016 | Aberg et al. | |
| 9,732,454 | B2 | 8/2017 | Davis et al. | |
| 9,877,876 | B2 | 1/2018 | Huang et al. | |
| 9,903,070 | B2 | 2/2018 | Mourad et al. | |
| 10,190,244 | B2 | 1/2019 | Ashraf | |
| 10,577,722 | B2 | 3/2020 | Ashraf et al. | |
| 2001/0029141 | A1 | 10/2001 | Mizutani et al. | |
| 2001/0053901 | A1 * | 12/2001 | Mizutani | A61F 13/51305 |
| | | | | 604/381 |
| 2002/0034914 | A1 * | 3/2002 | De Leon | D04H 1/49 |
| | | | | 442/384 |
| 2002/0052582 | A1 * | 5/2002 | Takai | A61F 13/512 |
| | | | | 604/358 |
| 2002/0068150 | A1 * | 6/2002 | Taneichi | A61F 13/5123 |
| | | | | 428/138 |
| 2002/0103469 | A1 | 8/2002 | Chen et al. | |
| 2002/0150431 | A1 | 10/2002 | Ofosu-Asante | |
| 2002/0153271 | A1 | 10/2002 | McManus et al. | |
| 2002/0180092 | A1 * | 12/2002 | Abba | D04H 1/732 |
| | | | | 264/112 |
| 2002/0193032 | A1 * | 12/2002 | Newkirk | D04H 5/08 |
| | | | | 442/401 |
| 2003/0008108 | A1 * | 1/2003 | Shizuno | D04H 3/11 |
| | | | | 428/156 |
| 2003/0021951 | A1 * | 1/2003 | Desai | B29C 55/146 |
| | | | | 428/131 |
| 2003/0028165 | A1 * | 2/2003 | Curro | A47L 13/17 |
| | | | | 604/378 |

(56) References Cited

U.S. PATENT DOCUMENTS

| | | |
|---|---|---|
| 2003/0050615 A1* | 3/2003 | Sakamoto ......... A61F 13/51104 604/358 |
| 2003/0073367 A1* | 4/2003 | Kopacz .................... B32B 5/26 442/381 |
| 2003/0082358 A1* | 5/2003 | Wenstrup ................ D04H 1/54 428/218 |
| 2003/0093045 A1 | 5/2003 | Jensen |
| 2003/0118777 A1* | 6/2003 | Chang ..................... D04H 3/14 428/156 |
| 2003/0119404 A1 | 6/2003 | Belau et al. |
| 2003/0125687 A1 | 7/2003 | Gubemick et al. |
| 2003/0143376 A1* | 7/2003 | Toyoshima ......... A61F 13/5116 428/156 |
| 2003/0162460 A1* | 8/2003 | Saka .................... D04H 1/5414 442/394 |
| 2003/0167044 A1* | 9/2003 | Toyoshima ............ D04H 1/542 604/367 |
| 2003/0203162 A1 | 10/2003 | Christopher et al. |
| 2003/0203691 A1* | 10/2003 | Fenwick .................. D04H 3/14 442/327 |
| 2003/0211802 A1 | 11/2003 | Keck et al. |
| 2003/0232558 A1* | 12/2003 | Moody, III ............. D04H 1/49 442/327 |
| 2004/0059309 A1 | 3/2004 | Nortman |
| 2004/0109911 A1* | 6/2004 | Boegli .................... B29C 59/04 425/363 |
| 2004/0111848 A1* | 6/2004 | Miyamoto ........ A61F 13/15699 28/165 |
| 2004/0254554 A1* | 12/2004 | Mavinkurve ..... A61F 13/51104 604/380 |
| 2005/0008825 A1* | 1/2005 | Casey ..................... D04H 3/14 428/174 |
| 2005/0148971 A1* | 7/2005 | Kuroda ................ A61F 13/512 604/380 |
| 2006/0005717 A1* | 1/2006 | Barge ....................... D04H 3/11 101/27 |
| 2006/0087053 A1 | 4/2006 | O'Donnell et al. |
| 2006/0105075 A1 | 5/2006 | Otsubo |
| 2006/0128247 A1* | 6/2006 | Skoog .................... D04H 3/14 442/384 |
| 2006/0131777 A1* | 6/2006 | Debyser ................ D04H 1/559 264/171.1 |
| 2006/0189954 A1 | 8/2006 | Kudo |
| 2006/0234586 A1* | 10/2006 | Wong ..................... D04H 3/10 442/327 |
| 2006/0286343 A1* | 12/2006 | Curro ..................... B32B 27/12 428/131 |
| 2006/0287636 A1* | 12/2006 | Sakai ...................... A61F 13/539 604/385.101 |
| 2007/0026753 A1* | 2/2007 | Neely ...................... D04H 3/02 442/327 |
| 2007/0045143 A1 | 3/2007 | Clough et al. |
| 2007/0045144 A1 | 3/2007 | Wheeler et al. |
| 2007/0074832 A1* | 4/2007 | Ampulski .............. D21C 9/005 162/109 |
| 2007/0074833 A1* | 4/2007 | Ampulski ............ D21H 25/005 162/109 |
| 2007/0128411 A1* | 6/2007 | Kawai ..................... B32B 3/263 428/170 |
| 2007/0163454 A1* | 7/2007 | Orlandi ................. B41F 17/003 101/45 |
| 2007/0179466 A1 | 8/2007 | Tremblay et al. |
| 2007/0255247 A1* | 11/2007 | Moberg-Alehammar ................. A61F 13/5116 604/385.101 |
| 2007/0298213 A1* | 12/2007 | Noda ..................... A61F 13/51 428/131 |
| 2007/0298214 A1 | 12/2007 | Noda et al. |
| 2007/0298220 A1* | 12/2007 | Noda ................ A61F 13/53717 428/152 |
| 2007/0298667 A1 | 12/2007 | Noda et al. |
| 2007/0299416 A1* | 12/2007 | Noda ................ A61F 13/15658 604/367 |
| 2008/0044622 A1* | 2/2008 | Noda ....................... D04H 1/74 428/131 |
| 2008/0044628 A1* | 2/2008 | Noda ....................... D04H 1/54 428/163 |
| 2008/0102250 A1* | 5/2008 | Ostendorf .............. D21H 27/02 428/153 |
| 2008/0102261 A1* | 5/2008 | Hupp ...................... D04H 11/08 428/218 |
| 2008/0149292 A1 | 6/2008 | Scherb |
| 2009/0123707 A1* | 5/2009 | Skoog .................... D04H 1/498 428/172 |
| 2009/0209156 A1* | 8/2009 | Pedoja .................... D04H 18/04 442/327 |
| 2009/0240222 A1 | 9/2009 | Tomoko et al. |
| 2010/0035014 A1* | 2/2010 | Hammons ........... A61F 13/4751 428/88 |
| 2010/0036346 A1* | 2/2010 | Hammons ........... A61F 13/51305 604/378 |
| 2010/0036349 A1* | 2/2010 | Hammons ............. A61F 13/512 604/385.01 |
| 2010/0048072 A1* | 2/2010 | Kauschke ............... A47L 13/16 442/1 |
| 2010/0130952 A1* | 5/2010 | Murai ..................... A61F 13/512 604/367 |
| 2010/0249740 A1* | 9/2010 | Miyamoto ........ A61F 13/51305 604/384 |
| 2010/0310845 A1* | 12/2010 | Bond ..................... A61F 13/5376 428/219 |
| 2010/0312208 A1* | 12/2010 | Bond ..................... A61F 13/538 604/366 |
| 2011/0073513 A1* | 3/2011 | Weisman .......... A61F 13/15203 206/494 |
| 2011/0123775 A1* | 5/2011 | Westwood ............ D04H 1/4382 428/172 |
| 2011/0196330 A1* | 8/2011 | Hammons ........... A61F 13/51305 604/383 |
| 2011/0250378 A1 | 10/2011 | Eaton et al. |
| 2011/0313385 A1* | 12/2011 | Hammons ......... A61F 13/51104 604/378 |
| 2012/0004633 A1 | 1/2012 | Marcelo et al. |
| 2012/0023693 A1* | 2/2012 | Pung ...................... A47L 13/16 15/209.1 |
| 2012/0064280 A1 | 3/2012 | Hammons |
| 2012/0107567 A1* | 5/2012 | Terada .................. D04H 1/5412 428/156 |
| 2012/0141742 A1* | 6/2012 | Yamaguchi ............ D04H 1/435 428/182 |
| 2012/0196091 A1* | 8/2012 | Mizutani ................. D04H 1/70 428/171 |
| 2012/0226250 A1* | 9/2012 | Sato ................... A61F 13/51104 604/367 |
| 2012/0237718 A1* | 9/2012 | Weisman ................ D04H 3/011 428/89 |
| 2012/0276239 A1* | 11/2012 | Coe ................... A61F 13/15731 425/418 |
| 2012/0276331 A1* | 11/2012 | Orr ........................ B32B 3/28 428/137 |
| 2012/0276341 A1* | 11/2012 | Lake ....................... B29C 55/18 428/174 |
| 2012/0277705 A1* | 11/2012 | Marinelli .............. A61F 13/534 604/374 |
| 2012/0277706 A1* | 11/2012 | Marinelli .................. B26F 1/24 604/374 |
| 2012/0282436 A1* | 11/2012 | Coe ........................... B31F 1/07 428/131 |
| 2013/0034686 A1* | 2/2013 | Mitsuno ................... D04H 3/16 428/131 |
| 2013/0095288 A1* | 4/2013 | Terada ................. D04H 1/5412 428/137 |
| 2013/0112584 A1 | 5/2013 | Gaspari et al. |
| 2013/0137328 A1* | 5/2013 | Mitsuno ................... D04H 3/02 442/327 |
| 2013/0139960 A1 | 6/2013 | Maruyama et al. |

(56) References Cited

U.S. PATENT DOCUMENTS

| | | | |
|---|---|---|---|
| 2013/0171421 A1* | 7/2013 | Weisman | C11D 17/047 428/171 |
| 2013/0178811 A1* | 7/2013 | Kikuchi | A61F 13/51104 604/365 |
| 2013/0178815 A1* | 7/2013 | Ohashi | A61F 13/514 604/380 |
| 2013/0211358 A1* | 8/2013 | Kikkawa | A61F 13/53708 604/367 |
| 2013/0232712 A1* | 9/2013 | Kawai | D04H 1/558 15/209.1 |
| 2013/0236700 A1* | 9/2013 | Yamanaka | A61F 13/5116 428/169 |
| 2013/0253461 A1* | 9/2013 | Xu | A61F 13/511 604/384 |
| 2013/0280481 A1* | 10/2013 | Mitsuno | D04H 5/06 428/131 |
| 2013/0003205 A1 | 12/2013 | Davis et al. | |
| 2013/0344286 A1* | 12/2013 | Mitsuno | A61F 13/513 428/137 |
| 2014/0004307 A1* | 1/2014 | Sheehan | B31F 1/07 428/156 |
| 2014/0023822 A1* | 1/2014 | Tai | A61F 13/15699 428/118 |
| 2014/0039434 A1* | 2/2014 | Xu | A61F 13/51456 604/368 |
| 2014/0039438 A1* | 2/2014 | Ferrer | A61F 13/84 604/385.01 |
| 2014/0121626 A1* | 5/2014 | Finn | B32B 3/30 604/384 |
| 2014/0127460 A1* | 5/2014 | Xu | A61F 13/51478 428/141 |
| 2014/0234575 A1* | 8/2014 | Mitsuno | B32B 5/145 428/137 |
| 2014/0276517 A1 | 9/2014 | Chester et al. | |
| 2014/0296815 A1* | 10/2014 | Takken | A61F 13/512 604/383 |
| 2014/0305570 A1 | 10/2014 | Matsunaga et al. | |
| 2014/0324009 A1* | 10/2014 | Lee | A61F 13/513 604/384 |
| 2014/0336605 A1* | 11/2014 | Hardie | A61F 13/512 604/369 |
| 2015/0038933 A1* | 2/2015 | Day | A61F 13/512 604/381 |
| 2015/0057627 A1* | 2/2015 | Noda | A61F 13/51108 604/367 |
| 2015/0173967 A1 | 6/2015 | Kreuzer et al. | |
| 2015/0250662 A1* | 9/2015 | Isele | A61F 13/5121 604/378 |
| 2015/0250663 A1* | 9/2015 | Wagner | A61F 13/51104 604/378 |
| 2015/0282999 A1* | 10/2015 | Arizti | A61F 13/52 604/385.06 |
| 2015/0283001 A1* | 10/2015 | Arizti | A61F 13/551 206/526 |
| 2016/0067119 A1 | 3/2016 | Weisman et al. | |
| 2016/0074254 A1* | 3/2016 | Orr | A61F 13/5121 428/162 |
| 2016/0074256 A1* | 3/2016 | Strube | D04H 1/559 428/171 |
| 2016/0076182 A1* | 3/2016 | Strube | B32B 3/28 28/134 |
| 2016/0076184 A1* | 3/2016 | Orr | A61F 13/51104 428/178 |
| 2016/0106633 A1 | 4/2016 | Nagata | |
| 2016/0129661 A1 | 5/2016 | Arora et al. | |
| 2016/0136009 A1 | 5/2016 | Weisman et al. | |
| 2016/0235590 A1* | 8/2016 | Coe | A61F 13/15804 |
| 2017/0014281 A1 | 1/2017 | Xie et al. | |
| 2017/0014291 A1 | 1/2017 | Tao et al. | |
| 2017/0027774 A1* | 2/2017 | Ashraf | A61F 13/15203 |
| 2017/0029993 A1 | 2/2017 | Ashraf et al. | |
| 2017/0029994 A1* | 2/2017 | Ashraf | D04H 3/11 |
| 2017/0056256 A1 | 3/2017 | Smith et al. | |
| 2017/0121873 A1 | 5/2017 | Kimura et al. | |
| 2017/0191198 A1* | 7/2017 | Ashraf | D04H 3/11 |
| 2017/0258650 A1 | 9/2017 | Rosati et al. | |
| 2017/0259524 A1* | 9/2017 | Neton | D04H 1/5412 |
| 2017/0260665 A1* | 9/2017 | Kauschke | D06C 15/08 |
| 2017/0282517 A1 | 10/2017 | Cabell et al. | |
| 2017/0348163 A1 | 12/2017 | Lakso et al. | |
| 2018/0168893 A1* | 6/2018 | Ashraf | D04H 3/147 |
| 2018/0177645 A1* | 6/2018 | Kimura | A41B 13/04 |
| 2018/0193208 A1* | 7/2018 | Hashimoto | A61F 13/15707 |
| 2018/0214318 A1* | 8/2018 | Ashraf | A61F 13/51401 |
| 2018/0214321 A1* | 8/2018 | Ashraf | A61F 13/5126 |
| 2018/0216269 A1* | 8/2018 | Ashraf | D04H 3/018 |
| 2018/0216270 A1 | 8/2018 | Ashraf et al. | |
| 2018/0216271 A1 | 8/2018 | Ashraf et al. | |
| 2018/0228659 A1* | 8/2018 | Conrad | A61F 13/15699 |
| 2018/0245252 A1* | 8/2018 | Groten | D04H 1/495 |
| 2019/0003079 A1* | 1/2019 | Ashraf | D04H 3/14 |
| 2019/0003080 A1* | 1/2019 | Ashraf | A61F 13/55115 |
| 2019/0060140 A1* | 2/2019 | Oshima | A61F 13/53 |
| 2019/0112737 A1 | 4/2019 | Ashraf | |
| 2019/0142654 A1* | 5/2019 | Uda | A61F 13/512 604/383 |
| 2020/0054501 A1 | 2/2020 | Seto et al. | |
| 2020/0149191 A1 | 5/2020 | Ashraf et al. | |
| 2020/0268571 A1* | 8/2020 | Miyama | D04H 1/435 |
| 2020/0299881 A1* | 9/2020 | Ashraf | A61F 13/51104 |

FOREIGN PATENT DOCUMENTS

| | | | | |
|---|---|---|---|---|
| CN | 1685099 | | 10/2005 | |
| CN | 1764533 A | | 4/2006 | |
| CN | 203400265 U | * | 1/2014 | |
| DE | 102007023356 A1 | * | 11/2008 | D04H 1/492 |
| EP | 1227181 A2 | * | 7/2002 | B29C 59/04 |
| EP | 2660377 | | 4/2014 | |
| JP | 10094558 A | * | 4/1998 | |
| JP | 2002249965 A | * | 9/2002 | |
| JP | 2003070841 A | * | 3/2003 | D04H 3/14 |
| JP | 2004113489 A | * | 4/2004 | |
| JP | 2006175688 A | * | 7/2006 | |
| JP | 2006175689 A | * | 7/2006 | |
| JP | 2008127706 A | * | 6/2008 | |
| JP | 2008132631 A | * | 6/2008 | |
| JP | 2008161302 A | * | 7/2008 | |
| JP | 2009-000512 | | 1/2009 | |
| JP | 2009000512 A | * | 1/2009 | |
| JP | 2009-101091 | | 5/2009 | |
| JP | 2009101091 A | * | 5/2009 | |
| JP | 2009185408 A | * | 8/2009 | |
| JP | 2009215667 A | * | 9/2009 | |
| JP | 2010-024573 | | 2/2010 | |
| JP | 2010024573 A | * | 2/2010 | |
| JP | 2011-015707 | | 1/2011 | |
| JP | 2012125629 A | * | 7/2012 | B29C 55/18 |
| JP | 2014-097257 | | 5/2014 | |
| JP | 2014-188042 | | 10/2014 | |
| TW | 200951264 A | * | 12/2009 | B29C 55/18 |
| WO | 2003015681 | | 2/2003 | |
| WO | WO-2004029349 A1 | * | 4/2004 | D04H 3/14 |
| WO | WO-2008051548 A2 | * | 5/2008 | B29C 55/18 |
| WO | WO-2008146594 A1 | * | 12/2008 | A61F 13/51104 |
| WO | WO-2011155284 A1 | * | 12/2011 | A61F 13/51305 |
| WO | WO201286730 | | 6/2012 | |
| WO | WO201318846 | | 2/2013 | |
| WO | WO 2013-084977 | | 6/2013 | |
| WO | WO201399625 | | 7/2013 | |
| WO | WO2013145966 | | 10/2013 | |
| WO | WO-2014115401 A1 | * | 7/2014 | D04H 3/007 |
| WO | 2016073686 A1 | | 5/2016 | |
| WO | WO 2017-105997 | | 6/2017 | |
| WO | WO2017110695 | | 6/2017 | |

OTHER PUBLICATIONS

Machine Translation of JP 2010024573 A, Feb. 2010 (Year: 2010).*
3D Nonwovens Developments for textured nonwovens; Detlef

(56) References Cited

OTHER PUBLICATIONS

Frey; http://web.archive.org/web/20170919080326/https://www.reicofil.com/en/pages/3d_nonwovens, Sep. 19, 2017.
PCT International Search Report U.S. Appl. No. 15/881,910 dated May 16, 2018—5 pages.
Written Opinion, PCT/US2018/015642, dated May 16, 2018.
All Office Actions U.S. Appl. No. 15/881,910.
All Office Actions U.S. Appl. No. 16/019,724.
All Office Actions U.S. Appl. No. 16/019,785.
All Office Actions, U.S. Appl. No. 16/744,516.
All Office Actions, U.S. Appl. No. 17/361,370.
Unpublished U.S. Appl. No. 17/361,370, filed Jun. 29, 2021, to Ashraf Arman et al.

\* cited by examiner

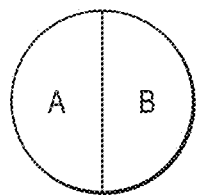
FIG. 8A
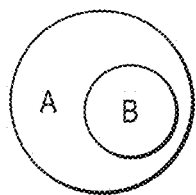
FIG. 8B
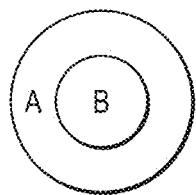
FIG. 8C
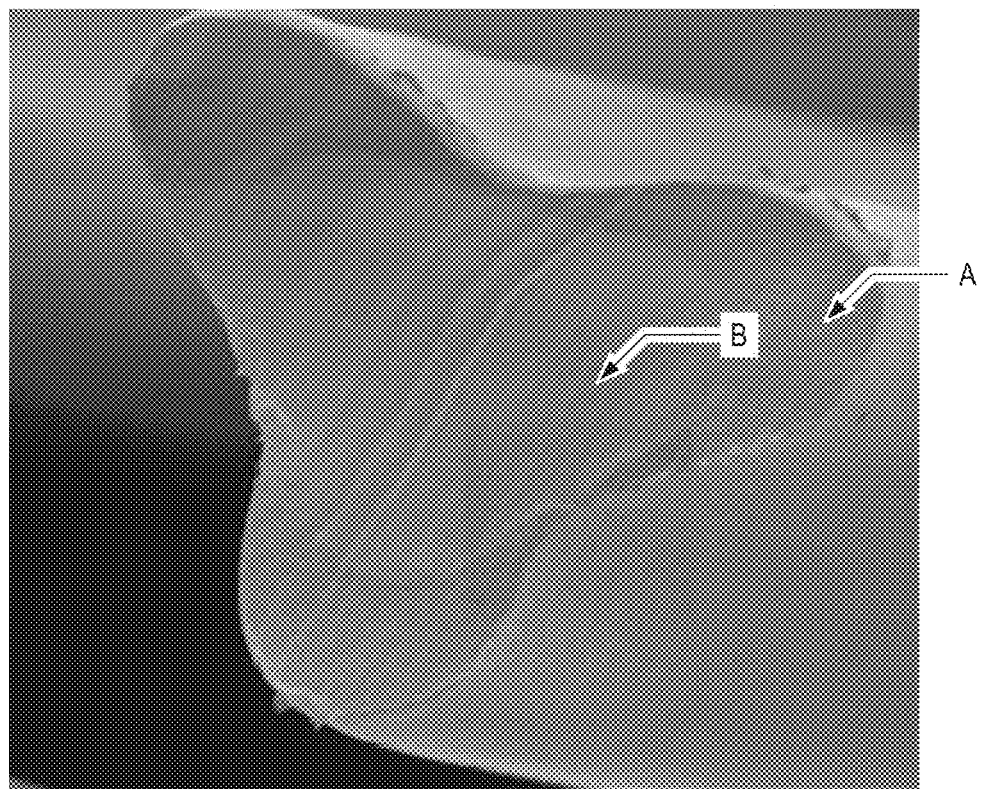
FIG. 9
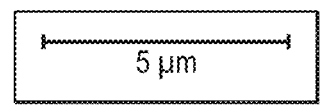

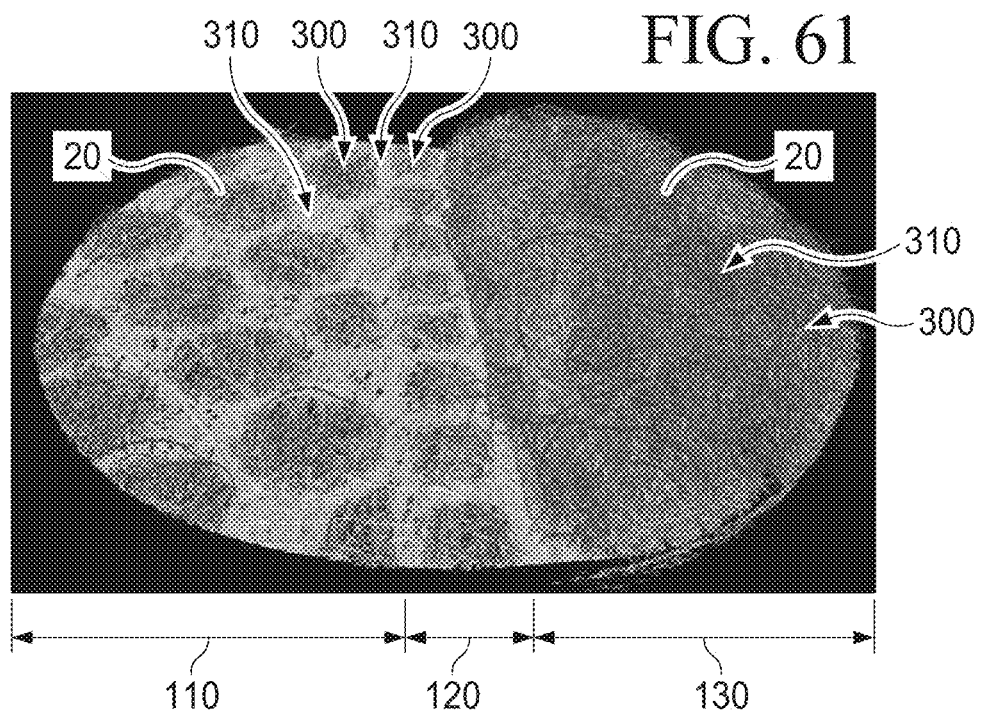
FIG. 61
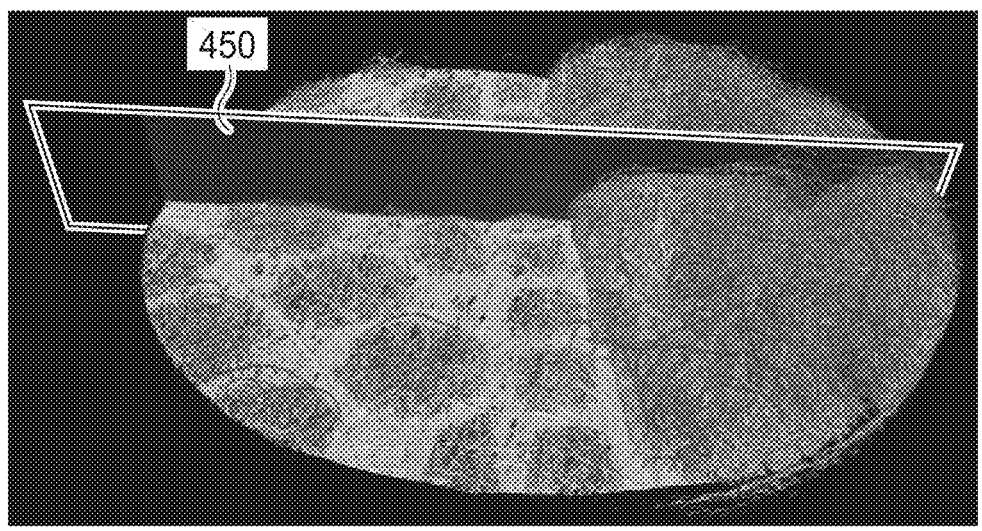
FIG. 62
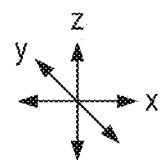

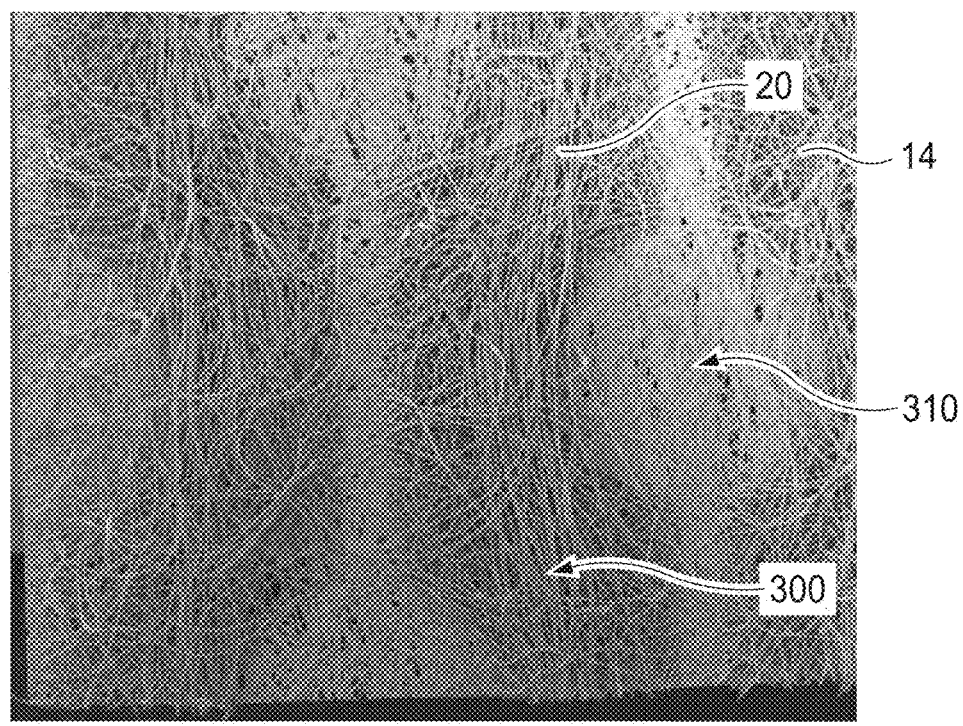

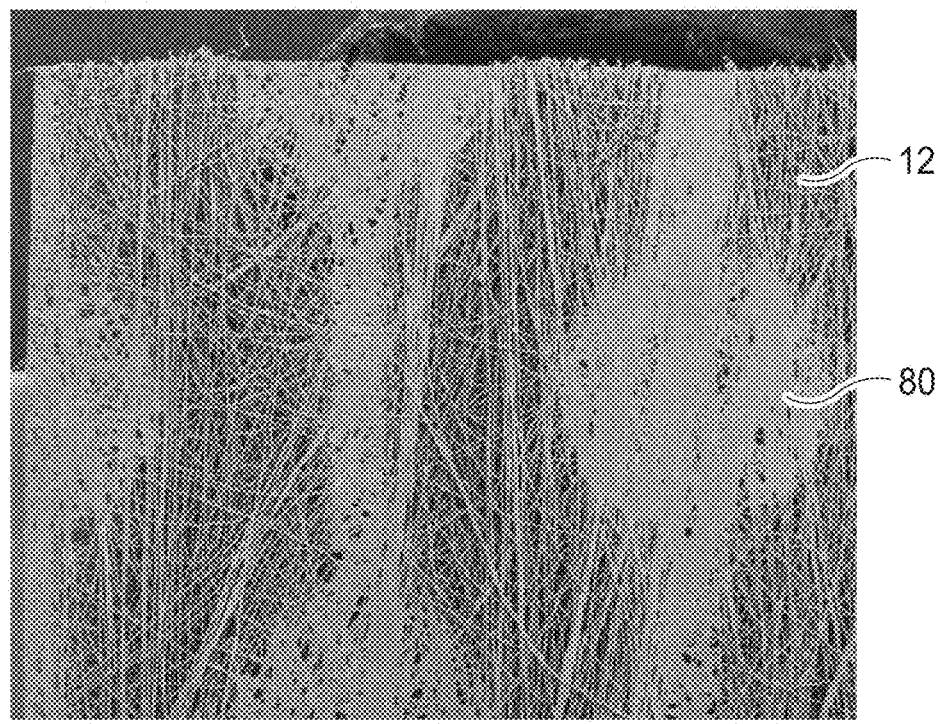

THREE-DIMENSIONAL SUBSTRATES AND ABSORBENT ARTICLES HAVING THE SAME

CROSS REFERENCE TO RELATED APPLICATIONS

This application is a continuation of, and claims priority under 35 U.S.C. § 120 to, U.S. patent application Ser. No. 15/881,910, filed on Jan. 29, 2018, which claims the benefit, under 35 U.S.C. § 119(e), of U.S. Provisional Patent Application Ser. No. 62/452,425, filed on Jan. 31, 2017, which are both hereby incorporated by reference in their entirety.

FIELD

This present disclosure generally relates to shaped, three-dimensional nonwoven fabrics or substrates and articles made with shaped, three-dimensional nonwoven fabrics. The present disclosure further relates to apertured nonwoven fabrics or substrates and articles including the same.

BACKGROUND

Nonwoven fabrics are useful for a wide variety of applications, including absorbent personal care products, garments, medical applications, and cleaning applications. Nonwoven personal care products include infant care items such as diapers, child care items such as training pants, feminine care items such as sanitary napkins, and adult care items such as incontinence products, pads, and pants. Nonwoven garments include protective workwear and medical apparel such as surgical gowns. Other nonwoven medical applications include nonwoven wound dressings and surgical dressings. Cleaning applications for nonwovens include towels and wipes. Still other uses of nonwoven fabrics are well known. The foregoing list is not considered exhaustive.

Various properties of nonwoven fabrics determine the suitability of nonwoven fabrics for different applications. Nonwoven fabrics may be engineered to have different combinations of properties to suit different needs. Variable properties of nonwoven fabrics include liquid-handling properties such as wettability, distribution, and absorbency, strength properties such as tensile strength and tear strength, softness properties, durability properties such as abrasion resistance, and aesthetic properties, which can include a visual impression of breathability and absorbency. The physical shape of a nonwoven fabric also affects the functionality and aesthetic properties of the nonwoven fabric.

Nonwoven fabrics are initially made into sheets which, when laid on a flat surface, may have a substantially planar, featureless surface or may have an array of surface features such as apertures, projections, or both. Nonwoven fabrics with apertures or projections are often referred to as three-dimensional shaped nonwoven fabrics. The apertures can be uniformly sized and shaped circular or ovate apertures throughout their area, and such circular or ovate apertures may be uniformly spaced in the cross-machine direction and/or the machine direction with respect to each other. The aperture patterns can allow for fluid penetration and/or absorbency throughout their area. However, in certain types of three-dimensional shaped nonwoven fabrics (e.g., variable basis weight nonwovens), apertures are typically not formed due to variability of the material and concerns about tearing.

Despite prior advances in the art of nonwoven fabrics, there remains a need for improved nonwoven fabrics having three-dimensional surface features. Further, there remains a need for processes and equipment for manufacturing improved nonwoven fabrics having three-dimensional surface features; articles, including absorbent articles, utilizing improved nonwoven fabrics having three-dimensional surface features, and absorbent articles utilizing nonwoven fabrics having three-dimensional surface features and which can be packaged in a compressed form while minimizing the loss of the three-dimensional surface features when opened from the package. In particular, there remains a need for packages of absorbent articles including soft nonwoven materials that have a reduced in-bag stack height compared to conventional absorbent article packages so the packages are convenient for caregivers to handle and store and so that manufacturers enjoy low distribution costs without a loss of aesthetics clarity, absorbency, or softness of the as-made absorbent article. Further, there remains a need for absorbent articles utilizing soft, spunbond nonwoven fabrics having three-dimensional surface features that have reduced fuzzing properties when in use; and improved nonwoven fabrics having three-dimensional surface features and physical integrity combined with softness. Additionally, there remains a need for three-dimensional shaped nonwoven fabrics, including variable basis weight nonwovens, that have apertures to provide improved fluid acquisition and visual impression of breathability and absorbency, as well as different combinations of apertured areas and zones having different intensive properties.

SUMMARY

In an example of the present disclosure, a three-dimensional, nonwoven substrate may comprise a first surface, a second surface, a first side edge, a second side edge, a first end edge, a second end edge, a central lateral axis, and a central longitudinal axis extending perpendicular to the central lateral axis. A line taken in a direction parallel to or perpendicular to the central lateral axis of the three-dimensional, nonwoven substrate may comprise a non-apertured, first visually discernible zone in the nonwoven substrate and a second visually discernible zone in the nonwoven substrate. The first visually discernable zone may have a pattern of three-dimensional features on the first surface or the second surface. At least some of the three-dimensional features may define a microzone having a first region and a second region. The first region and the second region may have a difference in value for an intensive property. The second visually discernable zone may define apertures. The apertures may have an Effective Aperture Area in a range of about 0.3 mm² to about 15 mm², according to the Aperture Test herein. The second visually discernable zone may have an Effective Open Area in a range of about 3% to about 50%, according to the Aperture Test herein.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting forms of the disclosure taken in conjunction with the accompanying drawings, wherein:

FIG. 8A is a schematic drawing illustrating the cross-section of a filament made with a primary component A and a secondary component B in a side-by-side arrangement.

FIG. 8B is a schematic drawing illustrating the cross-section of a filament made with a primary component A and a secondary component B in an eccentric sheath/core arrangement.

FIG. 8C is a schematic drawing illustrating the cross-section of a filament made with a primary component A and a secondary component B in a concentric sheath/core arrangement.

FIG. 9 is a photographic image depicting a perspective view of a tri-lobal, bicomponent fiber.

FIG. 61 is a Micro CT perspective view image of an example of a nonwoven fabric of the present disclosure.

FIG. 62 is a Micro CT perspective view image of an example of a nonwoven fabric of the present disclosure.

DETAILED DESCRIPTION

Various non-limiting forms of the present disclosure will now be described to provide an overall understanding of the principles of the structure, function, manufacture, and use of the shaped nonwoven fabrics and articles including the same disclosed herein. One or more examples of these non-limiting forms are illustrated in the accompanying drawings. Those of ordinary skill in the art will understand that the shaped nonwoven fabrics and articles including the same described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

Figure 1:
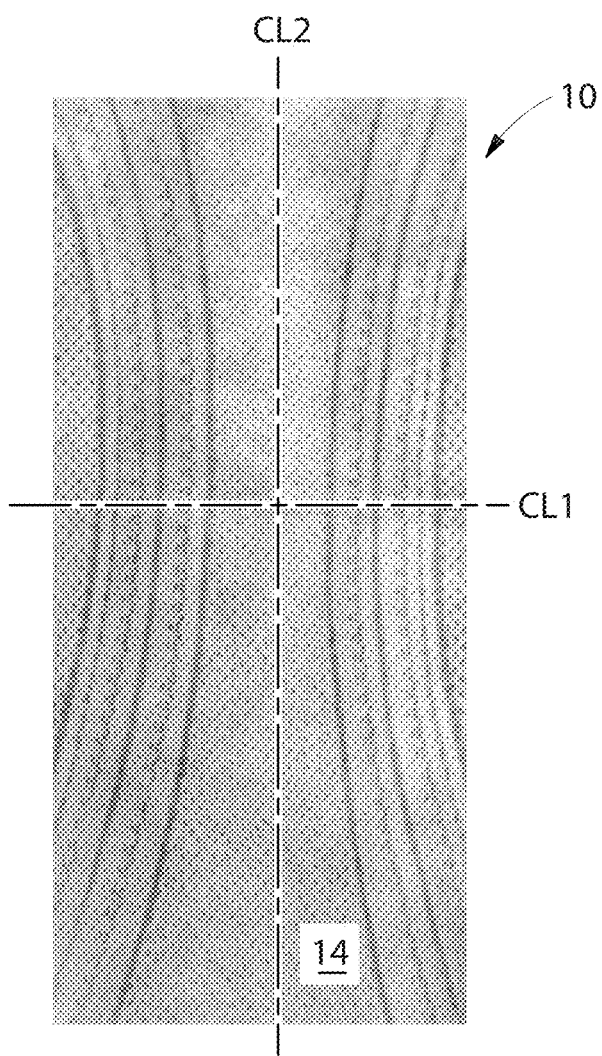
FIG. 1 is a photographic image of a portion of an example of a three-dimensional, variable basis weight, nonwoven fabric.
Figure 2:
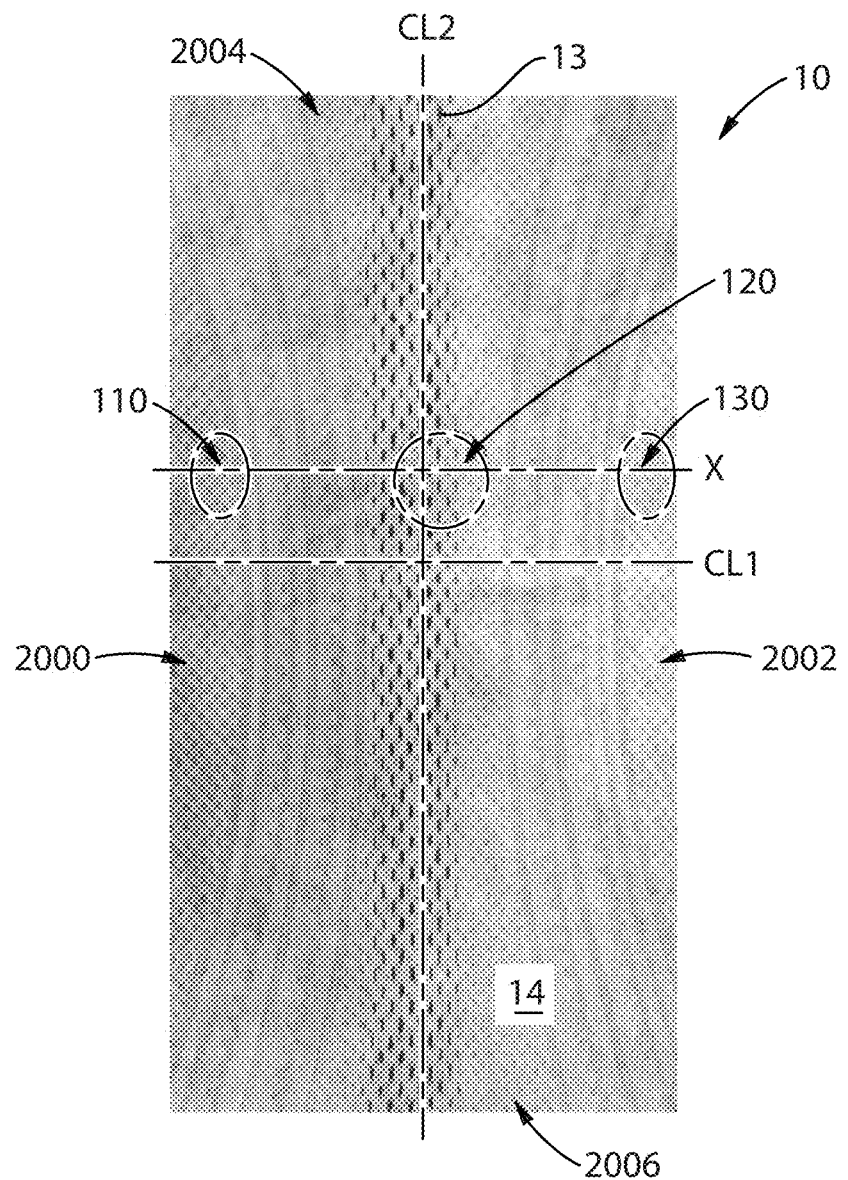
FIG. 2 is a photographic image of a portion of an example of a three-dimensional, variable basis weight, apertured nonwoven fabric of the present disclosure.

Three-dimensional, nonwoven substrates 10 of the present disclosure, as shown in FIGS. 1 and 2 and having a first surface 12 and a second surface 14, can comprise at least one non-apertured first visually discernible zone 110 having a pattern of three-dimensional features on the first surface 12 and/or the second surface 14. In FIGS. 1-2, the second surface 14 is facing the viewer and is opposite the first surface 12, which is shown in a cross-section of an example depicted in FIG. 7. Three-dimensional, nonwoven substrates 10 of the present disclosure can comprise at least one second visually discernible zone 120 that defines a plurality of apertures 13, as shown in FIG. 2. In certain examples, the plurality of apertures 13 may be organized in a pattern or in a plurality of patterns. The patterns may be the same or different. In certain examples, the nonwoven substrate 10 can comprise a first side edge 2000 and a second side edge 2002, a first end edge 2004 and a second end edge 2006, a central lateral axis CL1, and a central longitudinal axis CL2 extending perpendicularly to the central lateral axis CL1, such that a line X taken in a direction parallel to the central lateral axis CL1 can include each of the first visually discernible zone 110 and the second visually discernible zone 120. It will be appreciated that in certain examples, a plurality of apertures may define a strip that extends in a direction parallel to a central lateral axis (e.g., CL1), such that a line taken in a direction perpendicular to the central lateral axis can include each of a first visually discernible zone 110 and the and a second visually discernible zone.

Without wishing to be bound by theory, it is believed that while apertures are typically not formed in variable basis weight three-dimensional shaped nonwoven fabrics, apertures and patterns thereof can be provided within such nonwoven fabrics to provide improved fluid acquisition and visual impression of breathability. Further, it is believed that the three-dimensional shaped nonwoven fabrics can comprise different combinations of apertured zones and zones having different intensive properties to increase the overall effectiveness of a nonwoven substrate or an article, such as an absorbent article, in which one or more of the nonwoven substrates are employed. An example of a nonwoven substrate in an absorbent article is use as a topsheet of a diaper.

In certain examples, with respect to the first visually discernible zone 110, at least some of the three-dimensional features can define a microzone comprising a first region and a second region, where the first region and the second region can have a difference in value for one or more intensive properties. In certain examples, the second visually discernible zone 120 can comprise a pattern of other three-dimensional features on a first and/or second surface and at least some of the other three-dimensional features can define another microzone having a third region and a fourth region, where the third region and the fourth region can have a difference in value for one or more intensive properties. In other examples, the nonwoven substrate can further comprise a non-apertured, third visually discernible zone 130, in the line X taken in the direction parallel to the central lateral axis CL1, where the third visually discernible zone 130 can comprise a pattern of other three-dimensional features on a first and/or second surface and at least some of the other three-dimensional features can define another microzone having a fifth region and a sixth region, where the fifth region and the sixth region can have a difference in value for one or more intensive properties. Likewise, it will be appreciated that in examples where a plurality of apertures may define a strip that extends in a direction parallel to a central lateral axis (e.g., CL1), a nonwoven substrate can further comprise a non-apertured, third visually discernible zone in a line taken in a direction perpendicular to the central lateral axis or parallel to a central longitudinal axis (e.g., CL2).

With respect to any of the first, second, or third visually discernible zones 110, 120, 130, the one or more intensive properties can be basis weight, thickness, volumetric density, and/or any other suitable intensive properties described herein. It will be appreciated that any of a variety of suitable intensive properties can be exhibited in a first visually discernible zone. In certain examples, the one or more intensive properties (e.g., basis weight, thickness, or volumetric density) can be greater than zero. A difference in value of the one or more intensive properties between the first region and the second region or the third region and the fourth region or the fifth region and the sixth region can be an order of magnitude. In certain examples, the difference in value of the intensive property between the first region and the second region or the third region and the fourth region or the fifth region and the sixth region can be from about 1.2× to about 10×.

In certain examples, the second visually discernible zone 120 may include apertures 13 throughout the entirety of the zone or at least a portion of the zone. In certain examples, with respect to the second visually discernible zone 120, the apertures 13 can have an Effective Aperture Area in a range of about 0.3 mm$^2$ to about 15 mm$^2$; 0.3 mm$^2$ to about 14 mm$^2$; 0.4 mm$^2$ to about 12 mm$^2$; 0.3 mm$^2$ to about 10 mm$^2$; 0.5 mm$^2$ to about 8 mm$^2$; or 1.0 mm$^2$ to about 8 mm$^2$, specifically reciting all 0.05 mm$^2$ increments within the specified ranges and all ranges formed therein or thereby, according to the Aperture Test herein. A plurality of the apertures 13 in a three-dimensional shaped nonwoven fabric may be different in Effective Aperture Areas. The Relative Standard Deviation of the Effective Aperture Areas in a three-dimensional shaped nonwoven fabric may be at least about 50%, or at least about 55%, or at least about 60%/a, for example.

In certain examples, the second visually discernible zone 120 can have an Effective Open Area in the range of about 5% to about 50%; about 7% to about 50%, about 7% to about 11%, about 8% to about 10%, about 3% to about 50%; about 5% to about 40%; about 10% to about 40%; about 10% to about 35%; about 10% to about 30%; about 15% to about 30%, specifically reciting all 0.1% increments within the specified ranges and all ranges formed therein or thereby, according to the Aperture Test herein. In an example, the second visually discernible zone 120 can have an Effective Open Area from about 5% to about 25%, according to the Aperture Test. Without being bound by theory, it is believed that variable basis weight, apertured three-dimensional shaped nonwoven fabrics having a higher Effective Open Area may have utility as a topsheet or acquisition layer or system in an absorbent article (more functional to absorb bodily exudates), while variable basis weight, apertured three-dimensional shaped nonwoven fabrics having a lower Effective Open Area may have utility as an outer cover of an absorbent article (more decorative or for breathability purposes).

In certain examples, the second visually discernible zone 120 can comprise two or more different aperture patterns. Boundaries between the various zones (e.g., 110, 120, 130) may be linear or nonlinear.

Figure 3:
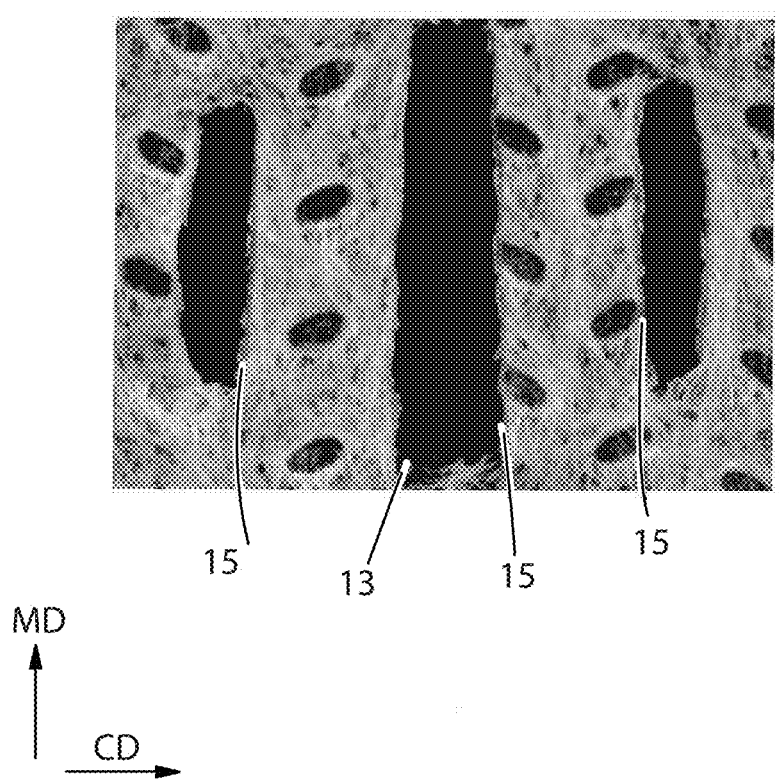
FIG. 3 is a photographic image of a nonwoven fabric including melt lips or fused portions surrounding apertures of the present disclosure.

In some examples, and referring to FIG. 3, portions of perimeters of at least some of the apertures can comprise one or more melt lips 15 or fused portions. In some examples, portions of perimeters of at least some of the apertures can be free of a melt lip. Thus, in certain examples, the one or more melt lips 15 may at least partially or fully surround the apertures 13. In an example, the one or more melt lips 15 may surround from about 25% of a perimeter of the apertures 13 to about 100% of the perimeter of the apertures 13. In certain examples, the one or more melt lips 15 may be formed on lateral sides of the apertures 13 and not on leading and/or trailing edges of the apertures 13 (see MD and CD arrows for reference in FIG. 3). It is believed that the one or more melt lips 15 may be formed during the overbonding step and may add strength to a substrate such as, for example, a three-dimensional shaped nonwoven fabric.

In certain examples, at least some of the apertures can have an aspect ratio of greater than 1, greater than 2, greater than 3, greater than 5, or greater than 10, but typically less than 15, according to the Aperture Test. In an example, at least some apertures can have an aspect ratio of from about 1.5 to about 10, specifically reciting all 0.1 increments within the specified range and all ranges formed therein. In certain examples, at least some of the apertures can have an aspect ratio of less than about 1.5. The aperture patterns in the variable basis weight, apertured, three-dimensional shaped nonwoven fabrics can comprise apertures having more than one aspect ratio, such as two or more distinct populations or having a substantially continuous distribution of aspect ratios having a slope greater than zero. Additionally, the aperture patterns of the variable basis weight, apertured, three-dimensional shaped nonwoven fabrics may comprise apertures with more than two effective aperture areas, either as two or more distinct populations or as a distribution of aperture areas having a slope greater than zero. The Relative Standard Deviation of the aperture aspect ratios in a variable basis weight, apertured, three-dimensional shaped nonwoven fabric may be at least about 30%, at least about 40%, or at least about 45%.

At least some of the variable basis weight, apertured, three-dimensional shaped nonwoven fabrics may have an aspect ratio, according to the Aperture Test herein, of greater than about 1.5:1, greater than about 1.8:1, greater than about 2:1, greater than about 2.5:1, greater than about 3:1, or in the range of about 1.5:1 to about 10:1, about 2:1 to about 6:1, about 2:1 to about 5:1, or about 2:1 to about 4:1, specifically reciting all 0.1 increments (e.g., 1.6:1, 1.7:1, 1.8:1) within the specified ranges and all ranges formed therein or thereby.

Figure 81:
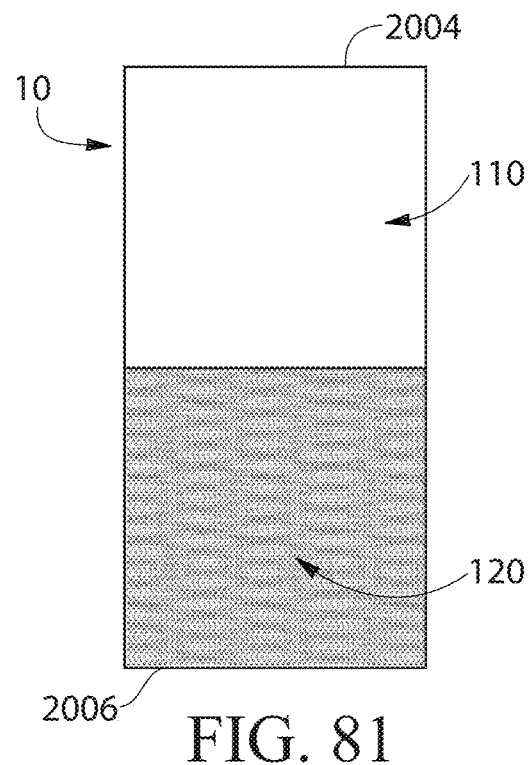
FIG. 81 is a schematic representation of an example of a nonwoven fabric of the present disclosure.

In certain examples, the first visually discernible zone 110 can be positioned proximate to the first end edge 2004 of the three-dimensional, nonwoven substrate 10 and the second visually discernible zone 120 can be positioned proximate to the second end edge 2006 of the three-dimensional, nonwoven substrate 10, as shown, for example, in FIG. 81. In other examples, the first visually discernible zone 110 can be positioned proximate to the second end edge 2006 and the second visually discernible zone 120 can be positioned proximate to the first end edge 2004. In certain examples having a third visually discernible zone 130, a portion of the first visually discernible zone 110 can be positioned proximate to the first side edge 2000 and a portion of the third visually discernible zone 130 can be positioned proximate to the second side edge 2002. In such examples, the second visually discernible zone 120 can be positioned intermediate the first visually discernible zone and the third visually discernible zone. In certain examples, a portion of the first visually discernible zone 110 can be positioned proximate to the first side edge 2000 and a portion of the third visually discernible zone 130 can be positioned proximate to the second side edge 2002. Similarly, in certain examples, a portion of the first visually discernible zone 110 can be positioned proximate to the first end edge 2004 and a portion of the third visually discernible zone 130 can be positioned proximate to the second end edge 2006. In some examples, a portion of the first visually discernible zone 110 can be positioned proximate to the first side edge 2000 and the first and/or second end edge 2004, 2006, and a portion of the third visually discernible zone 130 can be positioned proximate to the second side edge 2002 and the first and/or second end edge 2004, 2006. In such examples, the second visually discernible zone 120 may be entirely surrounded by the first and third visually discernible zones 110, 130, where the second visually discernible zone 120 may of any suitable size and shape, symmetric or asymmetric, and can be positioned centrally or in an off-center position. Similarly, a second visually discernible zone may be entirely surrounded by a first visually discernible zone 110 or vice versa. It will be appreciated that any number of visually discernible zones may be present in a substrate, such as more than three visually discernible zones, and each of such visually discernible zones may have any of a variety of suitable sizes and/or shapes. The various zones may be continuous or discontinuous.

Shaped Nonwovens

Shaped nonwoven fabrics, including those non-apertured visually discernible zones as well as other visually discernible zones prior to formation of the apertures, can be directly formed on a shaped forming belt with continuous spunbond filaments in a single forming process. The fabric of the present disclosure can assume a shape which corresponds to the shape of the forming belt. A fabric of the present disclosure made on a forming belt of the present disclosure in a method of the present disclosure can be particularly beneficial for use in personal care articles, garments, medical products, and cleaning products. The shaped nonwoven fabric can be fluid permeable for use as a topsheet, backsheet nonwoven, acquisition layer, distribution layer, or other component layer for a diaper, or a topsheet, backsheet nonwoven, acquisition layer, distribution layer, or other component layer for a sanitary napkin, a topsheet, backsheet nonwoven, acquisition layer, distribution layer, or other component layer for an adult incontinent pad or pant, or a pad for a floor cleaning implement.

The beneficial features of the nonwoven fabric will be described in some examples herein in the context of an overall area of the nonwoven fabric. The overall area can be an area determined by dimensions suitable for certain uses, for which the various features of the present disclosure provide beneficial properties. For example, the overall area of a fabric can be that of a fabric having dimensions making it suitable for use as a topsheet, backsheet nonwoven, acquisition layer, distribution layer, or other component layer for a diaper, or a topsheet, backsheet nonwoven, acquisition layer, distribution layer, or other component layer for a sanitary napkin, a topsheet, backsheet nonwoven, acquisition layer, distribution layer, or other component layer for an adult incontinent pad or pant, or a pad for a floor cleaning implement. Thus, the overall area can be based on width and length dimensions ranging from 3 cm wide to 50 cm wide and from 10 cm long to 100 cm long, resulting in overall areas of from 30 $cm^2$ to 500 $cm^2$. The aforementioned ranges can include as if explicitly stated every integer dimension between the range boundaries. By way of example, an overall area of 176 $cm^2$ defined by a width of 11 cm and a length of 16 cm is disclosed in the above ranges. As will be understood from the description herein, the overall area of a shaped nonwoven fabric may be a smaller area than the area of the web of nonwoven material of which it is a part when it is commercially made. That is, in a given commercially made web of nonwoven material, there can be a plurality of shaped nonwoven fabrics of the present disclosure, each of the shaped nonwoven fabrics of the present disclosure having an overall area less than the area of the web on which it is made.

Figure 4:
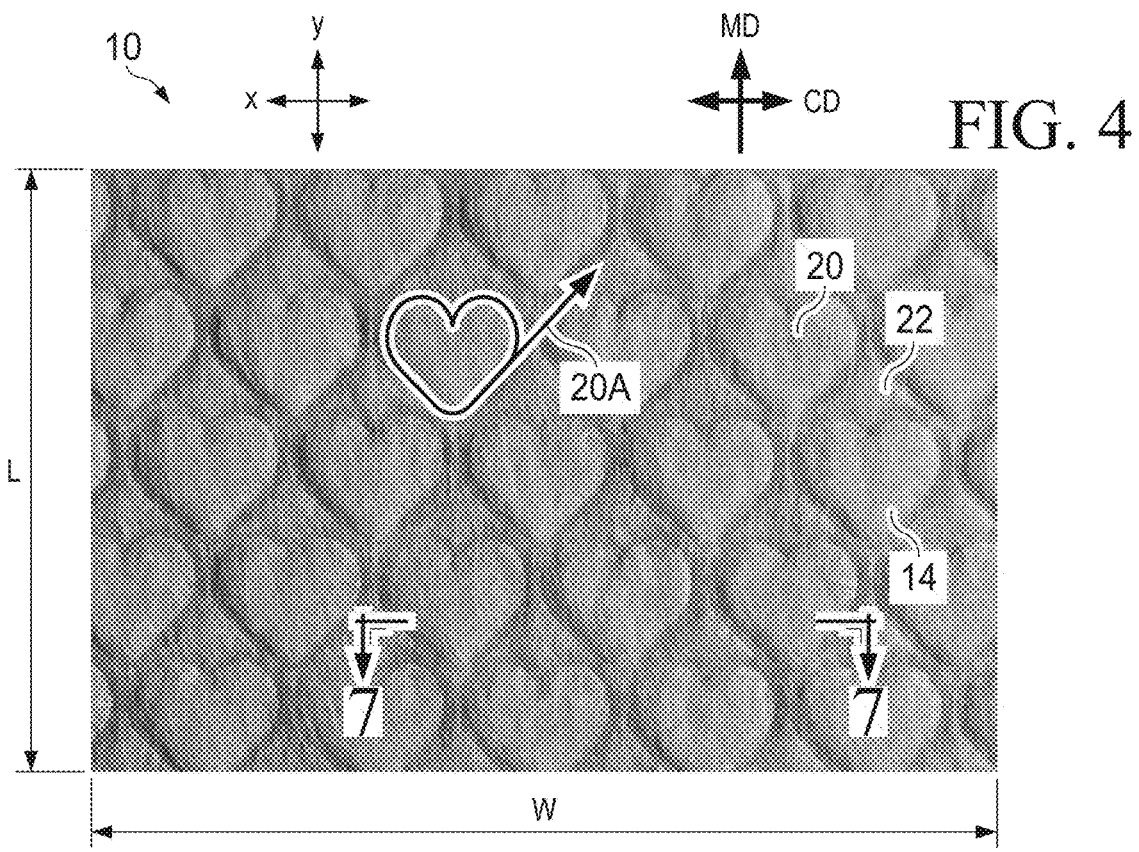
FIG. 4 is a photographic image of an example of a nonwoven fabric of the present disclosure.
Figure 5:
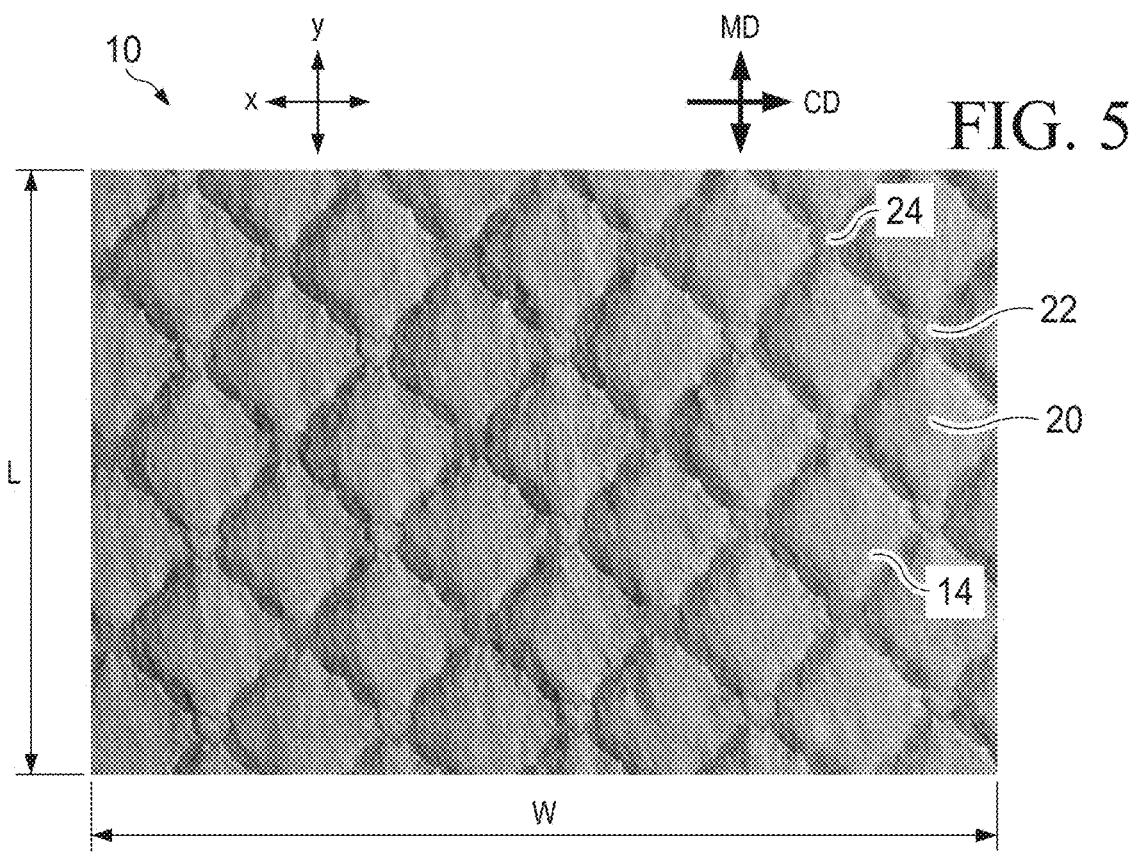
FIG. 5 is a photographic image of an example of a nonwoven fabric of the present disclosure.
Figure 6:
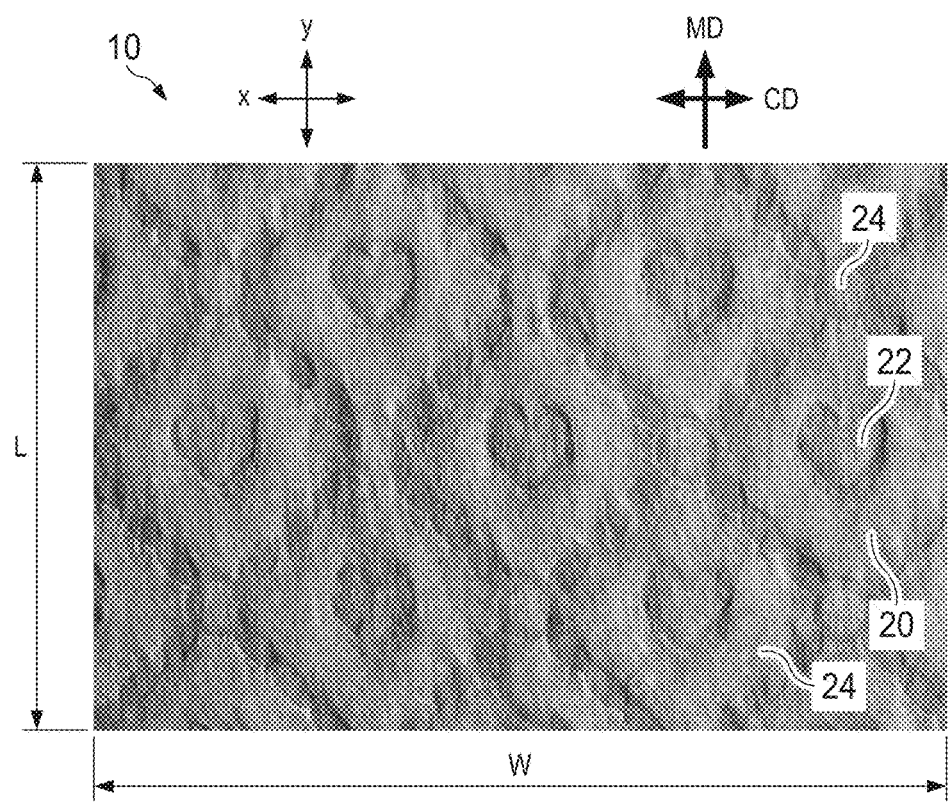
FIG. 6 is a photographic image of an example of a nonwoven fabric of the present disclosure.
Figure 7:
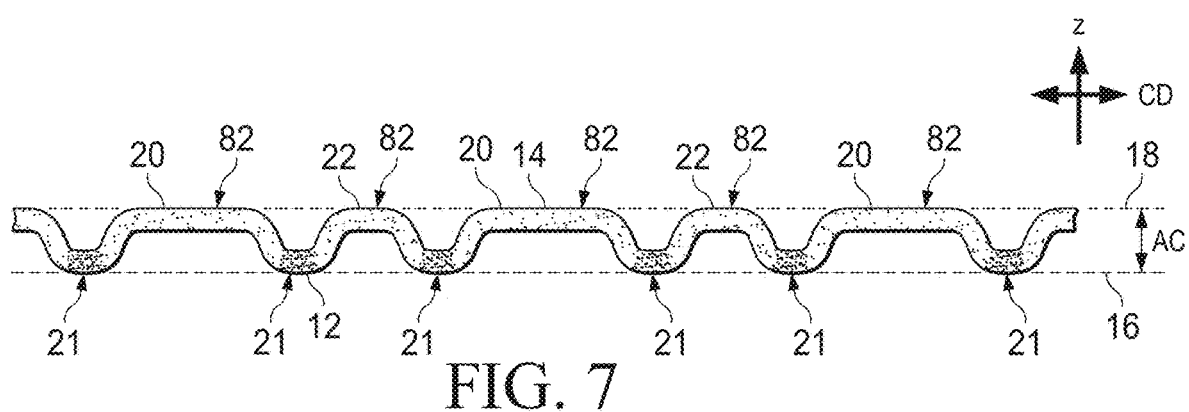
FIG. 7 is a cross-sectional view of a portion of the nonwoven fabric shown in FIG. 4.

Photographs of representative examples of shaped nonwoven fabrics 10 are shown in FIGS. 4-6. As in FIGS. 1 and 2, in FIGS. 4-6, the second surface 14 is facing the viewer and is opposite the first surface 12, which is depicted in FIG. 7. The term "surface" can be used broadly to refer to the two sides of a web for descriptive purposes, and is not intended to infer any necessary flatness or smoothness. Although the shaped nonwoven fabric 10 can be soft and flexible, it will be described in a flattened condition the context of one or more X-Y planes parallel to the flattened condition, and which correspond in web-making technology to the plane of the cross-machine direction, CD, and machine direction, MD, respectively, as shown in FIGS. 4-6. The length, L, in the MD and the width, W, in the CD can determine the overall area A for the nonwoven fabric 10. As shown in FIG. 7, which is a cross section of a portion of the nonwoven fabric 10 shown in FIG. 4, for descriptive purposes the three-dimensional features of the shaped nonwoven fabric are described as extending outwardly in a Z-direction from an X-Y plane of the first surface 16 (see, FIG. 7). In an example, a maximum dimension of three-dimensional features in the Z-direction can define the maximum distance between the plane of the first surface 16 and an X-Y plane of the second surface 18, which distance can be measured as the average caliper AC of the nonwoven fabric 10. The average caliper can be determined via optical, non-contact means, or it can be determined by instruments involving spaced apart flat plates that measure the caliper of the nonwoven placed between them under a predetermined pressure. It is not necessary that all the three-dimensional features have the same Z-direction maximum dimension, but a plurality of three-dimensional features can have substantially the same Z-direction maximum dimension determined by the fiber laydown process and the properties of the forming belt, discussed below.

The exemplary fabrics shown in FIGS. 4-7 (as well as other fabrics disclosed herein) are fluid permeable. In an example, the entire fabric can be considered fluid permeable. In an example, regions or zones can be fluid permeable. "Fluid permeable," as used herein with respect to the fabric, refers to the fabric having at least one zone which can permit liquid to pass through under in-use conditions of a consumer product. For example, if used as a topsheet on a disposable diaper, the fabric can have at least one zone having a level of fluid permeability permitting urine to pass through to an underlying absorbent core. "Fluid permeable," as used herein with respect to a region, refers to the region exhibiting a porous structure that can permit liquid to pass through.

As shown in FIGS. 4-7, the nonwoven fabric 10 can comprise a regular, repeating pattern of a plurality of discrete, recognizably different three-dimensional features, including a first three-dimensional feature 20 and a second three-dimensional feature 22, and a third three-dimensional feature 24, as shown in FIGS. 5 and 6. For example, in FIG. 4, heart-shaped first three-dimensional feature 20 can be recognizably different from the smaller, generally triangular-shaped second three-dimensional feature 22. The recognizable differences can be visual, such as recognizably different sizes and/or shapes.

The three-dimensional features of the nonwoven fabric 10 can be formed by depositing, such as by carding, air laying, spinning from solution, or melt spinning, fibers directly onto a forming belt having a pattern of corresponding three-dimensional features. In one sense the nonwoven fabric 10 can be molded onto a forming belt that can determine the shapes of the three-dimensional features of the fabric 10. However, importantly, as described herein, the apparatus and method of the present disclosure produce the nonwoven fabric 10 such that in addition to taking the shape of the forming belt, because of the attributes of the forming belt and the apparatus for forming the fabric, it can be imparted with beneficial properties for use in personal care articles, garments, medical products, and cleaning products. Specifically, because of the nature of the forming belt and other apparatus elements, as described above, the three-dimensional features of the nonwoven fabric 10 can have intensive properties that can differ between first and second regions within a microzone, or from feature to feature in ways that provide for beneficial properties of the nonwoven fabric 10 when used in personal care articles, garments, medical products, and cleaning products. For example, first three-dimensional feature 20 can have a basis weight or density that is different from the basis weight or density of second three-dimensional feature 22, and both can have a basis weight or density that is different from that of third three-dimensional feature 24, providing for beneficial aesthetic and functional properties related to fluid acquisition, distribution and/or absorption in diapers or sanitary napkins.

The intensive property differential between the various three-dimensional features of nonwoven fabric 10 is believed to be due to the fiber distribution and compaction resulting from the apparatus and method described below. The fiber distribution occurs during the fiber laydown process, as opposed to, for example, a post making process such as hydroentangling or embossing processes. Because the fibers can be free to move during a process such as a melt spinning process, with the movement determined by the nature of the features and air permeability of the forming belt and other processing parameters, the fibers are believed to be more stable and permanently formed in nonwoven fabric 10.

As can be seen in FIGS. 4-6, and as understood from the description herein, the distinct three-dimensional features may be bounded by visually discernible (with respect to the interior of a three-dimensional feature) regions that can be in the form of a closed figure (such as the heart shape in FIGS. 4 and 6, and the diamond shape of FIGS. 5 and 6). The closed figure can be a curvilinear closed figure, such as the heart shape in FIGS. 1 and 3. The outlining visually discernible regions can be the regions of the nonwoven fabric 10 that are most closely adjacent in the Z-direction to first surface 12, such as regions 21 as shown in FIG. 7, and which can lie at least partially in or on first plane 16 when in a flattened condition. For example, as shown in FIG. 4, first three-dimensional feature 20 is heart shaped, and as indicated as one exemplary first three-dimensional feature 20A is defined by a curvilinear closed heart-shaped element. A curvilinear element can be understood as a linear element having at any point along its length a tangential vector V, with the closed shape being such that the tangential vector V has both MD and CD components that change values over greater than 50% of the length of the linear element of the closed figure. Of course, the figure need not be entirely 100% closed, but the linear element can have breaks that do not take away from the overall impression of a closed figure. As discussed below in the context of the forming belt, the outlining visually discernible curvilinear closed heart-shaped element can be formed by a corresponding closed heart-shaped raised element on the forming belt to make the closed figure of a heart on fabric 10. In a repeating pattern, the individual shapes (in the case of first three-dimensional feature in FIG. 4, a heart shape) can result in aesthetically pleasing, soft, pillowy features across the overall area OA of the second surface 14 of fabric 10. In an example, in which the nonwoven fabric 10 is used as a topsheet for a diaper or sanitary napkin, the second surface 14 of nonwoven fabric 10 can be body-facing to deliver superior aesthetic and performance benefits related to softness, compression resistance, and fluid absorption. In certain examples, and in examples where aperture patterns are provided, the aperture patterns can coordinate with other patterns (e.g., heart or quilt shapes) shown in the above-described nonwovens. That is, in such examples, the aperture patterns can coordinate with patterns in non-apertured zones.

Specifically, in the regular repeating pattern of closed, three-dimensional features shown in FIG. 4-6, it is believed, without being bound by theory, that the dimensions of the various features, the average basis weight of the entire fabric 10 across its overall area, and other processing parameters described below which define the differing intensive properties can contribute to a beneficial improvement in compression recovery. It is believed that the plurality of relatively closely spaced, relatively small, and relatively pillowy three-dimensional features can act as springs to resist compression and recover once a compressive force is removed. Compression recovery can be important in topsheets, backsheet nonwovens, acquisition layers, distribution layers, or other component layers of personal care articles such as diapers, sanitary napkins, or adult incontinent pads, diapers, or pants for example, because such articles are typically packaged and folded in compressed conditions. Manufacturers of personal care products desire to retain most, if not all of the as-made caliper for aesthetic and performance purposes. The three-dimensionality of formed features can provide important aesthetic benefits due to the look and feel of softness and pleasing appearance of crisp, well-defined shapes, including very small shapes such as the small hearts shown in FIG. 5. The three-dimensional features can also provide for softness during use, improved absorbency, less leakage, and overall improved in-use experience. But the necessary compression during folding, packaging, shipping and storing of the personal care articles can cause permanent loss of caliper of a topsheet, backsheet nonwovens, acquisition layers, distribution layers, or other component layers of the absorbent article thereby degrading the as-made functional benefits. We have found unexpectedly the nonwoven fabrics of the present disclosure retain to a significant degree their as made three-dimensional features even after undergoing compression packaging and distribution in a compression packaged state.

Table 1 below shows compression recovery data for two examples of the present disclosure. Example 1 corresponds to the nonwoven fabric 10 shown in FIG. 4 and made on a forming belt as described with reference to FIGS. 15 and 17. Example 2 corresponds to the nonwoven fabric 10 shown in FIG. 5 and made on a forming belt as described with reference to FIGS. 18 and 19. As can be seen from the data, the fabrics 10 of the present disclosure show a significant benefit with respect to compression recovery when measured by the Compression Aging Test. In a form, packages of the absorbent articles having the compression recovery characteristics of the present disclosure can have a reduced in-bag stack height yet still deliver the aesthetic, absorbency, and softness benefits of the as made diaper; or as if it were never compression packaged. The present disclosure provides for reduced in-bag stack height packages which allow caregivers to easily handle and store the packages while also providing manufacturers with reduced distribution costs, both achieved while maintaining as made aesthetics clarity, absorbency, or softness performance of the absorbent article.

Example 1

A bicomponent spunbond nonwoven fabric that was produced by spinning a 50:50 ratio of polyethylene sheath (Aspun-6850-A obtained from Dow chemical company) and polypropylene core (PH-835 obtained from LyondellBasell) in a trilobal fiber configuration, as shown in FIG. 9, which is a scanning electron micrograph (SEM) showing a cross section of a bicomponent trilobal fiber. The nonwoven fabric was spun on a forming belt having a repeating pattern as described in FIG. 15 as described below with respect to FIGS. 10 and 11 moving at a linear speed of about 25 meters per minute to an average basis weight of 30 grams per square meter with a repeating pattern of heart shapes as shown in FIG. 4. Fibers of the fabric were further bonded on first surface 12 by heated compaction rolls 70, 72 (described below) at 130° C., and being wound on to a reel at winder 75.

Example 2

A bicomponent spunbond nonwoven fabric was produced by spinning a 50:50 ratio of polyethylene sheath (Aspun-6850-A obtained from Dow chemical company) and polypropylene core (PH-835 obtained from LyondellBasell) in a trilobal fiber configuration, as shown in FIG. 9, which is a scanning electron micrograph showing a cross section of a bicomponent trilobal fiber. The nonwoven fabric was spun on a forming belt having a repeating pattern as described in FIG. 19 as described below with respect to FIGS. 10 and 11 moving at a linear speed of about 25 meters per minute to form a fabric 10 having an average basis weight of 30 grams per square meter with a repeating pattern of diamond shapes as shown in FIG. 5. Fibers of the fabric were further bonded on first surface 12 by heated compaction rolls 70, 72 (described below) at 130° C.

TABLE 1

| | | Compression Recovery | | | | | |
|---|---|---|---|---|---|---|---|
| | Fresh (Nonwoven | 4 KPa (~96 mm IBSH) | | 14 KPa (~84 mm IBSH) | | 35 KPa (~68 mm IBSH) | |
| 3-D Nonwoven | off the roll) Caliper | Caliper after Compression | Percent Caliper Retention (%) | Caliper after Compression | Percent Caliper Retention (%) | Caliper after Compression | Percent Caliper Retention (%) |
| Example 1 | 0.45 | 0.38 | 84.44 | 0.35 | 77.78 | 0.34 | 75.56 |
| Example 2 | 0.43 | 0.36 | 83.72 | 0.36 | 83.72 | 0.31 | 72.09 |

As can be seen from Table 1, nonwoven fabrics 10 of the present disclosure can retain significant amounts of caliper after compression at relatively high pressures. For example, the Example 1 and Example 2 samples retain greater than 70%° of their original average caliper after being tested by the Compression Aging Test at a pressure of 35 KPa. The Compression Aging Test is a simulation of the conditions a nonwoven fabric would encounter if packaged in a high compression packaging of diapers and then remain in such a state during distribution to a consumer and then the package finally opened by a consumer.

The present disclosure can utilize the process of melt spinning. In melt spinning, there is no mass loss in the extrudate. Melt spinning is differentiated from other spinning, such as wet or dry spinning from solution, where a solvent is being eliminated by volatilizing or diffusing out of the extrudate resulting in a mass loss.

Melt spinning can occur at from about 150° C. to about 280° C., or, in some examples, at from about 190° C. to about 230° C. Fiber spinning speeds can be greater than 100 meters/minute, and can be from about 1,000 to about 10,000 meters/minute, from about 2,000 to about 7,000 meters/minute, and from about 2,500 to about 5,000 meters/minute. Spinning speeds can affect the brittleness of the spun fiber, and in general, the higher the spinning speed, the less brittle the fiber. Continuous fibers can be produced through spunbond methods or meltblowing processes.

A nonwoven fabric 10 of the present disclosure can comprise continuous multicomponent polymeric filaments comprising a primary polymeric component and a secondary polymeric component. The filaments can be continuous bicomponent filaments comprising a primary polymeric component A and an secondary polymeric component B. The bicomponent filaments can have a cross-section, a length, and a peripheral surface. The components A and B can be arranged in substantially distinct zones across the cross-section of the bicomponent filaments and can extend continuously along the length of the bicomponent filaments. The secondary component B can constitute at least a portion of the peripheral surface of the bicomponent filaments continuously along the length of the bicomponent filaments. The polymeric components A and B can be melt spun into multicomponent fibers on conventional melt spinning equipment. The equipment will be chosen based on the desired configuration of the multicomponent. Commercially available melt spinning equipment is available from Hills, Inc. located in Melbourne, Fla. The temperature for spinning can range from about 180° C. to about 230° C. The processing temperature can be determined by the chemical nature, molecular weights, and concentration of each component. The bicomponent spunbond filaments can have an average diameter from about 6 to about 40 microns, and preferably from about 12 to about 40 microns.

The components A and B can be arranged in either a side-by-side arrangement, as shown in FIG. 8A, or an eccentric sheath/core arrangement as shown in FIG. 8B to obtain filaments which exhibit a natural helical crimp. Alternatively, the components A and B can be arranged in a concentric sheath core arrangement as shown in FIG. 8C. Additionally, the component A and B can be arranged in multi-lobal sheath core arrangement as shown in FIG. 9. Other multicomponent fibers can be produced by using the compositions and methods of the present disclosure. The bicomponent and multicomponent fibers may be segmented pie, ribbon, islands-in-the-sea configuration, or any combination thereof. The sheath may be continuous or noncontinuous around the core. The ratio of the weight of the sheath to the core can be from about 5:95 to about 95:5. The fibers of the present disclosure may have different geometries that include round, elliptical, star shaped, rectangular, and other various eccentricities.

In certain forms, the nonwoven fabric may comprise one or more layered webs and/or gradient webs. The one or more layered webs and/or gradient webs may differ from each other based on one or more of surface energy, fiber diameter, and fiber crimp.

Methods for extruding multicomponent polymeric filaments into such arrangements are well-known to those of ordinary skill in the art.

A wide variety of polymers are suitable to practice the present disclosure including polyolefins (such as polyethylene, polypropylene and polybutylene), polyesters, polyamides, polyurethanes, elastomeric materials and the like. Non-limiting examples of polymer materials that can be spun into filaments can comprise natural polymers, such as starch, starch derivatives, cellulose and cellulose derivatives, hemicellulose, hemicelluloses derivatives, chitin, chitosan, polyisoprene (cis and trans), peptides, polyhydroxyalkanoates, and synthetic polymers including, but not limited to, thermoplastic polymers, such as polyesters, nylons, polyolefins such as polypropylene, polyethylene, polyvinyl alcohol and polyvinyl alcohol derivatives, sodium polyacrylate (absorbent gel material), and copolymers of polyolefins, such as polyethylene-octene or polymers comprising monomeric blends of propylene and ethylene, and biodegradable or compostable thermoplastic polymers such as polylactic acid filaments, polyvinyl alcohol, filaments, and polycaprolactone filaments. In an example, the polymer can be a thermoplastic polymer selected from the group consisting of: polypropylene, polyethylene, polyester, polylactic acid, polyhydroxyalkanoate, polyvinyl alcohol, polycaprolactone, styrene-butadiene-styrene block copolymer, styrene-isoprene-styrene block copolymer, polyurethane, and mixtures thereof. In another example, the thermoplastic polymer can be selected from the group consisting of: polypropylene, polyethylene, polyester, polylactic acid, polyhydroxyalkanoate, polyvinyl alcohol, polycaprolactone, and mixtures thereof. Alternatively, the polymer can comprise one derived from monomers which are biobased, such as bio-polyethylene or bio-polypropylene.

Primary component A and secondary component B can be selected so that the resulting bicomponent filament is providing improved nonwoven bonding and substrate softness. Primary polymer component A can have a melting temperature which is lower than the melting temperature of secondary polymer component B.

Primary polymer component A can comprise polyethylene or a random copolymer of propylene and ethylene. Secondary polymer component B can comprise polypropylene or random copolymer of propylene and ethylene. Polyethylenes can comprise linear low density polyethylene and high density polyethylene. In addition, secondary polymer component B may comprise additives for enhancing the natural helical crimp of the filaments, lowering the bonding temperature of the filaments, and enhancing the abrasion resistance, strength and softness of the resulting fabric.

Inorganic fillers such as the oxides of magnesium, aluminum, silicon, and titanium may be added as inexpensive fillers or processing aides. Other inorganic materials can comprise hydrous magnesium silicate, titanium dioxide, calcium carbonate, clay, chalk, boron nitride, limestone, diatomaceous earth, mica glass quartz, and ceramics.

The filaments of the present disclosure can also contain a slip additive in an amount sufficient to impart the desired haptics to the fiber. As used herein "slip additive" or "slip agent" means an external lubricant. The slip agent when melt-blended with the resin can gradually exude or migrate to the surface during cooling or after fabrication, hence forming a uniform, invisibly thin coating, thereby yielding permanent lubricating effects. The slip agent can preferably be a fast bloom slip agent, and can be a hydrocarbon having one or more functional groups selected from hydroxide, aryls and substituted aryls, halogens, alkoxys, carboxylates, esters, carbon unsaturation, acrylates, oxygen, nitrogen, carboxyl, sulfate and phosphate.

During the making or in a post-treatment or even in both, the nonwoven fabrics of the present disclosure can be treated with surfactants or other agents to either hydrophilize the web or make it hydrophobic. This is standard practice for nonwovens used in absorbent articles. For example, a nonwoven fabric used for a topsheet may be treated with a hydrophilizing material or surfactant so as to make it permeable to body exudates such as urine. For other absorbent articles, the topsheet may remain at its naturally hydrophobic state or made even more hydrophobic through the addition of a hydrophobizing material or surfactant.

Suitable materials for preparing the multicomponent filaments of the fabric of the present disclosure can comprise PH-835 polypropylene obtained from LyondellBasell and Aspun-6850-A polyethylene obtained from Dow chemical company.

When polyethylene is component A (sheath) and polypropylene is component B (core), the bicomponent filaments may comprise from about 5% to about 95% by weight polyethylene and from about 95% to about 5% polypropylene. The filaments can comprise from about 40% to about 60% by weight polyethylene and from about 60% to about 40% by weight polypropylene.

Figure 10:
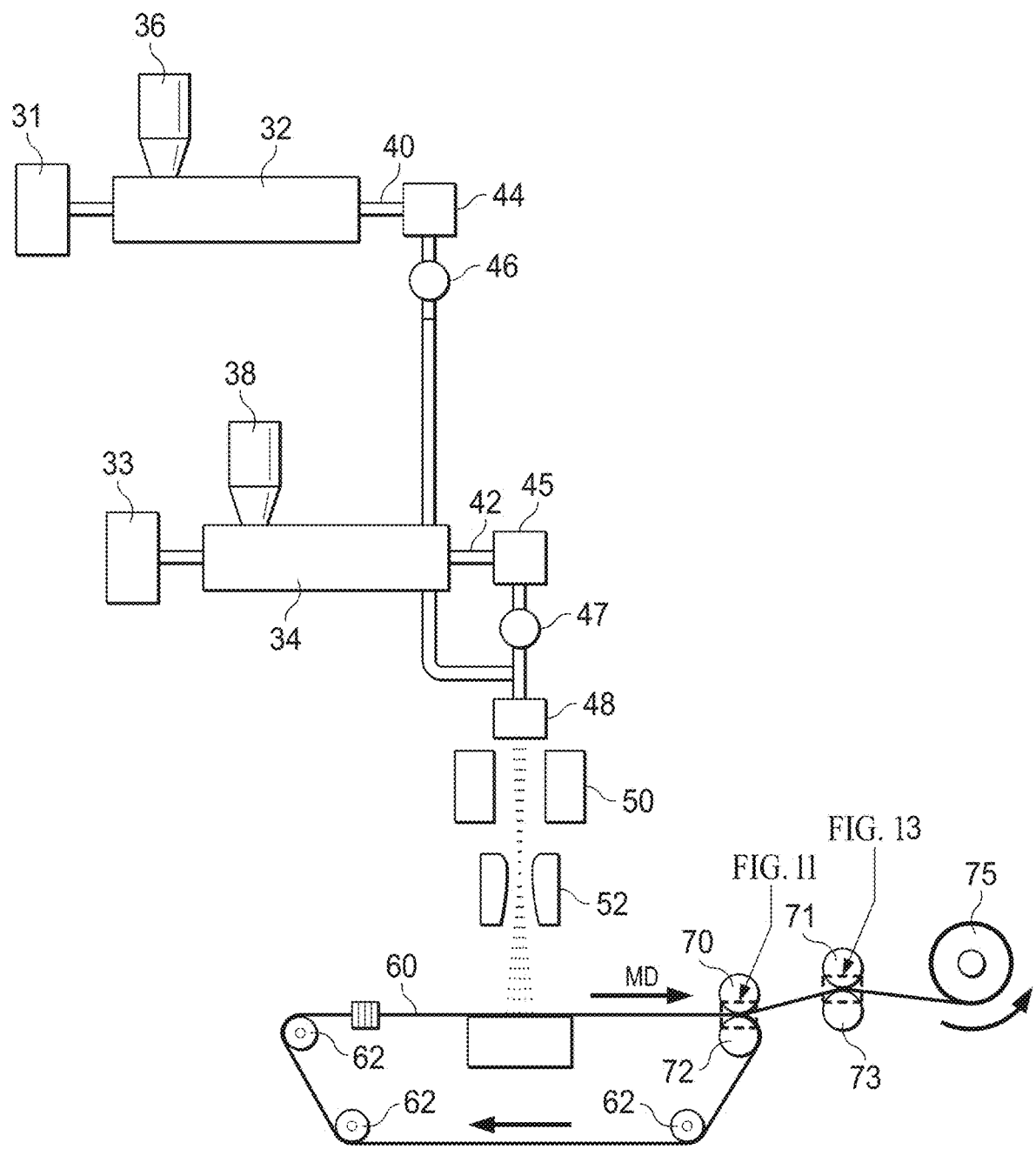
FIG. 10 is a schematic representation of an apparatus for making a fabric of the present disclosure.

Turning to FIG. 10, a representative process line 30 for preparing nonwoven fabrics 10 of the present disclosure is disclosed. The process line 30 can be arranged to produce a fabric of bicomponent continuous filaments, but it should be understood that the present disclosure comprehends nonwoven fabrics made with monocomponent or multicomponent filaments having more than two components. In certain examples, bicomponent filaments may be trilobal.

The process line 30 can comprise a pair of extruders 32 and 34 driven by extruder drives 31 and 33, respectively, for separately extruding the primary polymer component A and the secondary polymer component B. Polymer component A can be fed into the respective extruder 32 from a first hopper 36 and polymer component B can be fed into the respective extruder 34 from a second hopper 38. Polymer components A and B can be fed from the extruders 32 and 34 through respective polymer conduits 40 and 42 to filters 44 and 45 and melt pumps 46 and 47, which can pump the polymer into a spin pack 48. Spinnerets for extruding bicomponent filaments are well-known to those of ordinary skill in the art and thus are not described here in detail.

Generally described, the spin pack 48 can comprise a housing which can comprise a plurality of plates stacked one on top of the other with a pattern of openings arranged to create flow paths for directing polymer components A and B separately through the spinneret. The spin pack 48 can comprise openings arranged in one or more rows. The spinneret openings can form a downwardly extending curtain of filaments when the polymers are extruded through the spinneret. For the purposes of the present disclosure, spinnerets may be arranged to form sheath/core or side-by-side bicomponent filaments illustrated in FIGS. 8A, 8B, and 8C, as well as non-round fibers, such as tri-lobal fibers as shown in FIG. 9. Moreover, the fibers may be monocomponent comprising one polymeric component such as polypropylene.

The process line 30 can also comprise a quench blower 50 positioned adjacent the curtain of filaments extending from the spinneret. Air from the quench air blower 50 can quench the filaments extending from the spinneret. The quench air can be directed from one side of the filament curtain or both sides of the filament curtain.

An attenuator 52 can be positioned below the spinneret and can receive the quenched filaments. Fiber draw units or aspirators for use as attenuators in melt spinning polymers are well-known. Suitable fiber draw units for use in the process of the present disclosure can comprise a linear fiber attenuator of the type shown in U.S. Pat. No. 3,802,817 and eductive guns of the type shown in U.S. Pat. Nos. 3,692,618 and 3,423,266.

Generally described, the attenuator 52 can comprise an elongate vertical passage through which the filaments are drawn by aspirating air entering from the sides of the passage and flowing downwardly through the passage. A shaped, endless, at least partially foraminous, forming belt 60 can be positioned below the attenuator 52 and can receive the continuous filaments from the outlet opening of the attenuator 52. The forming belt 60 can be a belt and can travel around guide rollers 62. A vacuum 64 positioned below the forming belt 60 where the filaments are deposited can draw the filaments against the forming surface. Although the forming belt 60 is shown as a belt in FIG. 11, it should be understood that the forming belt can also be in other forms such as a drum. Details of particular shaped forming belts are explained below.

In operation of the process line 30, the hoppers 36 and 38 can be filled with the respective polymer components A and B. Polymer components A and B can be melted and extruded by the respective extruders 32 and 34 through polymer conduits 40 and 42 and the spin pack 48. Although the temperatures of the molten polymers may vary depending on the polymers used, when polyethylene and polypropylene are used as primary component A and secondary component B respectively, the temperatures of the polymers can range from about 190° C. to about 240° C.

As the extruded filaments extend below the spinneret, a stream of air from the quench blower 50 at least partially quenches the filaments, and, for certain filaments, to induce crystallization of molten filaments. The quench air can flow in a direction substantially perpendicular to the length of the filaments at a temperature of about 0° C. to about 35° C. and a velocity from about 100 to about 400 feet per minute. The filaments can be quenched sufficiently before being collected on the forming belt 60 so that the filaments can be arranged by the forced air passing through the filaments and forming surface. Quenching the filaments can reduce the tackiness of the filaments so that the filaments do not adhere to one another too tightly before being bonded and can be moved or arranged on the forming belt during collection of the filaments on the forming belt and formation of the web.

After quenching, the filaments can be drawn into the vertical passage of the attenuator 52 by a flow of the fiber draw unit. The attenuator is can be positioned 30 to 60 inches below the bottom of the spinneret.

The filaments can be deposited through the outlet opening of the attenuator 52 onto the shaped, traveling forming belt 60. As the filaments are contacting the forming surface of the forming belt 60, the vacuum 64 can draw the air and filaments against the forming belt 60 to form a nonwoven web of continuous filaments which assumes a shape corresponding to the shape of the forming surface. As discussed above, because the filaments are quenched, the filaments are not too tacky and the vacuum can move or arrange the filaments on the forming belt 60 as the filaments are being collected on the forming belt 60 and formed into the fabric 10.

The process line 30 can further comprise one or more bonding devices such as the cylinder-shaped compaction rolls 70 and 72, which can form a nip through which the fabric can be compacted, i.e., calendared, and which can be heated to bond fibers as well. One or both of the compaction rolls 70, 72 can be heated to provide enhanced properties and benefits to the nonwoven fabric 10 by bonding portions of the fabric. For example, it is believed that heating sufficient to provide thermal bonding can improve tensile properties of the fabric 10. The compaction rolls 70, 72 may be a pair of smooth surface stainless steel rolls with independent heating controllers. The compaction rolls 70, 72 may be heated by electric elements or hot oil circulation. The gap between the compaction rolls 70, 72 can be hydraulically controlled to impose desired pressure on the fabric as it passes through the compaction rolls on the forming belt. In an example, with a forming belt caliper of 1.4 mm, and a spunbond nonwoven having a basis weight of 30 gsm, the nip gap between the compaction rolls 70 and 72 can be about 1.4 mm.

Figure 11:
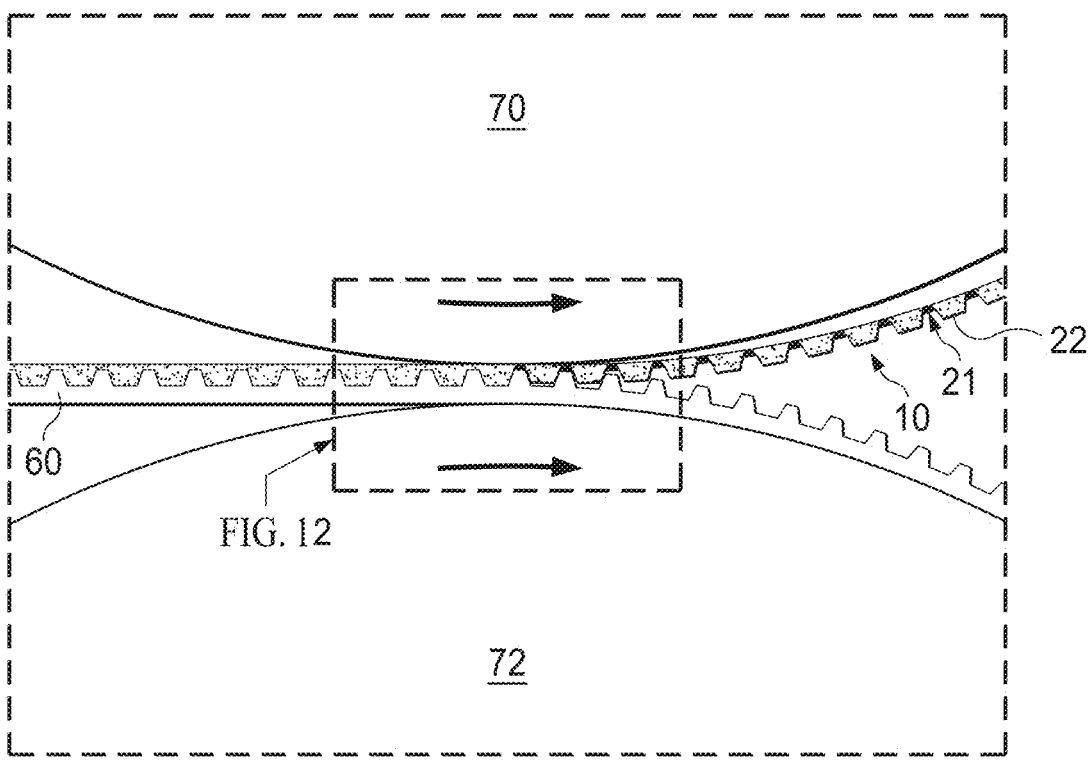
FIG. 11 is a detail of a portion of the apparatus for bonding a portion of a fabric of the present disclosure.
Figure 12:
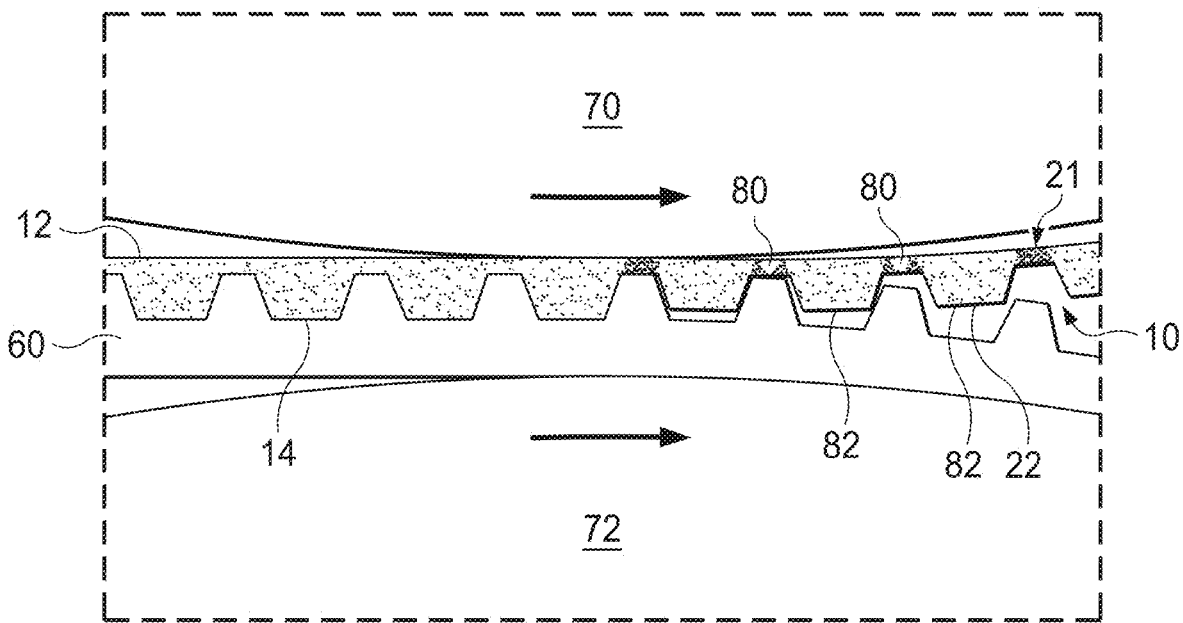
FIG. 12 is a further detail of a portion of the apparatus for bonding a portion of a fabric of the present disclosure.
Figure 13:
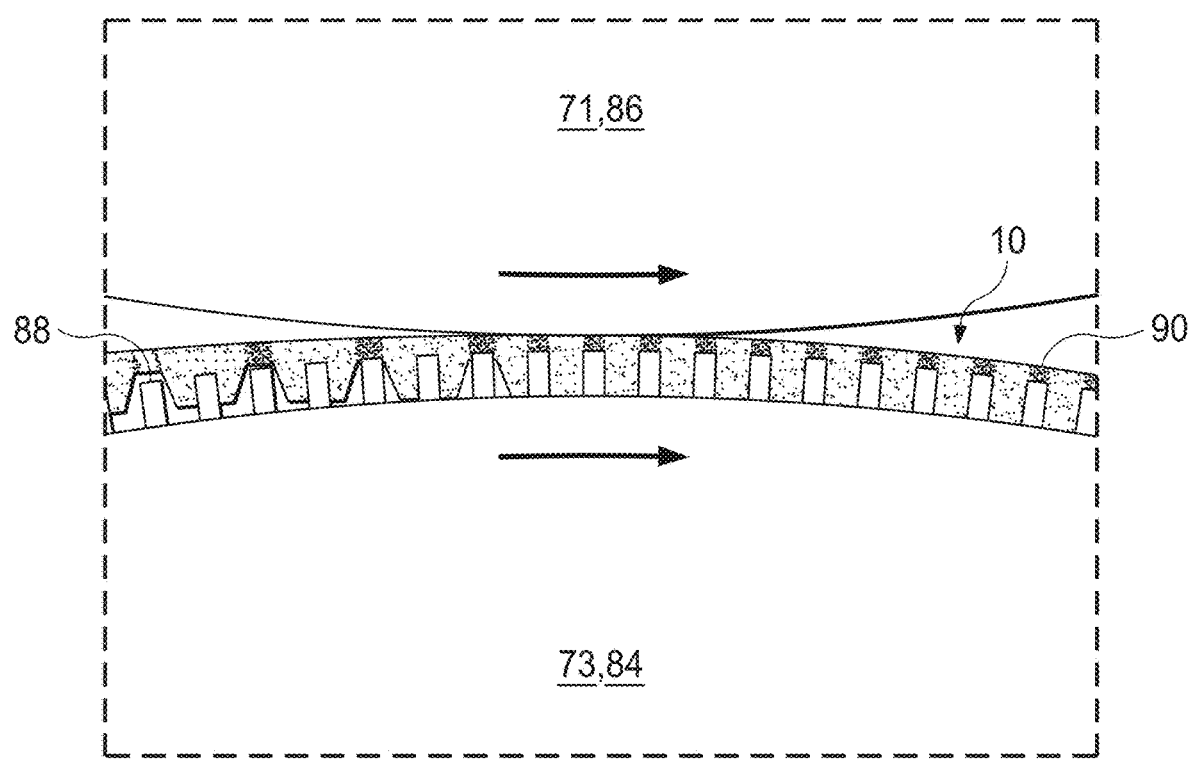
FIG. 13 is a detail of a portion of the apparatus for optional additional bonding of a portion of a fabric of the present disclosure.
Figure 14:
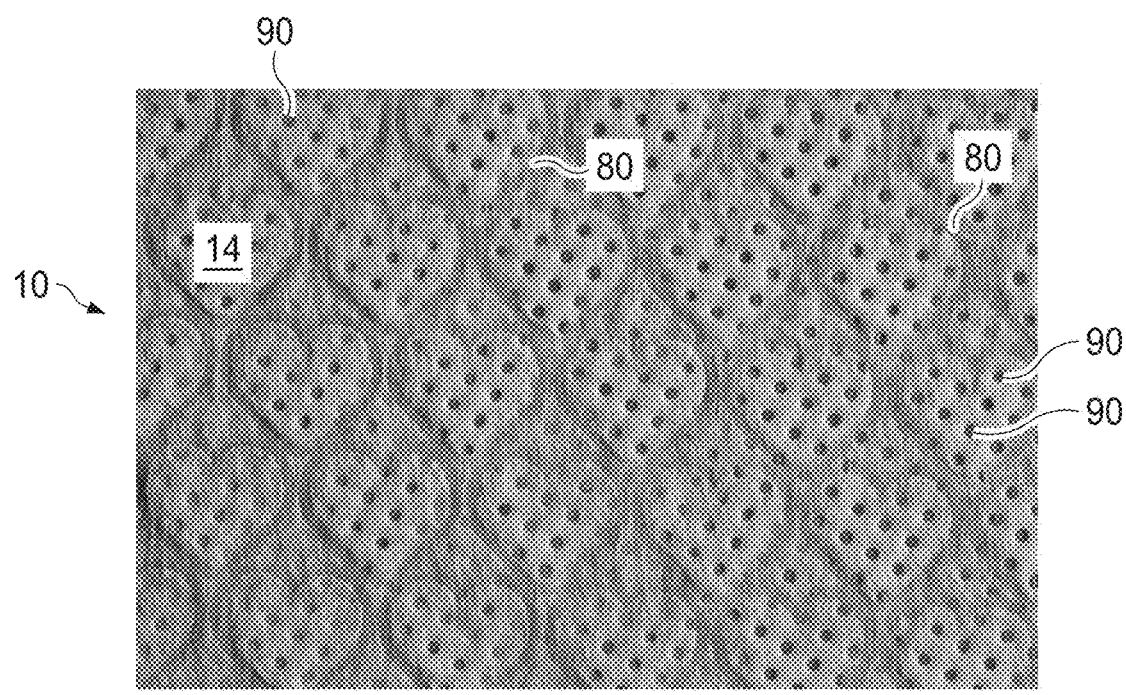
FIG. 14 is a photographic image of an example of a nonwoven fabric of the present disclosure.

In an example, upper compaction roll 70 can be heated sufficiently to melt bond fibers on the first surface 12 of the fabric 10, to impart strength to the fabric so that it can be removed from forming belt 60 without losing integrity. As shown in FIGS. 11 and 12, for example, as rolls 70 and 72 rotate in the direction indicated by the arrows, belt 60 with the spunbond fabric laid down on it enter the nip formed by rolls 70 and 72. Heated roll 70 can heat the portions of nonwoven fabric 10 that are pressed against it by the raised resin elements of belt 60, i.e., in regions 21, to create bonded fibers 80 on at least first surface 12 of the nonwoven fabric 10. As can be understood by the description herein, the bonded regions so formed can take the pattern of the raised elements of forming belt 60. For example, the bonded areas so formed can be a substantially continuous network or a substantially semi-continuous network on first surface 12 of regions 21 that make the same pattern as the hearts of FIG. 4 and FIG. 15. By adjusting temperature and dwell time, the bonding can be limited primarily to fibers closest to first surface 12, or thermal bonding can be achieved to second surface 14 as shown in FIG. 14 (which also shows point bonds 90, discussed more fully below), and FIGS. 66-70. Bonding can also be a discontinuous network, for example, as point bonds 90, discussed below.

The raised elements of the forming belt 60 may be selected to establish various network characteristics of the forming belt and the bonded regions of a nonwoven substrate 11 or nonwoven fabric 10. The network corresponds to the resin making up the raised elements of the forming belt 60 and may comprise substantially continuous, substantially semi-continuous, discontinuous, or combinations thereof options. These networks may be descriptive of the raised elements of the forming belt 60 as it pertains to their appearance or make-up in the X-Y planes of the forming belt 60 or the three dimensional features comprising the nonwoven substrate 11 or nonwoven fabric 10 of the present disclosure.

"Substantially continuous" network refers to an area within which one can connect any two points by an uninterrupted line running entirely within that area throughout the line's length. That is, the substantially continuous network has a substantial "continuity" in all directions parallel to the first plane and is terminated only at edges of that region. The term "substantially," in conjunction with continuous, is intended to indicate that while an absolute continuity can be achieved, minor deviations from the absolute continuity may be tolerable as long as those deviations do not appreciably affect the performance of the fibrous structure (or a molding member) as designed and intended.

"Substantially semi-continuous" network refers an area which has "continuity" in all, but at least one, directions parallel to the first plane, and in which area one cannot connect any two points by an uninterrupted line running entirely within that area throughout the line's length. The semi-continuous framework may have continuity only in one direction parallel to the first plane. By analogy with the continuous region, described above, while an absolute continuity in all, but at least one, directions is preferred, minor deviations from such a continuity may be tolerable as long as those deviations do not appreciably affect the performance of the fibrous structure.

"Discontinuous" network refer to discrete, and separated from one another areas that are discontinuous in all directions parallel to the first plane.

After compaction, the fabric can leave the forming belt 60 and be calendared through a nip formed by calendar rolls 71, 73, after which the fabric can be wound onto a reel. As shown in the schematic cross section of FIG. 10, the calendar rolls can be stainless steel rolls having an engraved pattern roll 84 and a smooth roll 86. The engraved roll 84 can comprise raised portions 88 that can provide for additional compaction and bonding to the fabric 10. Raised portions 88 can be a regular pattern of relatively small spaced apart "pins" that form a pattern of relatively small point bonds 90 in the nip of calendar rolls 71 and 73. The percent of point bonds in the nonwoven fabric 10 can be from 3% to 30%, or from 7% to 20%. The engraved pattern can be a plurality of closely spaced, regular, generally cylindrically-shaped, generally flat-topped pin shapes, with pin heights being in a range from ranging from 0.5 mm to 5 mm and preferably from 1 mm to 3 mm. Pin bonding calendar rolls can form closely spaced, regular point bonds 90 in nonwoven fabric 10, as shown in FIG. 14. Further bonding can be by hot-air through bonding, for example.

Through-air thermal bonding may be another approach to create higher loft nonwoven structures which may be suitable for this application. Through-air thermal bonding can involve the application of hot air to the surface of the nonwoven fabric. The hot air can flow through holes in a plenum positioned just above the nonwoven. However, the air is not pushed through the nonwoven, as in common hot air ovens. Negative pressure or suction, can pull the air through the open conveyor apron that supports the nonwoven as it passes thorough the oven. Pulling the air through the nonwoven fabric can allow much more rapid and even transmission of heat and minimizes fabric distortion. Aside from conventional through air bonding units, one could envision placing the bonding unit on top of the 3D belt while a vacuum is set under the belt to mimic the process of through air bonding for this specific application.

Binders used in through-air thermal bonding can comprise crystalline binder fibers, bicomponent binder fibers, and powders. When using crystalline binder fibers or powders, the binder can melt entirely and form molten droplets throughout the nonwoven's cross-section. Bonding can occur at these points upon cooling. In the case of sheath/core binder fibers, the sheath can be the binder and the core can be the carrier fiber. In an example, a nonwoven can comprise sheath/core binder fibers, where the sheath can comprise a polyethylene and the core can comprise polypropylene. For such a nonwoven, the through-air thermal bonding air temperature may be in the range of 110° C. to 150° C. and the residence time may be in the range of 0.5-10 seconds, 5-30 seconds, or 30-60 seconds as through air bonding time will depend upon basis weight, level of strength desired, and operating speed. Products manufactured using through-air ovens can tend to be bulky, open, soft, strong, extensible, breathable and absorbent.

Point bonding as used herein is a method of thermally bonding a nonwoven fabric, web, or substrate. This method can involve passing a web through a nip between two rolls consisting of heated male patterned or engraved metal roll and a smooth or patterned metal roll. The male patterned roll can comprise a plurality of raised, generally cylindrical-shaped pins that produce circular point bonds. The smooth roll may or may not be heated, depending on the application. In a nonwoven production line, the nonwoven fabric, which could be a non-bonded fiber web, can be fed into the calendar nip and the fiber temperature can be raised to the point for fibers to thermally fuse with each other at the tips of engraved points and against the smooth roll. The heating time is typically in the order of milliseconds. The fabric properties can be dependent on process settings such as roll temperatures, web line speeds, and nip pressures, all of which can be determined by the skilled person for the desired level of point bonding. Other types of point bonding known generally as hot calendar bonding may consist of different geometries for the bonds (other than circular shaped), such as oval, lines, circles, etc. In an example, the point bonding can produce a pattern of point bonds being 0.5 mm diameter circles with 10% overall bonding area. Other examples may comprise bonding shapes where the raised pins have a longest dimension across the bonding surface of a pin of from about 0.1 mm to 2.0 mm and the overall bonding area ranges from 5% to 30%.

As shown in FIG. 14, the heated compaction roll 70 can form a bond pattern, which can be a substantially continuous network bond pattern 80 (e.g., interconnected heart shaped bonds) on the first surface 12 of nonwoven fabric 10 (not shown in FIG. 14, as it faces away from the viewer), and engraved calendar roll 73 can form relatively small point bonds 90 on the second surface 14 of nonwoven fabric 10. The point bonds 90 can secure loose fibers that would otherwise be prone to fuzzing or pilling during use of the nonwoven fabric 10. The advantage of the resulting structure of nonwoven fabric 10 is most evident when used as a topsheet in a personal care article such as a diaper or sanitary napkin. In use in a personal care article, the first surface 12 of nonwoven fabric 10 can be relatively flat (relative to second surface 14) and have a relatively large amount of bonding due to the heated compaction roll forming bonds 80 at the areas of the fabric pressed by the raised elements of forming belt 60. This bonding can give the nonwoven fabric 10 structural integrity, but can be relatively stiff or rough to the skin of a user. Therefore, the first surface 12 of the nonwoven fabric 10 can be oriented in a diaper or sanitary napkin to face the interior of the article, i.e., away from the body of the wearer. Likewise, the second surface 14 can be body facing in use, and in contact with the body. The relatively small point bonds 90 can be less likely to be perceived visually or tactiley by the user, and the relatively soft three-dimensional features can remain visually free of fuzzing and pilling while feeling soft to the body in use. Further bonding can be used instead of, or in addition to, the above mentioned bonding.

Forming belt 60 can be made according to the methods and processes described in U.S. Pat. No. 6,610,173, issued to Lindsay et al. on Aug. 26, 2003, or U.S. Pat. No. 5,514,523 issued to Trokhan et al. on May 7, 1996, or U.S. Pat. No. 6,398,910 issued to Burazin et al. on Jun. 4, 2002, or U.S. Pub. No. 2013/0199741, published in the name of Stage et al. on Aug. 8, 2013, each with the improved features and patterns disclosed herein for making spunbond nonwoven webs. The Lindsay, Trokhan, Burazin, and Stage disclosures describe belts that are representative of papermaking belts made with cured resin on a woven reinforcing member, which belts, with improvements, can be utilized in the present disclosure as described herein.

Forming belt 60 having improved three-dimensional features and patterns for making spunbond nonwoven webs can also be made by the following methods and processes and/or on the following apparatuses, including with modifications as desired for structures taught herein: rotary screen processes as taught in U.S. Pat. No. 7,799,382 issued to Payne et al. on Sep. 21, 2010; polymer extrusion as taught in U.S. 2007-0170610 by Payne et al., published July 26, or U.S. 20072005-028018 by Sayers et al., published Dec. 22, 2005; resin system grafting as taught in U.S. Pat. No. 7,105,465 issued to Patel et al. on Sep. 12, 2006; perforated film as taught in U.S. Pat. No. 8,815,057 issued to Eberhardt et al. on Aug. 26, 2014; successive layer treatment as taught in U.S. 2006-0019567 by Sayers, published Jan. 26, 2006; polymeric droplet deposition as taught in U.S. Pat. No. 7,005,044 issued to Kramer et al. on Feb. 28, 2006; polymeric droplet deposition with a sacrificial material as taught in U.S. Pat. No. 7,014,735 issued to Kramer et al. on Mar. 21, 2006; air permeable film technology as taught by U.S. Pat. No. 8,454,800 issued to Mourad et al. on Jun. 4, 2013 or U.S. Pat. No. 8,822,009 issued to Riviere et al. on Sep. 9, 2014; multilayer belt structures as taught in U.S. 2016-0090692 by Eagles et al., published Mar. 31, 2016; laser etching as taught by U.S. Pat. No. 8,758,569 issued to Aberg et al. on Jun. 24, 2014 or U.S. Pat. No. 8,366,878 issued to Klerelid et al. on Feb. 5, 2013; extruded mesh technology as taught in U.S. 2014-0272269 by Hansen, published Sep. 18, 2014; nonwoven belts as described in U.S. 2008-0199655 by Monnerie et al., published Aug. 21, 2008; and additive manufacturing methods and processes as taught in U.S. 2015-0102526A1 by Ward et al., published Apr. 16, 2015, or U.S. 2016-0159007 by Miller et al., published Jun. 9, 2016, or WO 2016-085704 by Burazin et al., published Nov. 17, 2016, or U.S. 2016-0185041 by Lisagor et al., published Jun. 30, 2016.

Figure 15:
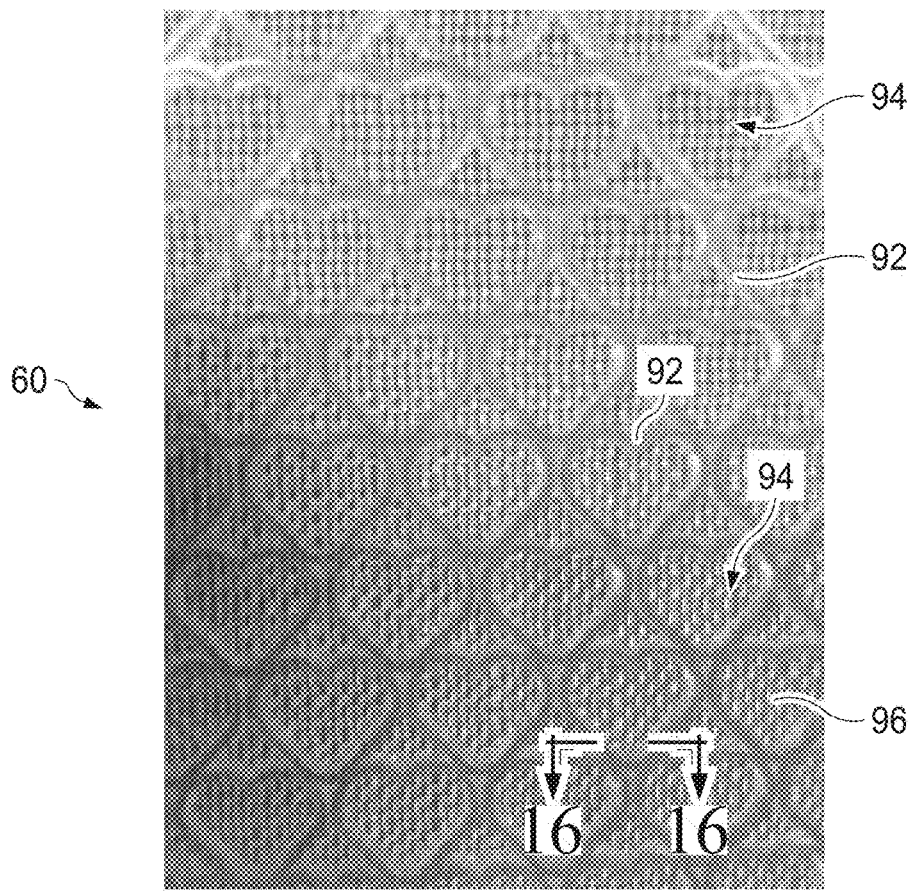
FIG. 15 is a photographic image of a portion of a forming belt useful for the present disclosure.

An example of a forming belt 60 of the type useful in the present disclosure and which can be made according to the disclosure of U.S. Pat. No. 5,514,523, is shown in FIG. 15. As taught therein, a reinforcing member 94 (such as a woven belt of filaments 96) can be thoroughly coated with a liquid photosensitive polymeric resin to a preselected thickness. A film or negative mask incorporating the desired raised element pattern repeating elements (e.g., FIG. 17) can be juxtaposed on the liquid photosensitive resin. The resin can then be exposed to light of an appropriate wave length through the film, such as UV light for a UV-curable resin. This exposure to light can cause curing of the resin in the exposed areas (i.e., white portions or non-printed portions in the mask). Uncured resin (resin under the opaque portions in the mask) can then be removed from the system leaving behind the cured resin forming the pattern illustrated, for example, the cured resin elements 92 shown in FIG. 15. Other patterns can also be formed, as discussed herein.

Figure 16:
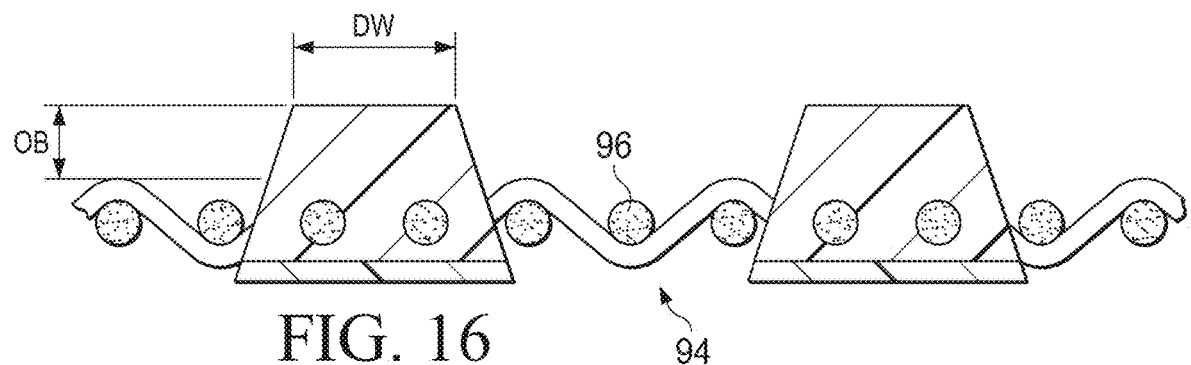
FIG. 16 is a cross-sectional depiction of a portion of the forming belt shown in FIG. 15.
Figure 17:
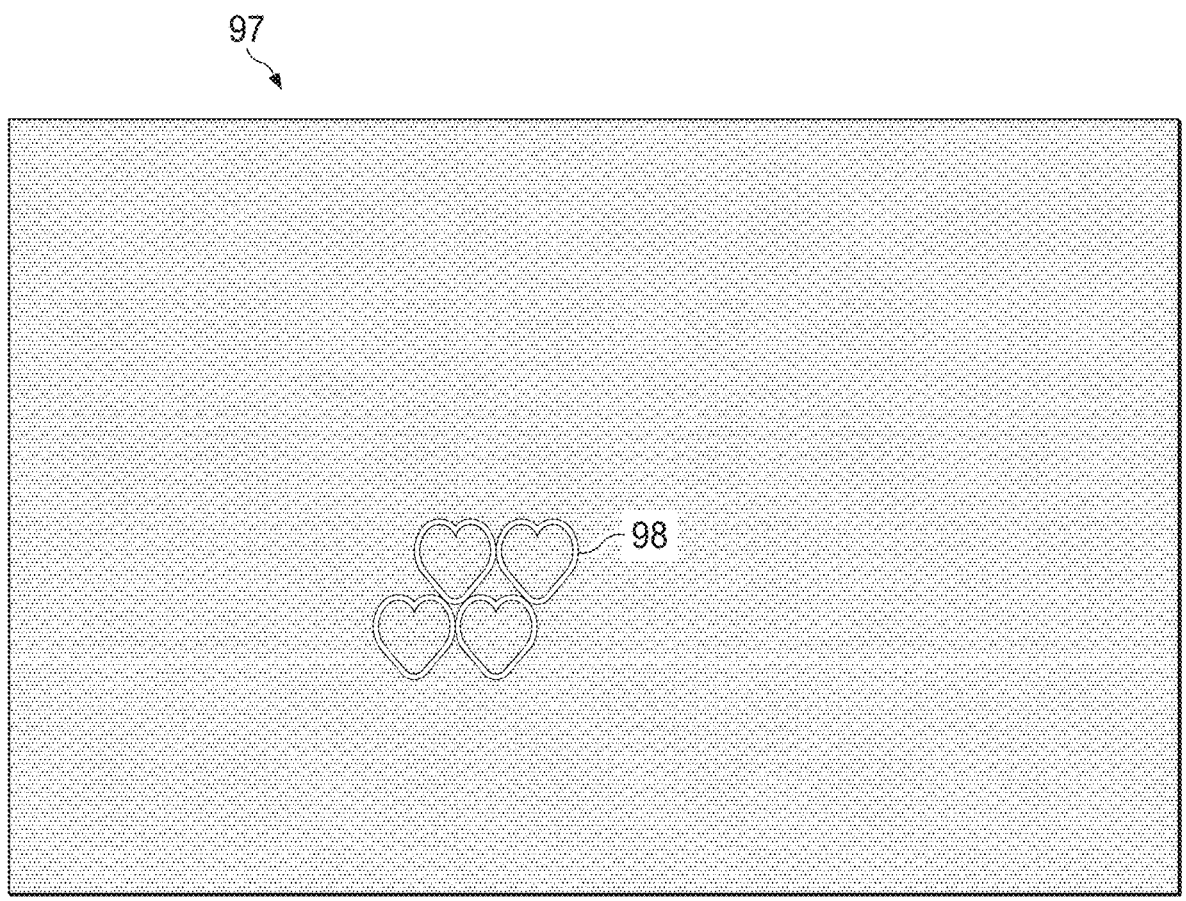
FIG. 17 is an image of a portion of a mask utilized to make the forming belt shown in FIG. 15.

FIG. 15 shows a portion of a forming belt 60 useful for making the nonwoven fabric 10 shown in FIG. 1. As shown, the forming belt 60 can comprise cured resin elements 92 on a woven reinforcing member 94. The reinforcing member 94 can be made of woven filaments 96 as is known in the art of papermaking belts, including resin coated papermaking belts. The cured resin elements can have the general structure depicted in FIG. 15, and can be made by the use of a mask 97 having the dimensions indicated in FIG. 17. As shown in schematic cross-section in FIG. 16, cured resin elements 92 can flow around and are cured to "lock on" to reinforcing member 94 and can have a width at a distal end DW of about 0.020 inch to about 0.060 inch, or from about 0.025 inch to about 0.030 inch, and a total height above the reinforcing member 94, referred to as over burden, OB, of about 0.030 inch to about 0.120 inch or about 0.50 to about 0.80 inch, or about 0.060 inch. FIG. 17 represents a portion of a mask 97 showing the design and representative dimensions for one repeat unit of the repeating hearts design in the nonwoven fabric 10 shown in FIG. 4. The white portion 98 can be transparent to UV light, and in the process of making the belt, as described in U.S. Pat. No. 5,514,523, can permit UV light to cure an underlying layer of resin which is cured to form the raised elements 92 on the reinforcing member 94. After the uncured resin is washed away, the forming belt 60 having a cured resin design as shown in FIG. 15 can be produced by seaming the ends of a length of the belt, the length of which can be determined by the design of the apparatus, as depicted in FIG. 10.

Figure 18:
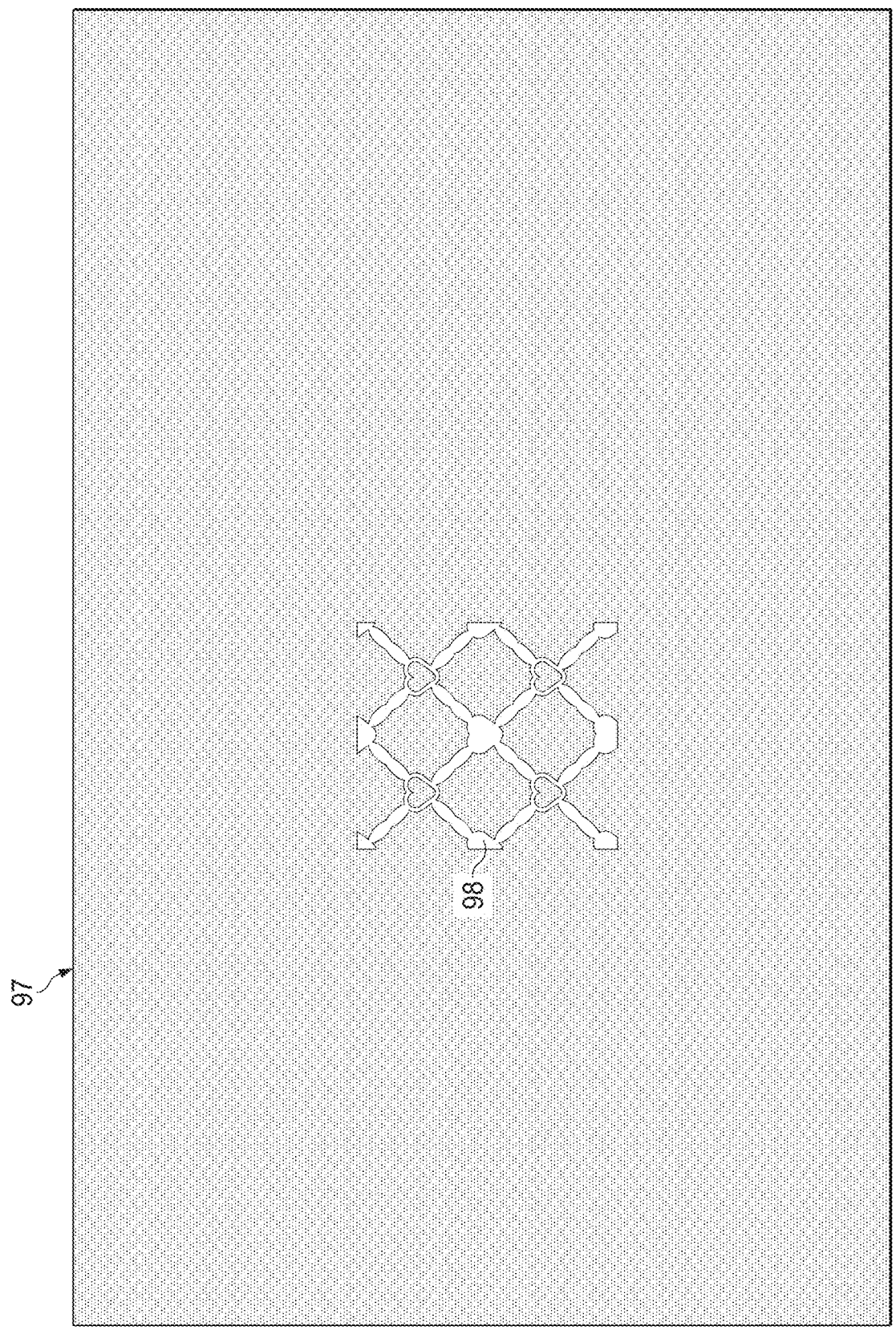
FIG. 18 is an image of a portion of a mask utilized to make a forming belt useful for the present disclosure.
Figure 19:
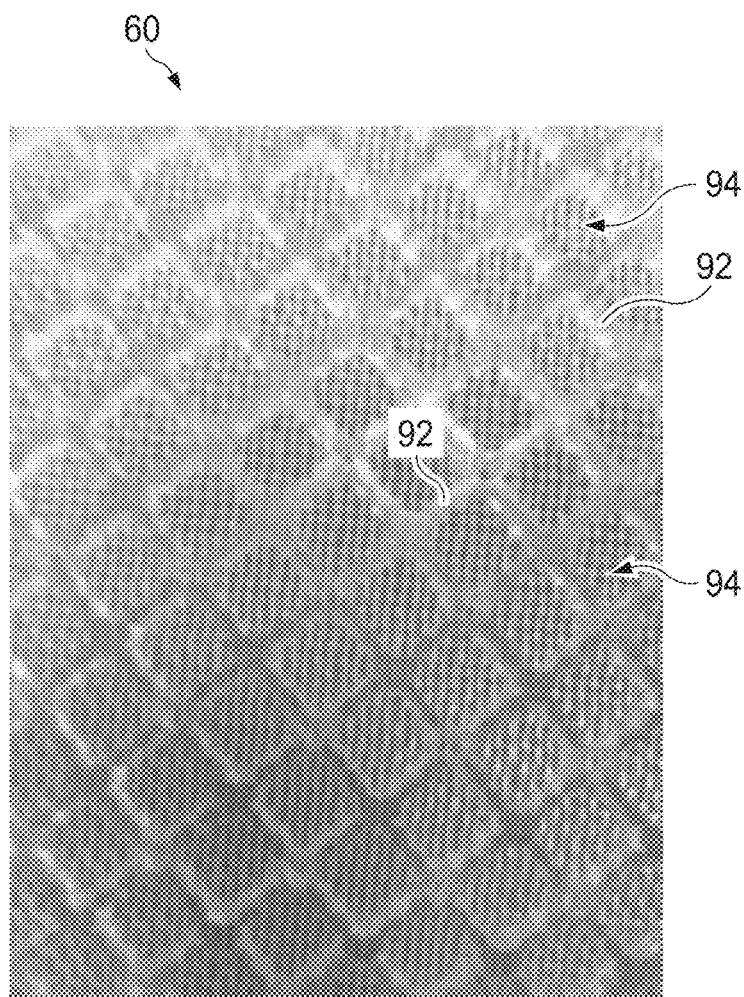
FIG. 19 is a photographic image of a portion of a forming belt formed from the mask referenced in FIG. 18.

In like manner, FIG. 18 represents a portion of a mask 97 showing the design for one repeat unit of the repeating design in the nonwoven fabric 10 shown in FIG. 5. The white portion 98 can be transparent to UV light, and in the process of making the belt can permit UV light to cure an underlying layer of resin which is cured to the reinforcing member 94. After the uncured resin is washed away, the forming belt 60 having a cured resin design as shown in FIG. 19 can be produced by seaming the ends of a length of the belt, the length of which can be determined by the design of the apparatus, as depicted in FIG. 10.

Figure 20:
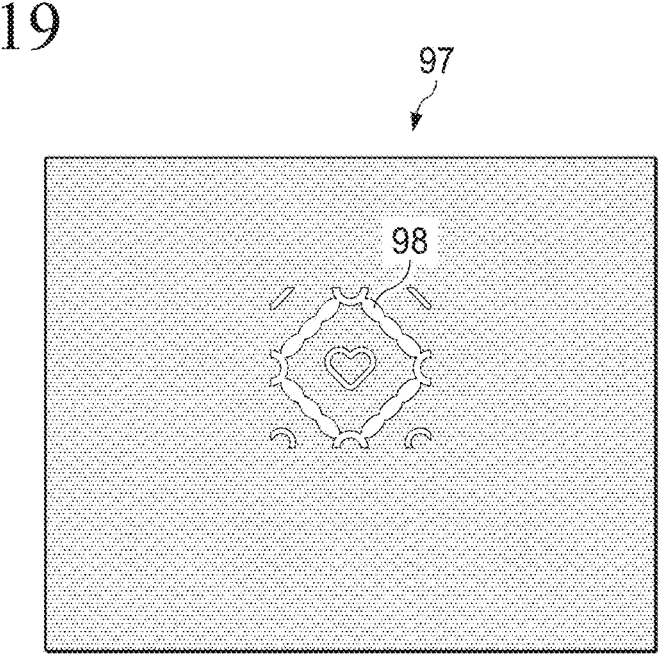
FIG. 20 is an image of a portion of a mask utilized to make a forming belt useful for the present disclosure.
Figure 21:
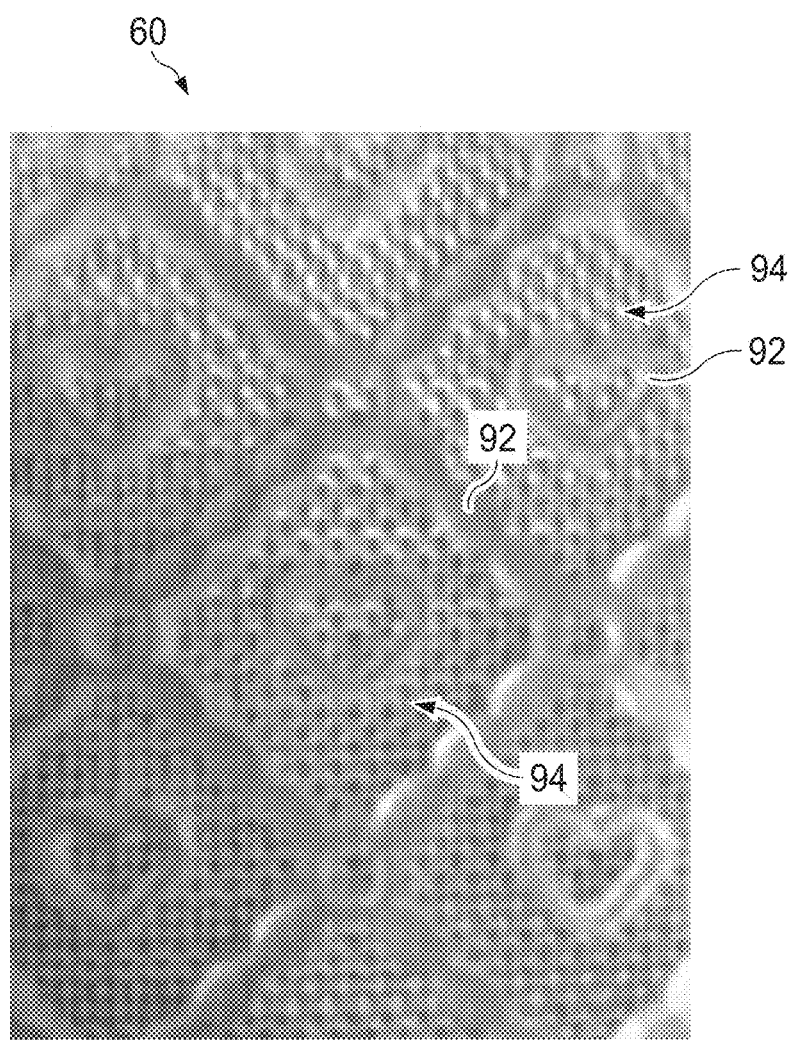
FIG. 21 is a photographic image of a portion of a forming belt formed from the mask referenced in FIG. 20.

Further, in another non-limiting example, FIG. 20 represents a portion of a mask showing the design for one repeat unit of the repeating design in the nonwoven fabric 10 shown in FIG. 21. The white portion 98 is transparent to UV light, and in the process of making the belt permits UV light to cure an underlying layer of resin which is cured to the reinforcing member 94. After the uncured resin is washed away, the forming belt 60 having a cured resin design as shown in FIG. 21 can be produced by seaming the ends of a length of nonwoven fabric 10.

Figure 22:
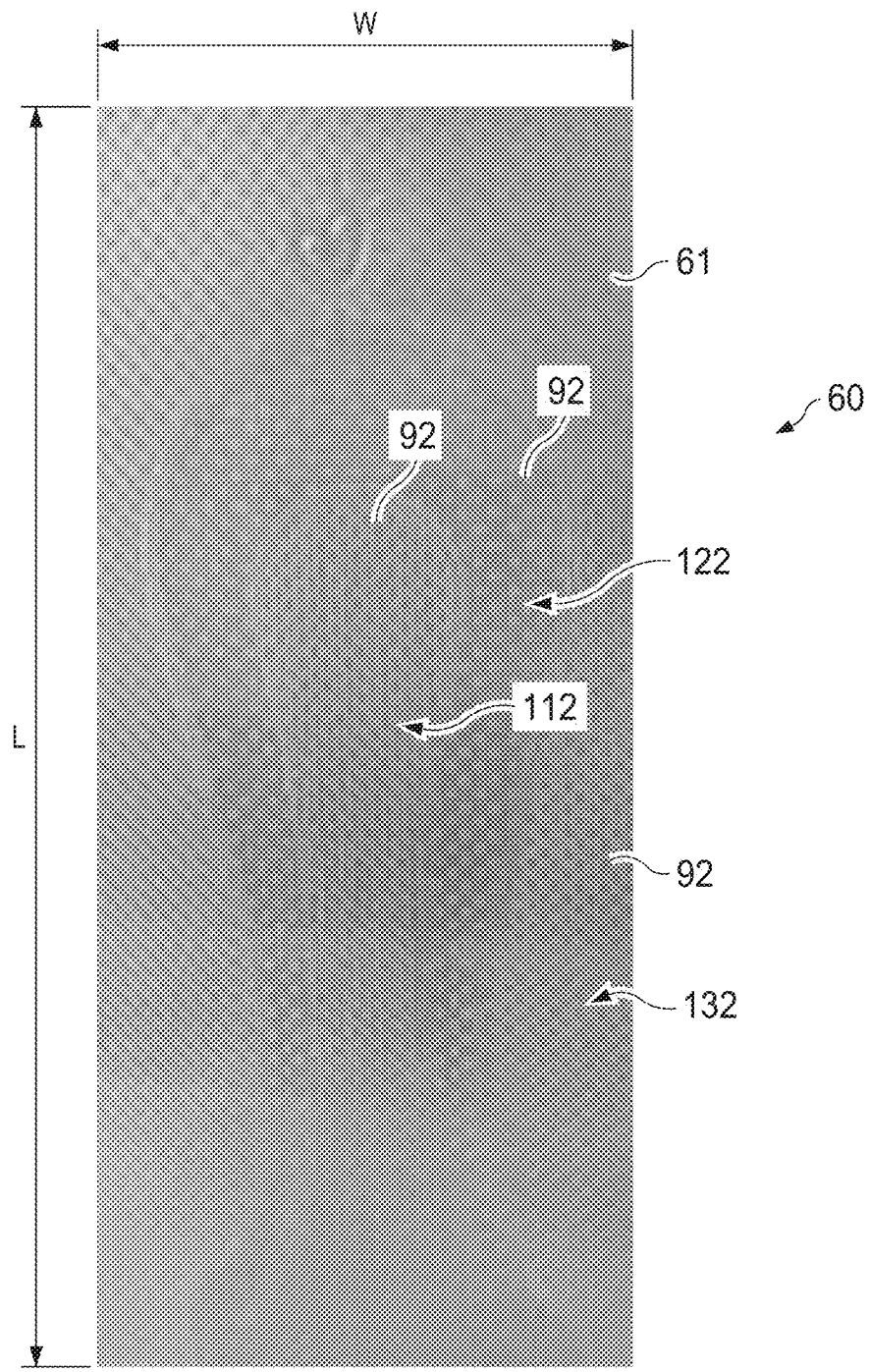
FIG. 22 is a photographic image of a portion of a forming belt useful for the present disclosure.
Figure 23:
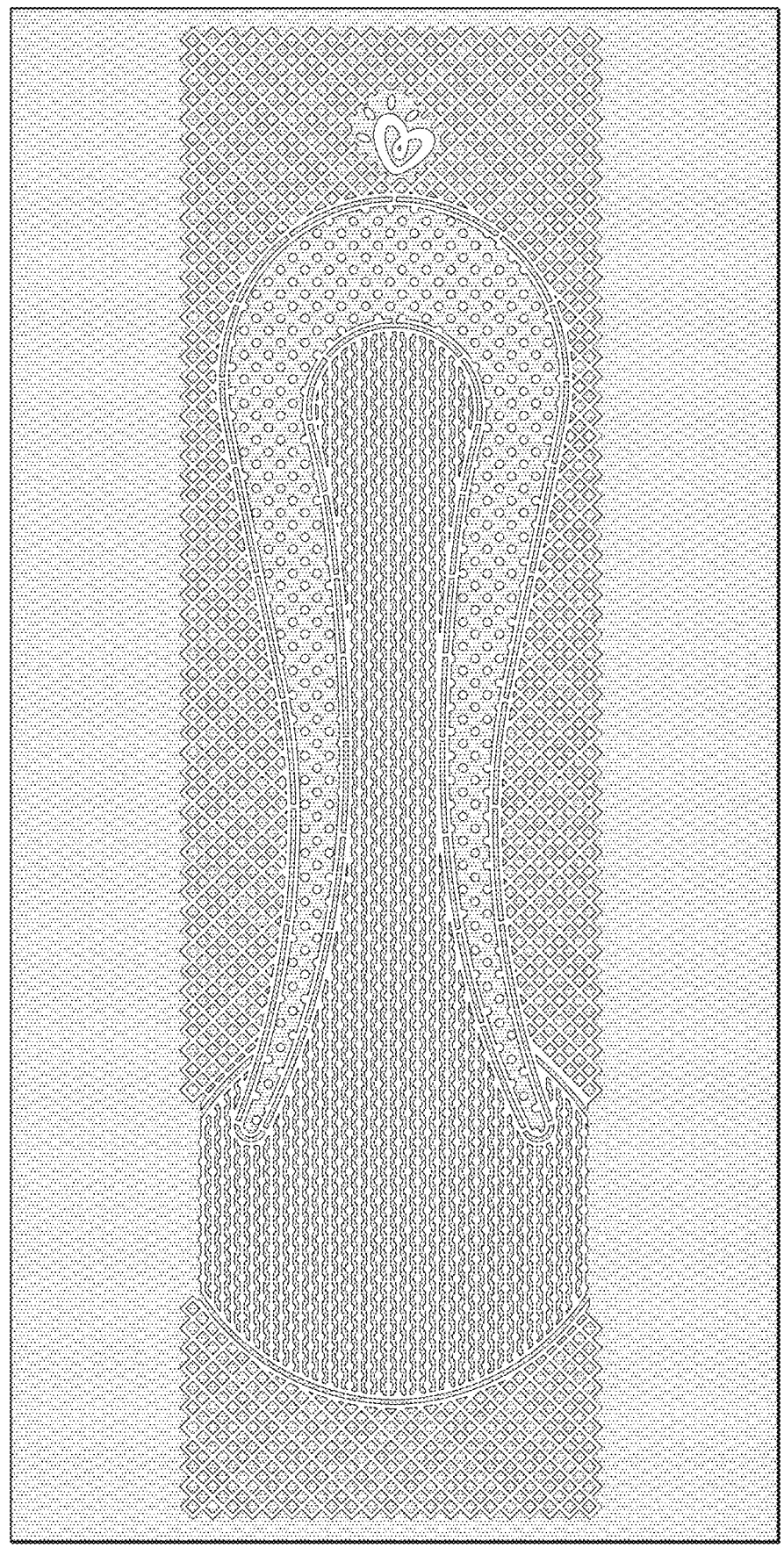
FIG. 23 is an image of a mask utilized to make the forming belt shown in FIG. 20.

Another example of a portion of a forming belt 60 of the type useful in the present disclosure is shown in FIG. 22. The portion of the forming belt 60 shown in FIG. 22 can be a discrete belt pattern 61 that can have a length L and width W corresponding to the length L and width W of the overall area OA of the nonwoven fabric 10. That is, the forming belt 60 can comprise discrete belt patterns 61 (as discussed more fully with reference to FIG. 25 below), each having a discrete belt pattern overall area DPOA that corresponds to the overall area OA of the nonwoven fabric 10. FIG. 23 represents a portion of a mask showing the design for one repeat unit of the repeating design in the nonwoven fabric 10 shown in FIG. 24. The white portion 98 can be transparent to UV light, and in the process of making the belt can permit UV light to cure an underlying layer of resin which is cured to the reinforcing member 94. After the uncured resin is washed away, the forming belt 60 having a cured resin design as shown in FIG. 22 can be produced by seaming the ends of a length of the belt.

The portion of the forming belt shown in FIG. 22 illustrates another benefit of the present disclosure. The portion of a forming belt 60 shown in FIG. 22 can make a nonwoven fabric 10 shown in FIG. 24. The nonwoven fabric 10 shown in FIG. 24 can have width W and length L dimensions and an overall area OA making it suitable for use as a topsheet in a disposable diaper, for example. The nonwoven fabric 10 made on a forming belt 60 as exemplified in FIG. 22 differs from that shown in FIGS. 4-6 in that the pattern of three-dimensional features formed by the discrete resin elements 92 on forming belt 60 are not in a regular, repeating pattern across the entire overall area. Rather, the pattern of three-dimensional raised elements in the discrete belt pattern overall area DPOA can be described as an irregular pattern encompassing distinct portions referred to as zones, as described above. The distinction between zones can be visual, i.e., a visually discernible difference, or in the nonwoven fabric 10 the distinction can produce a difference in average intensive properties such as basis weight or density, or combinations of visual and intensive properties. A visually discernible difference exists if an observer in ordinary indoor lighting conditions (20/20 vision, lighting sufficient to read by, for example) can visually discern a pattern difference between the zones, such as a first forming zone 112 and a second zone 122 of the forming belt 60.

Figure 24:
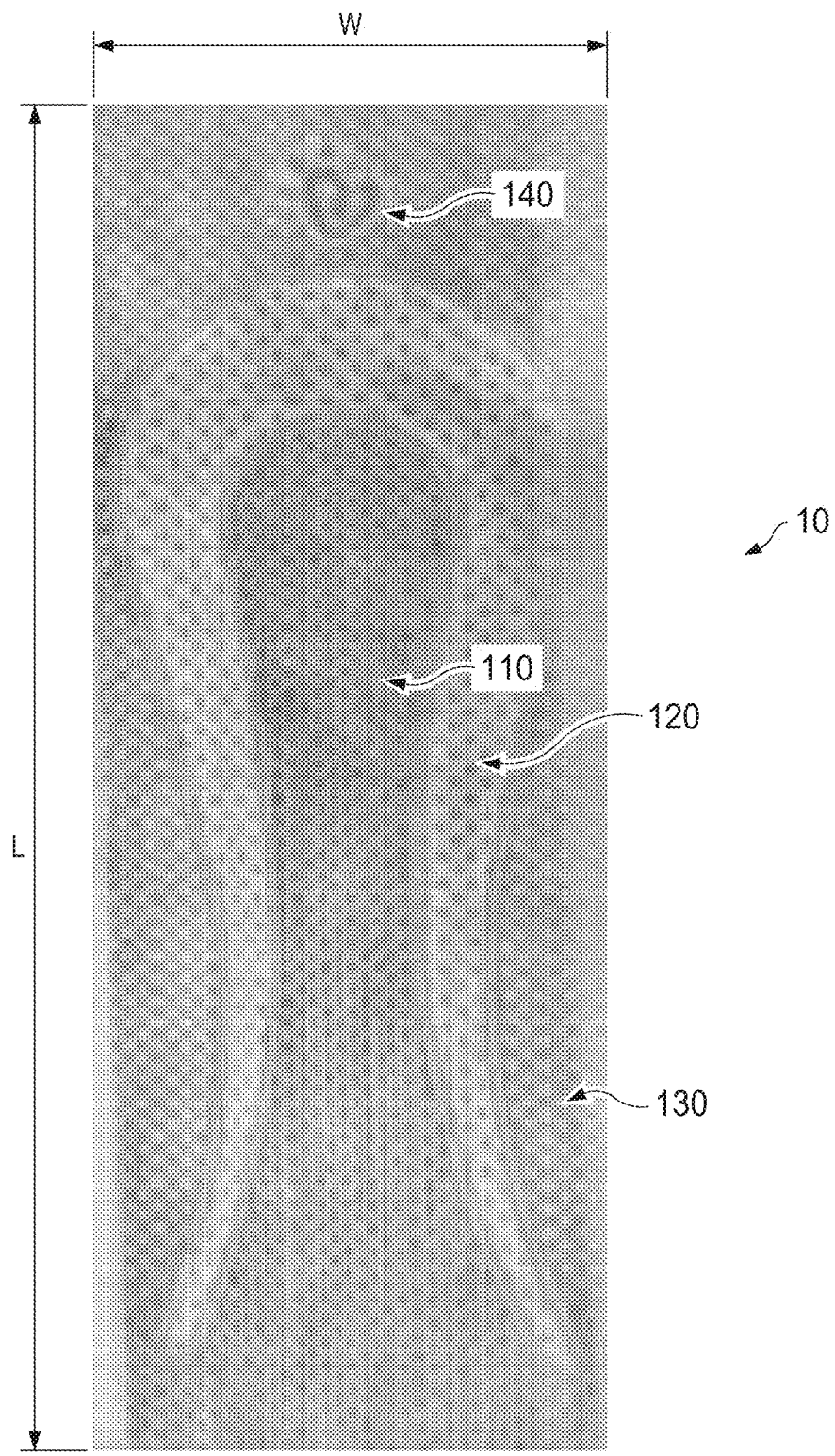
FIG. 24 is a photographic image of a nonwoven fabric of the present disclosure made on the forming belt shown in FIG. 22.

As described with reference to FIG. 2, the nonwoven fabric 10 can also comprise visually discernible zones corresponding to the zones of the forming belt. As shown in FIG. 24, for example, and described above, the nonwoven fabric 10 can comprise at least two, three, or four visually discernible zones. The first zone 110, having first pattern of three-dimensional features and first average intensive properties, can comprise a first area generally centrally located within the overall area OA. The second zone 120, having second pattern of three-dimensional features and second average intensive properties, can comprise a second area distributed generally about, and in an example, completely surrounding, the first zone 110 within the overall area OA. The third zone 130, having third pattern of three-dimensional features and third average intensive properties, can comprise a third area distributed generally about, and in an example, completely surrounding, the second zone 120 within the overall area OA. A fourth zone 140, having fourth three-dimensional features and fourth average intensive properties, can comprise a fourth area positioned within the overall area OA in any location, such as at a front area of a topsheet, such as the heart design shown in FIG. 24. In general, there can be n zones, with n being a positive integer. Each of the n zones can comprise an nth pattern of three-dimensional features and an nth area and nth average intensive properties. It will be appreciated that the zones can be arranged in any of a variety of suitable configurations, including but not limited to those described herein.

The visually discernible zones as shown in FIG. 24 may comprise visually discernible three-dimensional features. These distinct three-dimensional features may be bounded by relatively higher density (with respect to the interior of a three-dimensional feature) regions that may be in the form of a closed figure, such as the heart shape in FIGS. 4 and 6, and the diamond shape of FIGS. 5 and 6. In general, as discussed more fully below, including in the context of micro zones, the three-dimensional features can be defined by a first region and a second region, wherein the first region and second region are visually distinct and there is a common intensive property associated with each of the first and second regions and there is a difference in the first region's and second region's common intensive property value. In an example, the three-dimensional features can be defined by a first region and a second region, with the first region being at a higher elevation (dimension measured in the Z-direction) than the second region with respect to the plane of the first surface. In another example, the three-dimensional features can be defined by a first region and a second region, with the first region being at a higher basis than the second region.

As can be understood, rather than having a constant repeating pattern that is uniform across the entire forming belt, the forming belt 60 of the present disclosure allows the production of a nonwoven material that can have repeats of irregular discrete belt patterns 61, each discrete belt pattern 61 being like the discrete belt pattern shown in FIG. 22. The discrete belt patterns 61 each can be used to form one nonwoven fabric 10 having an overall area OA suitable for use in a disposable absorbent article, such as diaper or sanitary napkin, for example. The nonwoven fabrics 10 can be produced sequentially, i.e., in line, and, optionally sequentially in parallel lanes, each lane being a sequential line of nonwoven fabrics 10. The sequential line of nonwoven fabrics 10 can be produced in a machine direction along an axis parallel to the machine direction. The nonwoven material can then be slit or otherwise cut to size to produce nonwoven fabrics 10 utilized as a topsheet in disposable absorbent articles, such as diapers or sanitary napkins.

In an example, the pattern within each discrete belt pattern overall area DPOA can be the same or different. That is, the sequentially spaced discrete belt patterns can be substantially identical, or they can differ in visual appearance and/or in the intensive properties produced in nonwoven substrates produced thereon. For example, as shown schematically in FIG. 25, the pattern of three-dimensional raised elements in first forming zone 112 of discrete belt pattern 61A can be different from the pattern of three-dimensional raised elements in first forming zone 112 of discrete belt pattern 61B.

The forming belt 60 can thus offer flexibility in producing nonwoven fabrics 10 suitable for use in consumer goods, including disposable absorbent articles. For example, in one package of diapers, the topsheets of at least two diapers can be different because they were produced sequentially in a spunbond process as described herein, with sequential discrete belt patterns having different patterns of zones. In an example, the topsheet or backsheet nonwoven pattern for one size of diaper can be different from the topsheet or backsheet nonwoven of another size of diaper, thereby giving a caretaker a visual clue as to the size of a diaper. Likewise, sanitary napkins can utilize a nonwoven fabric 10 for a topsheet, with the visual pattern of three-dimensional features denoting the absorbency of the sanitary napkin. In any event, the various patterns of nonwoven fabrics 10 can be produced on a single belt by making the discrete belt patterns different as desired.

Figure 25:
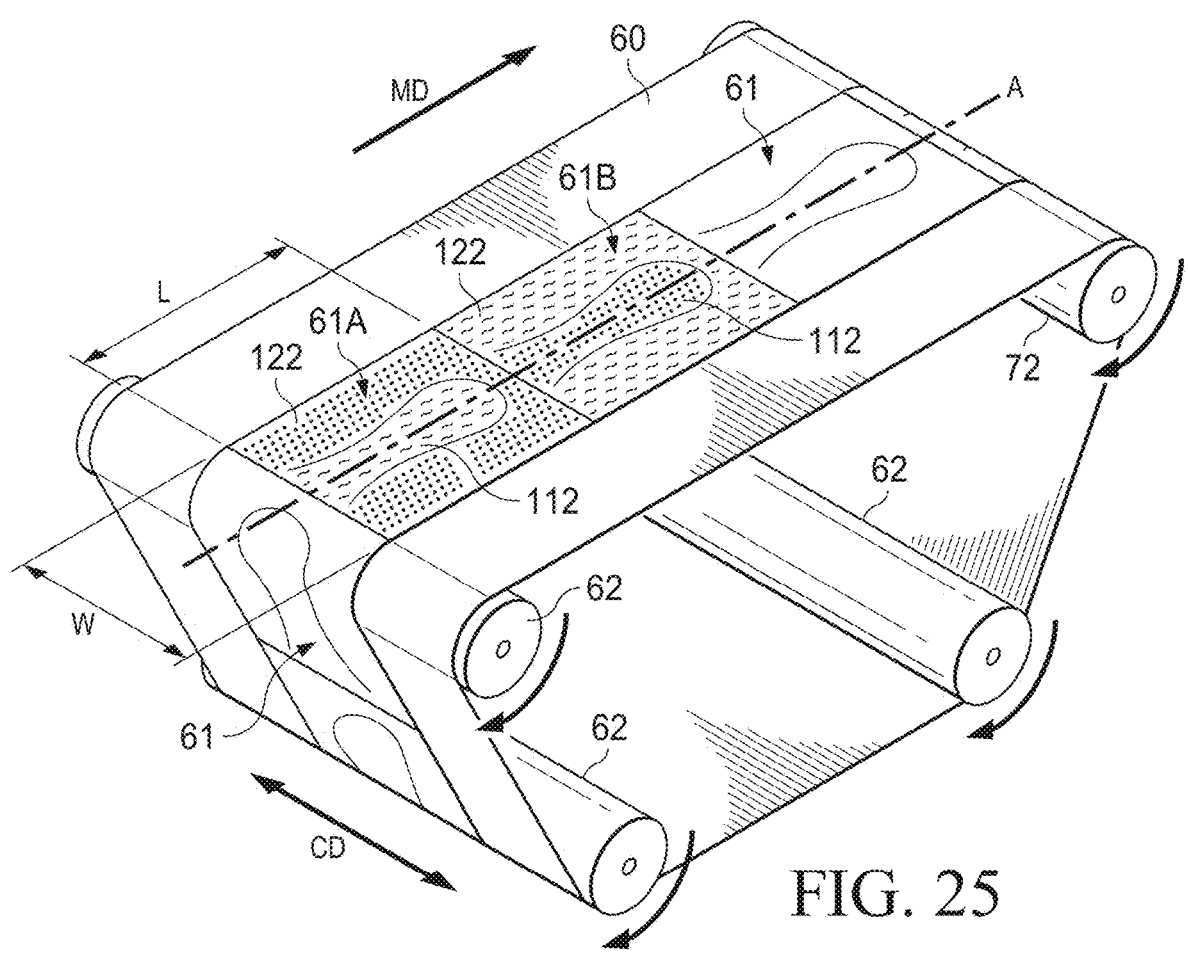
FIG. 25 is a perspective schematic view of a forming belt of the present disclosure.

Thus, the present disclosure describes, with reference to FIG. 25, a forming belt having an axis A parallel to a longitudinal direction which is a machine direction. The forming belt 60 can comprise a plurality of discrete belt patterns 61 ordered in at least one sequential relationship with respect to the longitudinal direction. Each discrete belt pattern 61 can have a discrete belt pattern overall area DPOA defined, in a rectangular-shaped pattern, by a length L and width W, as indicated with respect to discrete belt pattern 61A. Each discrete belt pattern within its overall area DPOA can comprise a first forming zone 112 having a first pattern of three-dimensional raised elements extending outwardly from the plane of the of the first surface and a second forming zone 122 having second three-dimensional raised elements extending outwardly from the plane of the of the first surface. The first forming zone can have a first air permeability value and the second forming zone can have a second air permeability value, and the first air permeability value can be different from the second air permeability value. The pattern within each sequentially ordered discrete belt pattern overall area DPOA can be the same or different.

By way of example, and referring to the discrete belt pattern 61 of forming belt 60 shown in FIG. 22 and the nonwoven fabric 10 shown in FIG. 24, the following properties were determined. The first zone 110 of the nonwoven fabric 10 can have an average basis weight of about 5 gsm to about 30 gsm; the second zone 120 can have an average basis weight of about 50 gsm to about 70 gsm; and the third zone 130 can have an average basis weight of about 25 gsm to about 60 gsm. The difference in basis weight from one zone to another can be attributed to a difference in air permeability of the forming belt 60. In the example used to make the nonwoven fabric 10 shown in FIG. 23, in which the basis weights for zones 110, 120, and 130, are 15 gsm, 53 gsm and 25 gsm, respectively, the air permeability of the respective forming zones 112, 122, and 132 of the forming belt 60 are 379 cfm, 805 cfm, and 625 cfm, respectively. Thus, by varying air permeability in zones in forming belt 60, the intensive properties of average basis weight and average density in zones can be facilitated across the overall area of nonwoven fabric 10.

Figure 26:
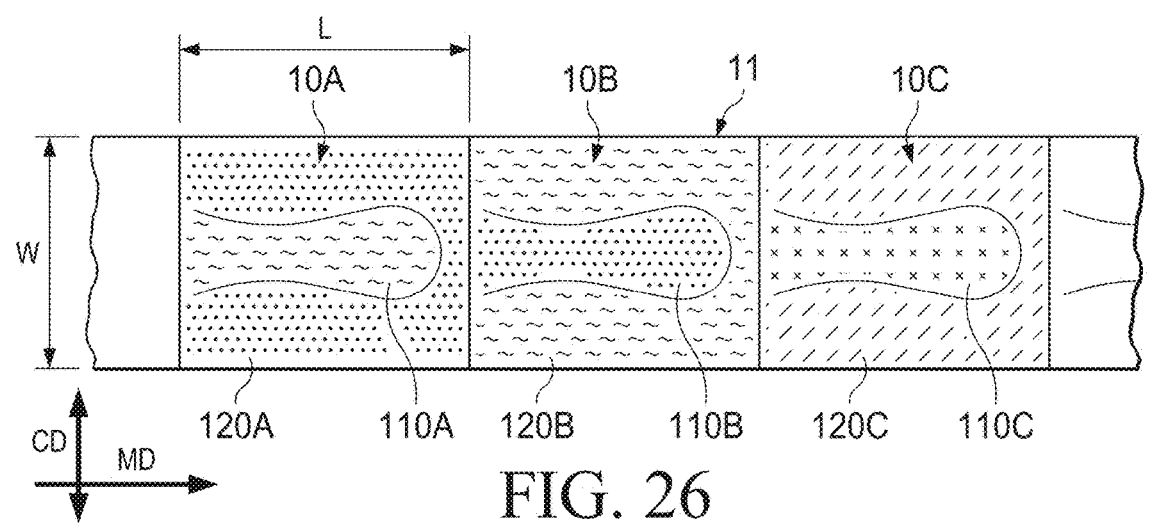
FIG. 26 is a plan view of a nonwoven substrate including nonwoven fabrics of the present disclosure.

As can be understood from the description of the forming belt 60 described in FIG. 25, and with reference to FIG. 26, the nonwoven substrate 11 made on belt 60 can be described as a nonwoven substrate 11 having a plurality of portions described herein as nonwoven fabrics 10 ordered in at least one sequential relationship with respect to the longitudinal direction, i.e., the machine direction when made on forming belt 60. FIG. 26 is a schematic representation of a spunbond nonwoven substrate 11 showing the sequentially ordered fabrics 10, each fabric 10 having a different pattern within the various zones. Each fabric 10 can have an overall area OA defined, in a rectangular-shaped pattern, by a length L and width W. Each sequentially disposed fabric 10 can have within its overall area OA at least a first zone 110, having a first pattern of three-dimensional features and first average intensive properties, and a first area located within the overall area OA; a second zone 120, having a second pattern of three-dimensional features and second average intensive properties, having a second area located within the overall area OA. Optionally, more zones, e.g., a third zone 130, having third pattern of three-dimensional features and third average intensive property and having a third area within the overall area OA can be present. As shown in the exemplary schematic representation of FIG. 26, the first pattern 110A of fabric 10A can be different from the first pattern 110B of fabric 10B, and can be different from first pattern 110C of fabric 10C. The same can be true for second zones 120A, 120B, and 120C.

In general, the sequentially ordered nonwoven fabrics 10 of the nonwoven material 11 made on forming belt 60 can vary in their respective overall areas, intensive properties, and visual appearances. A common intensive property is an intensive property possessed by more than one zone (with respect to zonal patterns, such as that shown in FIG. 24) or region (for three-dimensional features such as the regular repeating patterns, such as that shown in FIG. 4). Such intensive properties of the nonwoven fabrics 10 can be average values, and can include, without limitation, density, volumetric density, basis weight, thickness, and opacity. For example, if a density is a common intensive property of two differential zones or regions, a value of the density in one zone or region can differ from a value of the density in the other zone or region. Zones (such as, for example, a first zone and a second zone) can be identifiable areas distinguishable from one another visually and by distinct intensive properties averaged within the zone.

Figure 30:
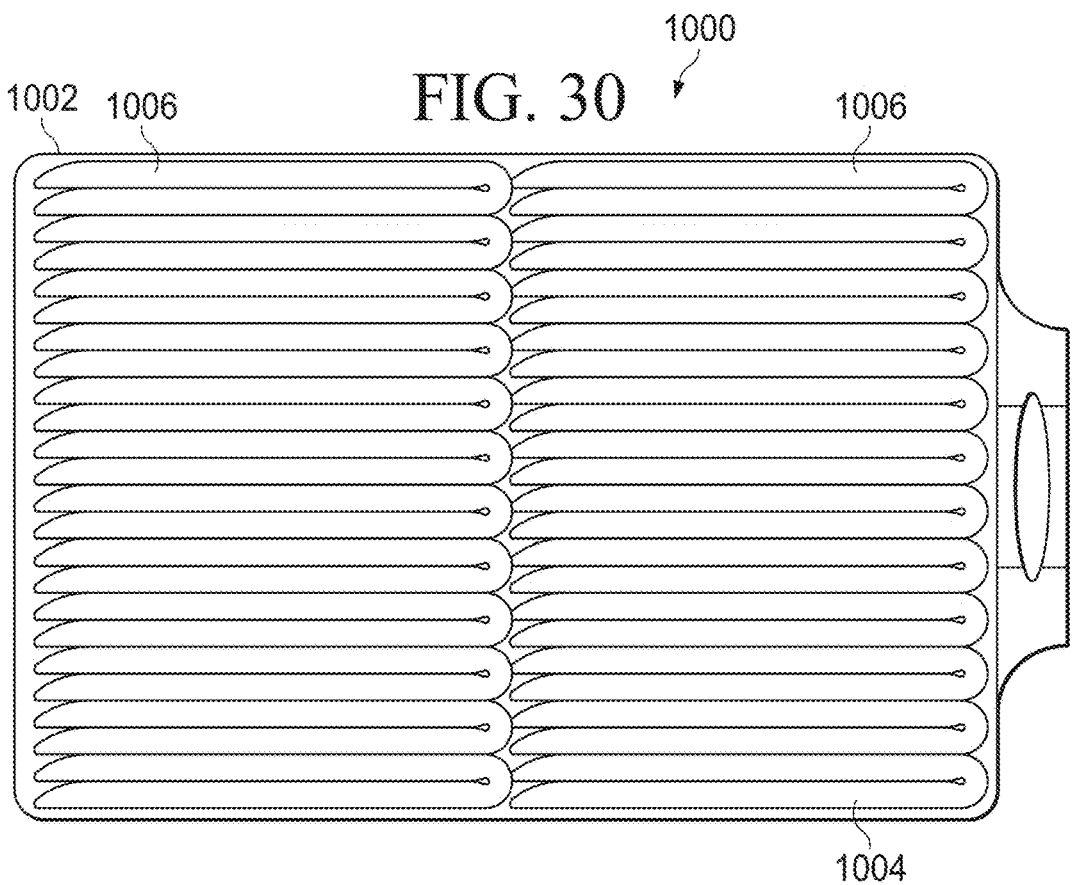
FIG. 30 is a schematic view of a package comprising absorbent articles comprising the three-dimensional, variable basis weight, nonwoven fabric of the present disclosure.

Once produced, the individual nonwoven fabrics 10 can be cut to size and utilized for their intended purposes, such as for topsheets in disposable absorbent articles. For example, a disposable diaper 1006 in a flattened orientation is shown in FIG. 30. One nonwoven fabric 10 is cut to the appropriate overall area and adhered into the diaper 1006 by means known in the art. Nonwoven fabrics 10 can be cut prior to being assembled into a diaper 1006, or during the diaper making process the nonwoven substrate 11 can be brought together with other diaper components in web form, and cut to size after assembly.

Figure 27:
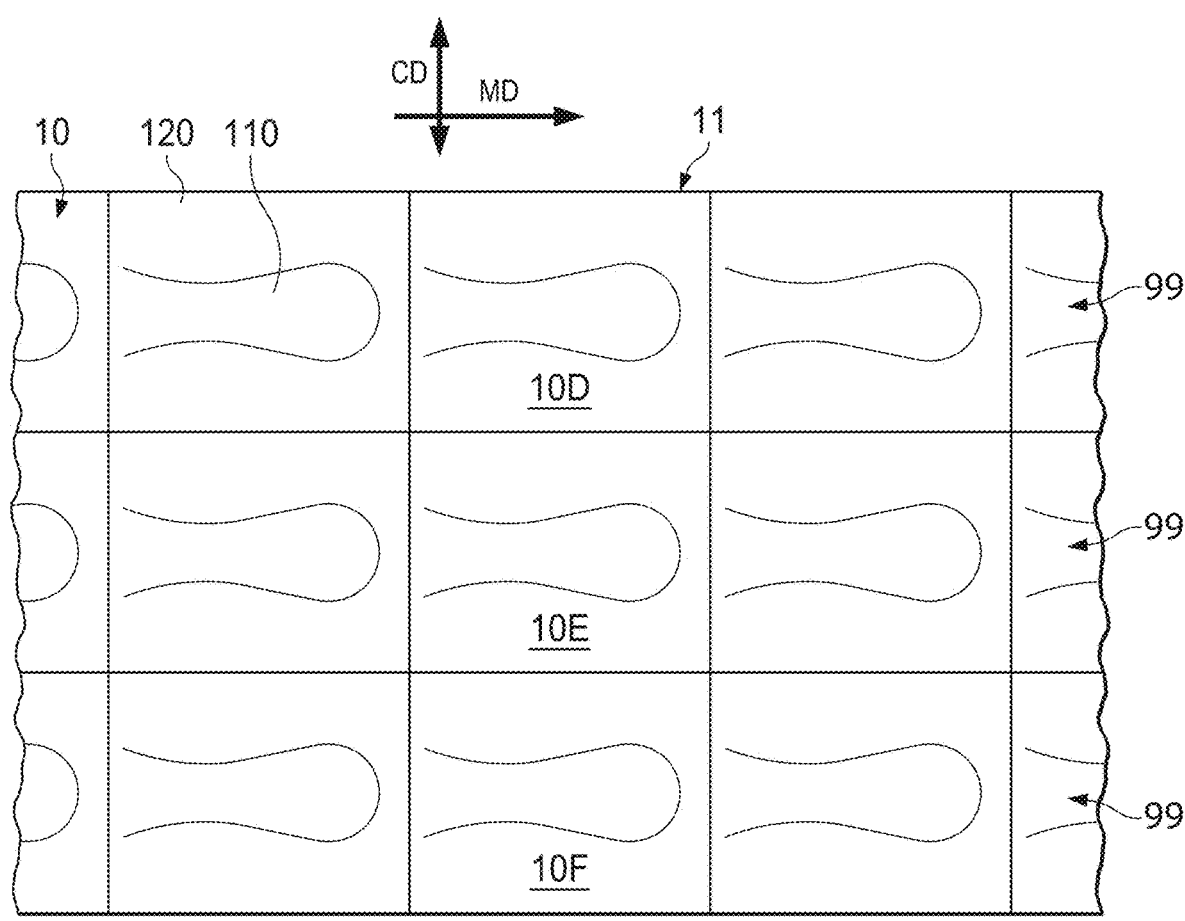
FIG. 27 is a plan view of a nonwoven substrate including nonwoven fabrics of the present disclosure.

As can be understood with reference to FIG. 27, the nonwoven substrate 11 made on forming belt 60 can be described as a nonwoven fabric 11 having a plurality of portions described herein as nonwoven fabrics 10 ordered in at least one sequential relationship with respect to the longitudinal direction, i.e., the machine direction when made on forming belt 60, in at least one side-by-side relationship, i.e., in the cross machine direction when made on forming belt 60. FIG. 27 is a schematic representation of a spunbond nonwoven substrate 11 showing the sequentially ordered nonwoven fabrics 10 in adjacent machine direction lanes 99, adjacent lanes having the side-by each nonwoven fabrics 10, called out in FIG. 27 as 10D, 10E, and 10F. Each nonwoven fabric 10 can have an overall area OA defined, in a rectangular-shaped pattern, by a length L and width W. Each sequentially disposed nonwoven fabric 10 can have within its overall area OA at least a first zone 110, having a first pattern of three-dimensional features and first average intensive properties, and a first area located within the overall area OA; a second zone 120, having a second pattern of three-dimensional features and second average intensive properties, having a second area located within the overall area OA. Optionally, more zones, e.g., a third zone 130, having third pattern of three-dimensional features and third average intensive property and having a third area within the overall area OA can be present. Each nonwoven fabric 10 in side-by-side lanes can be substantially identical, or they can be different with respect to size, visual appearance, and/or intensive properties. Once produced, the nonwoven substrate 11 can be reeled for slitting into lanes for processing into consumer products, or slit and then reeled.

By way of representative sample to compare basis weight differentials in a nonwoven fabric 10 made with a regular, repeating, uniform pattern and a nonwoven fabric 10 made with a non-uniform, zonal pattern, the nonwoven fabric 10 of Example 1 was compared with a fabric having a pattern similar to that shown in FIG. 24, and referred to as Example 3. Example 3 is a bicomponent spunbond nonwoven web produced on the apparatus disclosed herein by spinning 50:50 ratio of polyethylene sheath (Aspun-6850-A obtained from Dow chemical company) and polypropylene core (PH-835 obtained from LyondellBasell) in a trilobal fiber configuration. The spunbond, bicomponent, trilobal fibers were laid down on a forming belt 60 moving at a linear speed of about 25 meters per minute to an average basis weight of 30 grams per square meter on a forming belt with a zonal pattern as shown in FIG. 22. The second substrate was formed under identical conditions, but had at least one section having a regular, repeating, uniform pattern on a forming belt as shown in FIG. 19, from which basis weight was determined. Fiber spinning conditions, through-put, forming belt line speed and compaction roll bonding temperature were identical for both substrates.

Example 3

A bicomponent spunbond nonwoven fabric that was produced by spinning a 50:50 ratio of polyethylene sheath (Aspun-6850-A obtained from Dow chemical company) and polypropylene core (PH-835 obtained from LyondellBasell) in a trilobal fiber configuration to an average basis weight of 30 grams per square meter. A nonwoven fabric was produced as described with respect to FIGS. 10 and 11 moving at a forming belt linear speed of about 25 meters per minute to form a fabric having zonal pattern as shown in FIG. 23. Fibers of the fabric were further bonded on the first surface 12 by heated compaction rolls 70, 72 at 130° C., and the fabric was wound on to a reel at winder 75.

Example 4

A bicomponent spunbond nonwoven fabric that was produced by spinning a 50:50 ratio of polyethylene sheath (Aspun-6850-A obtained from Dow chemical company) and polypropylene core (PH-835 obtained from LyondellBasell) in a trilobal fiber configuration to an average basis weight of 30 grams per square meter. A nonwoven fabric was produced as described with respect to FIGS. 10 and 11 moving at a forming belt linear speed of about 25 meters per minute to form a fabric having repeating (non-zonal) pattern as shown in FIG. 5. Fibers of the fabric were further bonded on the first surface 12 by heated compaction rolls 70, 72 at 130° C., and being wound on to a reel at winder 75.

Figure 28A:
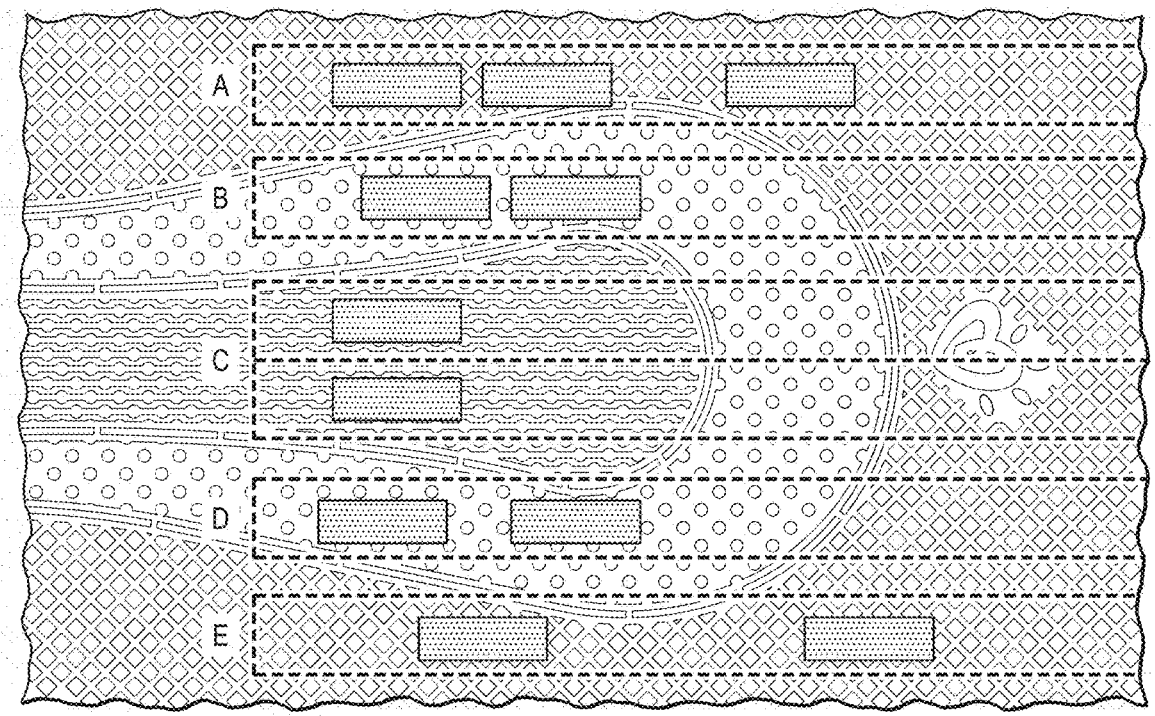
FIG. 28A is a plan view of a fabric of the present disclosure with portions removed for measurement of local basis weight.
Figure 28B:
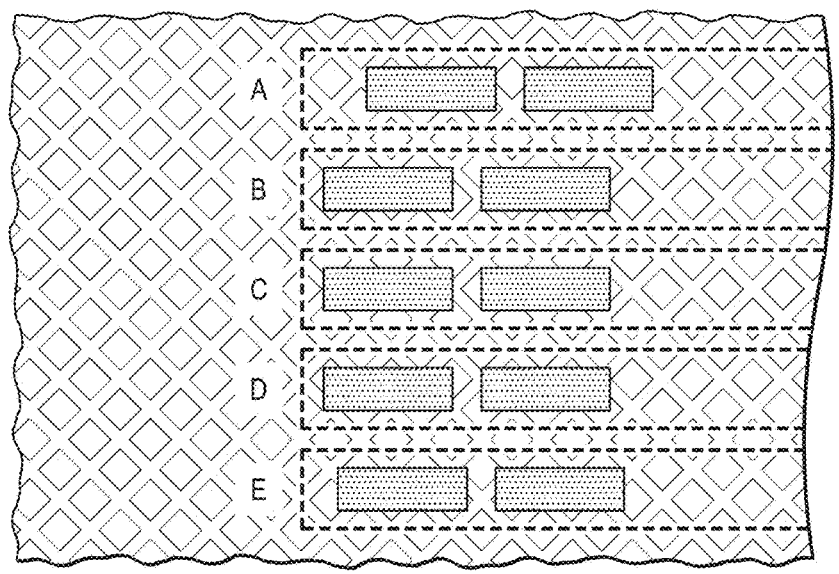
FIG. 28B is a plan view of a fabric of the present disclosure with portions removed for measurement of local basis weight.

Table 2 below shows average local basis weight, measured according to the Localized Basis Weight test method herein, and averaged over 10 samples. The samples for measurement were taken from the fabrics as shown in FIGS. 28A and 28B, in which the dark rectangles are where a 3 cm² sample was removed for measurement. As can be seen, the fabrics are labeled across the cross-direction (CD) as A-E. The measurements shown not only a significant difference in basis weight between zones of the zonal fabric, but a CD distribution which is depicted graphically in FIG. 29.

TABLE 2

Measured Average Basis Weight distribution in nonwoven fabric 10 in grams per square meter (gsm)

Figure 29:
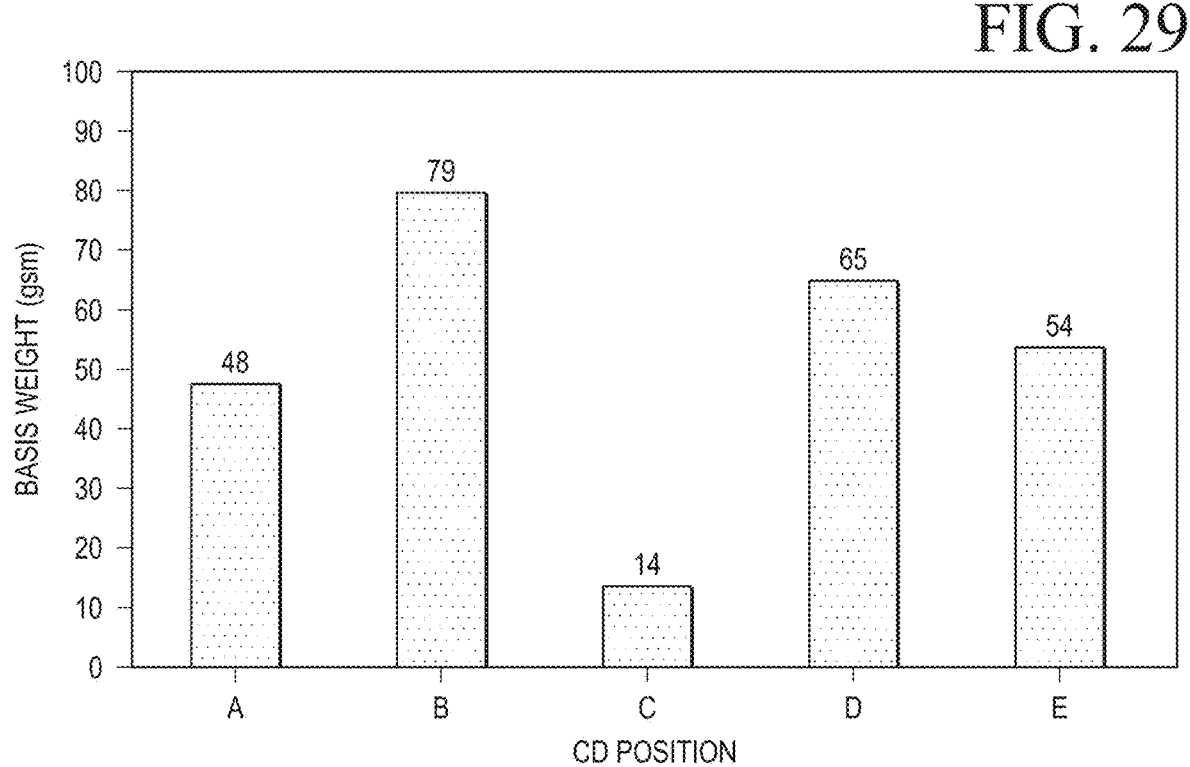
FIG. 29 is a graphical representation of cross-directional variation in basis weight in a fabric of the present disclosure.

| Region as Depicted in FIG. 29 | Example 3: Zonal Fabric Basis Weights | Example 4: Non-zonal Fabric Basis weights |
| --- | --- | --- |
| A | 48 gsm | 43 gsm |
| B | 79 gsm | 37 gsm |
| C | 14 gsm | 32 gsm |
| D | 65 gsm | 36 gsm |
| E | 54 gsm | 36 gsm |

As can be seen in Table 2, nonwoven fabrics 10 made on forming belts 60 having zones of differing air permeability demonstrate substantial variation in fiber laydown and thus basis weights within the CD of nonwoven fabric 10 suggesting the ability for fibers to travel with air into high permeability zones. The non-zonal, regular repeating pattern nonwoven fabric 10 exhibits approximately the same basis weights within the CD of fabric.

In addition to differences in air permeability of the various zones of the forming belt 60, the structure of forming belt 60 can affect other intensive properties of zones in the fabric 10, such as average caliper, average softness, average compression resistance, and fluid absorption properties.

Another aspect of the present disclosure relates to spunbond commercial lines where multiple beams are utilized for improved laydown opacity and uniformity of the fabric. In some cases, there the apparatus can comprise triple spunbond beams (known in the art as "SSS") and may be combined with meltblown (M), for example, in an apparatus known as an "SSMMS" spunbond line.

By calendaring the nonwoven fabric 10 to have point bonds 90, fuzzing can be reduced. Fuzzing refers to the tendency of fibers to become loose and removed from the fabric 10. Loosening and removal can be because of frictional engagement with manufacturing equipment during production of disposable absorbent articles, or another surface, such as the skin of a person interacting with the nonwoven fabric 10. In some uses, such as for topsheets in disposable absorbent articles, fuzzing is a negative consumer phenomenon. But bonding fibers in place can also be a consumer negative as it can produce roughness on the surface of an otherwise soft nonwoven substrate. We have found expectedly the nonwoven fabrics substrates and nonwoven fabrics of the present disclosure can endure an increase in bonding (and a consequent decrease in fuzzing) with minimal loss in softness. Bonding can be accomplished by relatively closely spaced point bonds 90, with the spacing being determined by the desired level of fuzzing reduction. Bonding can also be achieved by known methods for chemically or thermally bonding nonwoven fibers, such as thermal bonding, ultrasonic bonding, pressure bonding, latex adhesive bonding, and combinations of such methods. Fuzz reduction by bonding is illustrated with respect to Examples 5 and 6 below.

Example 5

Figure 57:
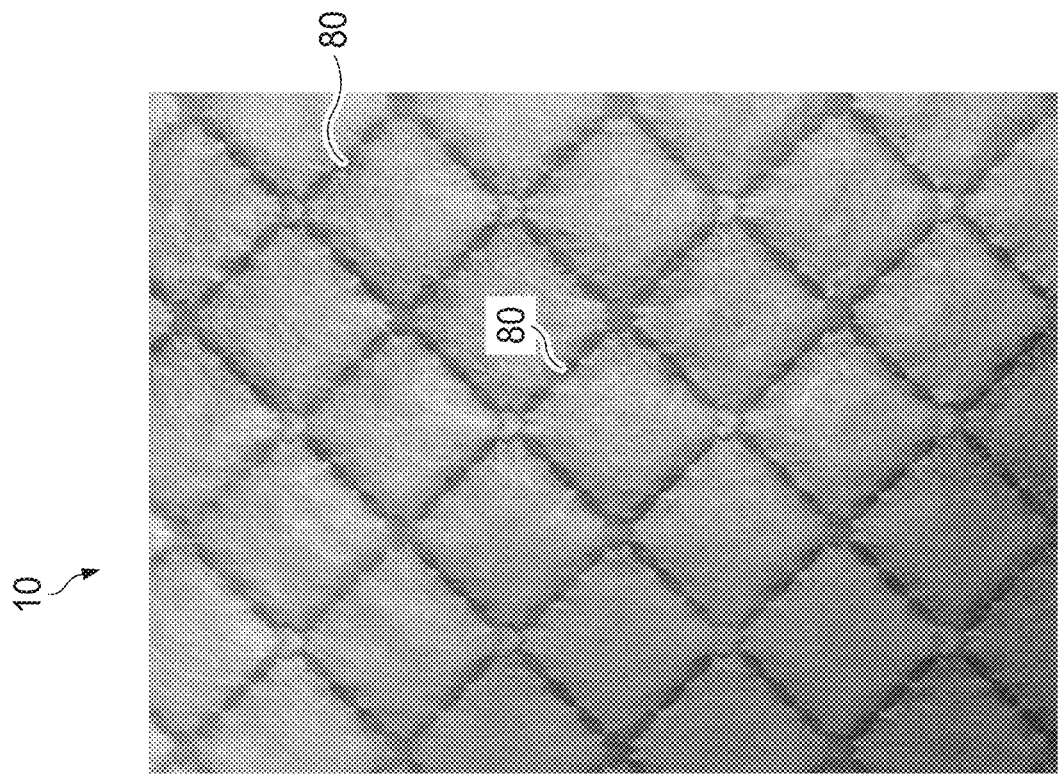
FIG. 57 is a photographic image of an example of a nonwoven fabric of the present disclosure.

A bicomponent spunbond nonwoven fabric was produced by spinning a 50:50 ratio of polyethylene sheath (Aspun- 6850-A obtained from Dow chemical company) and polypropylene core (PH-835 obtained from LyondellBasell) in a trilobal fiber configuration to an average basis weight of about 30 grams per square meter on a forming belt as described with respect to FIGS. 10 and 11 moving at a linear speed of about 25 meters per minute to form a fabric having the repeating pattern as shown in FIG. 57. Fibers of the fabric were further bonded on the first surface 12 by compaction rolls 70, 72 with compaction roll 70 heated to 130° C. to form substantially continuous bonds 80.

Example 6

Figure 58:
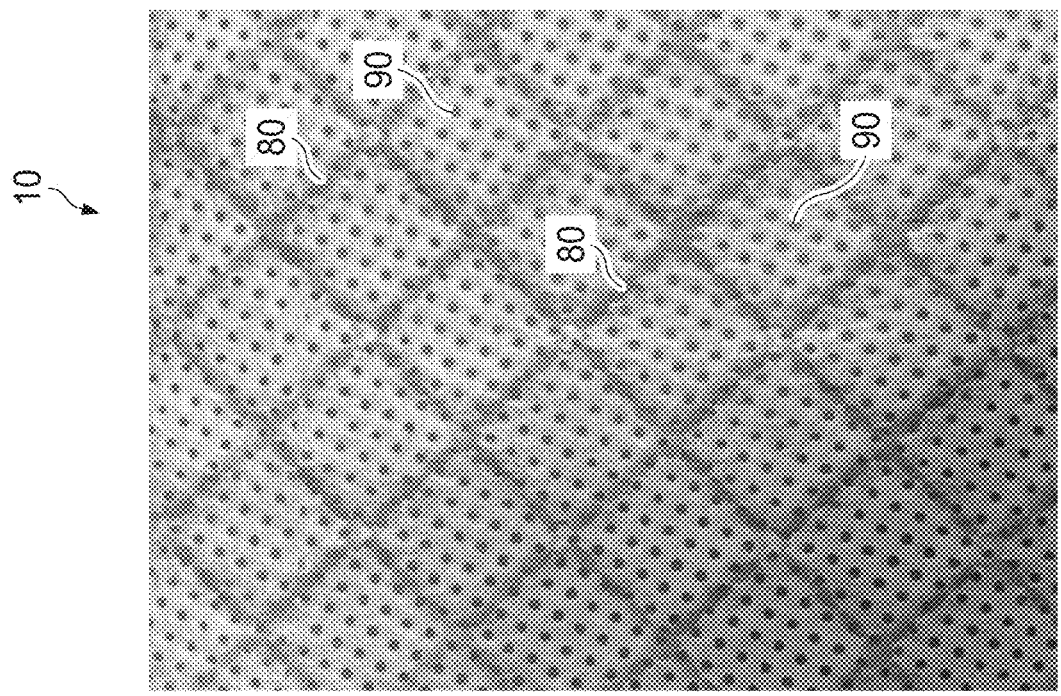
FIG. 58 is a photographic image of an example of a nonwoven fabric of the present disclosure.

A bicomponent spunbond nonwoven fabric was produced by spinning a 50:50 ratio of polyethylene sheath (Aspun-6850-A obtained from Dow chemical company) and polypropylene core (PH-835 obtained from LyondellBasell) in a trilobal fiber configuration to an average basis weight of about 30 grams per square meter on a forming belt as described with respect to FIGS. 10 and 11 moving at a linear speed of about 25 meters per minute to form a fabric having the repeating pattern described with respect to FIG. 58. Fibers of the fabric were further bonded on the first surface 12 by compaction rolls 70, 72 with compaction roll 70 heated to 130° C. to form substantially continuous bonds 80. Fibers of the fabric were further calendar bonded at calendar rolls 71, 73, with roll 73 being an engraved roll having raised portions 88 in the form of pins with 1.25 mm pin height and 0.62 mm open gap in a 10% point bonding pattern. The roll 73 was heated to 135° C. to form point bonds 90 on the second side 14 of the nonwoven fabric 10, as shown in FIG. 14.

The nonwoven fabrics 10 of Examples 5 and 6 differed only in the absence or presence of point bonds 90. The second side 14 of the nonwoven fabrics 10 underwent fuzz testing according to the Fuzz Level Test to determine the effectiveness of the point bonds in securing fibers to the surface of the fabric. The results of fuzz testing of Examples 5 and 6 are shown in Table 3.

TABLE 3

| | MD Fuzz Results |
|---|---|
| Sample No. | MD Fuzz Value (mg/cm$^2$) |
| Example 5 | 0.36 |
| Example 6 | 0.19 |

As shown above, the point bonds 90 result in a dramatic decrease in the MD Fuzz Value. It unexpectedly retained its softness, absorbency, and aesthetic benefits in spite of the bonding treatment and now also has the desired resistance to fuzz upon consumer use. Present disclosure absorbent articles are generally placed into packages for shipping, storing, and selling. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages. FIG. 30 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

Packages of the absorbent articles of the present disclosure may have an In-Bag Stack Height of less than about 100 mm, less than about 95 mm, less than about 90 mm, less than about 85 mm, less than about 85 mm, but greater than about 75 mm, less than about 80 mm, less than about 78 mm, less than about 76 mm, or less than about 74 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 100 mm, from about 70 mm to about 95 mm, from about 72 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Apertured Nonwoven Fabrics

Any suitable process for aperturing the nonwoven fabrics described herein may be utilized. For example, the variable basis weight, apertured, three-dimensional shaped nonwoven fabrics of the present disclosure may be made generally by using the process generally described in U.S. Pat. Nos. 5,628,097; 5,658,639; 5,916,661; 6,632,504 6,884,494; and 7,037,569 and U.S. Patent Publication 2003/0021951 entitled "High Elongation Apertured Nonwoven Web and Method of Making" which published Jan. 20, 2003.

Figure 31:
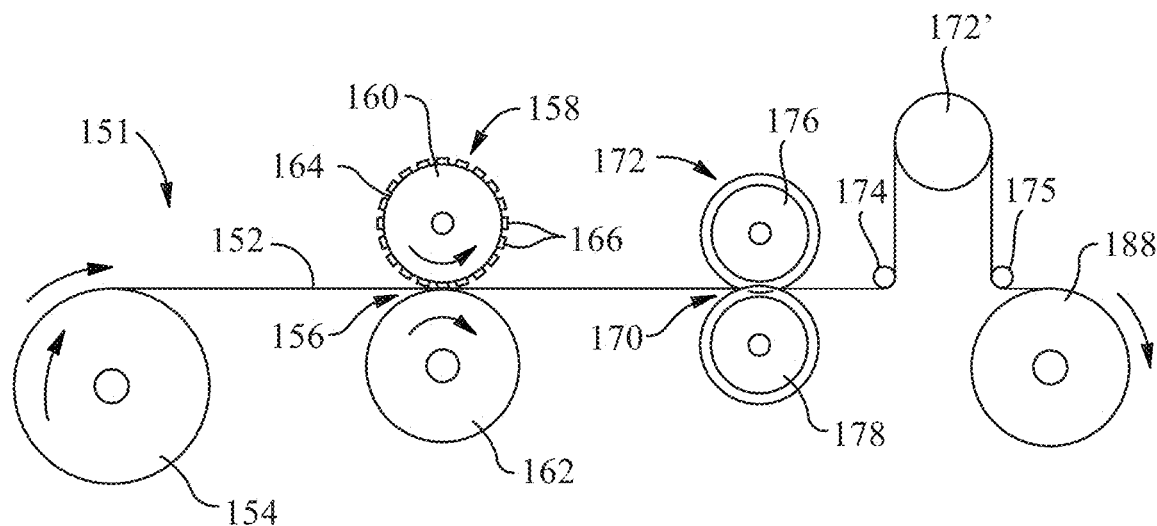
FIG. 31 is a schematic representation of an example method for producing an apertured nonwoven fabric of the present disclosure.

Referring to FIG. 31, for example, there is schematically illustrated at 151 one process for forming the variable basis weight, apertured, three-dimensional shaped nonwoven fabrics of the present disclosure. First, a precursor material 152 (e.g., the nonwoven fabric described herein) can be supplied as a starting material. The precursor material 152 can be supplied as discrete webs, e.g. sheets, patches, etc. of material for batch processing. For commercial processing, however, the precursor material 152 may be supplied as roll stock, and, as such it can be considered as having a finite width and an infinite length. In this context, the length can be measured in the machine direction (MD). Likewise, the width can be measured in the cross machine direction (CD).

The precursor material 152 may comprise the materials for the variable basis weight, three-dimensional shaped nonwoven fabrics described herein. The precursor material 152 may be a variable basis weight, three-dimensional shaped nonwoven fabric as one or more layers combined with one or more conventional nonwoven materials and/or films. The precursor material 152 may be purchased from a supplier and shipped to where the variable basis weight, three-dimensional shaped nonwoven fabrics are being formed or the precursor material 152 may be formed at the same location as where the variable basis weight, three-dimensional shaped nonwoven fabrics are being produced.

The precursor material 152 may be extensible, elastic, or nonelastic. Further, the precursor material 152 may be a single layer material or a multilayer material. In an instance, the precursor material 152 may be joined to a polymeric film or conventional nonwoven material to form a laminate.

The precursor material 152 may comprise or be made of mono-component, bicomponent, multi-constituent blends, or multi-component fibers comprising one or more thermoplastic polymers. In an example, the bicomponent fibers of the present disclosure may be formed of a polypropylene core and a polyethylene sheath. Further details regarding bicomponent or multi-component fibers and methods of making the same may be found in U.S. Patent Application Publ. No. 2009/0104831, published on Apr. 23, 2009, U.S. Pat. No. 8,226,625, issued on Jul. 24, 2012, U.S. Pat. No. 8,231,595, issued on Jul. 31, 2012, U.S. Pat. No. 8,388,594, issued on Mar. 5, 2013, and U.S. Pat. No. 8,226,626, issued on Jul. 24, 2012. The various fibers may be sheath/core, side-by-side, islands in the sea, or other known configurations of fibers. The fibers may be round, hollow, or shaped, such as trilobal, ribbon, capillary channel fibers (e.g., 4DG). The fibers may comprise microfibers or nanofibers.

In the example shown in FIG. 31, the precursor material 152 is shown to be unwound from a supply roll 154 and travel in a direction indicated by the arrow associated therewith as the supply roll 154 rotates in the direction indicated by the arrow associated therewith. The precursor material 152 passes through a nip 156 of a weakening roller (or overbonding) arrangement 158 formed by rollers 160 and 162, thereby forming a weakened precursor material. The weakened precursor material 152 has a pattern of overbonds, or densified and weakened areas, after passing through the nip 156. At least some of, or all of, these overbonds are used to form apertures in the precursor material 152. Therefore, the overbonds can correlate generally to patterns of apertures created in the precursor material 152.

Figure 32:
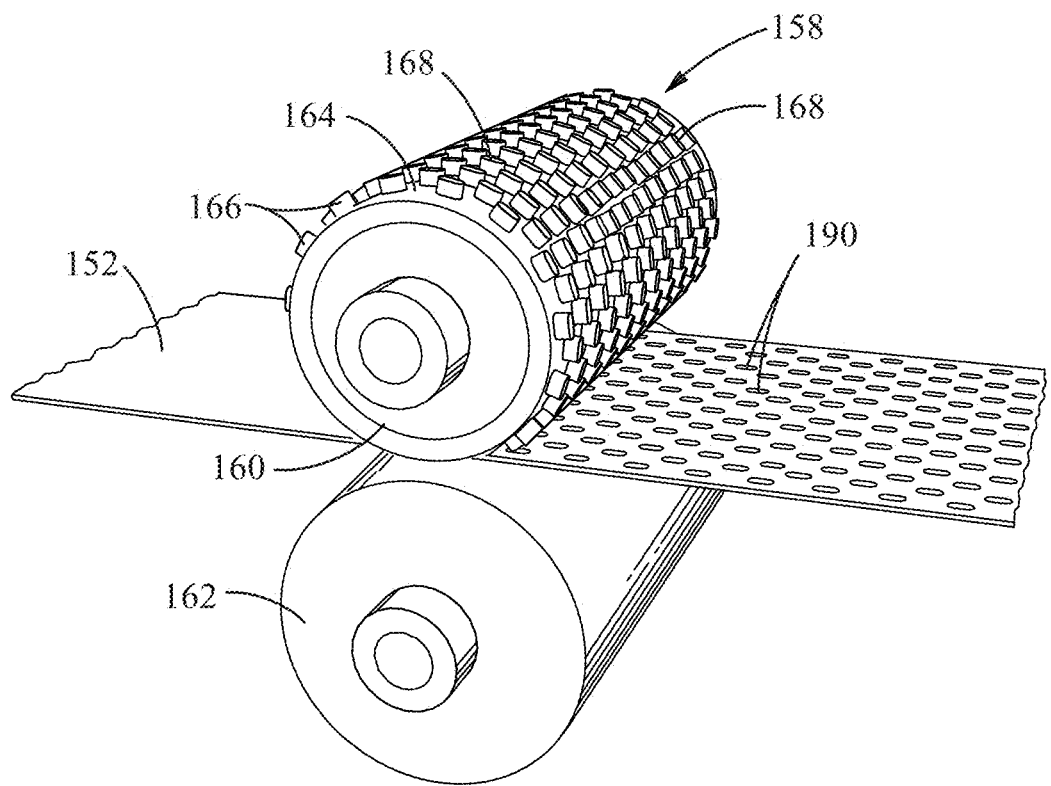
FIG. 32 is a perspective view of a web weakening arrangement of FIG. 31 of the present disclosure.

Referring to FIG. 32, the precursor material weakening roller arrangement 158 may comprises a patterned calendar roller 160 and a smooth anvil roller 162. One or both of the patterned calendar roller 160 and the smooth anvil roller 162 may be heated and the pressure between the two rollers may be adjusted by known techniques to provide the desired temperature, if any, and pressure to concurrently weaken and melt-stabilize (i.e., overbond) the precursor material 152 at a plurality of locations 190. The temperature of the calendar roller 160 (or portions thereof) and/or the smooth anvil roller 162 (or portions thereof) may be ambient temperature or may be in a range of about 100° C. to about 300° C., about 100° C. to about 250° C., about 100° C. to about 200° C., or about 100° C. to about 150° C., specifically reciting all 0.5° C. increments within the specified ranges and all ranges formed therein or thereby. The pressure between the calendar roller 160 and the smooth anvil roller 162 may be in a range of about 2,000 pli (pounds per linear inch) to about 10,000 pli, about 3,000 pli to about 8,000 pli, or about 4,500 pli to about 6,500 pli, specifically reciting all 0.1 pli increments within the specified ranges and all ranges formed therein or thereby. As will be discussed in further detail below, after the precursor material 152 passes through the weakening roller arrangement 158, the precursor material 152 may be stretched in the CD, or generally in the CD, by a cross directional tensioning force to at least partially, or fully, rupture the plurality of weakened, melt stabilized locations 190, thereby creating a plurality of at least partially formed apertures in the precursor material 152 coincident with the plurality of weakened, melt stabilized locations 190.

The patterned calendar roller 160 can be configured to have a cylindrical surface 164 and a plurality of protuberances or pattern elements 166, which can extend outwardly from the cylindrical surface 164. The pattern elements 166 are illustrated as a simplified example of a patterned calendar roller 160, but more detailed patterned calendar rollers that can be used to produce three-dimensional shaped nonwoven fabrics of the present disclosure will be illustrated in subsequent figures. The protuberances 166 may be disposed in a predetermined pattern with each of the protuberances 166 being configured and disposed to precipitate a weakened, melt-stabilized location in the precursor material 152 to affect a predetermined pattern of weakened, melt-stabilized locations 190 in the precursor material 152. The protuberances 166 may have a one-to-one correspondence to the pattern of melt stabilized locations in the precursor material 152. As shown in FIG. 32, the patterned calendar roller 160 may comprise a repeating pattern of the protuberances 166 which can extend about the entire circumference of surface 164. Alternatively, the protuberances 166 may extend around a portion, or portions of the circumference of the surface 164. Also, a single patterned calendar roller may comprise a plurality of patterns in various zones (i.e., first zone, first pattern, second zone, second pattern). The protuberances 166 may have a cross-directional width in the range of about 0.1 mm to about 10 mm, about 0.1 mm to about 5 mm, about 0.1 mm to about 3 mm, about 0.15 mm to about 2 mm, about 0.15 mm to about 1.5 mm, about 0.1 mm to about 1 mm, about 0.1 mm to about 0.5 mm, or about 0.2 mm to about 0.5 mm, specifically reciting all 0.05 mm increments within the specified ranges and all ranges formed therein or thereby. The protuberances 166 may have an aspect ratio in the range of about 10:1, about 9:1, about 8:1, about 7:1, about 6:1, about 5:1, about 4:1, about 3:1, about 2:1, about 1.5:1, or about 1.1:1, for example. Other aspect ratios of the protuberances 166 are also within the scope of the present disclosure. The protuberances 166, in some forms, may be angled, relative to the machine direction on either side, in the range of about 60 degrees to about 1 degree, about 50 degrees to about 2 degrees, about 45 degrees to about 2 degrees, about 45 degrees to about 5 degrees, about 40 degrees to about 5 degrees, or about 35 degrees to about 5 degrees, specifically reciting all 0.1 degree increments within the specified ranges and all ranges formed therein or thereby. Spacing between adjacent protuberances 166 in any direction may be greater than about 0.5 mm, greater than about 0.6 mm, greater than about 0.7 mm, greater than about 0.8 mm, greater than about 0.9 mm, greater than about 1 mm, greater than about 1.1 mm, greater than about 1.2 mm, greater than about 1.3 mm, greater than about 1.4 mm, greater than about 1.5 mm, greater than about 2 mm, greater than about 3 mm, or may be in the range of about 0.7 mm to about 20 mm, or about 0.8 mm to about 15 mm, specifically reciting all 0.1 mm increments within the specified ranges and all ranges formed therein or thereby.

The protuberances 166 may extend radially outwardly from surface 164 and can have distal end surfaces 168. The anvil roller 162 may be a smooth surfaced, circular cylinder of steel, rubber or other material. The anvil roller 162 and the patterned calendar roller 160 may be switched in position (i.e., anvil on top) and achieve the same result.

Figure 33:
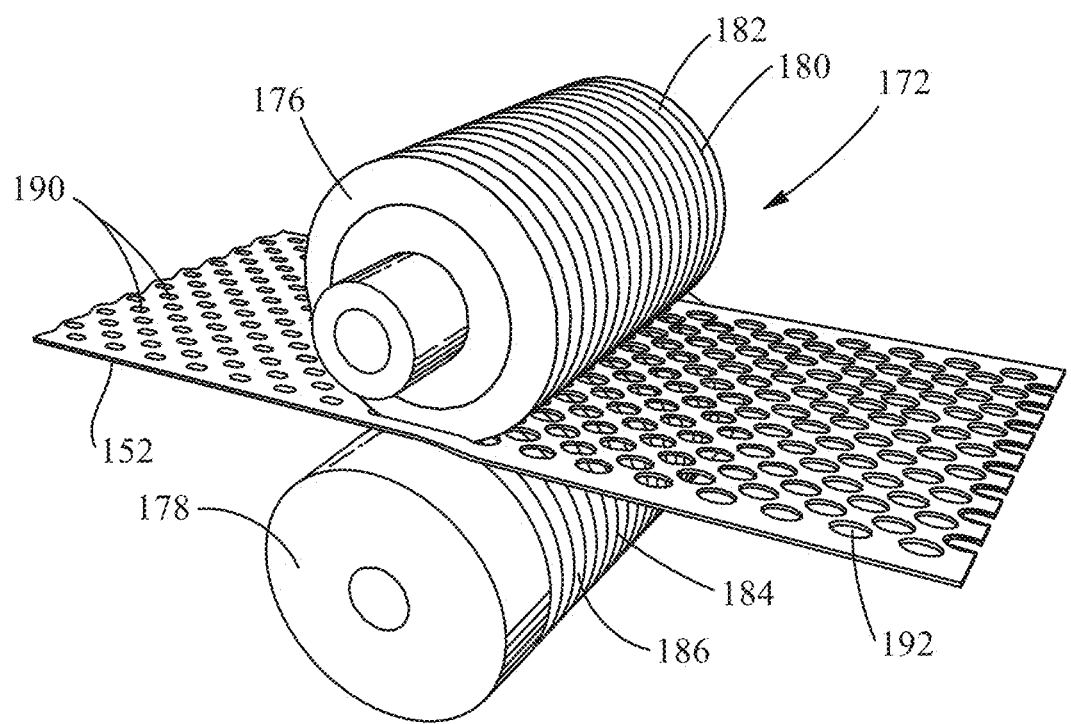
FIG. 33 is a perspective view of an incremental stretching system of the represented example method of FIG. 31 of the present disclosure.

From the weakening roller arrangement 158, the material 152 can pass through a nip 170 formed by an incremental stretching system 172, as shown in FIGS. 31 and 33, employing opposed pressure applicators having three-dimensional surfaces which at least to a degree may be complementary to one another.

Referring now to FIG. 33, there is shown a fragmentary enlarged view of the incremental stretching system 172 comprising two incremental stretching rollers 176 and 178. The incremental stretching roller 176 may comprise a plurality of teeth 180 and corresponding grooves 182 which may about the entire circumference of roller 176. The incremental stretching roller 178 may comprise a plurality of teeth 184 and a plurality of corresponding grooves 186. The teeth 180 on the roller 176 may intermesh with or engage the grooves 186 on the roller 178 while the teeth 184 on the roller 178 may intermesh with or engage the grooves 182 on the roller 176. The spacing and/or pitch of the teeth 184 and/or the grooves 186 may match the pitch and/or spacing of the plurality of weakened, melt stabilized locations 190 in the precursor material 152 or may be smaller or larger. As the precursor material 152 having weakened, melt-stabilized locations 202 passes through the incremental stretching system 172 the precursor material 152 is subjected to tensioning in the CD causing the material 152 to be extended (or activated) in the CD, or generally in the CD. Additionally the material 152 may be tensioned in the MD, or generally in the MD. The CD tensioning force placed on the material 152 is adjusted such that it causes the weakened, melt-stabilized locations 190 to at least partially, or fully rupture thereby creating a plurality of partially formed, or formed apertures 192 coincident with the weakened melt-stabilized locations 190 in the material 152. However, the bonds of the material 152 (in the non-overbonded areas) can be strong enough such that they do not rupture during tensioning, thereby maintaining the material 152 in a coherent condition even as the weakened, melt-stabilized locations rupture. However, it may be desirable to have some of the bonds rupture during tensioning.

Figure 34:
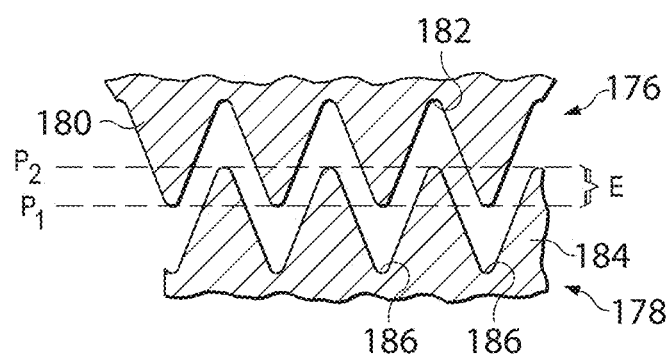
FIG. 34 is an enlarged view showing the details of teeth of the incremental stretching system of FIG. 33 of the present disclosure.

Referring to FIG. 34, a more detailed view of the teeth 180 and 184 and the grooves 182 and 186 on the rollers 176 and 178 is illustrated. The term "pitch" refers to the distance between the apexes of adjacent teeth. The pitch may be between about 0.02 inches to about 0.30 inches (about 0.51 mm to about 7.62 mm) or may be between about 0.05 inches and about 0.15 inches (about 1.27 mm to about 3.81 mm), specifically reciting all 0.001 inch increments within the above-specified ranges and all ranges formed therein or thereby. The height (or depth) of the teeth can be measured from the base of the tooth to the apex of the tooth, and may or may not be equal for all teeth. The height of the teeth may be between about 0.010 inches (about 0.254 mm) and about 0.90 inches (about 22.9 mm) or may be between about 0.025 inches (about 0.635 mm) and about 0.50 inches (about 12.7 mm), specifically reciting all 0.01 inch increments within the above-specified ranges and all ranges formed therein or thereby. The teeth 180 in one roll may be offset by about one-half of the pitch from the teeth 184 in the other roll, such that the teeth of one roll (e.g., teeth 180) mesh in the valley (e.g., groove 186) between teeth in the mating roll. The offset permits intermeshing of the two rolls when the rolls are "engaged" or in an intermeshing, operative position relative to one another. The teeth of the respective rolls may only be partially intermeshing in some instances. The degree to which the teeth on the opposing rolls intermesh is referred to herein as the "depth of engagement" or "DOE" of the teeth. The DOE may be constant or not constant. As shown in FIG. 34, the DOE, indicated as "E", is the distance between a position designated by plane P1 where the apexes of the teeth on the respective rolls are in the same plane (0% engagement) to a position designated by plane P2 where the apexes of the teeth of one roll extend inward beyond the plane P1 toward the groove on the opposing roll. The optimum or effective DOE for particular laminate webs may be dependent upon the height and the pitch of the teeth and/or the structure of the material. Some example DOEs may in the range of about 0.01 inches to about 0.5 inches, about 0.03 inches to about 0.2 inches, about 0.04 inches to about 0.08 inches, about 0.05 inches, or about 0.06 inches, specifically reciting all 0.001 inch increments within the above-specified ranges and all ranges formed therein or thereby.

As the material 152 having the weakened, melt-stabilized locations 190 passes through the incremental web stretching apparatus 172, the material 152 can be subjected to tensioning in the cross machine direction, or substantially in the cross machine direction, thereby causing the nonwoven web 152 to be extended in the cross machine direction. The tensioning force placed on the material 152 may be adjusted by varying the pitch, DOE, or teeth size, such that the incremental stretching is sufficient to cause the weakened, melt-stabilized locations 190 to at least partially, or fully rupture, thereby creating, or at least partially creating, a plurality of apertures 192 coincident with the weakened, melt-stabilized locations 190 in the material 152.

Figure 35:
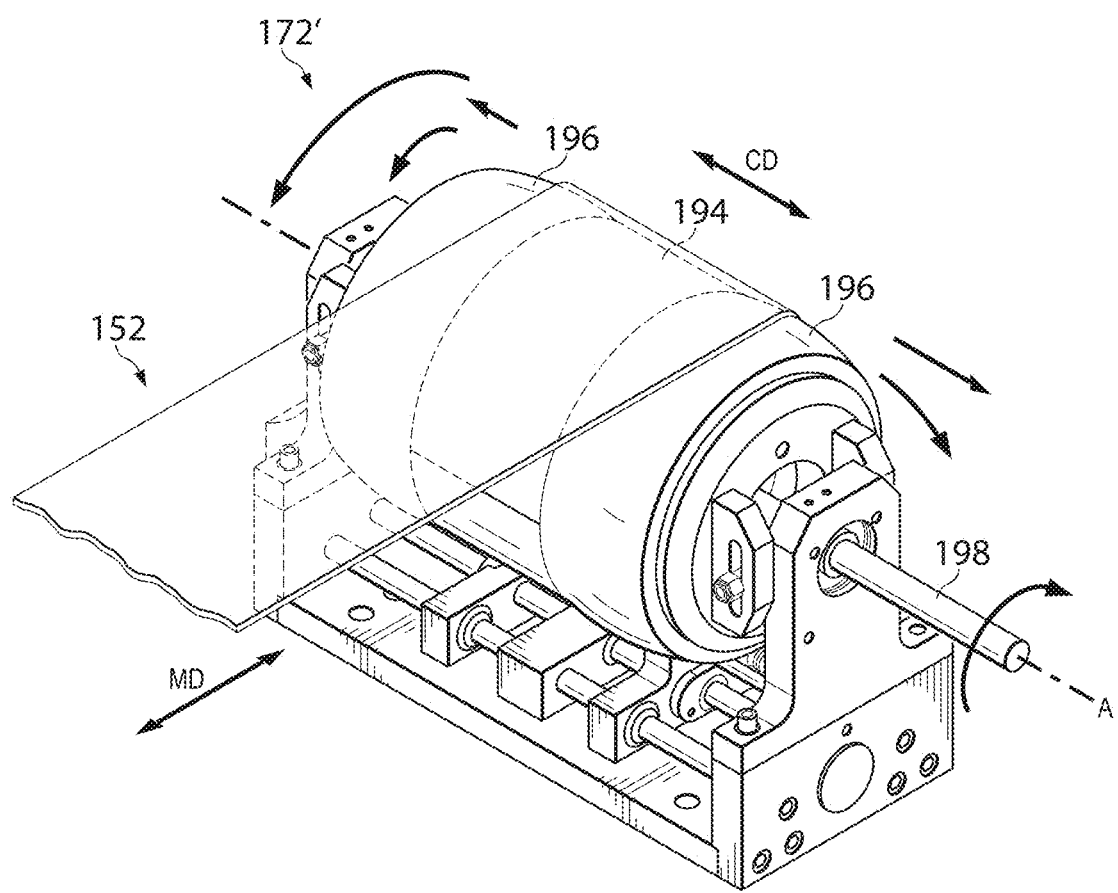
FIG. 35 is a perspective view of an example cross machine directional tensioning apparatus of the representative example method of FIG. 31 of the present disclosure.

After the material 152 passes through the incremental web stretching apparatus 172, the web 152 may be advanced to and at least partially around a cross machine directional tensioning apparatus 172' (see e.g., FIGS. 31 and 35). The cross machine directional tensioning apparatus 172' may be offset from the main processing line by running the web partially around two idlers 174 and 175 or stationary bars, for example. In other instances, the cross machine tensioning apparatus 172' may be positioned in line with the main processing line. The cross machine directional tensioning apparatus 172' may comprise a roll that comprises at least one outer longitudinal portion that expands along a longitudinal axis, A, of the roll, relative to a middle portion of the roll, to stretch and/or expand the material 152 in the cross machine direction. Instead of or in addition to expanding along the longitudinal axis, A, of the roll, the outer longitudinal portion may be angled relative to the longitudinal axis, A, of the roll in a direction away from the material 152 being advanced over the roll to stretch the material 152 in the cross machine direction or generally in the cross machine direction. In an example, a roll may comprise two outer longitudinal portions that each may expand in opposite directions generally along the longitudinal axis, A, of the roll. The two outer portions may both be angled downwards in a direction away from the material 152 being advanced over the roll. This movement or positioning of the outer longitudinal portions of the roll allows for generally cross machine directional tensioning of the material 152, which causes the plurality of weakened locations 190 to rupture and/or be further defined or formed into apertures 192.

The outer longitudinal portions of the roll may comprise vacuum, a low tack adhesive, a high coefficient of friction material or surface, such as rubber, and/or other mechanisms and/or materials to hold the material 152 to the outer lateral portions of the roll during movement of the outer longitudinal portion or portions relative to the middle portion of the roll. The vacuum, low tack adhesive, high coefficient of friction material or surface, and/or other mechanisms and/or materials may prevent, or at least inhibit, the held portions of the material 152 from slipping relative to the longitudinal axis, A, of the roll during stretching of the outer lateral portions of the material in the cross machine direction or generally in the cross machine direction.

FIG. 35 is a top perspective view of the example cross machine directional tensioning apparatus 172'. The cross machine directional tensioning apparatus 172' may comprise a roll comprising a middle portion 194 and two outer longitudinal portions 196 situated on either end of the middle portion 194. The roll may rotate about its longitudinal axis, A, on a drive shaft 198. The roll may rotate relative to the drive shaft 198 or in unison with the drive shaft 198, as will be recognized by those of skill in the art. The material 152 may be advanced over the entire cross machine directional width of the middle portion 194 and at least portions of the cross machine directional widths of the outer longitudinal portions 196. The material 152 may be advanced over at least about 5% up to about 80% of the circumference of the roll so that the cross machine directional stretching may be performed.

Figure 36:
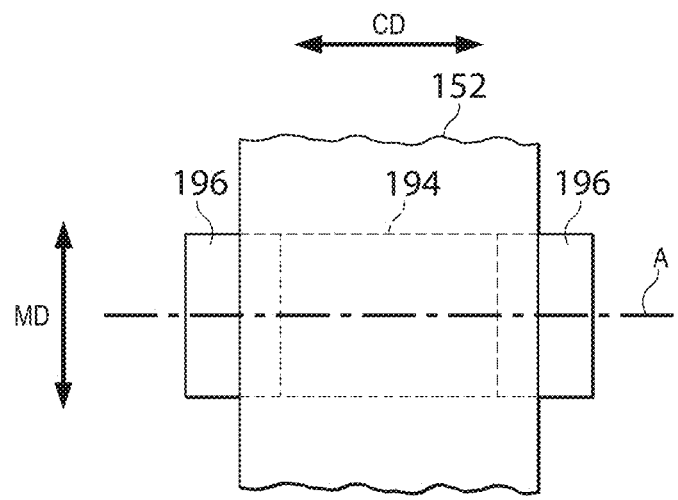
FIG. 36 is a schematic representation of a front view of an example cross machine directional tensioning apparatus with outer longitudinal portions in an unexpanded and non-angled position relative to a middle portion of the present disclosure.
Figure 37:
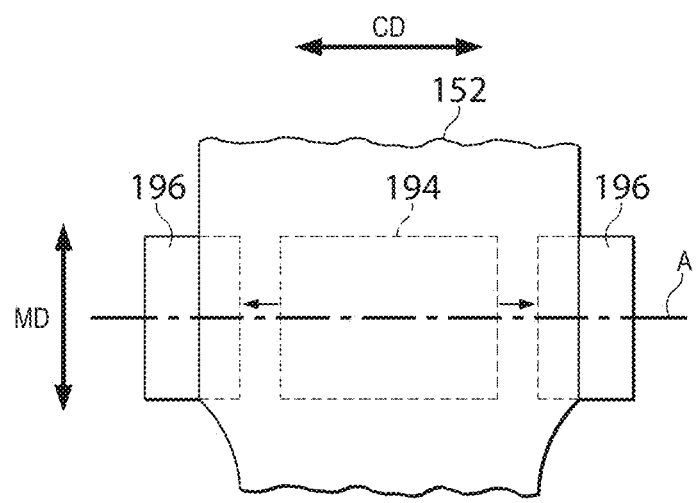
FIG. 37 is a schematic representation of a front view of the cross machine directional tensioning apparatus of FIG. 36 with the outer longitudinal portions in a longitudinally expanded position relative to the middle portion of the present disclosure.
Figure 38:
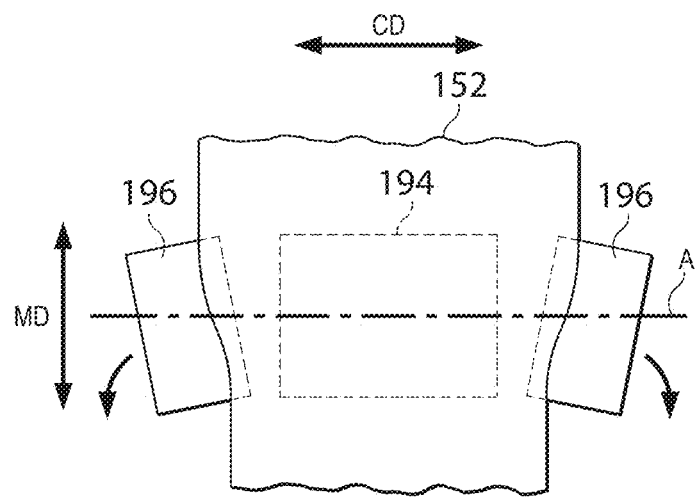
FIG. 38 is a schematic representation of a front view of the cross machine directional tensioning apparatus of FIG. 36 with the outer longitudinal portions in an angled and expanded position relative to the middle portion of the present disclosure.
Figure 39:
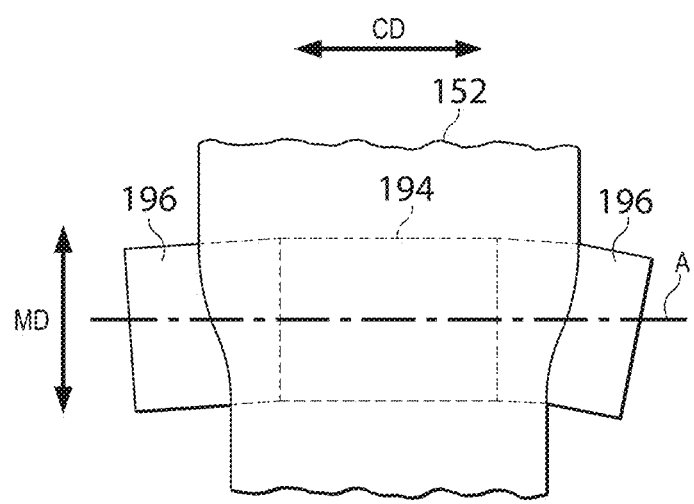
FIG. 39 is a schematic representation of a front view of a cross machine directional tensioning apparatus with outer longitudinal portions fixed in an angled position relative to a middle portion of the present disclosure.

FIG. 36 is a schematic representation of a front view of an example cross machine directional tensioning apparatus with outer longitudinal portions 196 in an unexpanded or non-angled position relative to the middle portion 194. FIG. 37 is a schematic representation of a front view of the cross machine directional tensioning apparatus of FIG. 33 with the outer longitudinal portions 196 in a longitudinally expanded position relative to the middle portion 194. FIG. 38 is a schematic representation of a front view of the cross machine directional tensioning apparatus of FIG. 37 with the outer longitudinal portions 196 in an angled and expanded position relative to the middle portion 194. In regard to FIG. 38, the outer longitudinal portions 196 may merely move or slide in a direction generally perpendicular to the machine direction of the material passing over the roll to apply the cross machine directional tensioning force to the material 152. FIG. 39 is a schematic representation of a front view of a cross machine directional tensioning apparatus with the outer longitudinal portions 196 fixed in an angled position relative to the middle portion 194 to apply the cross machine directional tensioning force to the material 152. In such a form, the middle portion 194 and each of the outer longitudinal portions 196 may comprise a separate roll.

Regardless of whether one or both of the outer longitudinal portions 196 is moved, slid, rotated, fixed, and/or expanded relative to the middle portion 194, this relative motion or positioning between the outer longitudinal portions 196 and the middle portion 194 can stretch the materials 152 in a cross machine direction to further rupture or further define the weakened locations 196 in the material 152 and create, or further form, a plurality the apertures 198 the material 152. The cross machine directional tensioning force applied by the cross machine directional tensioning apparatus 172' may be, for example, 10-25 grams or 15 grams. In an example, the cross machine directional tensioning apparatus may be similar to, or the same as, the incremental stretching apparatus 172 to apply the cross machine directional tensioning force. In other examples, any suitable cross machine directional tensioning apparatus may be used to apply the cross machine directional tensioning force to a material.

If desired, the incremental stretching step or the cross machine directional stretching step described herein may be performed at elevated temperatures. For example, the material 152 and/or the rolls may be heated. Utilizing heat in the stretching step may serve to soften the material, and may aid in extending the fibers without breaking.

Referring again to FIG. 31, the material 152 may be taken up on wind-up roll 188 and stored. Alternatively, the material 152 may be fed directly to a production line where it can be used to form a portion of an absorbent article or other consumer product.

It is important to note that the overbonding step illustrated in FIGS. 31 and 32 could be performed by the material supplier and then the material may be shipped to a consumer product manufacturer to perform step 172. In fact, the overbonding step may be used in the nonwoven production process to form overbonds, which may be in addition to, or in lieu of, primary bonds formed in the nonwoven production process. Alternatively, the material supplier may fully perform the steps illustrated in FIG. 31 and then the material may be shipped to the consumer product manufacturer. The consumer product manufacturer may also perform all of the steps in FIG. 31 after obtaining a nonwoven material from a nonwoven material manufacturer.

One of ordinary skill in the art will recognize that it may be advantageous to submit the material 152 to multiple incremental stretching processes depending on various desired characteristics of the finished product. Both the first and any additional incremental stretching may either be done on-line or off-line. Furthermore, one of ordinary skill will recognize that the incremental stretching may be done either over the entire area of the material or only in certain regions of the material depending on the final desired characteristics.

Figure 40:
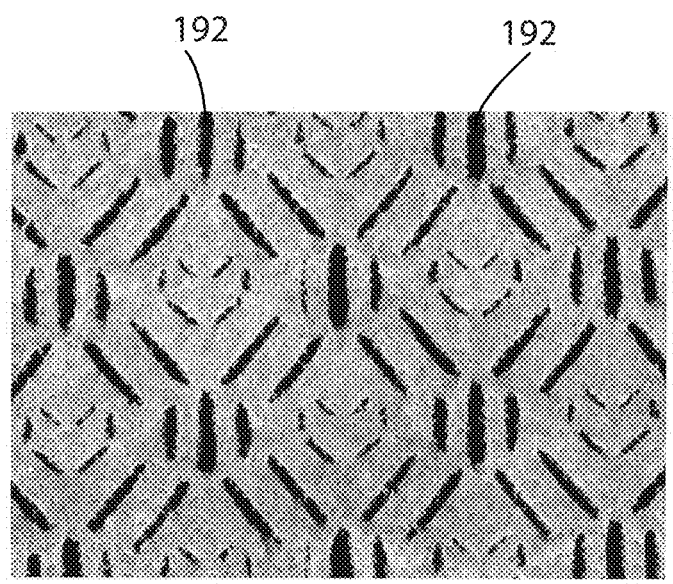
FIG. 40 is a photographic image of an example aperture pattern of the present disclosure.
Figure 41:
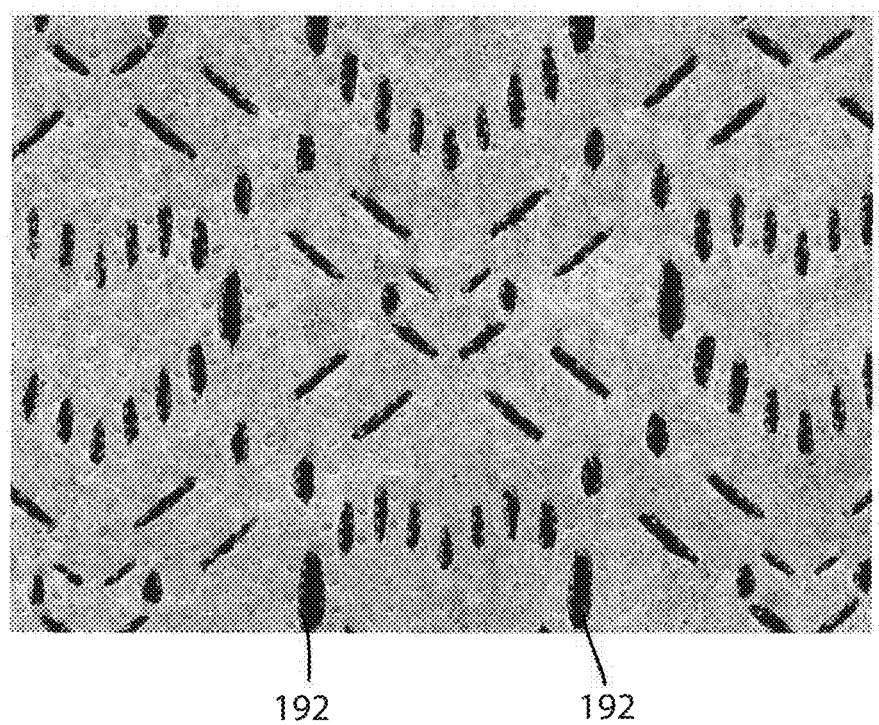
FIG. 41 is a photographic image of an example aperture pattern of the present disclosure.

Examples of aperture patterns are shown in FIGS. 40-45. In FIGS. 40 and 41, apertures 192 are shown to be arranged in various patterns. In the patterns shown in FIGS. 42 and 43, aperture arrays 193 are separated by continuous, interconnected land area patterns 195. In such examples, the land area patterns 195 may function as fluid distribution pathways and the aperture arrays 193 may function as fluid "drains," thereby promoting fluid access to an underlying absorbent material or absorbent core. In certain forms, the aperture arrays 193 may be shaped to enhance the ability of the aperture arrays 193 to manage fluid, such as bodily exudates (i.e., urine, runny BM, menses). In such examples, fluids may travel along land area in a concavity, for example, to a point where the concavity ends. At this location, fluids may enter an aperture in the direction of the fluid path or those on either side of the concavity if the fluid turns in either lateral direction. Example aperture array shapes having a concavity may include heart shapes, star shapes, some polygons, crescents, and chevrons, among other examples. In the patterns shown in FIGS. 44 and 45, apertures, or arrays thereof may form one or more continuous or semi-continuous patterns 197, resulting in discrete "macro" land areas 199. In such examples, the discrete macro land areas 199 may function as fluid deposition regions. Fluids moving from the discrete macro land areas 199 in any direction may be absorbed into the apertures of the continuous or semi-continuous pattern 197. While FIGS. 40-45 do not depict aperture patterns applied to variable basis weight, three-dimensional shaped nonwoven fabrics, it will be appreciated that such patterns, among other patterns and configurations, may be applied to variable basis weight, three-dimensional shaped nonwoven fabrics. Additional aperture patterns and configurations are disclosed in U.S. Pub. No. 2016/0136014.

As described herein, other suitable processes for aperturing the nonwoven fabrics described herein may be utilized. For example, the variable basis weight, apertured, three-dimensional shaped nonwoven fabrics may also be made by hydroforming carded webs, laser cutting, punching with a patterned roll, hot pin methods, or other suitable methods.

Figure 46:
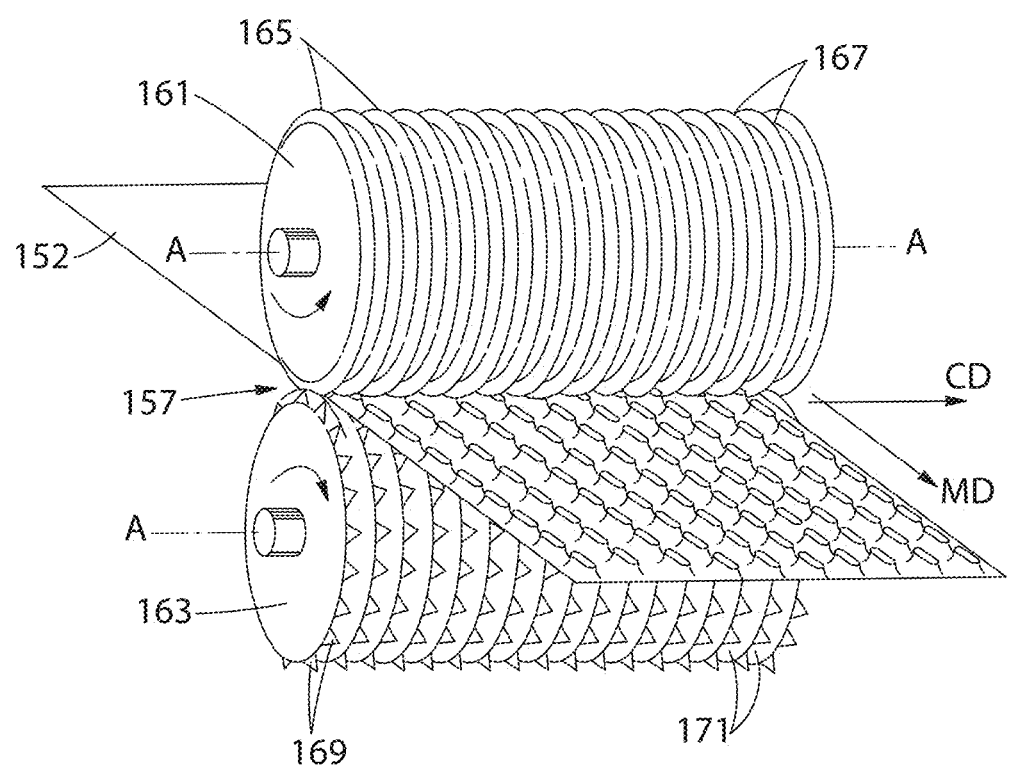
FIG. 46 is a schematic representation of another example method for producing an apertured nonwoven fabric of the present disclosure.

Alternatively, additional aperturing processes are described in U.S. Pat. Nos. 9,023,261 or 8,158,043; 8,241,543; and 8,679,391. For example, instead of the rollers 160 and 162 utilized in the process described herein, a pair of steel intermeshing rollers 161 and 163 may be utilized in an aperturing process, as shown in FIG. 46, and as described in, for example, U.S. Pat. No. 8,679,391. Each of the rollers 161 and 163 may rotate about an axis A, where the axes A may be parallel and in the same plane. A precursor material 152 may be received through nip 157 and exit as an apertured material.

As shown in FIG. 46, roller 161 may comprise a plurality of ridges 165 and corresponding grooves 167 which may extend unbroken about an entire circumference of roll 161. In certain examples, roller 161 may comprise ridges 165 where portions have been removed, such as by etching, milling or other machining processes, such that some or all of ridges 165 are not circumferentially continuous, but have breaks or gaps. The breaks or gaps can be arranged to form a pattern, including simple geometric patterns such as circles or diamonds, but also including complex patterns such as logos and trademarks. In an example, roller 161 may comprise teeth, similar to teeth 169 on roller 163, described below. In this manner, it is possible to have three dimensional apertures having portions extending outwardly on both sides of an apertured material.

Roller 163 may comprise a plurality of rows of circumferentially-extending ridges that have been modified to be rows of circumferentially-spaced teeth 169 that extend in spaced relationship about at least a portion of roller 163. The individual rows of teeth 169 of roller 163 may be separated by corresponding grooves 171. In operation, rollers 161 and 163 may intermesh such that the ridges 165 of roller 161 may extend into the grooves 171 of roll 163 and the teeth 169 of roller 163 extend into the grooves 167 of roller 161. Either or both of the rollers 161 or 163 may be heated by means known in the art, such as by incorporating hot oil filled rollers or electrically-heated rollers. Alternatively, either or both of the rollers 161 or 163 may be heated by surface convection or by surface radiation.

Figure 47:
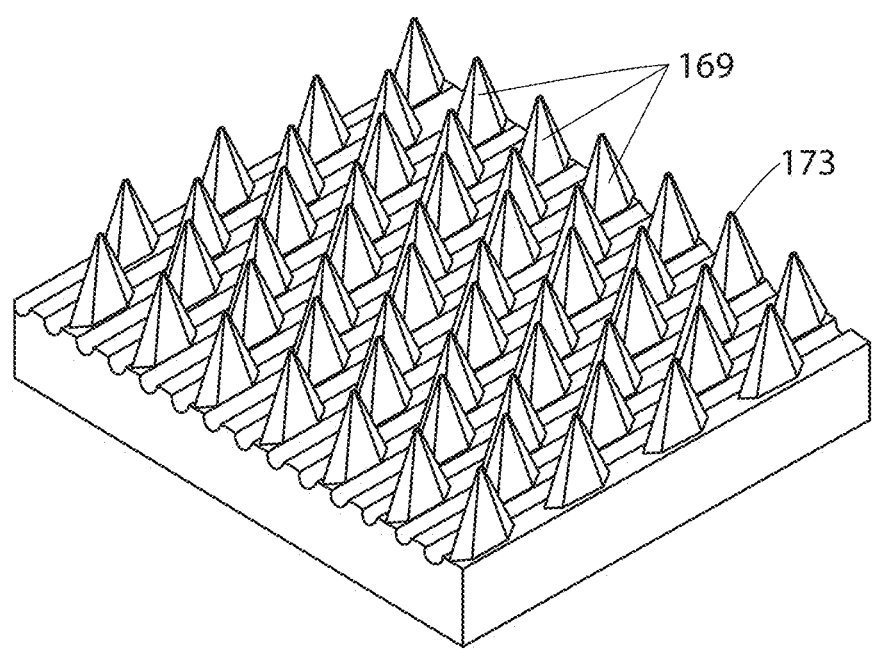
FIG. 47 is a perspective view of a roller system of the method of FIG. 46.
Figure 48:
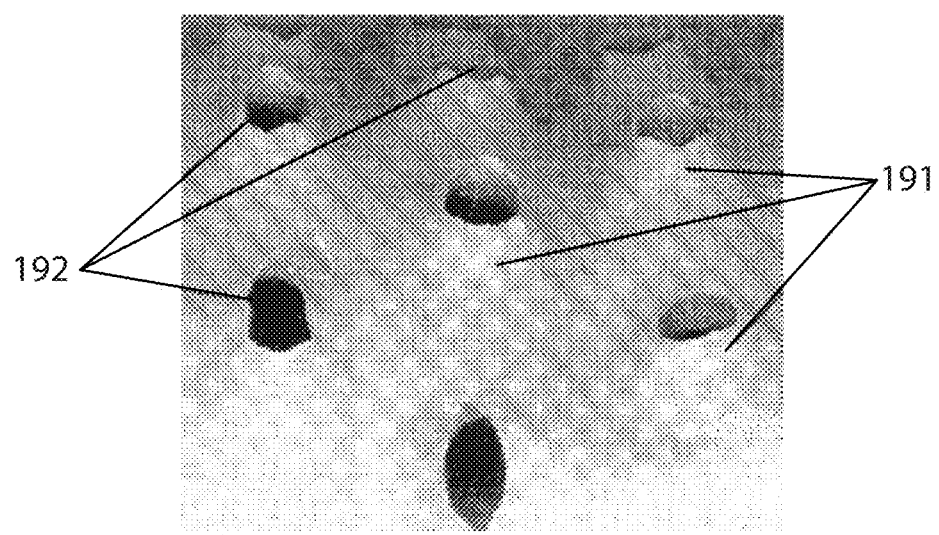
FIG. 48 is a photographic image of a highly magnified portion of an example aperture pattern made by the method of FIG. 46.

The teeth 169 may be joined to a base of the roller 163 by any method known in the art, such as by welding, compression fit, or integral attachment, where excess material may be removed from a roller. FIG. 47 shows a portion of the roller 163 having a plurality of teeth 169 useful in an aperturing process. A tooth tip 173 may be generally pointed, blunt pointed, or otherwise shaped so as to stretch and/or puncture the precursor material 152. A representative apertured material is shown in FIG. 48, where apertures 192 were formed by the action of teeth 169 on the heated roll 163 having stretched and pushed through the precursor material 152 to permanently deform the precursor material 152 to form a plurality of discrete, spaced apart volcano-like structures 191 extending outwardly therefrom.

The above-described apertures can further have an aperture density, according to the Aperture Test, of at least about 150, at least about 175, at least about 200, or at least about 300, for example.

At least some of the above-described apertures can further exhibit Absolute Feret Angles, according to the Aperture Test herein, of at least about 10 degrees, at least about 15 degrees, at least about 20 degrees, at least about 25 degrees, at least about 30 degrees, at least about 35 degrees, at least about 40 degrees, at least about 45 degrees, or in the range of about 10 degrees to about 45 degrees, or about 15 degrees to about 35 degrees, specifically reciting all 0.1 degree increments within the specified ranges and all ranges formed therein or thereby.

The patterned apertures may further comprise a first plurality of patterned apertures and a second plurality of patterned apertures. Central longitudinal axes of the first plurality of patterned apertures may extend in a first direction relative to the machine direction. Central longitudinal axes of the second plurality of apertures may extend in a second, different direction relative to the machine direction. The second different direction may be at least about 5 degrees, at least about 10 degrees, at least about 15 degrees, at least about 20 degrees, at least about 30 degrees, at least about 40 degrees, at least about 50 degrees, at least about 60 degrees, at least about 70 degrees, at least about 80 degrees, at least about 90 degrees, or in the range of about 10 degrees to about 90 degrees, or about 20 degrees to about 70 degrees, specifically reciting all 0.1 degree increments within the above-specified ranges and all ranges formed therein or thereby, different than the first direction. In certain examples, the first direction may have a positive slope relative to the machine direction and the second direction may have a negative slope relative to the machine direction. In other examples, the first direction and the second direction may both have a positive slope or may both have a negative slope. At least some of the plurality of the overbonds may form a diamond-shaped or diamond-like pattern in the web. Land areas may be formed at least partially around, or fully around, at least some of the plurality of the overbonds or the patterned apertures. At least some of the patterned apertures, such as 2 or more, 3 or more, or 4 or more may be non-homogenous, such that they can be designed to have a different size, shape, Absolute Feret Angle, according to the Aperture Test herein, and/or Aspect Ratio, according to the Aperture Test herein.

The three-dimensional shaped nonwoven fabrics or layers thereof may have apertures that have an Average Interaperture Distance of less than about 3.5 mm, less than about 3 mm, less than about 2.5 mm, less than about 2 mm, less than about 1.5 mm, less than about 1 mm, in the range of about 1 mm to about 3.5 mm, in the range of about 1 mm to about 3 mm, in the range of about 1 mm to about 2.5 mm, or in the range of about 3.5 mm to about 10 mm, specifically reciting all 0.1 mm increments within the above-specified ranges and all ranges formed therein or thereby, according to the Aperture Test herein.

A three-dimensional shaped nonwoven fabric may have Interaperture Distances, which can also be calculated according to the Aperture Test herein. The Interaperture Distances may have a distribution having a mean and a median. The mean may be greater than, different than, or less than the median. The mean may be greater than, different than, or less than the median in the range of about 3% to about 25%, about 4% to about 25%, about 5% to about 20%, about 8% to about 20%, or about 4% to about 15%, for example, specifically reciting all 0.1% increments within the above-specified ranges and all ranges formed therein or thereby. A first zone of a three-dimensional shaped nonwoven fabric may have Interaperture Distances. The Interaperture Distances of the first zone may have a first distribution having a first mean and a first median. The first mean may be greater than, different than, or less than the first median by the ranges set forth above in this paragraph. A second zone of the three-dimensional shaped nonwoven fabric may have Interaperture Distances. The Interaperture Distances of the second zone may have a second distribution having a second mean and a second median. The second mean may be greater than, less than, or different than the second median by the ranges set forth above in this paragraph. A third zone of the three-dimensional shaped nonwoven fabric may have Interaperture Distances. The Interaperture Distances of the third zone may have a third distribution having a third mean and a third median. The third mean may be greater than, different than, or less than the third median by the ranges set forth above in this paragraph. The first, second, and third means may be the same or different. The first, second, and third medians may be the same or different. The first, second, and third zones may be in a topsheet, a topsheet layer, an acquisition layer, an outer cover, an outer cover layer, or any other component of an absorbent article or other consumer products.

In other examples, a first portion of an absorbent article or other consumer product may have a first three-dimensional shaped nonwoven fabric that has Interaperture Distances, according to the Aperture Test herein. The Interaperture Distances of the first portion have a first distribution. A second portion of an absorbent article or other consumer product may have a second three-dimensional shaped nonwoven fabric that has Interaperture Distances, according to the Aperture Test herein. The Interaperture Distances of the second portion have a second distribution. A third portion of an absorbent article or other consumer product may have a third three-dimensional shaped nonwoven fabric that has Interaperture Distances, according to the Aperture Test herein. The Interaperture Distances of the third portion have a third distribution. The first, second, and third distributions may be the same or different. The first distribution may have a first mean and a first median. The first mean may be greater than, less than, or different than the first median in the range of about 3% to about 25%, about 4% to about 25%, about 5% to about 20%, about 8% to about 20%, or about 4% to about 15%, for example, specifically reciting all 0.1% increments within the above-specified ranges and all ranges formed therein or thereby. The second distribution may have a second mean and a second median. The second mean may be greater than, different than, or less than the second median by the ranges set forth above in this paragraph. The third distribution may have a second mean and a second median. The second mean may be greater than, different than, or less than the second median by the ranges set forth above in this paragraph. The first, second, and third means may be the same or different. The first, second, and third medians may be the same or different. The Relative Standard Deviation of the Interaperture Distances of a three-dimensional shaped nonwoven fabric may be at least about 50%/a, or at least about 55%. The Maximum Interaperture Distance in a given three-dimensional shaped nonwoven fabric may be at least about 8 mm, or at least about 10 mm, for example.

A three-dimensional shaped nonwoven fabric may have one or more apertures having an Absolute Ferret Angle, according to the Aperture Test herein, of at least about 15 degrees, at least about 18 degrees, at least about 20 degrees, at least about 22 degrees, at least about 25 degrees, at least about 30 degrees, at least about 35 degrees, at least about 40 degrees, in the range of about 15 degrees to about 80 degrees, in the range of about 20 degrees to about 75 degrees, in the range of about 20 degrees to about 70 degrees, or in the range of about 25 degrees to about 65 degrees, specifically reciting all 0.1 degrees increments within the above-specified ranges and all ranges formed therein or thereby.

A three-dimensional shaped nonwoven fabric may have a plurality of apertures having an Average Absolute Ferret Angle, according to the Aperture Test, of at least about 15 degrees, at least about 18 degrees, at least about 20 degrees, at least about 22 degrees, at least about 25 degrees, at least about 30 degrees, at least about 35 degrees, at least about 40 degrees, in the range of about 15 degrees to about 80 degrees, in the range of about 20 degrees to about 75 degrees, in the range of about 20 degrees to about 70 degrees, or in the range of about 25 degrees to about 65 degrees, specifically reciting all 0.1 degrees increments within the above-specified ranges and all ranges formed therein or thereby. These apertures may all be within a single repeat unit of the three-dimensional shaped nonwoven fabric. The Relative Standard Deviation of the Absolute Ferret Angles in a three-dimensional shaped nonwoven fabric may be at least about 30%, or at least about 40%, or at least about 50%. A repeat unit is an area in a three-dimensional shaped nonwoven fabric that can be identified as having a full aperture pattern or array. Multiple repeat units may be present in a three-dimensional shaped nonwoven fabric, with one full aperture pattern or array being present in each repeat unit.

At least two, at least 3, at least 4, at least 5, at least 6, at least 7, at least 8, at least 9, or at least 10 of the apertures in a three-dimensional shaped nonwoven fabric, or a repeat unit of a three-dimensional shaped nonwoven fabric, may each have a different Absolute Feret Angle, according to the Aperture Test herein. In other instances, some of the apertures may have Absolute Feret Angles that are the same, while other of the apertures may have Absolute Feret Angles that are different. In addition to having different Absolute Feret Angles, the at least two, at least 3, at least 4, at least 5, at least 6, at least 7, at least 8, at least 9, or at least 10 apertures may have different sizes and/or shapes. At least some of the at least two, at least 3, at least 4, at least 5, at least 6, at least 7, at least 8, at least 9, or at least 10 apertures may also have the same size and/or shape, while having different Absolute Feret Angles. The Absolute Feret Angles of at least some of the apertures within a repeat unit may differ by at least about 5 degrees, at least about 10 degrees, at least about 15, degrees, at least about 20 degrees, at least about 25 degrees, or at least about 30 degrees, for example.

Some of the three-dimensional shaped nonwoven fabrics may have land area widths of at least about 4 mm, at least about 5 mm, at least about 6 mm, at least about 7 mm, at least about 8 mm, at least about 9 mm, at least about 10 mm, or in the range of about 4 mm to about 15 mm, specifically reciting all 0.1 mm increments within the specified range and all ranges formed therein.

General Description of an Absorbent Article

Figure 49:
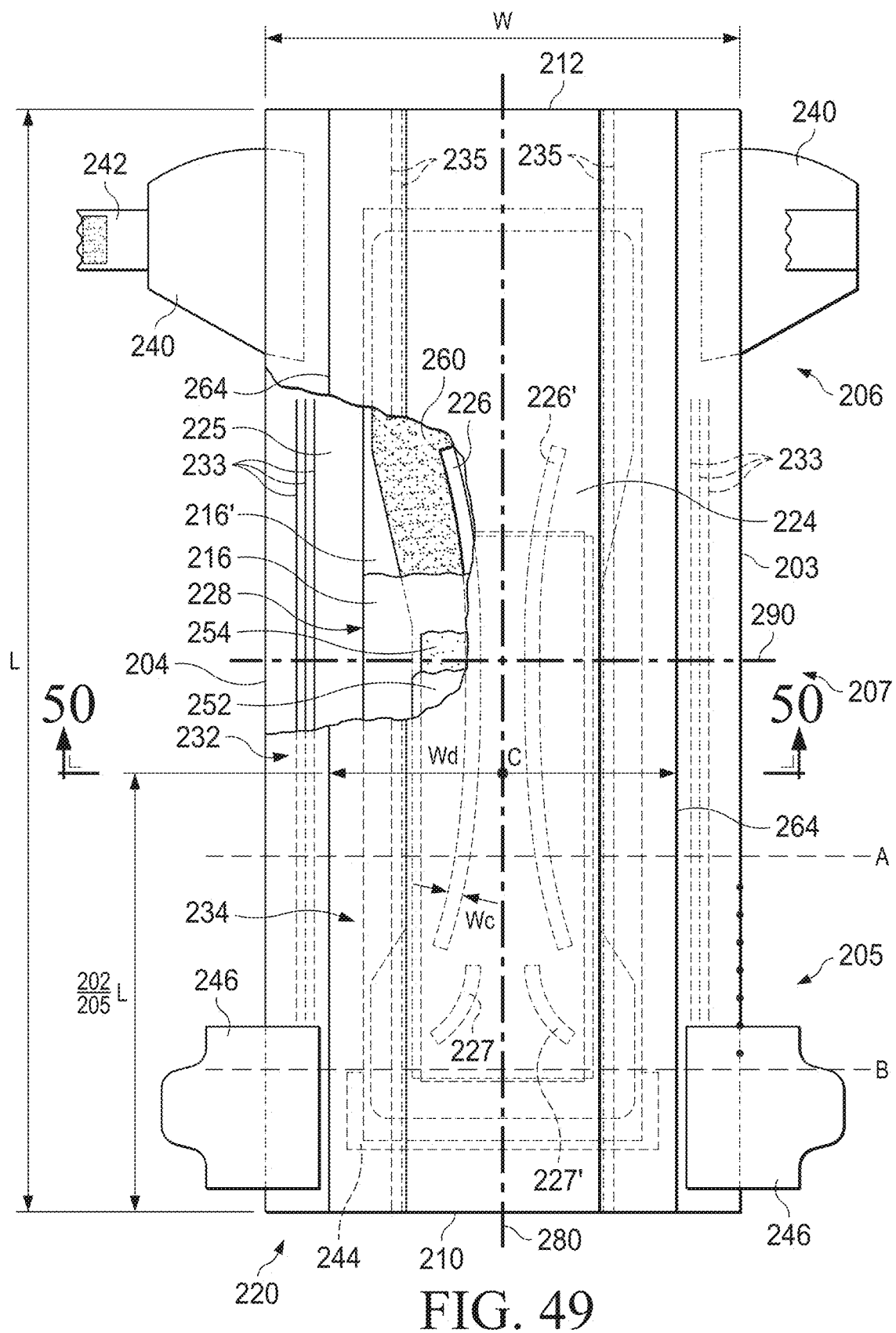
FIG. 49 is a plan view of an example absorbent article of the present disclosure.
Figure 50:
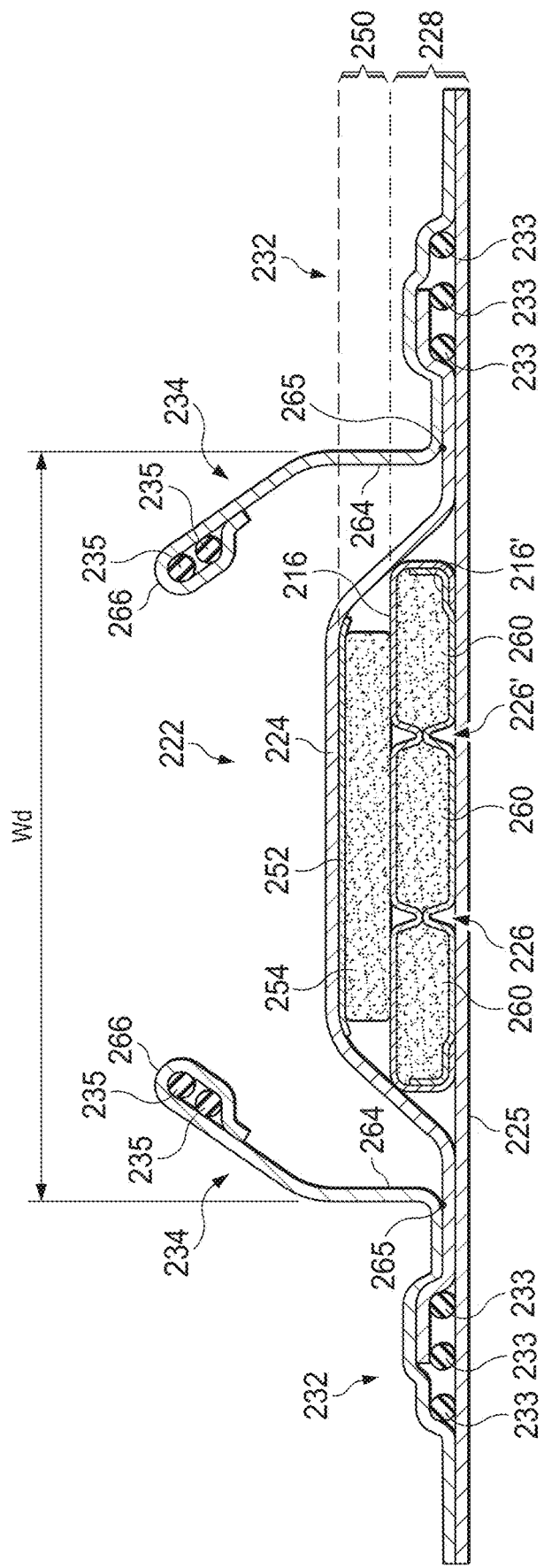
FIG. 50 is a cross-sectional view along section 50-50 of FIG. 49.
Figure 51:
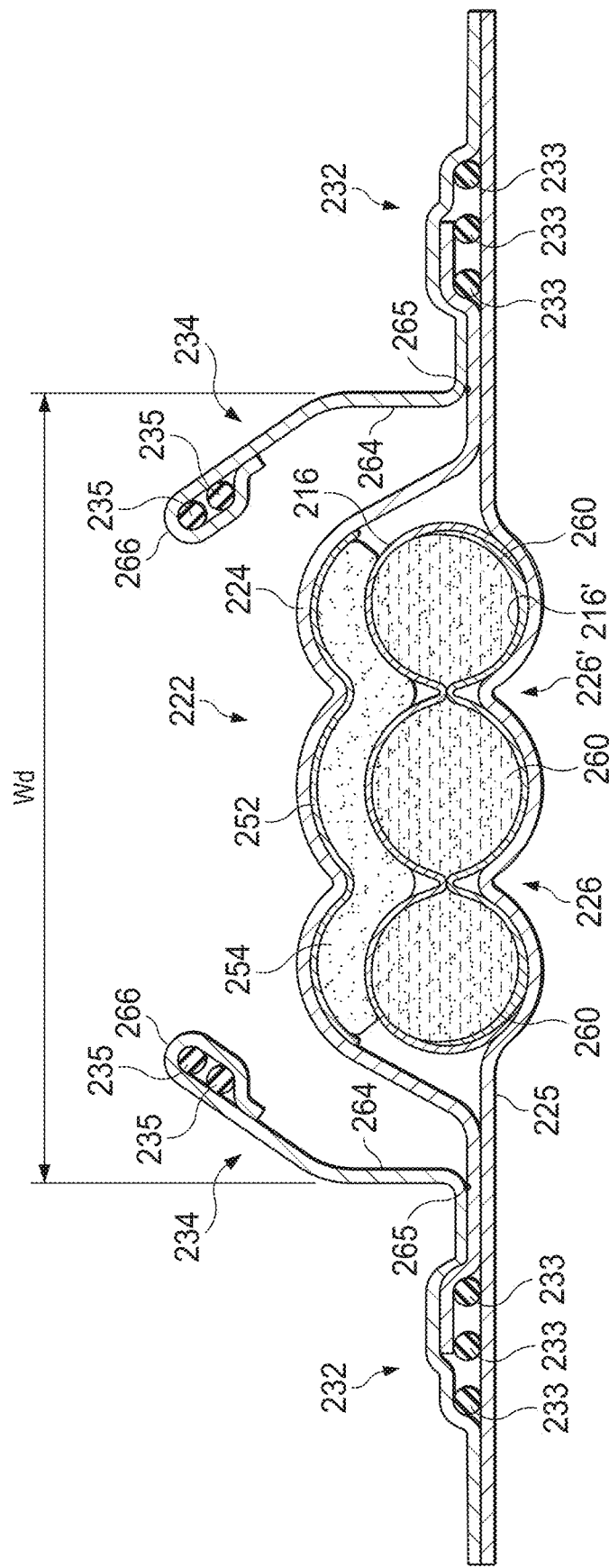
FIG. 51 is another cross-sectional view along section 50-50 of FIG. 49.

An absorbent article can comprise a liquid permeable material comprising a variable basis weight, apertured, three-dimensional shaped nonwoven fabrics material, as described above; a liquid impermeable material; and an absorbent core including an absorbent material, where the absorbent core can be positioned at least partially intermediate the liquid permeable material and the liquid impermeable material. That is, in certain examples, the three-dimensional nonwoven fabrics 10 of the present disclosure, as well as the apertured material 152 described above, can be utilized as a component of absorbent articles, such as diapers, child care items such as training pants, feminine care items such as sanitary napkins, and adult care items such as incontinence products, pads, and pants An example absorbent article in the form of a diaper 220 is represented in FIGS. 49-51. FIG. 49 is a plan view of the example diaper 220, in a flat, laid-out state, with portions of the structure being cut-away to more clearly show the construction of the diaper 220. The wearer-facing surface of the diaper 220 of FIG. 49 is facing the viewer. This diaper 220 is shown for illustration purpose only as the three-dimensional nonwoven materials of the present disclosure may be used as one or more components of an absorbent article, such as the topsheet, the acquisition layer, the topsheet and the acquisition layer, or the topsheet and the acquisition and/or the distribution system ("ADS"). In any event the three-dimensional nonwoven materials of the present disclosure may be liquid permeable, as described above.

The absorbent article 220 may comprise a liquid permeable material or topsheet 224, a liquid impermeable material or backsheet 225, an absorbent core 228 positioned at least partially intermediate the topsheet 224 and the backsheet 225, and barrier leg cuffs 234. The absorbent article may also comprise an ADS 250, which in the example represented comprises a distribution layer 254 and an acquisition layer 252, which will be further discussed below. The absorbent article 220 may also comprise elasticized gasketing cuffs 232 comprising elastics 233 joined to a chassis of the absorbent article, typically via the topsheet and/or backsheet, and substantially planar with the chassis of the diaper.

Figure 52:
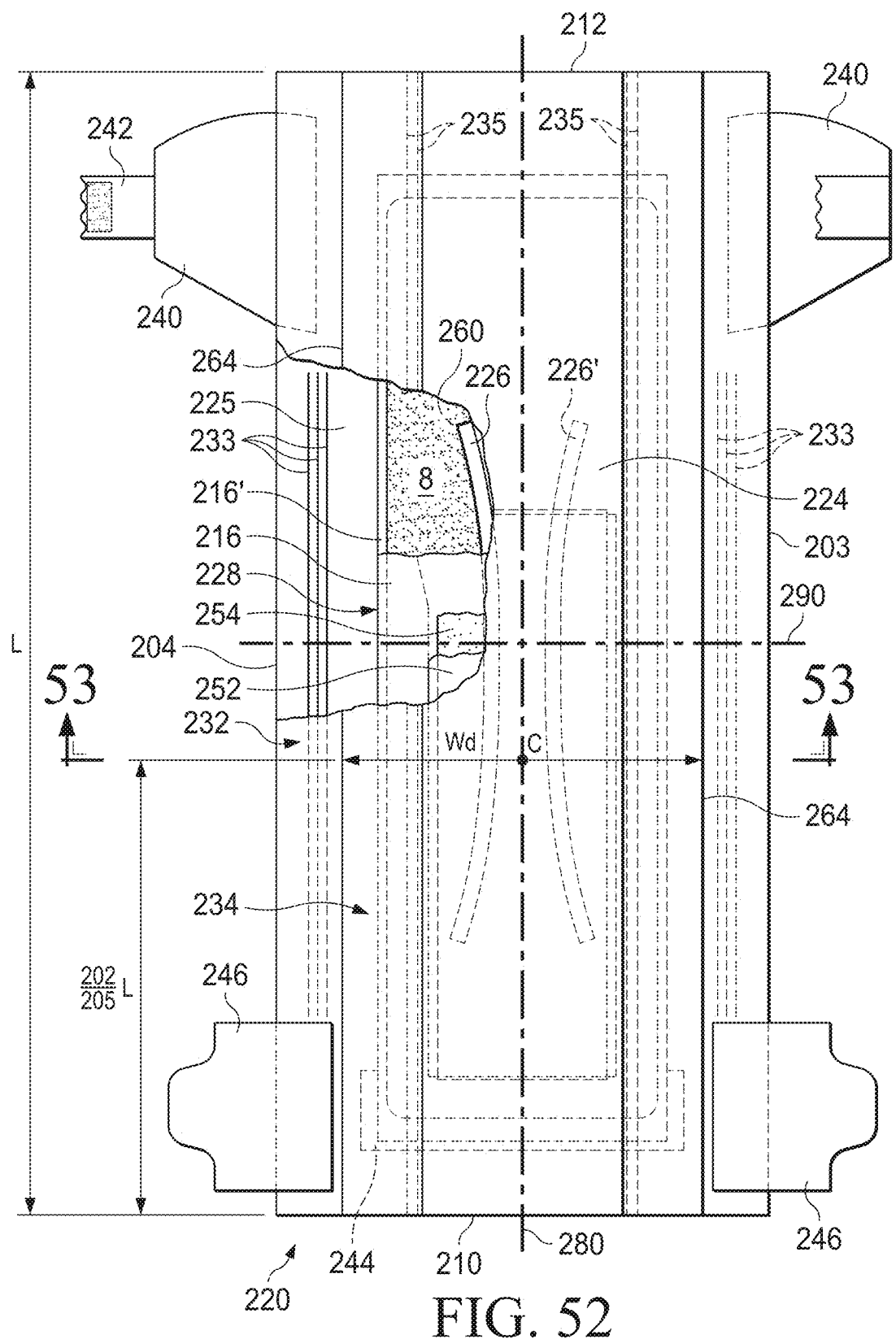
FIG. 52 is a plan view of an absorbent article of the present disclosure.

FIGS. 49 and 52 also show typical taped diaper components such as a fastening system comprising tabs 242 attached towards the rear edge of the article and cooperating with a landing zone 244 on the front of the absorbent article. The absorbent article may also comprise other typical elements, which are not represented, such as a rear elastic waist feature, a front elastic waist feature, transverse barrier cuff(s), and/or a lotion application, for example.

The absorbent article 220 can comprise a front waist edge 210, a rear waist edge 212 longitudinally opposing the front waist edge 210, a first side edge 203, and a second side edge 204 laterally opposing the first side edge 203. The front waist edge 210 can be the edge of the article which is intended to be placed towards the front of the user when worn, and the rear waist edge 212 can be the opposite edge. The absorbent article 220 may have a longitudinal axis 280 extending from the lateral midpoint of the front waist edge 210 to a lateral midpoint of the rear waist edge 212 of the article and dividing the article in two substantially symmetrical halves relative to the longitudinal axis 280, with the article placed flat, laid-out and viewed from above as in FIG. 49. The absorbent article 220 may also have a lateral axis 290 extending from the longitudinal midpoint of the first side edge 203 to the longitudinal midpoint of the second side edge 204. The length, L, of the article may be measured along the longitudinal axis 280 from the front waist edge 210 to the rear waist edge 212. The width, W, of the absorbent article may be measured along the lateral axis 290 from the first side edge 203 to the second side edge 204. The absorbent article may comprise a crotch point C defined herein as the point placed on the longitudinal axis at a distance of two fifth (⅖) of L starting from the front edge 210 of the article 220. The article may comprise a front waist region 205, a rear waist region 206, and a crotch region 207. The front waist region 205, the rear waist region 206, and the crotch region 207 may each define ⅓ of the longitudinal length, L, of the absorbent article.

The topsheet 224, the backsheet 225, the absorbent core 228, and the other article components may be assembled in a variety of configurations, in particular by gluing or heat embossing, for example.

The absorbent core 228 may comprise an absorbent material comprising at least 80% by weight, at least 85% by weight, at least 90% by weight, at least 95% by weight, or at least 99% by weight of superabsorbent polymers, and a core wrap enclosing the superabsorbent polymers. The core wrap may typically comprise two materials, substrates, or nonwoven materials 216 and 216' for the top side and the bottom side of the core. These types of cores are known as airfelt-free cores. The core may comprise one or more channels, represented in FIG. 49 as the four channels 226, 226' and 227, 227'. The channels 226, 226', 227, and 227' are optional features. Instead, the core may not have any channels or may have any number of channels.

These and other components of the example absorbent articles will now be discussed in more details.

Topsheet

In the present disclosure, the topsheet (the portion of the absorbent article that contacts the wearer's skin and receives the fluids) may be formed of a portion of, or all of, one or more of the three-dimensional nonwoven materials described herein and/or have one or more of the nonwoven materials positioned thereon and/or joined thereto, so that the nonwoven material(s) contact(s) the wearer's skin. Other portions of the topsheet (other than the three-dimensional nonwoven materials) may also contact the wearer's skin. The three-dimensional nonwoven materials may be positioned as a strip or a patch on top of the typical topsheet 224. Alternatively, the three-dimensional nonwoven material may only form a central CD area of the topsheet. The central CD area may extend the full MD length of the topsheet or less than the full MD length of the topsheet.

The topsheet 224 may be joined to the backsheet 225, the absorbent core 228 and/or any other layers as is known to those of skill in the art. Usually, the topsheet 224 and the backsheet 225 are joined directly to each other in some locations (e.g., on or close to the periphery of the absorbent article) and are indirectly joined together in other locations by directly joining them to one or more other elements of the article 220.

The topsheet 224 may be compliant, soft-feeling, and non-irritating to the wearer's skin. Further, a portion of, or all of, the topsheet 224 may be liquid permeable, permitting liquids to readily penetrate through its thickness. Furthermore, a portion of, or all of, the topsheet 224 may be treated with surfactants or other agents to either hydrophilize the web or make it hydrophobic. Any portion of the topsheet 224 may be coated with a lotion and/or a skin care composition as is generally disclosed in the art. The topsheet 224 may also comprise or be treated with antibacterial agents.

Backsheet

The backsheet 225 is generally that portion of the absorbent article 220 positioned adjacent the garment-facing surface of the absorbent core 228 and which prevents, or at least inhibits, the fluids and bodily exudates absorbed and contained therein from soiling articles such as bedsheets and undergarments. The backsheet 225 can be typically impermeable, or at least substantially impermeable, to fluids (e.g., urine). The backsheet may, for example, be or comprise a thin plastic film such as a thermoplastic film having a thickness of about 0.012 mm to about 0.051 mm. Other suitable backsheet materials may comprise breathable materials which can permit vapors to escape from the absorbent article 220, while still preventing, or at least inhibiting, fluids from passing through the backsheet 225.

The backsheet 225 may be joined to the topsheet 224, the absorbent core 228, and/or any other element of the absorbent article 220 by any attachment methods known to those of skill in the art.

The absorbent article may comprise a backsheet comprising an outer cover or an outer cover nonwoven. An outer cover or outer cover nonwoven of the absorbent article 220 may cover at least a portion of, or all of, the backsheet 225 to form a soft garment-facing surface of the absorbent article. The outer cover or outer cover nonwoven may be formed of the high loft, three-dimensional nonwoven materials described herein. Alternatively, the outer cover or outer cover nonwoven may comprise one or more known outer cover materials. If the outer cover comprises one of the three-dimensional nonwoven materials of the present disclosure, the three-dimensional nonwoven material of the outer cover may or may not match (e.g., same material, same pattern) a three-dimensional nonwoven material used as the topsheet or the topsheet and the acquisition layer of the absorbent article. In other instances, the outer cover may have a printed or otherwise applied pattern that matches or visually resembles the pattern of the three-dimensional nonwoven materials used as the topsheet or the topsheet and the acquisition layer laminate of the absorbent article. The outer cover may be joined to at least a portion of the backsheet 225 through mechanical bonding, ultrasonic, thermal bonding, adhesive bonding, or other suitable methods of attachment.

Absorbent Core

The absorbent core is the component of the absorbent article that has the most absorbent capacity and that comprises an absorbent material and a core wrap or core bag enclosing the absorbent material. The absorbent core does not include the acquisition and/or distribution system or any other components of the absorbent article which are not either integral part of the core wrap or core bag or placed within the core wrap or core bag. The absorbent core may comprise, consist essentially of, or consist of, a core wrap, an absorbent material (e.g., superabsorbent polymers and little or no cellulose fibers) as discussed, and glue.

The absorbent core 228 may comprise an absorbent material with a high amount of superabsorbent polymers (herein abbreviated as "SAP") enclosed within the core wrap. The SAP content may represent 70%-100% or at least 70%, 75%, 80%, 85%, 90%, 95%, 99%, or 100%, by weight of the absorbent material, contained in the core wrap. The core wrap is not considered as absorbent material for the purpose of assessing the percentage of SAP in the absorbent core. The absorbent core may contain airfelt with or without superabsorbent polymers.

By "absorbent material" it is meant a material which has some absorbency property or liquid retaining properties, such as SAP, cellulosic fibers as well as synthetic fibers. Typically, glues used in making absorbent cores have no or little absorbency properties and are not considered as absorbent material. The SAP content may be higher than 80%, for example at least 85%, at least 90%, at least 95%, at least 99%, and even up to and including 100% of the weight of the absorbent material contained within the core wrap. This airfelt-free core is relatively thin compared to a conventional core typically comprising between 40-60% SAP by weight and a high content of cellulose fibers. The absorbent material may in particular comprises less than 15% weight percent or less than 10% weight percent of natural, cellulosic, or synthetic fibers, less than 5% weight percent, less than 3% weight percent, less than 2% weight percent, less than 1% weight percent, or may even be substantially free of natural, cellulosic, and/or synthetic fibers.

As referenced above, the airfelt-free cores with very little or no natural, cellulosic and/or synthetic fibers are quite thin compared to conventional cores, thereby making the overall absorbent article thinner than absorbent articles with cores comprising mixed SAP and cellulosic fibers (e.g., 40%-60% cellulose fibers). This core thinness can lead to consumer perceptions of reduced absorbency and performance, although technically this is not the case. Presently, these thin cores have typically been used with substantially planar topsheets. Furthermore, absorbent articles having these thin airfelt-free cores have reduced capillary void space since there is little or no natural, cellulosic, or synthetic fibers in the cores. Thus, there may sometimes not be enough capillary void space in the absorbent article to fully accept multiple insults of bodily exudates or a single large insult.

To solve such problems, the present disclosure provides absorbent articles with these thin airfelt-free cores in combination with one of the high-loft, three-dimensional nonwoven materials described herein as a topsheet or as a topsheet and acquisition layer laminate. In such an instance, consumer perception of absorbency and performance, through the increased thickness of the absorbent article owing to the additional thickness provided by the high-loft, three-dimensional nonwoven material, is increased. Furthermore, the three-dimensional nonwoven materials, when used with these thin airfelt-free cores and as the topsheet or the topsheet and acquisition layer laminate, add capillary void space back into the absorbent articles, while still allowing for minimal stack heights, thereby passing cost savings onto consumers and manufactures. As such, the absorbent articles of the present disclosure may easily absorb multiple bodily exudate insults or single large insults owing to this increased capillary void space. Additionally, absorbent articles that comprise the nonwoven materials as the topsheet or the topsheet and acquisition layer laminate can provide consumers with an aesthetically pleasing topsheet relative to a planar topsheet with an increased thickness and thus the consumer perceptions of absorbency and performance.

Figure 42:
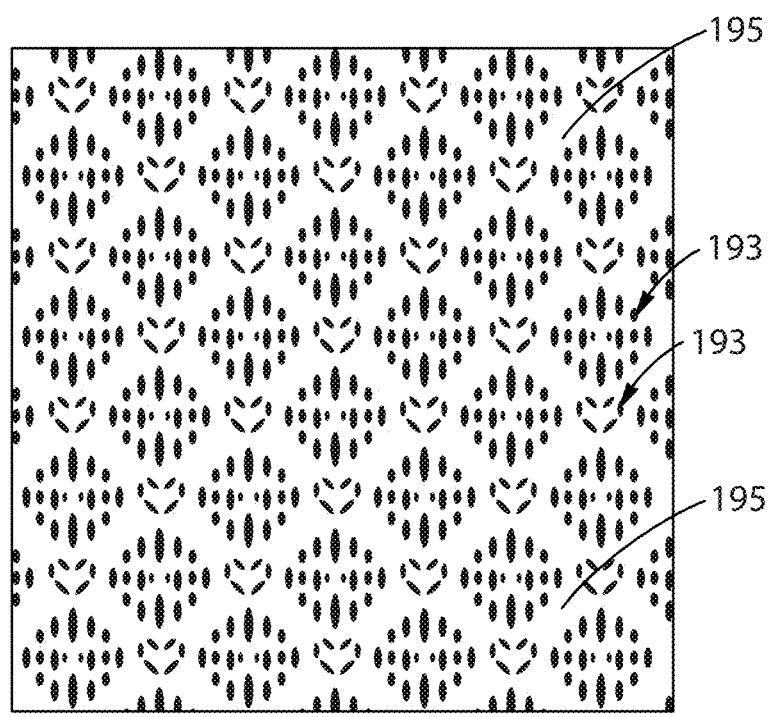
FIG. 42 is a schematic representation of an example aperture pattern of the present disclosure.
Figure 43:
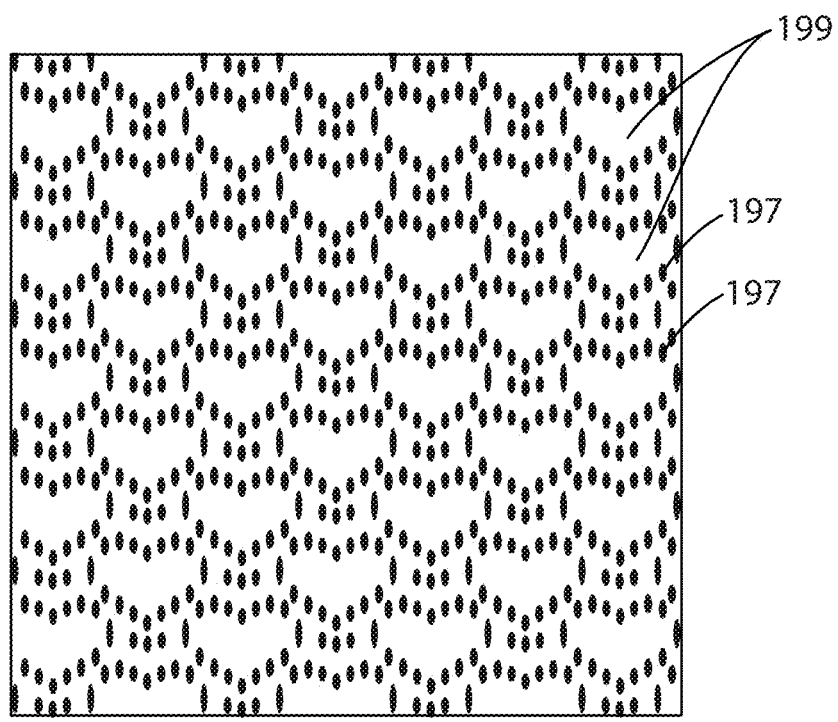
FIG. 43 is a schematic representation of an example aperture pattern of the present disclosure.
Figure 44:
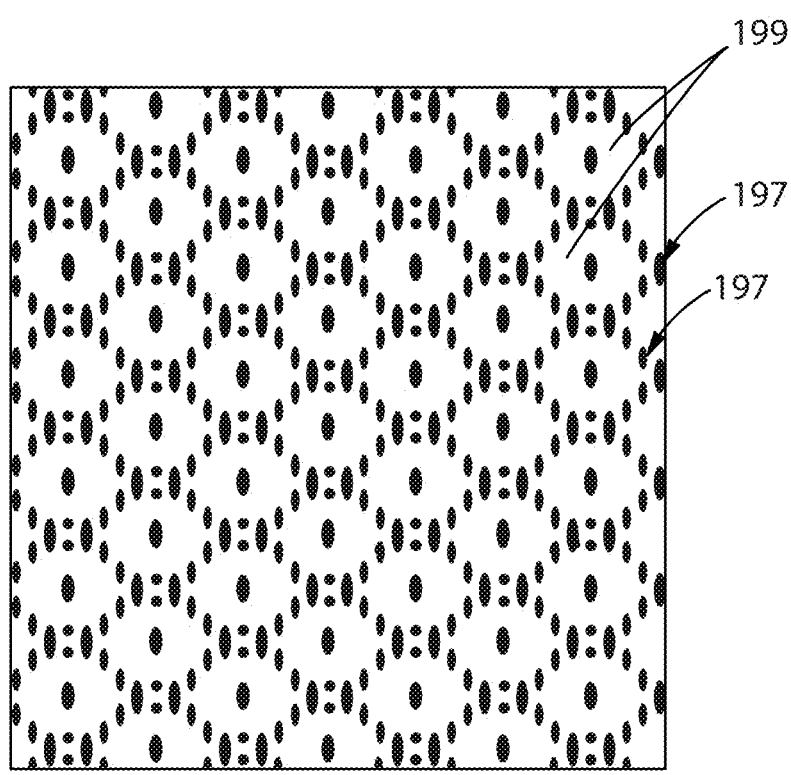
FIG. 44 is a schematic representation of an example aperture pattern of the present disclosure.
Figure 45:
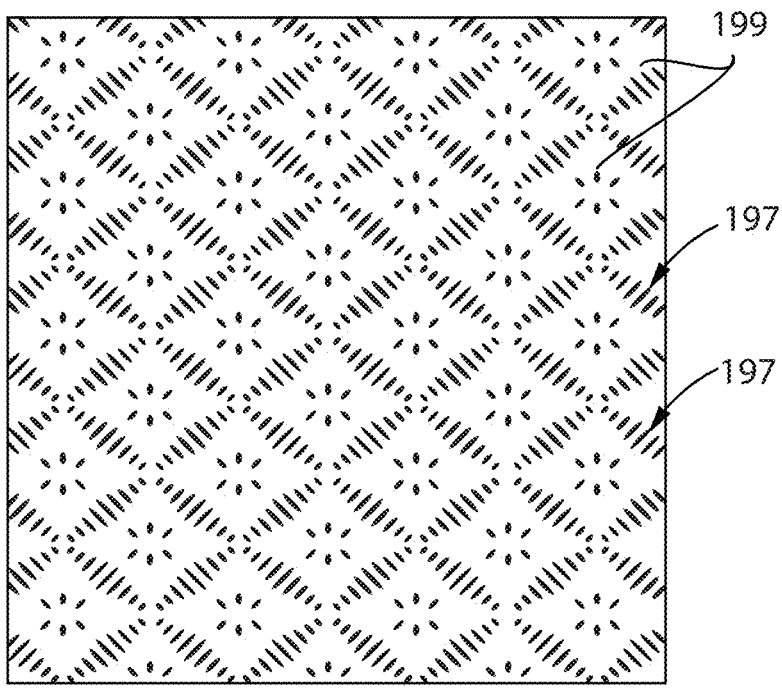
FIG. 45 is a schematic representation of an example aperture pattern of the present disclosure.
Figure 53:
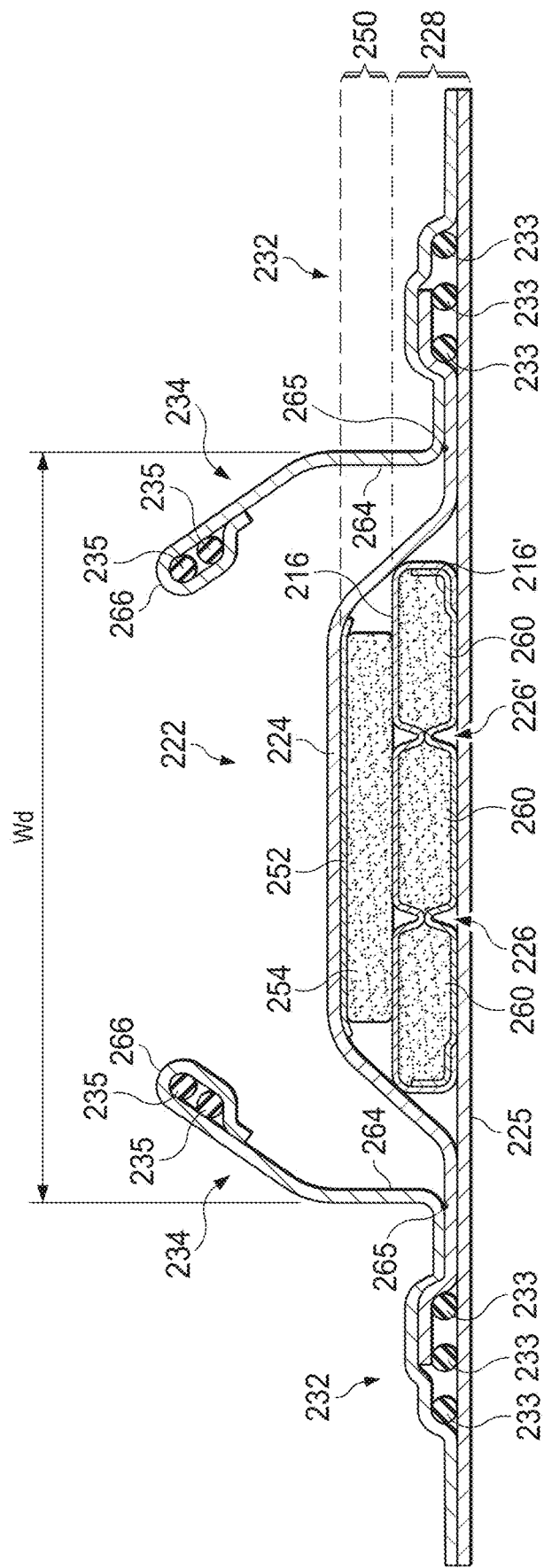
FIG. 53 is a cross-sectional view along section 53-53 of FIG. 52.
Figure 55:
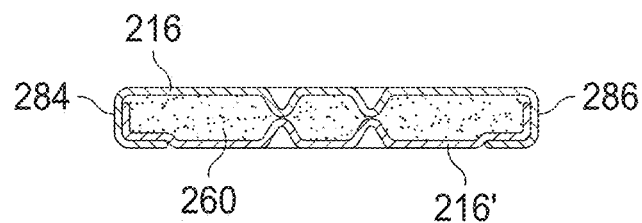
FIG. 55 is a cross-sectional view along section 55-55 of FIG. 54.

The example absorbent core 228 of the absorbent article 220 of FIGS. 52 and 53 is shown in isolation in FIGS. 42-44. The absorbent core 228 may comprise a front side 480, a rear side 282, and two longitudinal sides 284, 286 joining the front side 480 and the rear side 282. The absorbent core 228 may also comprise a generally planar top side and a generally planar bottom side. The front side 480 of the core can be the side of the core intended to be placed towards the front waist edge 210 of the absorbent article. The core 228 may have a longitudinal axis 280' corresponding substantially to the longitudinal axis 280 of the absorbent article 220, as seen from the top in a planar view as in FIG. 49. The absorbent material may be distributed in higher amount towards the front side 480 than towards the rear side 282 as more absorbency may be required at the front in particular absorbent articles. The front and rear sides 480 and 282 of the core may be shorter than the longitudinal sides 284 and 286 of the core. The core wrap may be formed by two nonwoven materials, substrates, laminates, or other materials, 216, 216' which may be at least partially sealed along the sides 284, 286 of the absorbent core 228. The core wrap may be at least partially sealed along its front side 480, rear side 282, and two longitudinal sides 284, 286 so that substantially no absorbent material leaks out of the absorbent core wrap. The first material, substrate, or nonwoven 216 may at least partially surround the second material, substrate, or nonwoven 216' to form the core wrap, as illustrated in FIG. 55. The first material 216 may surround a portion of the second material 216' proximate to the first and second side edges 284 and 286.

The absorbent core may comprise adhesive, for example, to help immobilizing the SAP within the core wrap and/or to ensure integrity of the core wrap, in particular when the core wrap is made of two or more substrates. The adhesive may be a hot melt adhesive, supplied, by H.B. Fuller, for example. The core wrap may extend to a larger area than strictly needed for containing the absorbent material within.

Figure 56:
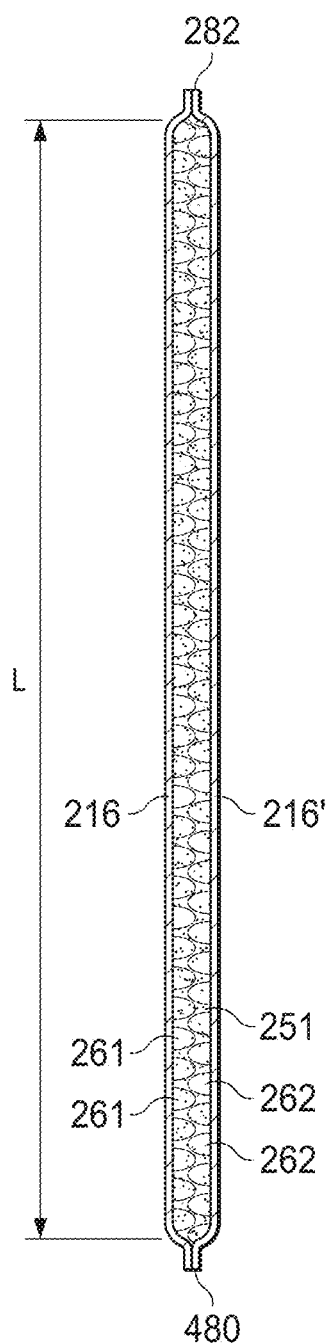
FIG. 56 is a cross-sectional view along section 56-56 of FIG. 54.

The absorbent material may be a continuous layer present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two absorbent layers having discontinuous absorbent material application patterns, wherein the resulting layer is substantially continuously distributed across the absorbent particulate polymer material area, as disclosed in U.S. Pat. Appl. Pub. No. 2008/0312622A1 (Hundorf), for example. The absorbent core 228 may comprise a first absorbent layer and a second absorbent layer. The first absorbent layer may comprise the first material 216 and a first layer 261 of absorbent material, which may be 100% or less of SAP. The second absorbent layer may comprise the second material 216' and a second layer 262 of absorbent material, which may also be 100% or less of SAP. The absorbent core 228 may also comprise a fibrous thermoplastic adhesive material 251 at least partially bonding each layer of absorbent material 261, 262 to its respective material 216 or 216'. This is illustrated in FIGS. 55 and 56, as an example, where the first and second SAP layers have been applied as transversal stripes or "land areas" having the same width as the desired absorbent material deposition area on their respective substrate before being combined. The stripes may comprise different amounts of absorbent material (SAP) to provide a profiled basis weight along the longitudinal axis of the core 280. The first material 216 and the second material 216' may form the core wrap.

The fibrous thermoplastic adhesive material 251 may be at least partially in contact with the absorbent material 261, 262 in the land areas and at least partially in contact with the materials 216 and 216' in the junction areas. This can impart an essentially three-dimensional structure to the fibrous layer of thermoplastic adhesive material 251, which in itself can be essentially a two-dimensional structure of relatively small thickness, as compared to the dimension in length and width directions. Thereby, the fibrous thermoplastic adhesive material may provide cavities to cover the absorbent material in the land areas, and thereby immobilizes this absorbent material, which may be 100% or less of SAP.

The thermoplastic adhesive used for the fibrous layer may have elastomeric properties, such that the web formed by the fibers on the SAP layer is able to be stretched as the SAP swell.

Superabsorbent Polymer (SAP)

The SAP useful with the present disclosure may comprise a variety of water-insoluble, but water-swellable polymers capable of absorbing large quantities of fluids.

The superabsorbent polymer may be in particulate form so as to be flowable in the dry state. Particulate absorbent polymer materials may be made of poly(meth)acrylic acid polymers. However, starch-based particulate absorbent polymer material may also be used, as well as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

The SAP may be of numerous shapes. The term "particles" refers to granules, fibers, flakes, spheres, powders, platelets and other shapes and forms known to persons skilled in the art of superabsorbent polymer particles. The SAP particles may be in the shape of fibers, i.e., elongated, acicular superabsorbent polymer particles. The fibers may also be in the form of a long filament that may be woven. SAP may be spherical-like particles. The absorbent core may comprise one or more types of SAP.

For most absorbent articles, liquid discharges from a wearer occur predominately in the front half of the absorbent article, in particular for a diaper. The front half of the article (as defined by the region between the front edge and a transversal line placed at a distance of half L from the front waist edge 210 or rear waist edge 212) may therefore comprise most of the absorbent capacity of the core. Thus, at least 60% of the SAP, or at least 65%, 70%, 75%, 80%, or 85% of the SAP may be present in the front half of the absorbent article, while the remaining SAP may be disposed in the rear half of the absorbent article. Alternatively, the SAP distribution may be uniform through the core or may have other suitable distributions.

The total amount of SAP present in the absorbent core may also vary according to expected user. Diapers for newborns may require less SAP than infant, child, or adult incontinence diapers. The amount of SAP in the core may be about 5 g to 60 g or from 5 g to 50 g. The average SAP basis weight within the (or "at least one", if several are present) deposition area 8 of the SAP may be at least 50, 100, 200, 300, 400, 500 or more g/m$^2$. The areas of the channels (e.g., 226, 226', 227, 227') present in the absorbent material deposition area 8 are deduced from the absorbent material deposition area to calculate this average basis weight.

Core Wrap

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, as illustrated, for example, in FIGS. 50 and 55, the longitudinal and/or transversal edges of one of the substrates can be folded over the other substrate to form flaps. These flaps can then be bonded to the external surface of the other substrate, typically by gluing.

The core wrap may be formed by any materials suitable for receiving and containing the absorbent material. Typical substrate materials used in the production of conventional cores may be used, in particular paper, tissues, films, wovens or nonwovens, or laminates or composites of any of these.

The substrates may also be air-permeable (in addition to being liquid or fluid permeable). Films useful herein may therefore comprise micro-pores.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

Figure 54:
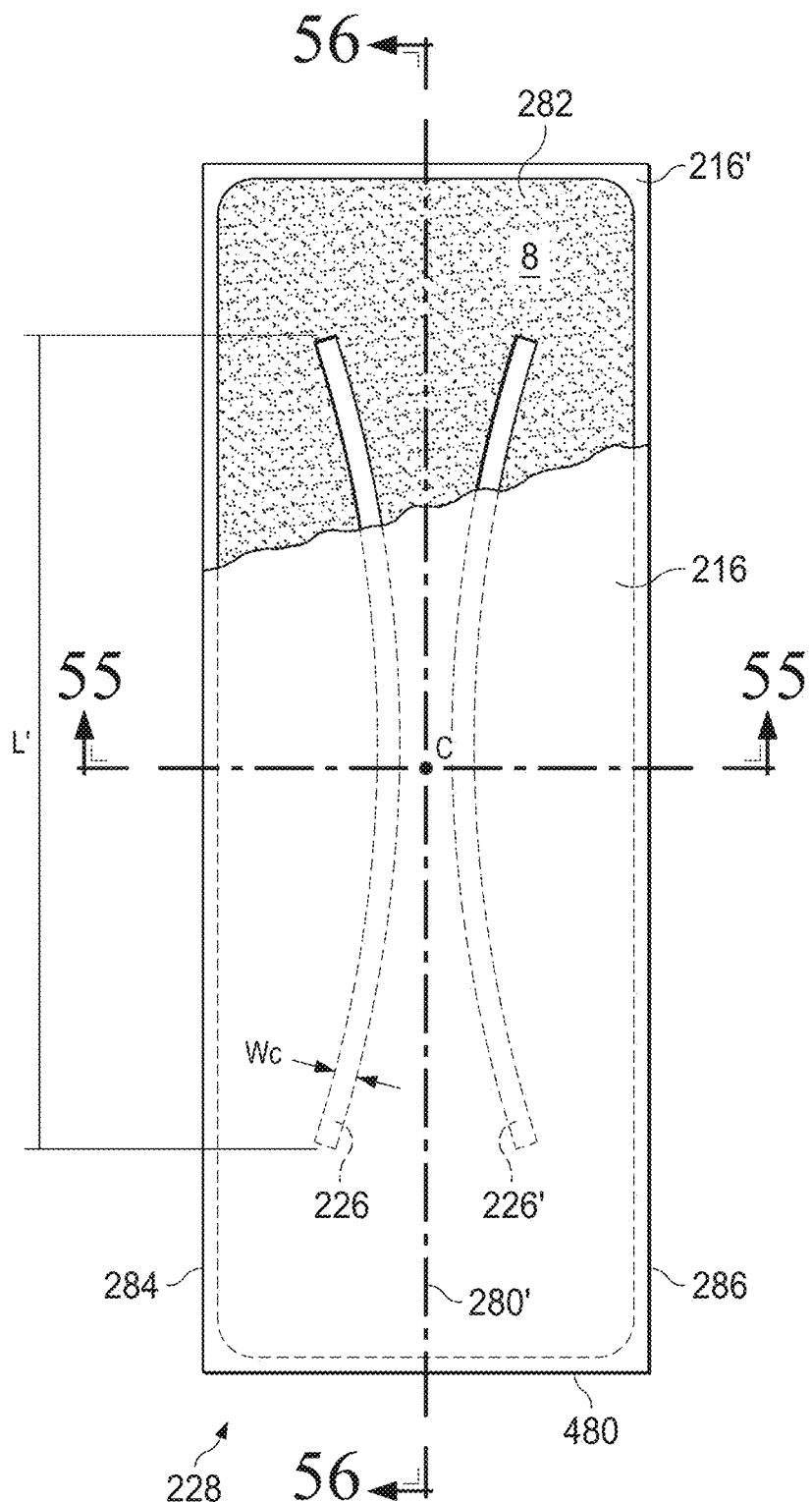
FIG. 54 is a plan view of an absorbent article of the present disclosure.

If the core wrap is formed by two substrates 216, 216', four seals may be used to enclose the absorbent material 260 within the core wrap. For example, a first substrate 216 may be placed on one side of the core (the top side as represented in FIGS. 54-56) and extend around the core's longitudinal edges to at least partially wrap the opposed bottom side of the core. The second substrate 216' may be present between the wrapped flaps of the first substrate 216 and the absorbent material 260. The flaps of the first substrate 216 may be glued to the second substrate 216' to provide a strong seal. This so called C-wrap construction may provide benefits such as improved resistance to bursting in a wet loaded state compared to a sandwich seal. The front side and rear side of the core wrap may then also be sealed by gluing the first substrate and second substrate to another to provide complete encapsulation of the absorbent material across the whole of the periphery of the core. For the front side and rear side of the core, the first and second substrates may extend and may be joined together in a substantially planar direction, forming for these edges a so-called sandwich construction. In the so-called sandwich construction, the first and second substrates may also extend outwardly on all sides of the core and be sealed flat, or substantially flat, along the whole or parts of the periphery of the core typically by gluing and/or heat/pressure bonding. In an example, neither the first nor the second substrates need to be shaped, so that they may be rectangularly cut for ease of production but other shapes are also within the scope of the present disclosure.

The core wrap may also be formed by a single substrate which may enclose as in a parcel wrap the absorbent material and be sealed along the front side and rear side of the core and one longitudinal seal.

SAP Deposition Area

The absorbent material deposition area 208 may be defined by the periphery of the layer formed by the absorbent material 260 within the core wrap, as seen from the top side of the absorbent core. The absorbent material deposition area 208 may have various shapes, in particular, a so-called "dog bone" or "hour-glass" shape, which shows a tapering along its width towards the middle or "crotch" region of the core. In this way, the absorbent material deposition area 8 may have a relatively narrow width in an area of the core intended to be placed in the crotch region of the absorbent article, as illustrated in FIG. 49. This may provide better wearing comfort. The absorbent material deposition area 8 may also be generally rectangular, for example as shown in FIGS. 52-54, but other deposition areas, such as a rectangular, "T," "Y," "sand-hour," or "dog-bone" shapes are also within the scope of the present disclosure. The absorbent material may be deposited using any suitable techniques, which may allow relatively precise deposition of SAP at relatively high speed.

Channels

The absorbent material deposition area 208 may comprise at least one channel 226, which is at least partially oriented in the longitudinal direction of the article 280 (i.e., has a longitudinal vector component) as shown in FIGS. 49 and 50. Other channels may be at least partially oriented in the lateral direction (i.e., has a lateral vector component) or in any other direction. In the following, the plural form "channels" will be used to mean "at least one channel". The channels may have a length L' projected on the longitudinal axis 280 of the article that is at least 10% of the length L of the article. The channels may be formed in various ways. For example, the channels may be formed by zones within the absorbent material deposition area 208 which may be substantially free of, or free of, absorbent material, in particular SAP. In another example, the channels may be formed by zones within the absorbent material deposition area 208 where the absorbent material of the core comprises cellulose, airfelt, SAP, or combinations thereof and the channels may be substantially free of, or free of, absorbent material, in particular the SAP, cellulose, or airfelt In addition or alternatively, the channel(s) may also be formed by continuously or discontinuously bonding the top side of the core wrap to the bottom side of the core wrap through the absorbent material deposition area 208. The channels may be continuous, but it is also envisioned that the channels may be intermittent. The acquisition-distribution system or layer 250, or another layer of the article, may also comprise channels, which may or not correspond to the channels of the absorbent core.

In some instances, the channels may be present at least at the same longitudinal level as the crotch point C or the lateral axis 260 in the absorbent article, as represented in FIG. 49 with the two longitudinally extending channels 226, 226'. The channels may also extend from the crotch region 207 or may be present in the front waist region 205 and/or in the rear waist region 206 of the article.

The absorbent core 228 may also comprise more than two channels, for example, at least 3, at least 4, at least 5, or at least 6 or more. Shorter channels may also be present, for example in the rear waist region 206 or the front waist region 205 of the core as represented by the pair of channels 227, 227' in FIG. 49 towards the front of the article. The channels may comprise one or more pairs of channels symmetrically arranged, or otherwise arranged relative to the longitudinal axis 280.

The channels may be particularly useful in the absorbent core when the absorbent material deposition area is rectangular, as the channels may improve the flexibility of the core to an extent that there is less advantage in using a non-rectangular (shaped) core. Of course channels may also be present in a layer of SAP having a shaped deposition area.

The channels may be completely oriented longitudinally and parallel to the longitudinal axis or completely oriented transversely and parallel to the lateral axis, but also may have at least portions that are curved.

In order to reduce the risk of fluid leakages, the longitudinal main channels may not extend up to any of the edges of the absorbent material deposition area 208, and may therefore be fully encompassed within the absorbent material deposition area 208 of the core. The smallest distance between a channel and the closest edge of the absorbent material deposition area 208 may be at least 5 mm.

The channels may have a width We along at least part of their length which is at least 2 mm, at least 3 mm, at least 4 mm, up to for example 20 mm, 16 mm, or 12 mm, for example. The width of the channel(s) may be constant through substantially the whole length of the channel or may vary along its length. When the channels are formed by absorbent material-free zone within the absorbent material deposition area 208, the width of the channels can be considered to be the width of the material free zone, disregarding the possible presence of the core wrap within the channels. If the channels are not formed by absorbent material free zones, for example mainly though bonding of the core wrap through the absorbent material zone, the width of the channels can be the width of this bonding.

At least some or all of the channels may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the upper side and lower side of the core wrap (e.g., the first substrate 216 and the second substrate 216') and/or the topsheet 224 to the backsheet 225 together through the channels. Typically, an adhesive may be used to bond both sides of the core wrap or the topsheet and the backsheet through the channels, but it is possible to bond via other known processes, such as pressure bonding, ultrasonic bonding, heat bonding, or combination thereof. The core wrap or the topsheet 224 and the backsheet 225 may be continuously bonded or intermittently bonded along the channels. The channels may advantageously remain or become visible at least through the topsheet and/or backsheet when the absorbent article is fully loaded with a fluid. This may be obtained by making the channels substantially free of SAP, so they will not swell, and sufficiently large so that they will not close when wet. Furthermore, bonding the core wrap to itself or the topsheet to the backsheet through the channels may be advantageous.

Barrier Leg Cuffs

The absorbent article may comprise a pair of barrier leg cuffs 234. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs can be delimited by a proximal edge 264 joined directly or indirectly to the topsheet 224 and/or the backsheet 225 and a free terminal edge 266, which is intended to contact and form a seal with the wearer's skin. The barrier leg cuffs 234 can extend at least partially between the front waist edge 210 and the rear waist edge 212 of the absorbent article on opposite sides of the longitudinal axis 280 and are at least present at the level of the crotch point (C) or crotch region. The barrier leg cuffs may be joined at the proximal edge 264 with the chassis of the article by a bond 265 which may be made by gluing, fusion bonding, or a combination of other suitable bonding processes. The bond 265 at the proximal edge 264 may be continuous or intermittent. The bond 265 closest to the raised section of the leg cuffs delimits the proximal edge 264 of the standing up section of the leg cuffs.

The barrier leg cuffs may be integral with the topsheet 224 or the backsheet 225 or may be a separate material joined to the article's chassis. Each barrier leg cuff 234 may comprise one, two or more elastic strings 235 close to the free terminal edge 266 to provide a better seal.

In addition to the barrier leg cuffs 234, the article may comprise gasketing cuffs 232, which are joined to the chassis of the absorbent article, in particular to the topsheet 224 and/or the backsheet 225 and are placed externally relative to the barrier leg cuffs. The gasketing cuffs 232 may provide a better seal around the thighs of the wearer. Each gasketing leg cuff may comprise one or more elastic strings or elastic elements 233 in the chassis of the absorbent article between the topsheet 224 and backsheet 225 in the area of the leg openings. All, or a portion of, the barrier leg cuffs and/or gasketing cuffs may be treated with a lotion or another skin care composition.

Acquisition-Distribution System

The absorbent articles of the present disclosure may comprise an acquisition-distribution layer or system 250 ("ADS"). One function of the ADS is to quickly acquire one or more of the fluids and distribute them to the absorbent core in an efficient manner. The ADS may comprise one, two or more layers, which may form a unitary layer or may remain as discrete layers which may be attached to each other. In an example, the ADS may comprise two layers: a distribution layer 254 and an acquisition layer 252 disposed between the absorbent core and the topsheet, but the present disclosure is not so limited.

In an example, the high loft, three-dimensional nonwoven materials of the present disclosure may comprise the topsheet and the acquisition layer as a laminate. A distribution layer may also be provided on the garment-facing side of the topsheet/acquisition layer laminate.

Carrier Layer

In an instance where the high loft, three-dimensional nonwoven materials of the present disclosure encompass a topsheet and acquisition layer laminate, the distribution layer may need to be supported by a carrier layer (not illustrated) that may comprise one or more nonwoven materials or other materials. The distribution layer may be applied to or positioned on the carrier layer. As such, the carrier layer may be positioned intermediate the acquisition layer and the distribution layer and be in a facing relationship with the acquisition layer and the distribution layer.

Distribution Layer

The distribution layer of the ADS may comprise at least 50% by weight of cross-linked cellulose fibers. The cross-linked cellulosic fibers may be crimped, twisted, or curled, or a combination thereof including crimped, twisted, and curled. This type of material is disclosed in U.S. Pub. No. 2008/0312622 A1 (Hundorf). The cross-linked cellulosic fibers provide higher resilience and therefore higher resistance to the first absorbent layer against the compression in the product packaging or in use conditions, e.g., under wearer weight. This may provide the core with a higher void volume, permeability, and liquid absorption, and hence reduced leakage and improved dryness.

The distribution layer comprising the cross-linked cellulose fibers of the present disclosure may comprise other fibers, but this layer may advantageously comprise at least 50%, or 60%, or 70%, or 80%, or 90%, or even up to 100%, by weight of the layer, of cross-linked cellulose fibers (including the cross-linking agents).

Acquisition Layer

If a three-dimensional nonwoven material of the present disclosure is provided as only the topsheet of an absorbent article, the ADS 250 may comprise an acquisition layer 252. The acquisition layer may be disposed between the distribution layer 254 and the topsheet 224. In such an instance, the acquisition layer 252 may be or may comprise a nonwoven material, such as a hydrophilic SMS or SMMS material, comprising a spunbonded, a melt-blown and a further spunbonded layer or alternatively a carded staple fiber chemical-bonded nonwoven. The nonwoven material may be latex bonded.

Fastening System

The absorbent article may comprise a fastening system. The fastening system may be used to provide lateral tensions about the circumference of the absorbent article to hold the absorbent article on the wearer as is typical for taped diapers. This fastening system may not be necessary for training pant articles since the waist region of these articles is already bonded. The fastening system may comprise a fastener such as tape tabs, hook and loop fastening components, interlocking fasteners such as tabs & slots, buckles, buttons, snaps, and/or hermaphroditic fastening components, although any other suitable fastening mechanisms are also within the scope of the present disclosure. A landing zone 244 is normally provided on the garment-facing surface of the front waist region 205 for the fastener to be releasably attached thereto.

Front and Rear Ears

The absorbent article may comprise front ears 246 and rear ears 240. The ears may be an integral part of the chassis, such as formed from the topsheet 224 and/or backsheet 226 as side panels. Alternatively, as represented on FIG. 49, the ears may be separate elements attached by gluing, heat embossing, and/or pressure bonding. The rear ears 240 may be stretchable to facilitate the attachment of the tabs 242 to the landing zone 244 and maintain the taped diapers in place around the wearer's waist. The rear ears 240 may also be elastic or extensible to provide a more comfortable and contouring fit by initially conformably fitting the absorbent article to the wearer and sustaining this fit throughout the time of wear well past when absorbent article has been loaded with fluids or other bodily exudates since the elasticized ears allow the sides of the absorbent article to expand and contract.

Elastic Waist Feature

The absorbent article 220 may also comprise at least one elastic waist feature (not represented) that helps to provide improved fit and containment. The elastic waist feature can be generally intended to elastically expand and contract to dynamically fit the wearer's waist. The elastic waist feature may extend at least longitudinally outwardly from at least one waist edge of the absorbent core 228 and can generally form at least a portion of the end edge of the absorbent article. Disposable diapers may be constructed so as to have two elastic waist features, one positioned in the front waist region and one positioned in the rear waist region.

Color Signals

In a form, the absorbent articles of the present disclosure may have different colors in different layers, or portions thereof (e.g., the topsheet and the acquisition layer, the topsheet and the nonwoven core cover, a first portion and a second portion of a topsheet, a first portion and second portion of the acquisition layer). The different colors may be shade of the same color (e.g., dark blue and light blue) or may be actual different colors (e.g., purple and green). The different colors may have a Delta E in the range of about 1.5 to about 10, about 2 to about 8, or about 2 to about 6, for example. Other Delta E ranges are also within the scope of the present disclosure.

In an instance, various layers of the absorbent articles may be joined using a colored adhesive. The colored adhesive may be laid down on any suitable layer or layers in a pattern. The pattern of the adhesive may or may not complement the pattern of the topsheet. Such a pattern may increase the appearance of depth in an absorbent article. In certain instances, the colored adhesive may be blue.

In other instances, any of the layers may comprise indicia, such as a printed ink to aid in the appearance, depth impression, absorbency impression, or quality impression of the absorbent articles.

In other instances, the colors may be complimentary, or registered with, the patterns of three-dimensional features of the nonwoven fabric 10 utilized as a component in an absorbent article. For example, a fabric having first and second zones of visually distinct patterns of three-dimensional features may also have printed thereon color to emphasize, highlight, contrast with, or otherwise change the visual appearance of the nonwoven fabric 10. The color enhancements can be beneficial in communicating to a user of an absorbent article certain functional characteristics of the nonwoven fabric 10 when in use. Thus, color can be used in combination with structural, three-dimensional features in one component, or in combinations of components to deliver a visually distinctive absorbent article. For example, a secondary topsheet or acquisition layer may have printed thereon a pattern of color or colors that compliments the pattern of three-dimensional features of a nonwoven fabric 10 utilized as a topsheet in an absorbent article. Another example is an absorbent article comprising 1) an absorbent core comprising a channel, 2) a topsheet with a three dimensional pattern registered or highlighting the channel or channels in the core, and 3) a graphic, colored component, printed ink, or indicia visible from the topsheet viewing (body contacting surface) or the backsheet viewing surface (garment facing surface) to further emphasize the functional features of the core channel or channels and the overall performance of the absorbent article.

Further characterization of the novel aspects of the present disclosure can be realized by focusing on the three-dimensional features within a visually discernible zone. Each zone, such as Zones 110, 120, and 130, discussed above, can be described further with respect to microzones. As described above, a microzone is a portion of the nonwoven fabric 10 within a zone, that can have at least two visually discernible regions where there can be a common intensive property difference between these two regions. A microzone may comprise a portion of the nonwoven fabric 10 which can cross two or more zone boundaries that has at least two visually discernible regions and there is a common intensive property difference between these two regions The benefit of considering microzones in the present disclosure is to illustrate that in addition to differences in average intensive properties with a zone, such as zones 110, 120, and 130, as discussed above, the present disclosure also provides for fabrics having differences in actual and/or average intensive properties between regions defined by the three-dimensional features within a zone, with the three-dimensional features precisely placed according to the design of the forming belt used to produce the fabrics. The difference between intensive properties between regions of the three-dimensional features provides for additional visual as well as functional benefits. The sharp visual contrast between regions can provide for extremely fine visually distinctive designs within a zone and between zones. Likewise, the precise placement of regions afforded by the precisely manufactured forming belt can provide for excellent and tailored softness, strength, and fluid handling properties of the zones. Thus, in an example, the present disclosure provides for the unexpected combination of differences in average intensive properties between zones and simultaneously differences in intensive properties of the regions making up a microzone.

Figure 59:
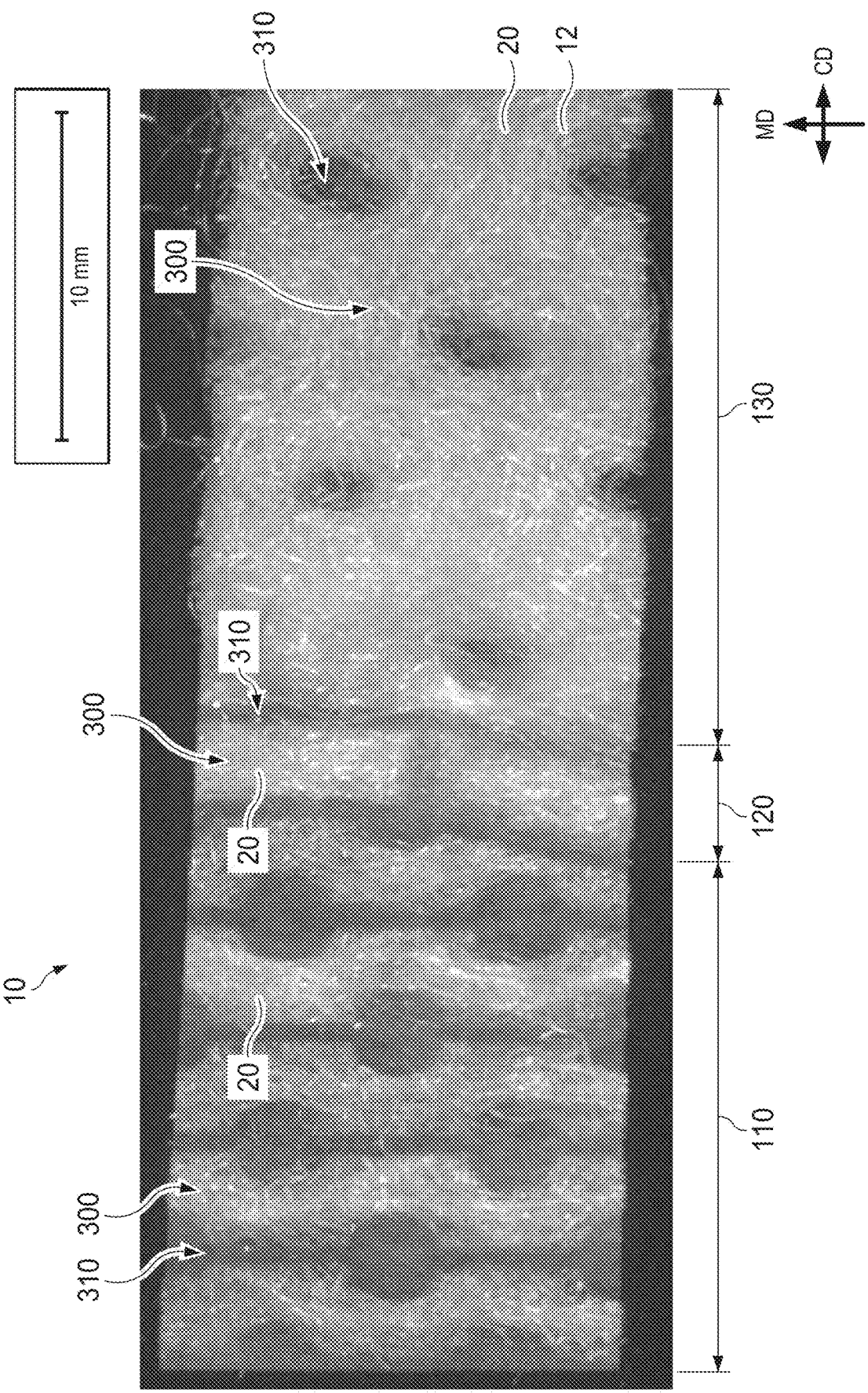
FIG. 59 is a photographic image of an example of a nonwoven fabric of the present disclosure.
Figure 60:
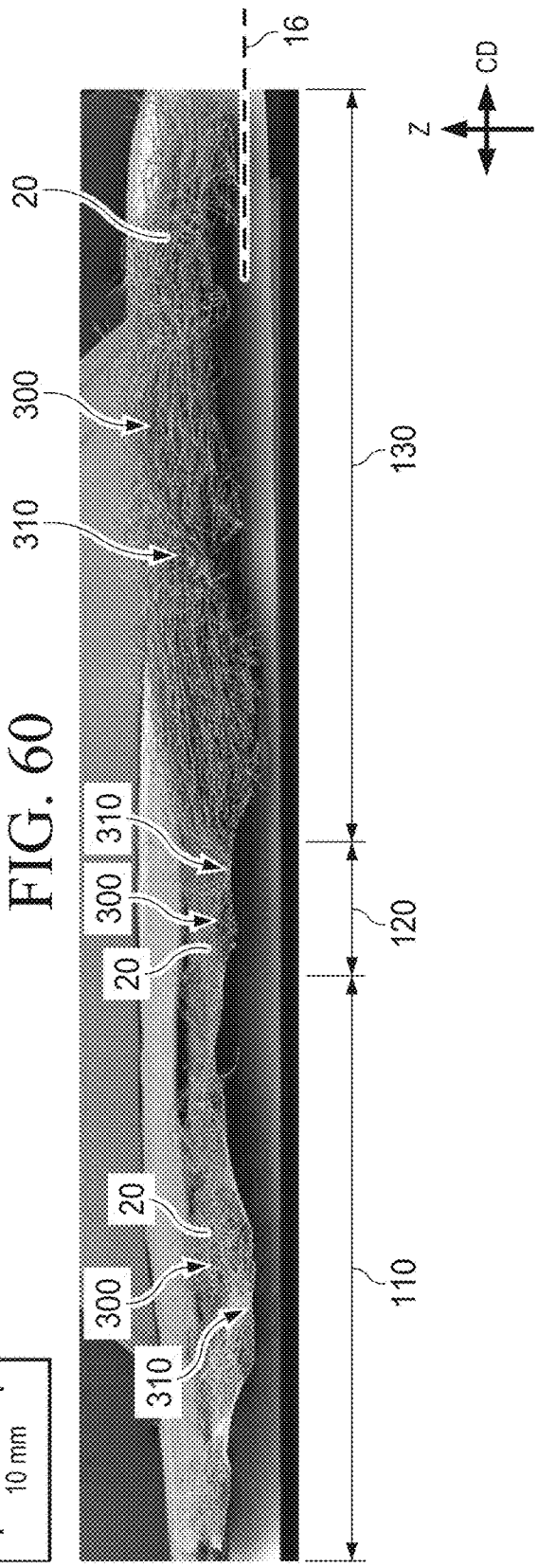
FIG. 60 is a photographic image of cross-section of the example shown in FIG. 59.

Regions defined by three-dimensional features can be understood with reference to FIG. 59 and FIG. 60. FIG. 59 shows a light microscope image of a portion of a fabric 10 according to the present disclosure, and FIG. 60 is a scanning electron micrograph (SEM) of a cross-section of the portion of the fabric shown in FIG. 59. Thus, FIGS. 59 and 60 show a portion of a nonwoven fabric 10 magnified for more precise description of the otherwise visually discernible features of the fabric. The portion of the nonwoven fabric 10 shown in FIG. 59 is approximately 36 mm in the CD and exhibits portions of at least three visually distinct zones as discussed below.

In FIGS. 59 and 60, which show a portion of one pattern of a nonwoven fabric 10, a first zone 110 (on the left side of FIG. 50) is characterized by generally MD-oriented rows of variable width first regions 300 separated by MD-oriented rows of variable width second regions 310. The first region is also the three-dimensional feature 20 that defines the first and second regions 300, 310. In an example, a three-dimensional feature is a portion of the nonwoven fabric 10 that was formed between or around a raised element of the forming belt, which in this description is the first region 300, such that the resulting structure has a relatively greater dimension in the Z-direction. The adjacent second region 310 generally has a common intensive property with first region 300, and in an example, has relatively lower thickness values, i.e., lesser dimension in the Z-direction. The relative dimensions in the Z direction with respect to a plane of the first surface 16 as described above, can be seen in FIG. 51. Absolute dimensions are not critical; but the dimensional differences can be visually discernible on the nonwoven fabric 10 without magnification.

The present disclosure permits beneficial characteristics best expressed with respect to the regions defined by three-dimensional features in microzones. For example, as shown in FIG. 59, in the first zone 110 for each three dimensional features 20 there is a visible distinction between a first region 300 and a second region 310. As stated above, the visible distinction can exist in the nonwoven fabric 10 without magnification; the magnified views used herein are for purposes of clear disclosure. Any area that extends across the boundary between enough of first region 300 and second region 310 such that a difference in their respective intensive properties can be ascertained within the area can be a microzone. Additionally, light microscopy or Micro-CT imagery of a structure can also be used to establish the location of regions and the area of a microzone.

The portion of nonwoven fabric 10 shown in FIG. 59 further illustrates another beneficial characteristic of the nonwoven fabric 10, in that the differences in intensive properties between adjacent regions can be differences across zones. Thus, a microzone that spans an area encompassing second region 310 of zone 120 and first region 300 of the third zone 130 can be identified. In certain examples, including in the nonwoven fabric 10 shown in FIGS. 59 and 60, the difference in intensive properties exhibited by regions in microzones that a zone boundary can be significantly different in magnitude than the differences between intensive properties exhibited by regions within a zone.

Regardless of which zone, or which zonal boundary a particular microzone encompasses, the three-dimensional features can be characterized by the differences between intensive properties of the regions defined by them. In general, the nonwoven of the present disclosure can be a spunbond nonwoven fabric having a first surface defining a plane of the first surface. The fabric can comprise a plurality of three-dimensional features, each three dimensional feature defining a first region and a second region, the regions having a common intensive property that has a different value between them. In an example, the first region can be distinguished as being at a higher elevation than the second region with respect to the plane of the first surface, hence exhibiting a difference in each region's common intensive property of thickness. The two regions can also be distinguished as having different densities, basis weights, and volumetric densities. That is, the two regions can be distinguished within a micro zone of the spunbond nonwoven fabric as being different with respect to common intensive properties, including properties such as thickness, density, basis weight, and volumetric density. In an example, one or both regions of a microzone can be fluid permeable. In an example, the higher density region of a microzone can be fluid permeable.

Within the first zone 110 of the portion of fabric shown in FIG. 59, for example, there can be three-dimensional features 20 defining at least two regions, a first region 300 and a second region 310. The difference in thickness, basis weight, and volumetric density between the first and second regions for the first zone 110 shown in FIG. 59 can be 274 microns, 1 gsm, and 0.437 g/cc, respectively.

Likewise, within the third zone 130 of the portion of fabric shown in FIG. 59, for example, there can be three-dimensional features 20 defining at least two regions, a first region 300 and a second region 310. The difference in thickness, basis weight, and volumetric density between the first and second regions for the third zone 130 shown in FIG. 59 can be 2083 microns, 116 gsm, and 0.462 g/cc, respectively.

Additionally, within the second zone 120 of the portion of fabric shown in FIG. 59, for example, there can be three-dimensional features 20 defining at least two regions, a first region 300 and a second region 310. The difference in thickness, basis weight, volumetric density between the first and second regions for the portion of fabric shown in FIG. 59 can be 204 microns, 20 gsm, 0.53 g/cc, respectively. In the example shown, the second zone 120 forms what appears in an unmagnified view of nonwoven fabric 10 to be a stitched boundary between the first and third zones 110, 130.

Further, a zone that encompasses the boundary between the second and third zones 120, 130 of the portion of fabric shown in FIG. 59, for example, there are at least two regions, a first region 300 in the third zone 130 and a second region 310 in the second zone 120. The difference in thickness, basis weight, and volumetric density between the first and second regions for the portion of fabric shown in FIG. 59 can be 2027 microns, 58 gsm, and 0.525 g/cc, respectively.

Figure 63:
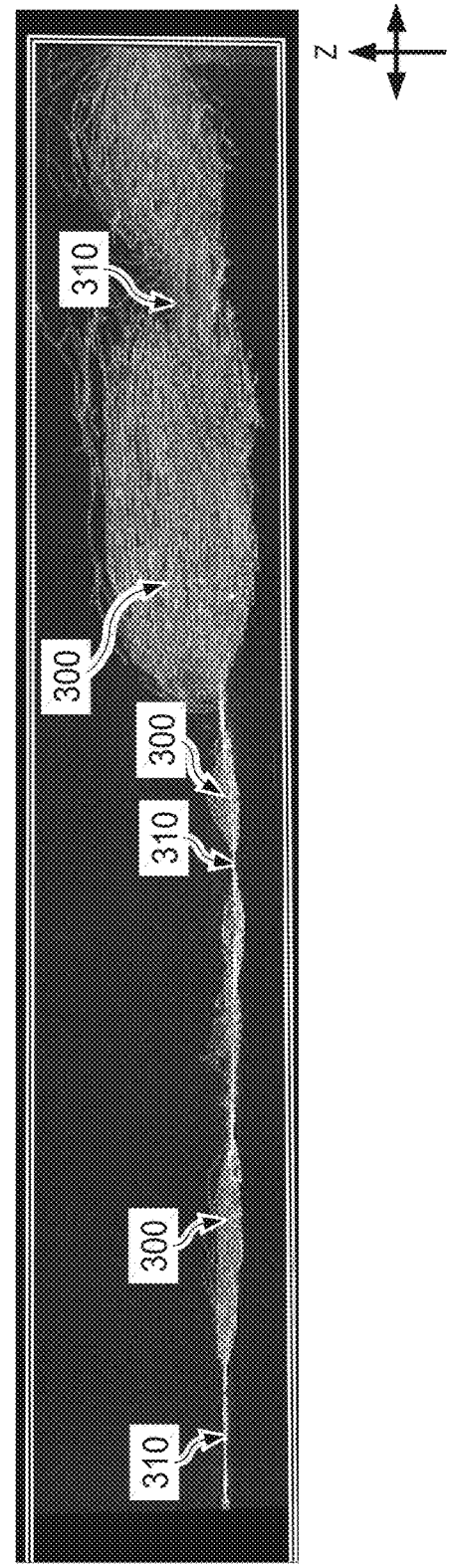
FIG. 63 is a Micro CT image of a cross-section of the example shown in FIGS. 61 and 62.

Microzones are discussed in more detail with reference to FIGS. 61-63 and the data depicted in FIG. 65. FIGS. 61-63 are Micro-CT scans of a portion of a nonwoven fabric 10 similar in pattern to that of the nonwoven fabric 10 shown in FIG. 59. The Micro-CT scan permits description of the same features as shown in FIG. 59 in a slightly different manner and in a way that permits very precise measurement of intensive properties.

As shown in FIG. 61, zones 110, 120, and 130 are clearly visible, with their respective three-dimensional features 20. As depicted in FIGS. 61 and 62, the three-dimensional features are the dark-colored portions, with the dark color also representing the first region 300 of a three-dimensional feature 20, and the adjacent light-colored portions being the second region 310 for the three-dimensional feature 20.

The Micro-CT scan permits the image to be "cut" and cross-sectioned, as shown by the cut plane 450 in FIG. 62. A cut plane can be placed anywhere on the image; for the purposes of the present disclosure, the cut plane 450 cuts a cross section substantially parallel to the Z axis so as to produce the cross-sectional image in FIG. 63.

The Micro-CT technology permits intensive properties to be precisely and directly measured. Thickness measurements can be made directly from imaged cross sections based on the scale magnification, such as the cross section shown in FIG. 63. Further, the color differential between first regions and second regions is representative and proportional to differences in basis weight, volumetric density, and other intensive properties, which can likewise be directly measured. Micro-CT methodology is explained below in the Test Methods section.

Figure 64:
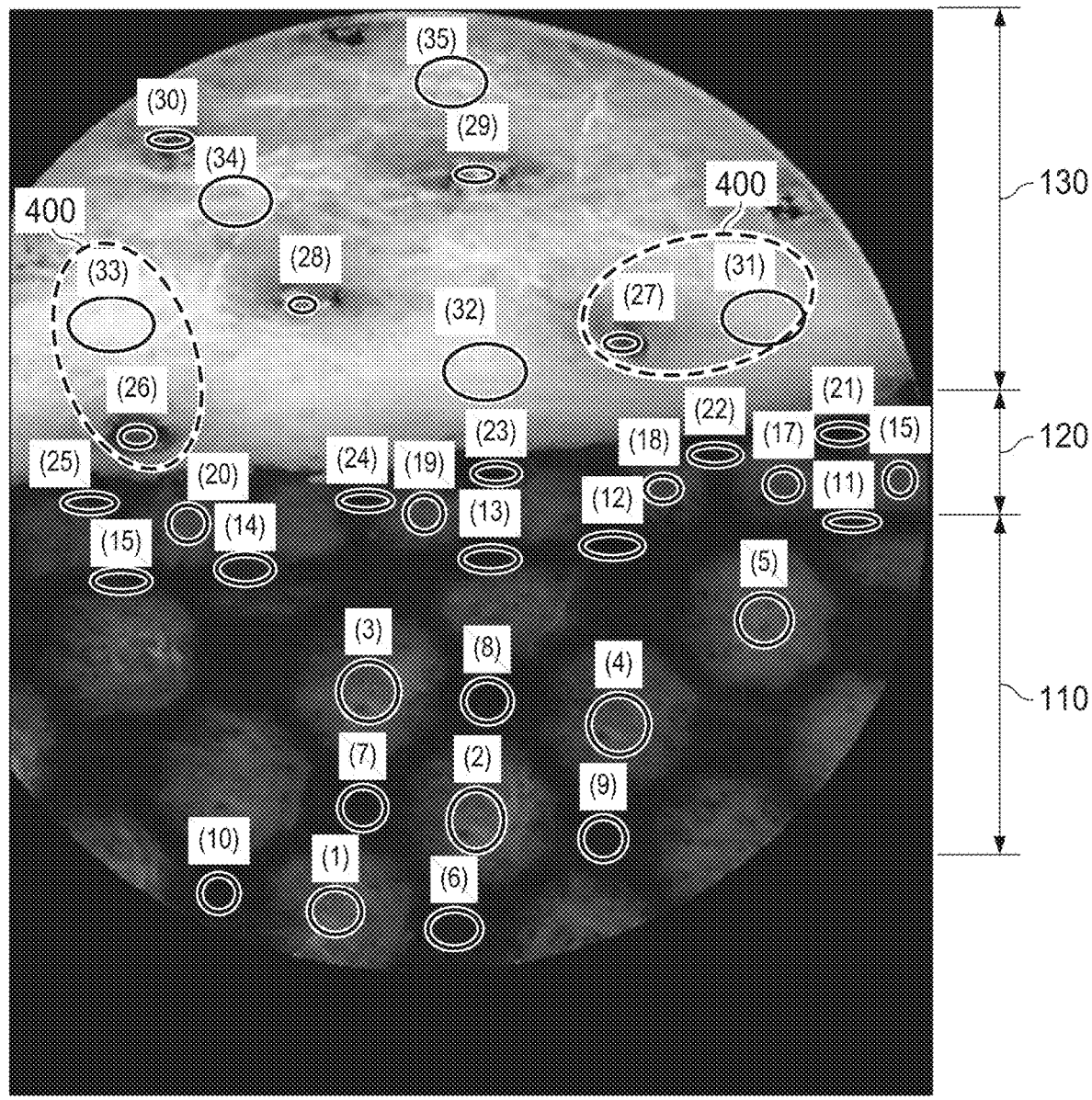
FIG. 64 is a Micro CT plan view image of the example shown in FIGS. 61 and 62.

FIG. 64 is a Micro-CT scan image of the portion of nonwoven fabric 10 shown in FIGS. 61 and 63. Utilizing specific first and second regions shown as numbered portions of the nonwoven fabric 10 can then be analyzed. In FIG. 64, specific regions were manually selected and analyzed to measure thickness, basis weight, and volumetric density, and the data is produced in FIG. 65.

Figure 65:
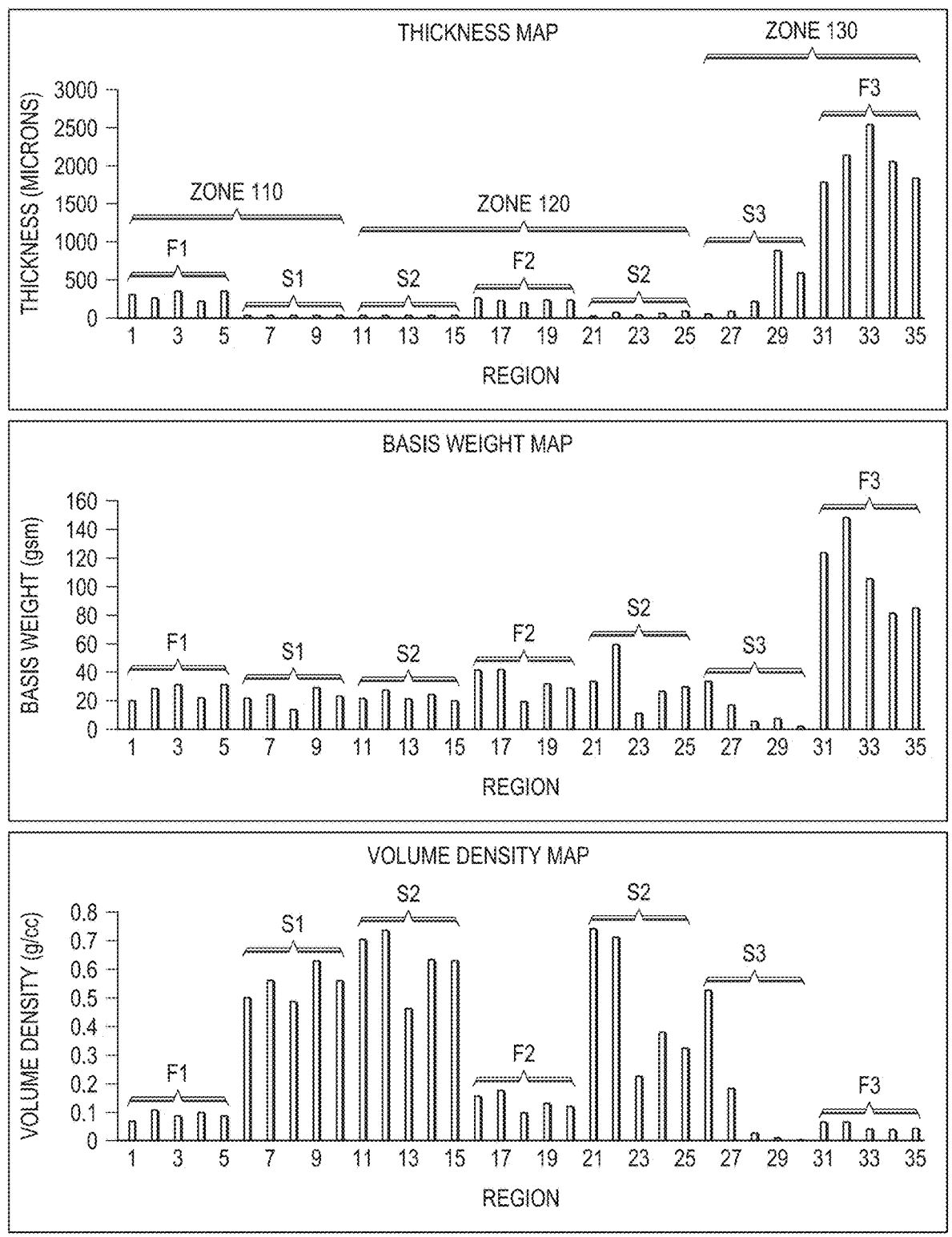
FIG. 65 is a graphical depiction of various benefits of the present disclosure.

FIG. 65 shows data for groupings of first and second region measurements made within the three zones depicted in FIG. 65. The x-axis is the regions, with the numbers corresponding to the numbered regions on FIG. 64. First region measurements are labeled as Fn (e.g., F1) and second regions measurements are labeled as Sn (e.g., S1). Thus, regions 1-5 are first regions F1, each being in the first zone 110. Regions 6-10 are second regions S1, also being in the first zone 110. Likewise, first regions F2 are regions 16-20 in the second zone 120, and regions 11-15 and 21-25 are second regions S2 in the second zone 120. Finally, regions 31-35 are first regions F3 in the third zone 130 and regions 26-30 are second regions S2 in the third zone 130. The numbered regions are consistently depicted across all three graphs of FIG. 56, but for simplicity, the zones 110, 120, and 130 are depicted only on the Thickness Map.

The graphs shown in FIG. 65 represent graphically the magnitude of difference in intensive properties between first regions and second regions within any one of the zones, and can be used to see graphically the difference in intensive properties for pairs of regions making up a microzone. For example, one can see that in the first zone 110 that basis weight between the two regions can be substantially the same, but the thickness (caliper) can vary from about 400 microns in the first regions to about 40 microns in the second regions, or about a 10× differential. The volumetric density in the first zone 110 can vary from about 0.1 g/cc to about 0.6 g/cc. Similar quantifiable distinctions can be understood for each of the zones shown.

Thus, with reference to FIG. 64 and FIG. 65 together, further characterization of the beneficial structure of a nonwoven fabric 10 of the present disclosure can be understood. The nonwoven fabric 10 can be described as having at least two visually distinct zones, e.g., first and second zones 110, 120, with each of the zones having a pattern of three-dimensional features, each of the three-dimensional features defining a microzone comprising first and second regions, e.g., regions 300, 310, and wherein the difference in values for at least one of the microzones in the first zone 110 is quantifiably different from the difference in values for at least one of the microzones in the second zone 120. For example, in FIG. 64, two representative microzones 400 in the third zone 130 are designated as the pair of regions marked as areas 31 and 27 and 33 and 26. That is, first region 31 and second region 27 form a microzone, and first region 33 and second region 26 form a microzone. Likewise, two representative microzones 400 in the second zone 120 are designated as the pair of regions marked as areas 19 and 24 and 17 and 22. From FIG. 65, Tables 4-7 can be populated as shown:

TABLE 4

Illustrative examples of differences in thickness in microzones

| | | | Thickness (microns) | Difference in Thickness (microns) |
|---|---|---|---|---|
| Zone 130 | Microzone 1 | First Region 31 | 1802 | 1709 |
| | | Second Region 27 | 93 | |
| | Microzone 2 | First Region 33 | 2548 | 2484 |
| | | Second Region 26 | 64 | |
| Zone 120 | Microzone 1 | First Region 19 | 242 | 172 |
| | | Second Region 24 | 70 | |

TABLE 4-continued

Illustrative examples of differences in thickness in microzones

| | | | Thickness (microns) | Difference in Thickness (microns) |
|---|---|---|---|---|
| | Microzone 2 | First Region 17 | 235 | 183 |
| | | Second Region 23 | 52 | |

TABLE 5

Illustrative examples of differences in basis weight in microzones

| | | | Basis weights (gsm) | Difference in Basis weights (gsm) |
|---|---|---|---|---|
| Zone 130 | Microzone 1 | First Region 31 | 124 | 107 |
| | | Second Region 27 | 17 | |
| | Microzone 2 | First Region 33 | 106 | 72 |
| | | Second Region 26 | 34 | |
| Zone 120 | Microzone 1 | First Region 19 | 32 | 5 |
| | | Second Region 24 | 27 | |
| | Microzone 2 | First Region 17 | 42 | 30 |
| | | Second Region 23 | 12 | |

TABLE 6

Illustrative examples of differences in volumetric density in microzones

| | | | Volumetric Density (g/cc) | Difference in Volumetric Density (g/cc) |
|---|---|---|---|---|
| Zone 130 | Microzone 1 | First Region 31 | 0.069 | 0.116 |
| | | Second Region 27 | 0.185 | |
| | Microzone 2 | First Region 33 | 0.041 | 0.49 |
| | | Second Region 26 | 0.531 | |
| Zone 120 | Microzone 1 | First Region 19 | 0.133 | 0.251 |
| | | Second Region 24 | 0.384 | |
| | Microzone 2 | First Region 17 | 0.185 | 0.044 |
| | | Second Region 23 | 0.229 | |

TABLE 7

Illustrative examples of differences in intensive properties within different zones:

| | Thickness (Microns) | Thickness Differences | Basis Weights (gsm) | Basis Weights Differences | Volumetric Density (g/cc) | Volumetric Density Differences |
|---|---|---|---|---|---|---|
| Zone 130 First Region 32 | 2147 | 2118 | 149 | 135 | 0.069 | 0.423 |

TABLE 7-continued

Illustrative examples of differences in intensive properties within different zones:

| | Thickness (Microns) | Thickness Differences | Basis Weights (gsm) | Basis Weights Differences | Volumetric Density (g/cc) | Volumetric Density Differences |
|---|---|---|---|---|---|---|
| Zone 110 Second Region 8 | 29 | | 14 | | 0.492 | |

The four representative microzones from two zones are shown in Tables 4-6 for illustration. But as can be understood, each pair of first and second regions in FIG. 64 could likewise be quantified to further populate additional rows in Table 4, but for purposes of conciseness are not. In general, for any fabric having two or more zones, each zone having a pattern of three-dimensional features defining microzones, the intensive properties can be measured and tabulated as illustrated herein with reference to FIGS. 64 and 65 to understand both the difference in values for intensive properties within a zone, and differences in values of intensive properties between one region in first zone to another region in a second zone.

A microzone spanning two zones, such as the first and third zones 110, 130, can have an even greater difference in intensive properties relative to a microzone within a single zone. For example, viewing the data for a microzone spanning a first region of the third zone 130, for example at first region 32, and a second region of the first zone 110, for example at second region 8, the microzone exhibits dramatic differences in all of thickness, basis weight and volumetric density. The thickness of first region 32 of the third zone 130 is about 2100 microns, while the thickness of second region 8 of the first zone 110 is about 29 microns, or about a 72× differential. Likewise, the basis weight of first region 32 of the third zone 130 can be as high as 150 gsm, while the basis weight of second region 8 of the first zone 110 can be about 14 gsm, or about a 10× differential. Further, the volumetric density of first region 32 of the third zone 130 can be about 0.069 g/cc, while the volumetric density of second region 8 of the first zone 110 can be 0.492 g/cc, or about a 7× differential.

For each of the measured intensive property parameters of the various regions of a microzone, such a measurement is done using the Micro-CT method described herein. The resolution of the method supports establishing the intensive properties of microzone regions so differences and ratios comparisons of regions as described herein can be dimensioned.

Figure 66:
FIG. 66 is a photographic image of a portion of an example of a nonwoven fabric of the present disclosure.
Figure 67:
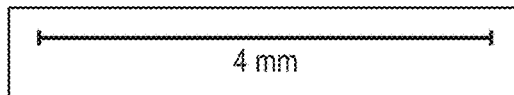
FIG. 67 is a photographic image of a portion of an example of a nonwoven fabric of the present disclosure.
Figure 68:
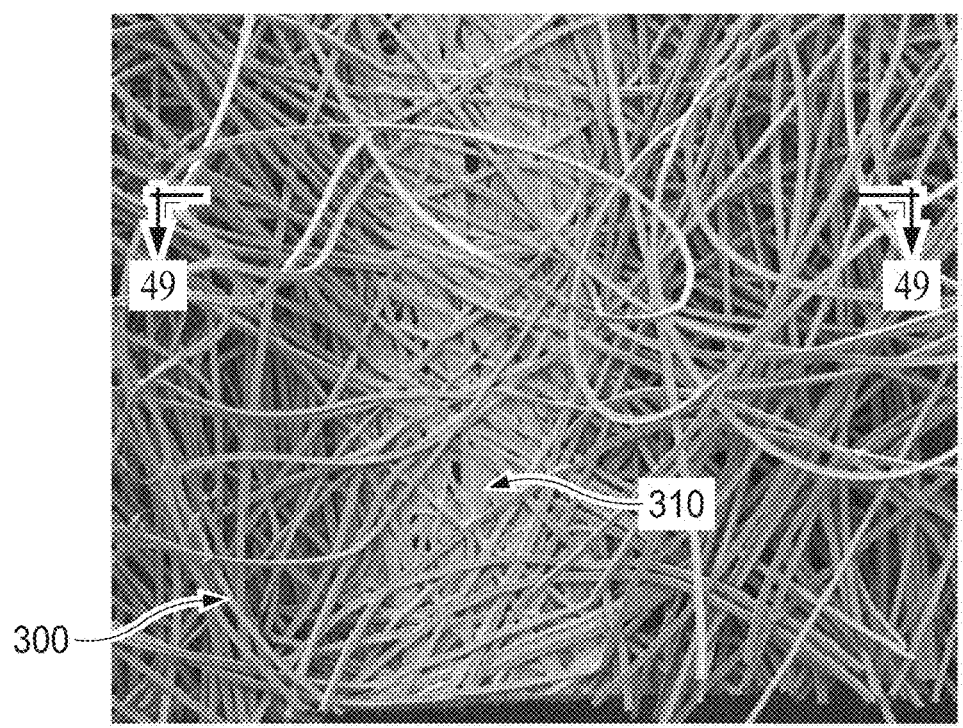
FIG. 68 is a photographic image of a portion of an example of a nonwoven fabric of the present disclosure.

Further characterization of a nonwoven fabric 10 can be made with reference to FIGS. 66-70, which are SEMs showing in greater detail certain aspects of the nonwoven fabric 10 and regions therein. FIGS. 66-70 are photographs of magnified portions of the first zone 110 of the fabric shown in FIG. 59. The nonwoven fabric 10 shown in FIG. 59 was made according to the process described above with reference to FIG. 10 in which the fabric was processed through a nip formed by compaction rolls 70 and 72, with roll 72 which contacts first side 12 being heated to cause partial bonding of fibers in the second regions 301. FIGS. 66 (facing the belt) and 67 (facing the heated compaction roll) are SEMs of a portion of the second surface 14 and first surface 12, respectively, magnified to 20×. FIGS. 68 (facing the belt) and 69 (facing the heated compaction roll) are photographs of a portion of the second surface 14 and first surface 12, respectively, magnified to 90×, and show in detail the beneficial structural characteristic of the partial bonding of fibers formed by compaction rolls 70 and 72.

Figure 69:
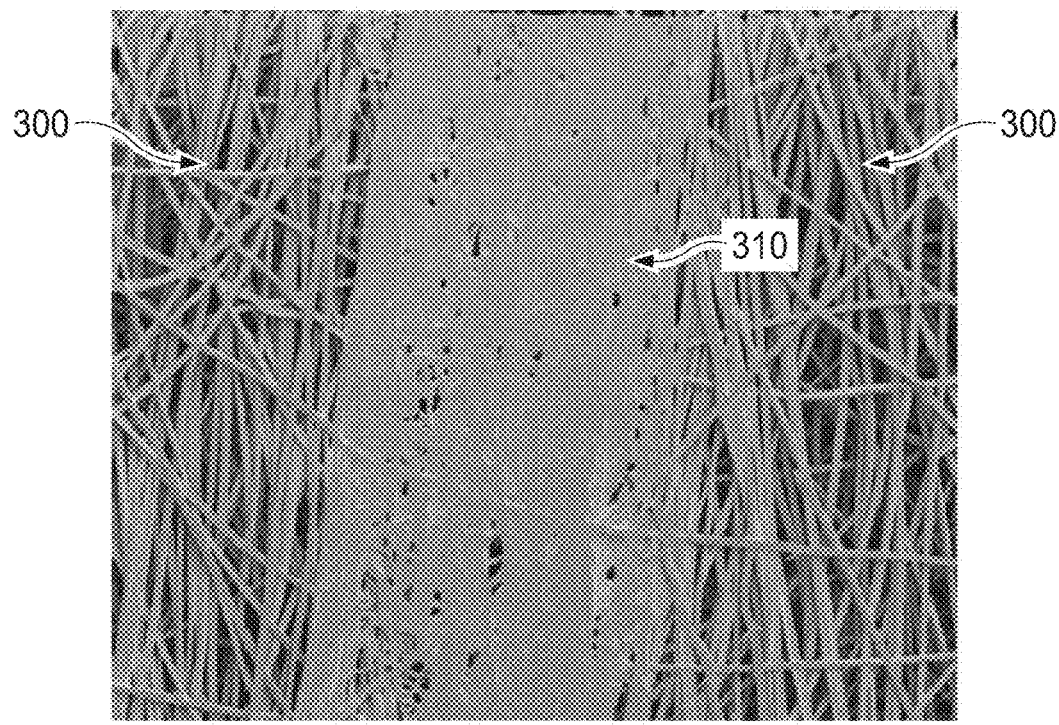
FIG. 69 is a photographic image of a portion of an example of a nonwoven fabric of the present disclosure.
Figure 70:
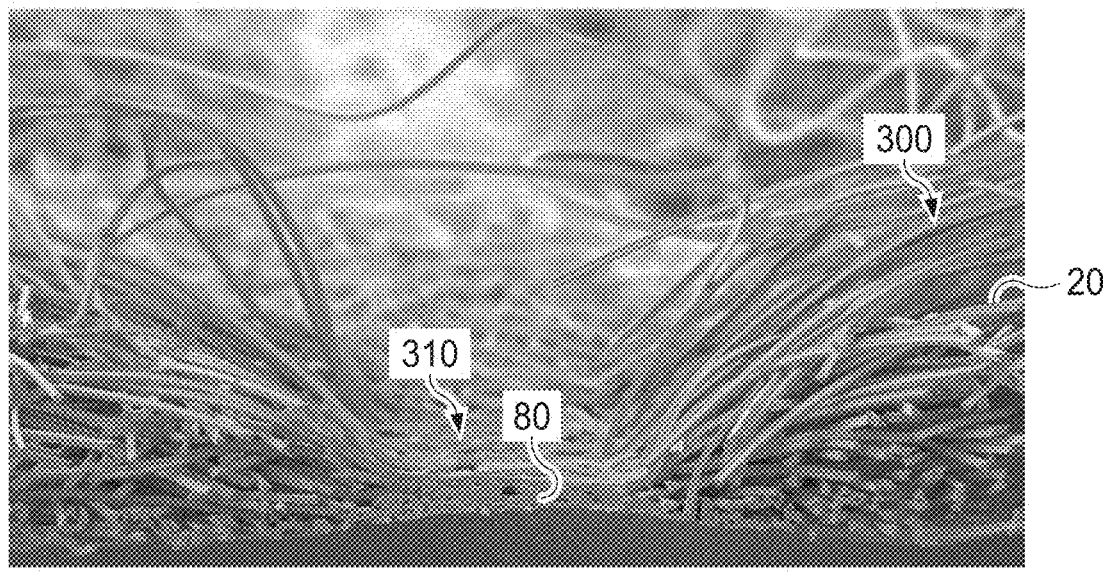
FIG. 70 is a photographic image of a cross-section of the example shown in FIGS. 68 and 69.
Figure 71:
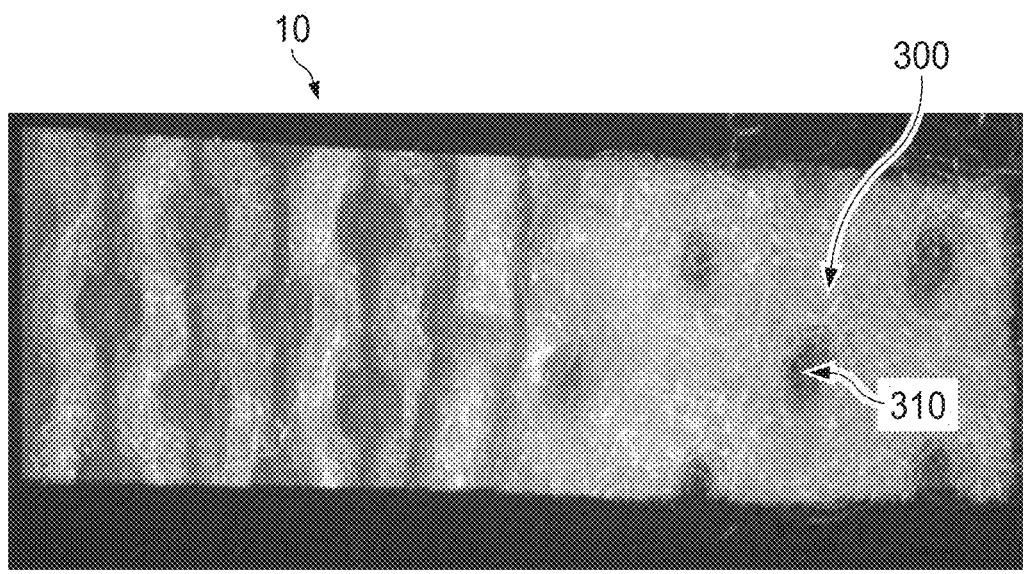
FIG. 71 is a photographic image of a portion of an example of a nonwoven fabric of the present disclosure.

As can best be seen in FIGS. 68 and 69, as well as the cross sectional view of FIG. 70, the heated compaction rolls can cause thermal bonding of fibers to different degrees with a beneficial effect on the overall nonwoven fabric 10. As shown, the fibers in contact with a heated roll, e.g., roll 70 in contact with first surface 12 of nonwoven fabric 10, can be melt bonded such that the first surface 12 experiences relatively greater fiber-to-fiber bonding than does the second surface 14. In an example, the bonded fibers 80 of the first surface can be substantially completely melt bonded to form, in effect, a film skin of bonded fibers, while the fibers in the second region 310 on the second side 14 can experience little to no bonding. This feature permits a nonwoven fabric 10 for use in a disposable absorbent article, e.g., as a topsheet, to maintain physical integrity during manufacture and use, as well as relative softness on one side, which can be the user-facing, skin-contacting side.

Even in the microzones with the greatest thickness differential, this "bond skinning" effect serves the purpose of maintaining web integrity, while not significantly impacting softness, or other beneficial properties such as fluid handling properties. As can be understood with reference to FIGS. 71-74, the differential in the extent of thermal bonding of fibers can be such that fibers on the first surface 12 at a second region 310 can be complete, or substantially complete, while the extent of thermal bonding of fibers on the second surface 14 at a first region 300 can be minimal, to no thermal bonding.

Figure 72:
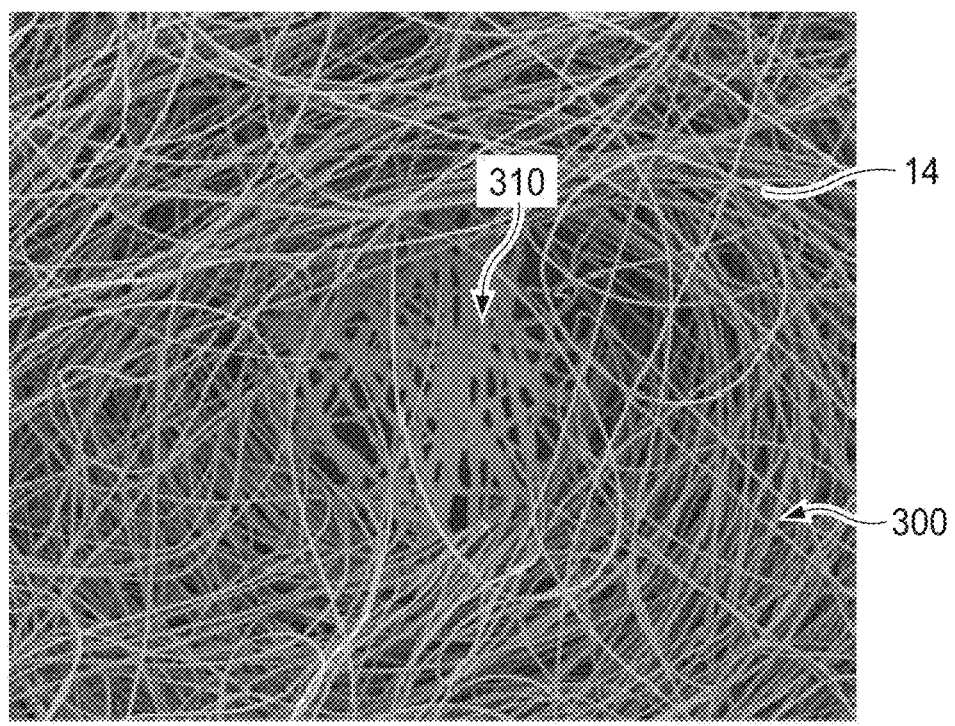
FIG. 72 is a photographic image of a portion of an example of a nonwoven fabric of the present disclosure.
Figure 73:
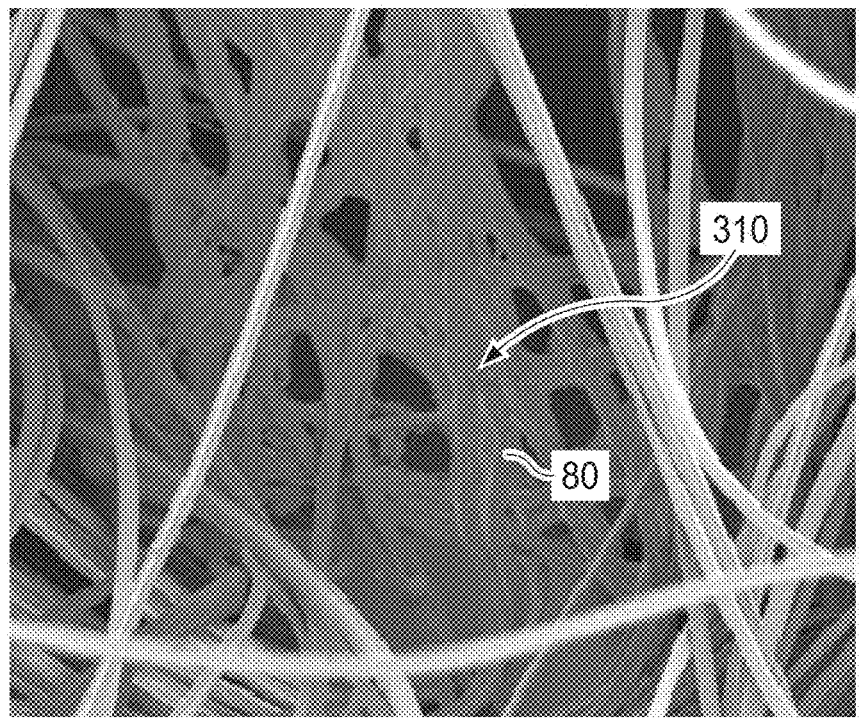
FIG. 73 is a photographic image of a portion of an example of a nonwoven fabric of the present disclosure.
Figure 74:
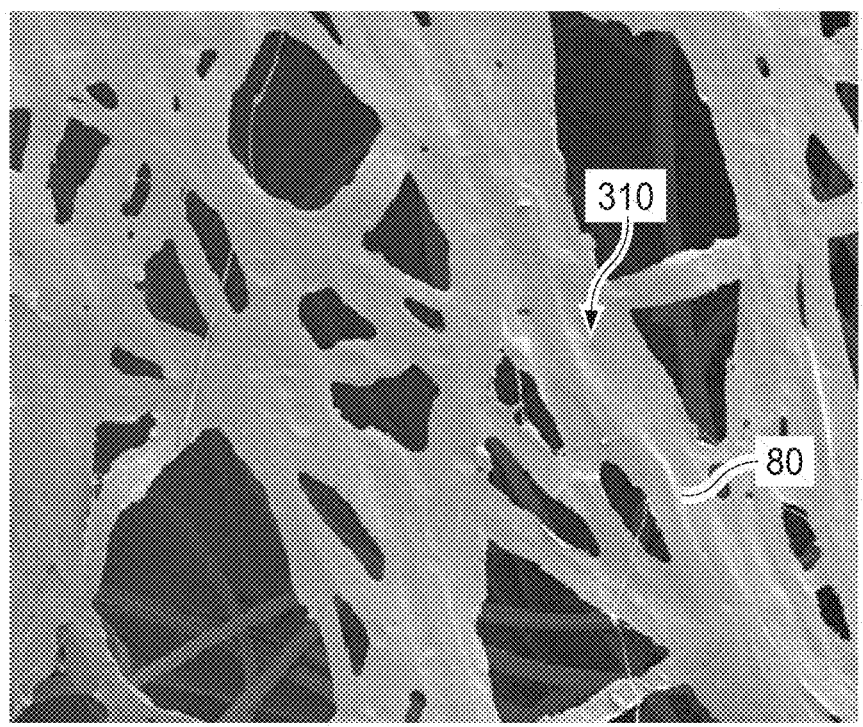
FIG. 74 is a photographic image of a portion of an example of a nonwoven fabric of the present disclosure.

FIG. 71 shows again the portion of nonwoven fabric 10 shown in FIG. 59. FIGS. 72-74 show magnified images of one microzone, indicated in FIG. 61 as a first region 300 and second region 310, which visually appears to be a hole or an aperture. FIGS. 72 and 73 show the microzone as it appears on the second surface 14 magnified to 40× and 200×, respectively. FIG. 74 shows the second region 310 as it appears on the first side 12 under 200× magnification. Fibers in the second region 310 are completely, or substantially completely bonded, while fibers in the first region 300 are completely, or substantially completely unbonded. The benefit of the illustrated structure is that a microzone can function as a fluid pervious aperture, while the bonded regions of the second region 310 simultaneously functioning to maintain physical integrity of the nonwoven fabric 10.

Microzones, therefore, play a significant role in the overall physical structure and functioning of a nonwoven fabric 10 of the present disclosure. Producing relatively closely spaced, precisely designed three-dimensional features, enabled by the forming belt of the present disclosure, a nonwoven fabric 10 can exhibit visually distinct zones, microzones, and three-dimensional features that provide for functional superiority in the areas of, at least, softness and fluid handling, as well as visually attractive aesthetic designs. The potential difference in physical properties of the first and second surfaces permits the nonwoven fabric 10 to be designed for both strength and softness, both form and function.

Figure 75:
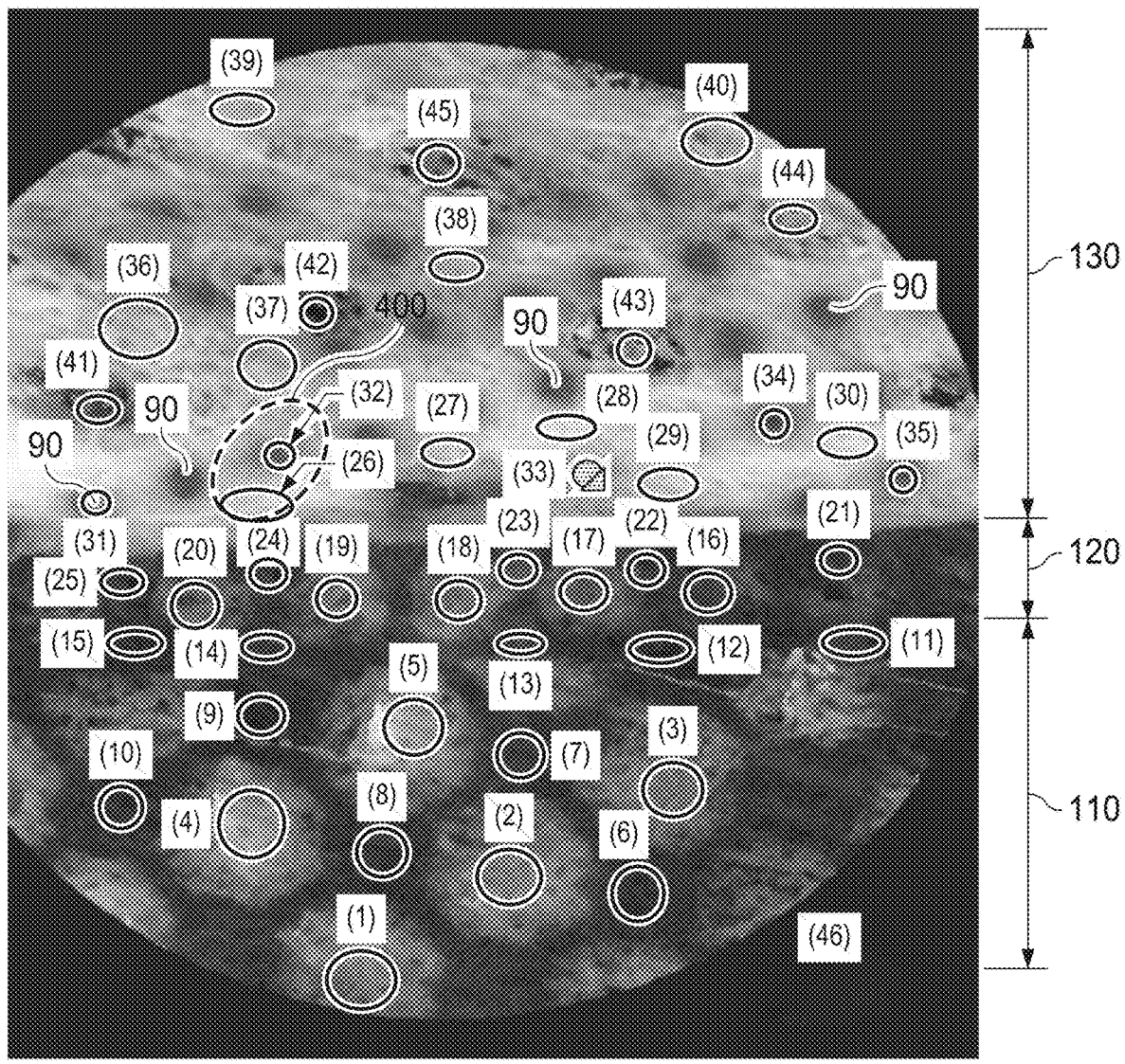
FIG. 75 is a Micro CT plan view image of the example shown in FIGS. 61 and 62 after experiencing additional processing.

FIG. 75 is a Micro-CT scan image of the portion of nonwoven fabric 10 similar to that shown in FIGS. 61 and 62, but having been subjected to the additional processing step of forming point bonds 90 in the nip of calendar rollers 71 and 73. As above, with respect to the discussion of FIGS. 64 and 65, for specific point bond microzones 400 first and second regions shown as numbered portions of the nonwoven fabric 10 can be analyzed, and comprise regions of point bonds, specifically in the numbered areas 31-35. For example, adjacent regions 32 and 26 form a microzone 400 in the third zone 130. In FIG. 75, the specific regions were visually discerned to identify regions including the added point bond regions and analyzed to measure thickness, basis weight, and volumetric density, and the data is produced in FIG. 76, where the thickness, basis weight and volumetric density of all the regions, including the point bond regions are quantified and compared.

Figure 76:
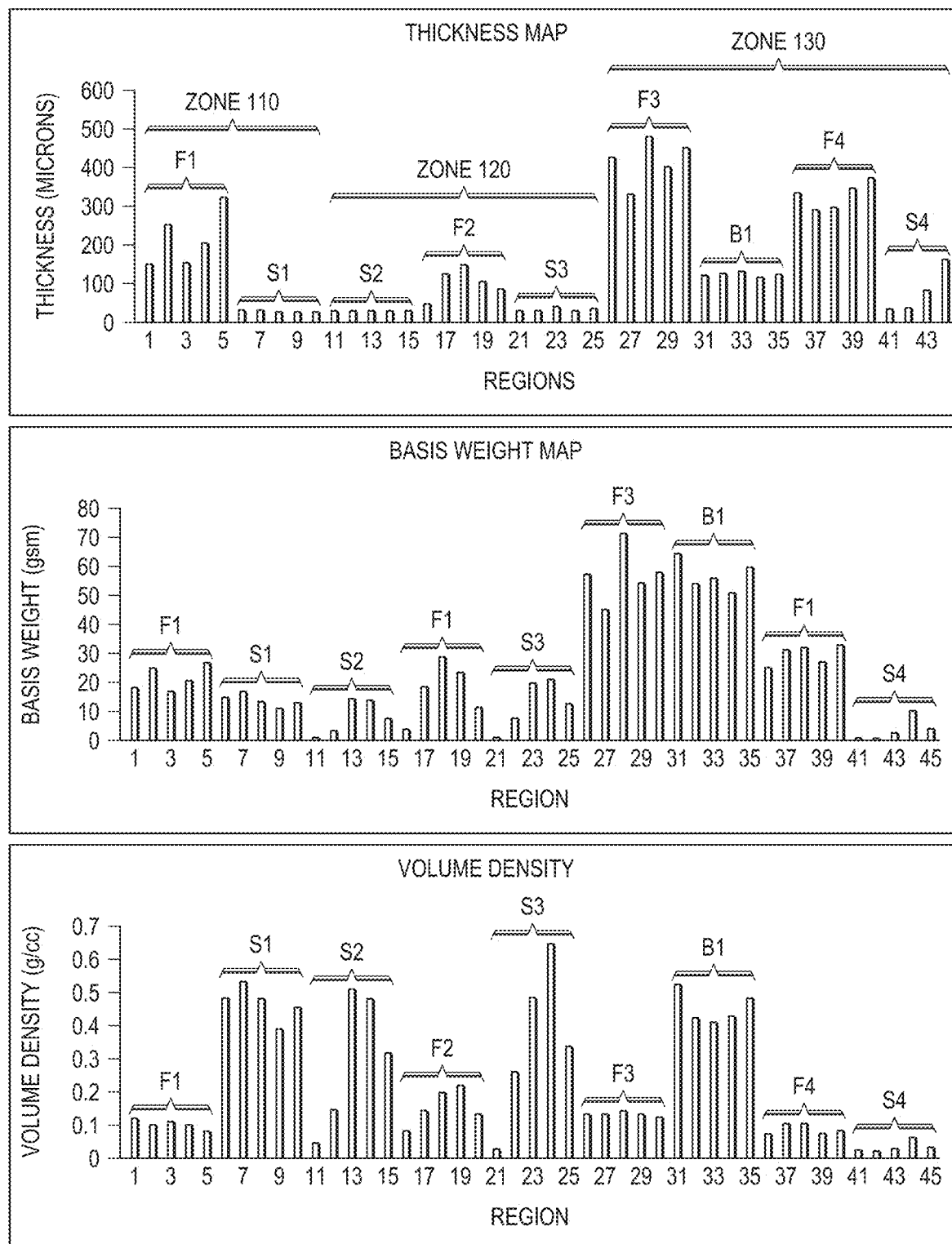
FIG. 76 is a graphical depiction of various benefits of the present disclosure shown in FIG. 75.

FIG. 76 shows data for groupings of first and second region measurements made within the three zones depicted in FIG. 75. The x-axis is the regions, with the numbers corresponding to the numbered regions on FIG. 64. First region measurements are labeled as Fn (e.g., F1) and second regions measurements are labeled as Sn (e.g., S1). Thus, regions 1-5 are first regions F1, each being in the first zone 110. Regions 6-10 are second regions S1, also being in the first zone 110. Likewise, first regions F2 are regions 16-20 in the second zone 120, and regions 11-15 and 21-25 are second regions S2 in the second zone 120. Finally, regions 31-35 are second regions but are point bonds 90 denoted on FIG. 76 as B1 to distinguish them in this disclosure as having been formed by a point bonding process. First regions F3 in the third zone 130 are regions 26-30 and 36-40, while regions 41-44 are second regions S2 in the third zone 130. The numbered regions are consistently depicted across all three graphs of FIG. 76, but for simplicity, the zones 110, 120, and 130 are depicted only on the Thickness Map.

The graphs shown in FIG. 75 represent graphically the magnitude of difference in intensive properties between first regions and second regions within any one of the zones of a fabric subjected to a calendaring point bonding step, and can be used to see graphically the difference in intensive properties for pairs of regions making up a microzone. For example, one can see that in the first zone 110 that basis weight between the two regions can vary within a range narrower than does thickness or volumetric density. For example, the thickness (caliper) can vary from about 325 microns in the first regions to about 29 microns in the second regions of the first zone 110, or about a 10× differential. The volumetric density in the first zone 110 can vary from about 0.08 g/cc to about 0.39 g/cc. Similar quantifiable distinctions can be understood for each of the zones shown.

In general, regions of a microzone can have broadly varying values for basis weight, thickness, and volumetric density.

Thus, with reference to FIG. 75 and FIG. 76 together, further characterization of the beneficial structure of a nonwoven fabric 10 of the present disclosure can be understood specifically with respect to the thermal calendar point bonds 90. Focusing for purposes of description on the third zone 130, three-dimensional features defining a microzone comprising first and second regions which are point bonded regions can be identified and the values of intensive properties quantified. For example, in FIG. 75, a representative point bond microzone 400 in the third zone 130 can be the pair of regions marked as areas 26 and 32 or 30 and 35. That is, first region 26 and second region 32 form a point bond microzone 400, and first region 30 and second region 35 form a point bond microzone 400.

The differences in certain intensive properties for point bond microzones can be seen in FIG. 67. For example, taking the two point bond microzones 400 described above, e.g., the two point bond microzones 400 of regions 26 and 32 and 30 and 35, respectively, one can see there is a slight difference in basis weight between the first regions and second regions ranging from about 55 to about 60 gsm, but the same regions exhibit a significant difference in thickness of from about 430 microns to about 460 microns to about 125 microns, and a significant difference in volumetric density of from about 0.13-0.14 g/cc to about 0.41-0.48 g/cc. Other differences in intensive properties can be observed by reference to FIG. 66.

Bond points 90 may play a significant role in the overall physical structure and functioning of a nonwoven fabric 10 of the present disclosure. By adding bond points 90 to the nonwoven fabric 10 comprising relatively closely spaced, precisely designed three-dimensional features, enabled by the forming belt of the present disclosure, a nonwoven fabric 10 can be further improved to exhibit an unexpected combination of visually distinct zones, microzones, and three-dimensional features that provide for functional superiority in the high performance combination of softness, strength, low fuzz, and fluid handling, as well as visually attractive aesthetic designs. The bond point feature provides for a nonwoven fabric 10 to be designed for the highest combined performance of strength, softness, fluid handling, and visual aesthetics, especially considering both form and function.

Figure 77:
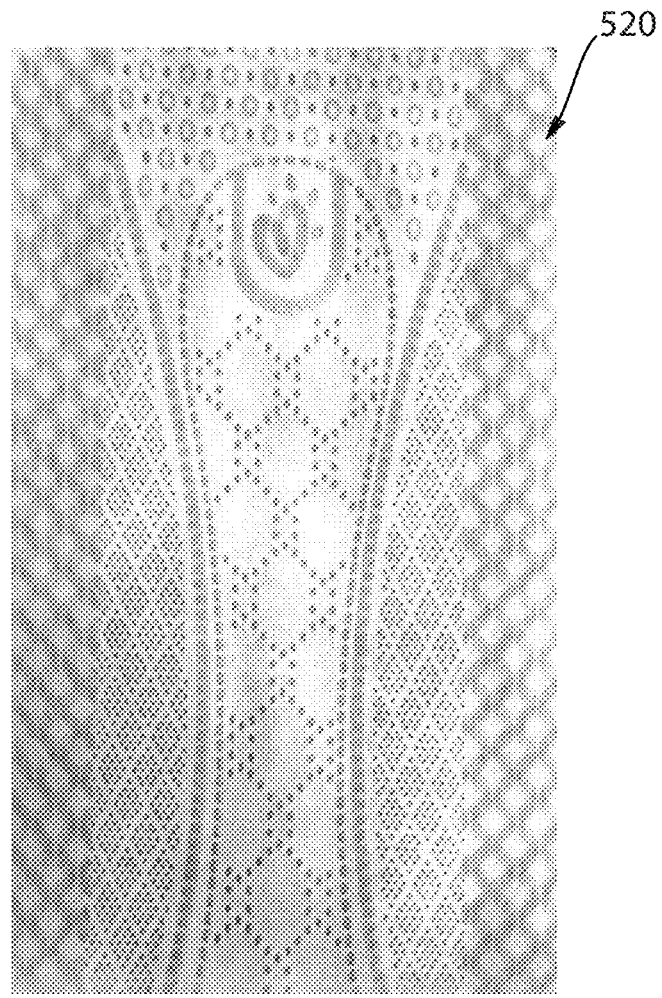
FIG. 77 is a photographic image of a portion of an example of a three-dimensional, variable basis weight, nonwoven fabric.
Figure 78:
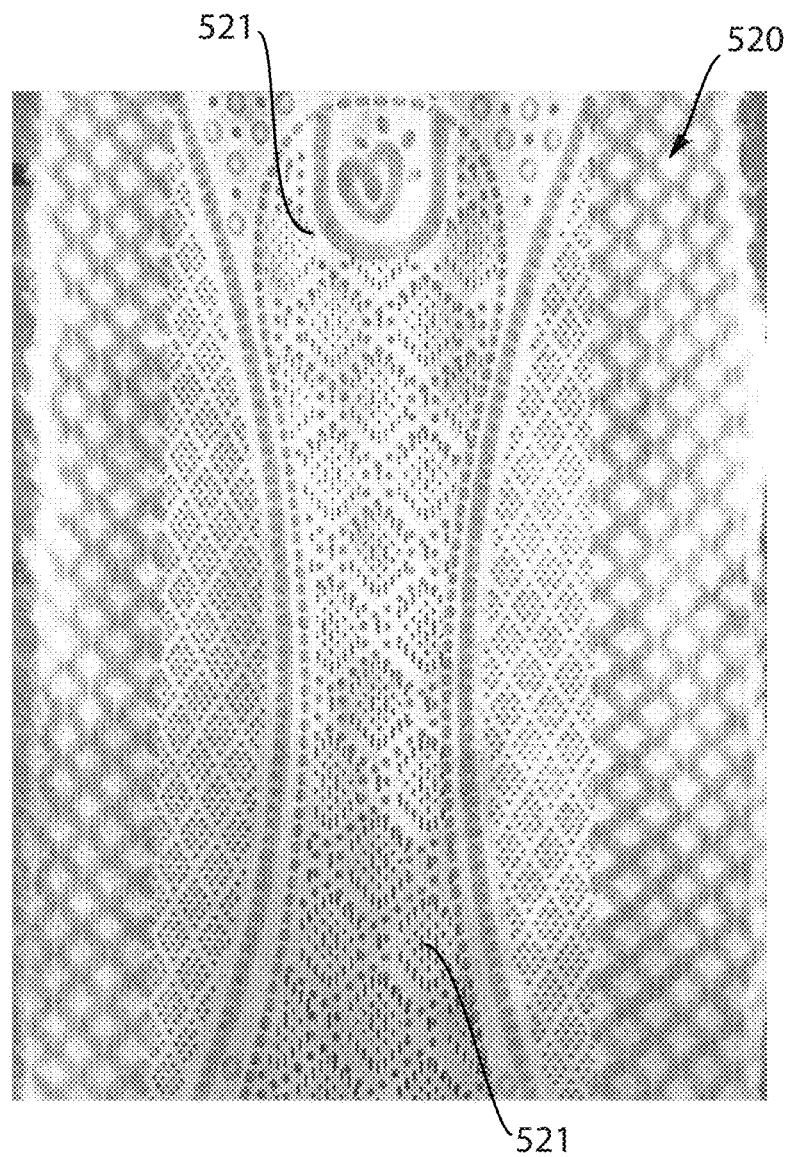
FIG. 78 is a photographic image of a portion of an example of a three-dimensional, variable basis weight, apertured nonwoven fabric of the present disclosure.

FIG. 77 shows an example of a variable basis weight, three-dimensional shaped nonwoven fabric 520 as described herein, but without any apertures. FIG. 78 shows an example variable basis weight, apertured, three-dimensional shaped nonwoven fabric 520 as described herein. As shown in FIG. 78, the variable basis weight, apertured, three-dimensional shaped nonwoven fabric 520 comprises a plurality of apertures 521 in one of the central zones, where the plurality of apertures 521 were formed as a result of overbonding and stretching in the CD to rupture the overbonds, as described herein. It is believed that such apertures 521 can facilitate fluid acquisition and provide a visual impression of breathability and absorbency when used as a component (e.g., topsheet, outercover nonwoven) in an absorbent article.

Figure 79:
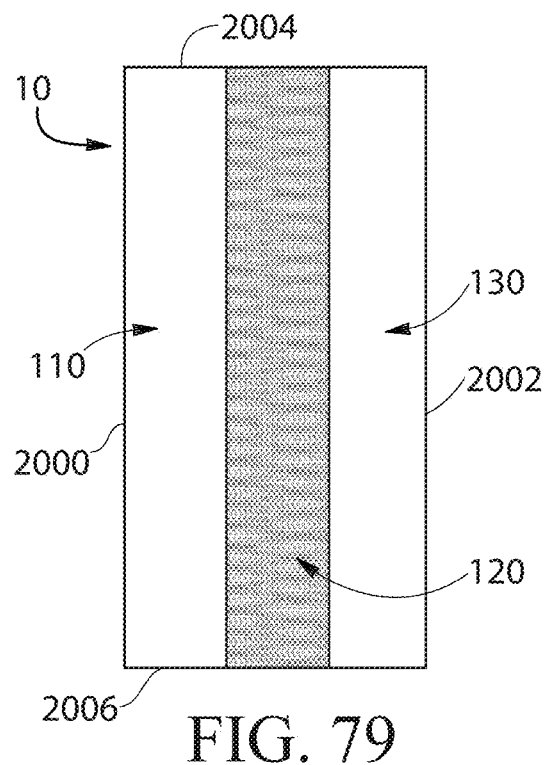
FIG. 79 is a schematic representation of an example of a nonwoven fabric of the present disclosure.
Figure 80:
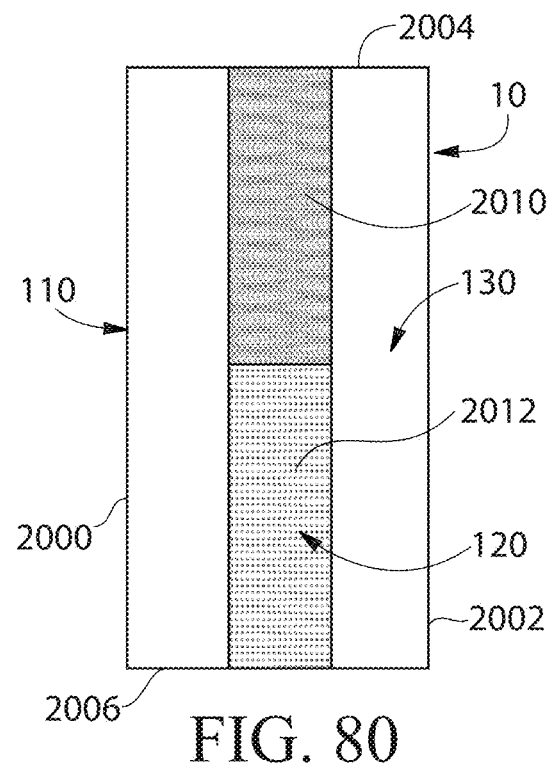
FIG. 80 is a schematic representation of an example of a nonwoven fabric of the present disclosure.
Figure 82:
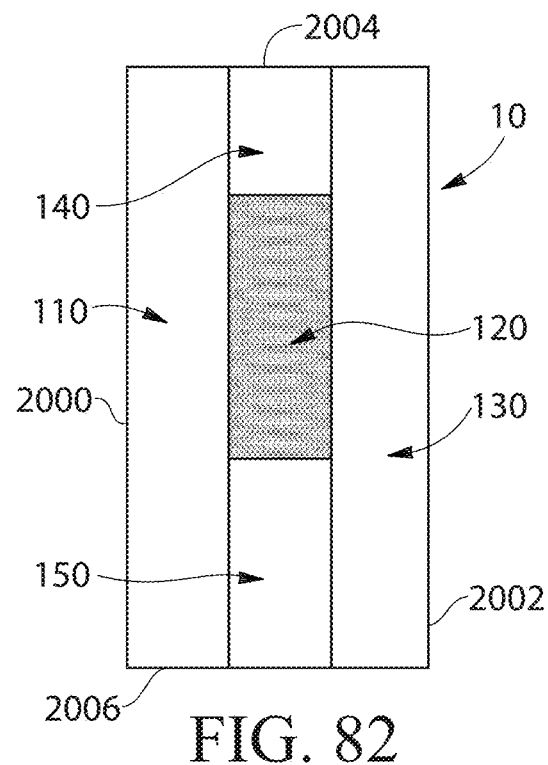
FIG. 82 is a schematic representation of an example of a nonwoven fabric of the present disclosure.

FIGS. 79-82 show additional example configurations for zones in a variable basis weight, three-dimensional shaped nonwoven fabric or substrate 10. For example, as shown in FIGS. 79 and 80, and as described herein, a portion of the first visually discernible zone 110 can be positioned proximate to the first side edge 2000 and a portion of the third visually discernible zone 130 can be positioned proximate to the second side edge 2002. The second visually discernible zone 120 can be positioned intermediate the first visually discernible zone 110 and the third visually discernible zone 130. As shown in FIG. 80, the second visually discernible zone 120 may comprise an area having a first aperture pattern 2010 and an area having a second aperture pattern 2012. In FIG. 81, the first visually discernible zone 110 can be positioned proximate to the first end edge 2004 of the three-dimensional, nonwoven fabric or substrate 10 and the second visually discernible zone 120 can be positioned proximate to the second end edge 2006. It will be appreciated that in an example, a first visually discernible zone can be positioned proximate to a second end edge of a three-dimensional, nonwoven substrate and a second visually discernible zone can be positioned proximate to a first end edge. As described herein, the second visually discernible zone 120 can be surrounded by one or more non-apertured visually discernible zones. For example, and as shown in FIG. 82, the second visually discernible zone 120 can be surrounded by the first visually discernible zone 110 and the third visually discernible zone 100. A portion of the first visually discernible zone 110 can be positioned proximate to the first side edge 2000 and a portion of the third visually discernible zone 130 can be positioned proximate to the second side edge 2002. A fourth visually discernible zone 140 and a fifth visually discernible zone 150 may be provided. A portion of the fourth visually discernible zone 140 can be positioned proximate to the first end edge 2004 and a portion of the fifth visually discernible zone 150 can be positioned proximate to the second end edge 2006. In such examples, non-apertured zones (e.g., 110, 130) may stretch and expand along with apertured zones (e.g., 120). However, it will be appreciated that the zones described herein may be arranged in any of a variety of configurations.

Test Methods:

Compression Aging Test

Initial Caliper Measurement:
  Cut five 3 inch by 3 inch samples per nonwoven fabric to be measured.
  Number each sample from 1 to 5.
  Measure caliper at 0.5 kPa with Standard 65 mm foot using Thwing-Albert caliper tester according to standard procedures.
  Report initial caliper for each of the five samples.
  Report the average caliper of the five samples.

Aged Compression Method and Aged Caliper Measurement
  Stack the five samples in an alternating mode with each separated by a paper towel, the stack starting and ending with a Sample Number 1 and 5, respectively.
  Place the alternating stacked samples in an aluminum sample holder with an appropriate weight on top of the samples (4 KPa, 14 KPa or 35 KPa).
  Place the stacked samples with the weight in oven at 40° C. for 15 hours.
  Remove the weight after 15 hours, separate the samples and measure the caliper of each sample at 0.5 kPa with Standard 65 mm foot Thwing-Albert caliper tester according to standard procedures.
  Report aged caliper value for each of the five samples.
  Report the average aged caliper of the five samples.

Analysis Reports:
  Report average initial and aged calipers by position number
  Report Caliper Recovery Index:
    (Average Aged Caliper/Average Initial Caliper)*100

Localized Basis Weight

Localized basis weight of the nonwoven fabric may be determined by several available techniques, but a simple representative technique involves a punch die having an area of 3.0 cm$^2$ which is used to cut a sample piece of the web from the selected region from the overall area of a nonwoven fabric. The sample piece is then weighed and divided by its area to yield the localized basis weight of the nonwoven fabric in units of grams per meter squared. Results are reported as a mean of 2 samples per selected region.

Fuzz Level Test

The Fuzz Level Test is used to determine the quantity of fibers removed from a nonwoven materials under an abrasive force (i.e., the fuzz level).

The Fuzz Level Test utilizes the following materials:
Sutherland Ink Rub Tester with 2 lb. weight, available from Danilee Co, San Antonio, Tex.
Aluminum oxide cloth 320 grit shop rolls made by Plymouth Coatings, (617) 447-7731. This material can also be ordered through McMaster Carr, part number 468.7A51, (330) 995-5500.
Two sided tape, 3M #409, available from Netherland Rubber Company, (513) 733-1085.
Fiber Removal Tape, 3M #3187, available from Netherland Rubber Company, (513) 733-1085.
Analytical Balance (+/−0.0001 g)
Paper cutter
2200 g weight (metal) 170 mm×63 mm.
Thick-style release paper liner cardboard—0.0445 in (1.13 mm) caliper.

Materials Preparation

Measure and cut aluminum oxide cloth to 7.5 in (19.0 cm) in length. Measure and cut pieces of 3M #3187 tape 6.5 inches (16.5 cm) in length, two tapes for each specimen. Fold under approximately 0.25 inch (0.6 cm) on each end of the 3M #3187 tape to facilitate handling. Lay 3M #3187 tape on the thick-style release paper for use later.

Sample Preparation

Before handling or testing any of the materials, wash hands with soap and water to remove excess oils from hands. Optionally, latex gloves may be worn. Cut a sample of the nonwoven fabric to be tested to a size at least 11 cm in the MD and 4 cm in the CD. Lay out the sample of nonwoven fabric to be tested with the side to be tested facing down. Cut a piece of 3M #409 two-sided tape off roll at least 11 cm long. Remove the backing and apply the side of two-sided tape that was facing the backing to the sample nonwoven fabric lengthwise in the machine direction (MD). Replace the backing over the exposed tape. Using the paper cutter, cut test samples within the taped area 11 cm MD and 4 cm CD.

Test Procedure

1. Mount the cut piece of aluminum oxide cloth on Sutherland Ink Rub Tester using the 2 lb. weight. Lay a second cut piece of aluminum oxide cloth on top of the thick-style release paper liner cardboard (a new piece is used for each test). Lay both on top of the 2 lb. weight. The sides will fold down into clips—make sure aluminum oxide cloth and the thick-style release paper liner cardboard are flat.
2. Mount the specimen onto Sutherland Ink Rub Tester platform, centering on the metal plate. Place the 2200 g weight on top of specimen for 20 seconds.
3. Attach the metal plate and 2 lb. weight to Sutherland Ink Rub Tester.
4. Turn Rub Tester on. If the counter light is not illuminated press the reset button. Press the counter button to set the rub cycles to 20 cycles. Select Speed 1, the slow speed, (light is not illuminated) by using the Speed button. Press "Start".
5. When Rub Tester has shut off, carefully remove the aluminum oxide cloth/weight, being sure not to lose any of the loose microfibers (fuzz). In some cases, the microfibers will be attached to both the aluminum oxide cloth and the surface of Sample nonwoven. Lay the weight upside down on the bench.
6. Weigh the fiber removal tapes with release paper attached. Holding the fiber removal tape by its folded ends, remove release paper and set aside. Gently put the tape onto the aluminum oxide cloth to remove all of the fuzz. Remove the fiber removal tape and put back on release paper. Weigh and record the weight of the fiber removal tapes.

7. Hold another piece of the pre-weighed fiber removal tape by its folded ends. Gently put the fiber removal tape onto the surface of the rubbed nonwoven sample. Lay a flat metal plate on top of the fiber removal tape.
8. Lay the 2200 g weight on top of the metal plate for 20 seconds. Remove the fiber removal tape. Hold the pre-weighed fiber removal tape by its folded ends to avoid fingerprints. Put pre-weighed fiber removal tape back on release paper. Weigh and record the weight of the fiber removal tapes.
9. The fuzz weight is the sum of weight-increase of both fiber removal tapes.
10. The fuzz weight is reported as the average of 10 measurements.

Calculations

For a given sample, add the weight in grams of fuzz collected from the aluminum oxide cloth and the weight in grams of fuzz collected from the abraded Sample nonwoven. Multiply the combined weight in grams by 1000 to convert to milligrams (mg). To convert this measurement from absolute weight loss to weight loss per unit area, divide the total weight of fuzz by the area of the abraded area.

Air Permeability Test

The Air Permeability Test is used to determine the level of air flow in cubic feet per minute (cfm) through a forming belt. The Air Permeability Test is performed on a Textest Instruments model FX3360 Portair Air Permeability Tester, available from Textest AG, Sonnenbergstrasse 72, CH 8603 Schwerzenbach, Switzerland. The unit utilizes a 20.7 mm orifice plate for air permeability ranges between 300-1000 cfm. If air permeability is lower than 300 cfm the orifice plate needs to be reduced; if higher than 1000 cfm the orifice plate needs to be increased. Air permeability can be measured in localized zones of a forming belt to determine differences in air permeability across a forming belt.

Test Procedure

1. Power on the FX3360 instrument.
2. Select a pre-determined style having the following setup:
   a. Material: Standard
   b. Measurement Property: Air Permeability (AP)
   c. Test Pressure: 125 Pa (pascals)
   d. T-factor: 1.00
   e. Test point pitch: 0.8 inch.
3. Position the 20.7 mm orifice plate on the top side of the forming belt (the side with the three-dimensional protrusions) at the position of interest.
4. Selecting "Spot Measurement" on the touch screen of the testing unit.
5. Reset the sensor prior to measurement, if necessary.
6. Once reset, select the "Start" button to begin measurement.
7. Wait until the measurement stabilizes and record the cfm reading on the screen.
8. Select the "Start" button again to stop measurement.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850-1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 30). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

Micro-CT Intensive Property Measurement Method

The Micro-CT intensive property measurement method measures the basis weight, thickness and volumetric density values within visually discernable regions of a substrate sample. It is based on analysis of a 3D x-ray sample image obtained on a Micro-CT instrument (a suitable instrument is the Scanco µCT 50 available from Scanco Medical AG, Switzerland, or equivalent). The Micro-CT instrument is a cone beam microtomograph with a shielded cabinet. A maintenance free x-ray tube is used as the source with an adjustable diameter focal spot. The x-ray beam passes through the sample, where some of the x-rays are attenuated by the sample. The extent of attenuation correlates to the mass of material the x-rays have to pass through. The transmitted x-rays continue on to the digital detector array and generate a 2D projection image of the sample. A 3D image of the sample is generated by collecting several individual projection images of the sample as it is rotated, which are then reconstructed into a single 3D image. The instrument is interfaced with a computer running software to control the image acquisition and save the raw data. The 3D image is then analyzed using image analysis software (a suitable image analysis software is MATLAB available from The Mathworks, Inc., Natick, Mass., or equivalent) to measure the basis weight, thickness and volumetric density intensive properties of regions within the sample.

Sample Preparation:

To obtain a sample for measurement, lay a single layer of the dry substrate material out flat and die cut a circular piece with a diameter of 30 mm.

If the substrate material is a layer of an absorbent article, for example a topsheet, backsheet nonwoven, acquisition layer, distribution layer, or other component layer; tape the absorbent article to a rigid flat surface in a planar configuration. Carefully separate the individual substrate layer from the absorbent article. A scalpel and/or cryogenic spray (such as Cyto-Freeze, Control Company, Houston Tex.) can be used to remove a substrate layer from additional underlying layers, if necessary, to avoid any longitudinal and lateral extension of the material. Once the substrate layer has been removed from the article proceed with die cutting the sample as described above.

If the substrate material is in the form of a wet wipe, open a new package of wet wipes and remove the entire stack from the package. Remove a single wipe from the middle of the stack, lay it out flat and allow it to dry completely prior to die cutting the sample for analysis.

A sample may be cut from any location containing the visually discernible zone to be analyzed. Within a zone, regions to be analyzed are ones associated with a three-dimensional feature defining a microzone. The microzone comprises a least two visually discernible regions. A zone, three-dimensional feature, or microzone may be visually discernable due to changes in texture, elevation, or thickness. Regions within different samples taken from the same substrate material can be analyzed and compared to each other. Care should be taken to avoid folds, wrinkles or tears when selecting a location for sampling.

Image Acquisition:

Set up and calibrate the Micro-CT instrument according to the manufacturer's specifications. Place the sample into the appropriate holder, between two rings of low density material, which have an inner diameter of 25 mm. This will allow the central portion of the sample to lay horizontal and be scanned without having any other materials directly adjacent to its upper and lower surfaces. Measurements should be taken in this region. The 3D image field of view is approximately 35 mm on each side in the xy-plane with a resolution of approximately 5000 by 5000 pixels, and with a sufficient number of 7 micron thick slices collected to fully include the z-direction of the sample. The reconstructed 3D image resolution contains isotropic voxels of 7 microns. Images are acquired with the source at 45 kVp and 133 µA with no additional low energy filter. These current and voltage settings may be optimized to produce the maximum contrast in the projection data with sufficient x-ray penetration through the sample, but once optimized held constant for all substantially similar samples. A total of 1500 projections images are obtained with an integration time of 1000 ms and 3 averages. The projection images are reconstructed into the 3D image, and saved in 16-bit RAW format to preserve the full detector output signal for analysis.

Image Processing:

Load the 3D image into the image analysis software. Threshold the 3D image at a value which separates, and removes, the background signal due to air, but maintains the signal from the sample fibers within the substrate.

Three 2D intensive property images are generated from the thresheld 3D image. The first is the Basis Weight Image. To generate this image, the value for each voxel in an xy-plane slice is summed with all of its corresponding voxel values in the other z-direction slices containing signal from the sample. This creates a 2D image where each pixel now has a value equal to the cumulative signal through the entire sample.

In order to convert the raw data values in the Basis Weight Image into real values a basis weight calibration curve is generated. Obtain a substrate that is of substantially similar composition as the sample being analyzed and has a uniform basis weight. Follow the procedures described above to obtain at least ten replicate samples of the calibration curve substrate. Accurately measure the basis weight, by taking the mass to the nearest 0.0001 g and dividing by the sample area and converting to grams per square meter (gsm), of each of the single layer calibration samples and calculate the average to the nearest 0.01 gsm. Following the procedures described above, acquire a Micro-CT image of a single layer of the calibration sample substrate. Following the procedure described above process the Micro-CT image, and generate a Basis Weight Image containing raw data values. The real basis weight value for this sample is the average basis weight value measured on the calibration samples. Next, stack two layers of the calibration substrate samples on top of each other, and acquire a Micro-CT image of the two layers of calibration substrate. Generate a basis weight raw data image of both layers together, whose real basis weight value is equal to twice the average basis weight value measured on the calibration samples. Repeat this procedure of stacking single layers of the calibration substrate, acquiring a Micro-CT image of all of the layers, generating a raw data basis weight image of all of the layers, the real basis weight value of which is equal to the number of layers times the average basis weight value measured on the calibration samples. A total of at least four different basis weight calibration images are obtained. The basis weight values of the calibration samples must include values above and below the basis weight values of the original sample being analyzed to ensure an accurate calibration. The calibration curve is generated by performing a linear regression on the raw data versus the real basis weight values for the four calibration samples. This linear regression must have an R2 value of at least 0.95, if not repeat the entire calibration procedure. This calibration curve is now used to convert the raw data values into real basis weights.

The second intensive property 2D image is the Thickness Image. To generate this image the upper and lower surfaces of the sample are identified, and the distance between these surfaces is calculated giving the sample thickness. The upper surface of the sample is identified by starting at the uppermost z-direction slice and evaluating each slice going through the sample to locate the z-direction voxel for all pixel positions in the xy-plane where sample signal was first detected. The same procedure is followed for identifying the lower surface of the sample, except the z-direction voxels located are all the positions in the xy-plane where sample signal was last detected. Once the upper and lower surfaces have been identified they are smoothed with a 15×15 median filter to remove signal from stray fibers. The 2D Thickness Image is then generated by counting the number of voxels that exist between the upper and lower surfaces for each of the pixel positions in the xy-plane. This raw thickness value is then converted to actual distance, in microns, by multiplying the voxel count by the 7 µm slice thickness resolution.

The third intensive property 2D image is the Volumetric Density Image. To generate this image divide each xy-plane pixel value in the Basis Weight Image, in units of gsm, by the corresponding pixel in the Thickness Image, in units of microns. The units of the Volumetric Density Image are grams per cubic centimeter (g/cc).

Micro-CT Basis Weight, Thickness and Volumetric Density Intensive Properties:

Begin by identifying the region to be analyzed. A region to be analyzed is one associated with a three-dimensional feature defining a microzone. The microzone comprises a least two visually discernible regions. A zone, three-dimensional feature, or microzone may be visually discernable due to changes in texture, elevation, or thickness. Next, identify the boundary of the region to be analyzed. The boundary of a region is identified by visual discernment of differences in intensive properties when compared to other regions within the sample. For example, a region boundary can be identified based by visually discerning a thickness difference when compared to another region in the sample. Any of the intensive properties can be used to discern region boundaries on either the physical sample itself of any of the Micro-CT intensive property images. Once the boundary of the region has been identified, draw an oval or circular "region of interest" (ROI) within the interior of the region. The ROI should have an area of at least 0.1 mm2, and be selected to measure an area with intensive property values representative of the identified region. From each of the three intensive property images calculate the average basis weight, thickness and volumetric density within the ROI. Record these values as the region's basis weight to the nearest 0.01 gsm, thickness to the nearest 0.1 micron and volumetric density to the nearest 0.0001 g/cc.

Aperture Test

Aperture dimensions, Effective Aperture Area, % Effective Open Area, Interaperture Distance measurements, among other measurements, are obtained from specimen images acquired using a flatbed scanner. The scanner is capable of scanning in reflectance mode at a resolution of 6400 dpi and 8 bit grayscale (a suitable scanner is an Epson Perfection V750 Pro from Epson America Inc., Long Beach Calif. or equivalent). The scanner is interfaced with a computer running an image analysis program (a suitable program is ImageJ v. 1.47 or equivalent, National Institute of Health, USA). The specimen images are distance calibrated against an acquired image of a ruler certified by NIST. A steel frame is used to mount the specimen, which is then backed with a black glass tile (P/N 11-0050-30, available from HunterLab, Reston, Va.) prior to acquiring the specimen image. The resulting image is then thresheld, separating open aperture regions from specimen material regions, and analyzed using the image analysis program. All testing is performed in a conditioned room maintained at about 23±2° C. and about 50±2% relative humidity.

Sample Preparation:

To obtain a specimen, tape an absorbent article to a rigid flat surface in a planar configuration. Any leg elastics may be cut to facilitate laying the article flat. A rectilinear steel frame (100 mm square, 1.5 mm thick with an opening 60 mm square) is used to mount the specimen. Take the steel frame and place double-sided adhesive tape on the bottom surface surrounding the interior opening. Remove the release paper of the tape, and adhere the steel frame to the apertured layer of the article. Align the frame so that it is parallel and perpendicular to a machine direction (MD) and a cross direction (CD) of the apertured layer. Using a razor blade excise the apertured layer from the underlying layers of the article around the outer perimeter of the frame. Carefully remove the specimen such that its longitudinal and lateral extension is maintained to avoid distortion of the apertures. A cryogenic spray (such as Cyto-Freeze, Control Company, Houston Tex.) may be used to remove the specimen from the underlying layers if necessary. Five replicates obtained from five substantially similar articles are prepared for analysis. If the apertured layer of interest is too small to accommodate the steel frame, reduce the frame dimensions accordingly to accomplish the goals of removal of the specimen without distortion of the apertures while leaving an opening of sufficient size to allow for scanning a significant portion of the apertured layer. An apertured substrate raw material is prepared for testing by extending or activating it under the same process conditions, and to the same extent, as it would be for use on the absorbent article, and then in its extended state adhering it to the steel frame as described above for testing. Condition the samples at about 23±2° C. and about 50±2% relative humidity for 2 hours prior to testing.

Image Acquisition:

Place the ruler on the scanner bed, oriented parallel to sides of the scanner glass, and close the lid. Acquire a calibration image of the ruler in reflectance mode at a resolution of 6400 dpi (approximately 252 pixels per mm) and 8 bit grayscale, with the field of view corresponding to the dimensions of an interior of the steel frame. Save the calibration image as an uncompressed TIFF format file. Lift the lid and remove the ruler. After obtaining the calibration image, all specimens are scanned under the same conditions and measured based on the same calibration file. Next, place the framed specimen onto the center of the scanner bed, lying flat, with the outward facing surface of the specimen facing the scanner's glass surface. Orient the specimen so that sides of the frame are aligned parallel with and perpendicular to the sides of the scanner's glass surface, so that the resulting specimen image will have the MD vertically running from top to bottom. Place the black glass tile on top of the frame covering the specimen, close the lid and acquire a scanned image. Scan the remaining four replicates in like fashion. If necessary, crop all images to a rectangular field of view circumscribing the apertured region, and resave the files.

% Effective Open Area Calculation:

Open the calibration image file in the image analysis program and perform a linear distance calibration using the imaged ruler. This distance calibration scale will be applied to all subsequent specimen images prior to analysis. Open a specimen image in the image analysis program and set the distance scale. View the 8 bit histogram (0 to 255, with one bin per GL) and identify the gray level (GL) value for the minimum population located between the dark pixel peak of the aperture holes and the lighter pixel peak of the specimen material. Threshold the image at the minimum gray level value to generate a binary image. In the binary image the apertures appear as black, with a GL value of 255, and specimen as white, with a GL value of 0.

Using the image analysis program, analyze each of the discrete aperture regions. Measure and record all of the individual aperture areas to the nearest 0.01 mm$^2$, including partial apertures along the edges of the image. Discard any apertures with an area less than 0.3 mm$^2$ as "non-effective". Sum the remaining aperture areas (including whole and partial apertures), divide by the total area included in the image and multiply by 100. Record this value as the % effective open area to the nearest 0.01%.

In like fashion, analyze the remaining four specimen images. Calculate and report the average % effective open area values to the nearest 0.01% for the five replicates.

Effective Aperture Dimension Measurements:

Open the calibration image (containing the ruler) file in the image analysis program. Resize the resolution of the original image from 6400 dpi to 640 dpi (approximately 25.2 pixels per mm) using a bicubic interpolation. Perform a linear distance calibration using the imaged ruler. This distance calibration scale will be applied to all subsequent specimen images prior to analysis. Open a specimen image in the image analysis program. Resize the resolution of the original image from 6400 dpi to 640 dpi (approximately 25.2 pixels per mm) using a bicubic interpolation. Set the distance scale. View the 8 bit histogram (0 to 255, with one bin per GL) and identify the gray level (GL) value for the minimum population located between the dark pixel peak of the aperture holes and the lighter pixel peak of the specimen material. Threshold the image at the minimum gray level value to generate a binary image. In the binary image, the apertures appear as black, with a GL value of 255, and specimen as white, with a GL value of 0. Next, two morphological operations are performed on the binary image. First, a closing (a dilation operation followed by an erosion operation, iterations=1, pixel count=1), which removes stray fibers within an aperture hole. Second, an opening (an erosion operation followed by a dilation operation, iterations=1, pixel count=1), which removes isolated black pixels. Pad the edges of the image during the erosion step to ensure that black boundary pixels are maintained during the operation. Lastly, fill any remaining voids enclosed within the black aperture regions.

Using the image analysis program, analyze each of the discrete aperture regions. During the analysis exclude measurements of partial apertures along the edges of the image, so that only whole apertures are measured. Measure and record all of the individual effective aperture areas, perimeters, feret diameters (length of the apertures) along with its corresponding angle of orientation in degrees from 0 to 180, and minimum feret diameters (width of the apertures). Record the measurements for each of the individual elements areas to the nearest 0.01 mm$^2$, the perimeters and feret diameters (length and width), to the nearest 0.01 mm, and angles to the nearest 0.01 degree. Discard any apertures with an area less than 0.3 mm$^2$ as "non-effective". Record the number of remaining apertures, divide by the area of the image and record as the Aperture Density value. The angle of orientation for an aperture aligned with the MD (vertical in the image) will have an angle of 90 degrees. Apertures with a positive slope, increasing from left to right, will have an angle between zero and 90 degrees. Apertures with a negative slope, decreasing from left to right, will have an angle between 90 and 180 degrees. Using the individual aperture angles calculate an Absolute Feret Angle by subtracting 90 degrees from the original angle of orientation and taking its absolute value. In addition to these measurements, calculate an Aspect Ratio value for each individual aperture by dividing the aperture length by its width. Repeat this analysis for each of the remaining four replicate images. Calculate and report the statistical mean and standard deviation for each of the effective aperture dimension, the Absolute Feret Angle, and the Aspect Ratio measurements using all of the aperture values recorded from the replicates. Record the average of the individual Absolute Feret Angle measurements as the Average Absolute Feret Angle value. Calculate and report the % relative standard deviation (RSD) for each of the aperture dimension, the Absolute Feret Angle, and the Aspect Ratio measurements by dividing the standard deviation by the mean and multiplying by 100.

Inter-Aperture Distance Measurements:

The mean, standard deviation, median, and maximum distance between the apertures can be measured by further analyzing the binary image that was analyzed for the aperture dimension measurements. First, obtain a duplicate copy of the resized binary image following the morphological operations, and using the image analysis program, perform a Voronoi operation. This generates an image of cells bounded by lines of pixels having equal distance to the borders of the two nearest pattern apertures, where the pixel values are outputs from a Euclidian distance map (EDM) of the binary image. An EDM is generated when each interaperture pixel in the binary image is replaced with a value equal to that pixel's distance from the nearest pattern aperture. Next, remove the background zeros to enable statistical analysis of the distance values. This is accomplished by using the image calculator to divide the Voronoi cell image by itself to generate a 32-bit floating point image where all of the cell lines have a value of one, and the remaining parts of the image are identified as Not a Number (NaN). Lastly, using the image calculator, multiply this image by the original Voronoi cell image to generate a 32-bit floating point image where the distance values along the cell lines remain, and all of the zero values have been replaced with NaN. Next, convert the pixel distance values into actual inter-aperture distances by multiplying the values in the image by the pixel resolution of the image (approximately 0.04 mm per pixel), and then multiply the image again by 2 since the values represent the midpoint distance between apertures. Measure and record the mean, standard deviation, median and maximum inter-aperture distances for the image to the nearest 0.01 mm. Repeat this procedure for all replicate images. Calculate the % relative standard deviation (RSD) for the interaperture distance by dividing the standard deviation by the mean and multiplying by 100.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A three-dimensional, nonwoven substrate comprising:
a first surface and a second surface;
a first side edge and a second side edge connecting a first end edge and a second end edge;
a central lateral axis extending between the first end edge and the second end edge; and
a central longitudinal extending between the first side edge and the second side edge perpendicular to the central lateral axis;
wherein a line taken in a direction parallel or perpendicular to the central lateral axis of the three-dimensional, nonwoven substrate comprises:
a non-apertured, first visually discernable zone in the nonwoven substrate; and
an apertured second visually discernible zone in the nonwoven substrate;

wherein the first visually discernible zone comprises a first pattern of first three-dimensional features on the first surface and/or the second surface, wherein at least some of the first three-dimensional features define a first microzone comprising a first region and a second region, wherein the first region and the second region have a difference in value for at least one intensive property, wherein the at least one intensive property is basis weight, thickness, and/or volumetric density;

wherein the second visually discernible zone comprises a second pattern of second three-dimensional features on the first surface and/or the second surface, wherein at least some of the second three-dimensional features define a second microzone comprising a third region and a fourth region, wherein the third region and the fourth region have a difference in value for at least one intensive property, wherein the at least one intensive property is basis weight, thickness, and/or volumetric density, and a pattern of apertures such that the second visually discernable zone has an Effective Open Area in a range of about 3% to about 50%;

wherein the first and second three-dimensional features are formed prior to the formation of the apertures and correspond to the shape of a shaped forming belt; and wherein the nonwoven substrate retains greater than 70% of an original caliper after compression at a pressure of 35 kPa.

2. The nonwoven substrate of claim 1, wherein the apertures have an Effective Aperture Area in a range of about 0.3 mm².

3. The nonwoven substrate of claim 1, wherein the apertures have an Effective Aperture Area in a range of about 0.5 mm² to about 8 mm², and wherein the second zone has an Effective Open Area in a range of about 5% to about 25%.

4. The nonwoven substrate of claim 1, wherein at least one of the apertures overlaps with at least one of the second three-dimensional features in a plan view.

5. The nonwoven substrate of claim 1, wherein the first visually discernible zone is positioned proximate to one of the first end edge or the second end edge, and wherein the second visually discernible zone is positioned proximate to the other of the first end edge or the second end edge.

6. The nonwoven substrate of claim 1, wherein portions of perimeters of at least some of the apertures comprise one or more fused portions.

7. The nonwoven substrate of claim 6, wherein the one or more fused portions surround at least 25% of the perimeter.

8. The nonwoven substrate of claim 7, wherein the one or more fused portions are formed on lateral sides of the apertures and not on leading or trailing edges of the apertures.

9. The nonwoven substrate of claim 6, wherein portions of perimeters of at least some of the apertures are free of fused portions.

10. The nonwoven substrate of claim 1, wherein at least some of the apertures have an aspect ratio in a range of about 1.5 to about 10.

11. The nonwoven substrate of claim 1, wherein at least some of the apertures have an aspect ratio of less than about 1.5.

12. The nonwoven substrate of claim 1, wherein the difference in value for the intensive property for the first region and the second region is an order of magnitude.

13. The nonwoven substrate of claim 1, wherein the difference in value for the intensive property of the first region and the second region is about 1.2× to about 10×.

14. The nonwoven substrate of claim 1, wherein the intensive property for the third region and the fourth region is about 1.2× to about 10×.

15. The nonwoven substrate of claim 1, wherein the intensive property of the first visually discernible zone is basis weight, and wherein the basis weight of every region is greater than zero.

16. The nonwoven substrate of claim 1, wherein the intensive property of the first visually discernible zone is thickness, and wherein the thickness of every region is greater than zero.

17. The nonwoven substrate of claim 1, wherein the intensive property of the first visually discernible zone is volumetric density, and wherein the volumetric density of every region is greater than zero.

18. The nonwoven substrate of claim 1, wherein the intensive property for the second visually discernible zone is basis weight, thickness, and/or volumetric density, and wherein the basis weight, thickness, and/or volumetric density is greater than zero.

19. The nonwoven substrate of claim 1, wherein the line taken in the direction parallel or perpendicular to the central lateral axis of the three-dimensional nonwoven substrate comprises:

a non-apertured, third visually discernible zone in the nonwoven substrate; and wherein the third visually discernible zone comprises a third pattern of third three-dimensional features on the first surface and/or the second surface, wherein at least some of the third three-dimensional features define a third microzone comprising a fifth region and a sixth region, wherein the fifth region and the sixth region have a difference in value for at least one intensive property, wherein the at least one intensive property is basis weight, thickness, and/or volumetric density;

wherein the third three-dimensional features are also formed prior to the formation of the apertures and correspond to the shape of the shaped forming belt; and wherein the second visually discernible zone is positioned intermediate the first visually discernible zone and the third visually discernible zone.

20. The nonwoven substrate of claim 19, wherein a portion of the first visually discernible zone is positioned proximate to the first side edge, and wherein a portion of the third visually discernible zone is positioned proximate to the second side edge.

21. The nonwoven substrate of claim 19, wherein a portion of the first visually discernible zone is positioned proximate to the first end edge, and wherein a portion of the third visually discernible zone is positioned proximate to the second end edge.

22. The nonwoven substrate claim 1, wherein the nonwoven substrate is a spunbond nonwoven substrate.

23. An absorbent article comprising:
a liquid permeable material comprising the three-dimensional, nonwoven substrate of claim 1;
a liquid impermeable material; and
an absorbent core comprising an absorbent material, wherein the absorbent core is positioned intermediate the liquid permeable material and the liquid impermeable material.

24. A package comprising a plurality of the absorbent articles of claim 23, wherein the In-Bag Stack Height is in the range of about 70 mm to about 90 mm, according to the In-Bag Stack Height Test.

* * * * *